US008273772B2

(12) United States Patent
Sutton et al.

(10) Patent No.: US 8,273,772 B2
(45) Date of Patent: Sep. 25, 2012

(54) HETEROARYL COMPOUNDS AS P2Y$_1$ RECEPTOR INHIBITORS

(75) Inventors: James C. Sutton, Pleasanton, CA (US); Zulan Pi, Pennington, NJ (US); Rejean Ruel, Saint-Lambert (CA); Alexandre L'Heureux, Ste-Julie (CA); Carl Thibeault, Mascouche (CA); Patrick Y. S. Lam, Chadds Ford, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 434 days.

(21) Appl. No.: 12/619,702

(22) Filed: Nov. 17, 2009

(65) Prior Publication Data

US 2010/0093689 A1 Apr. 15, 2010

Related U.S. Application Data

(62) Division of application No. 11/333,050, filed on Jan. 17, 2006, now Pat. No. 7,645,778.

(60) Provisional application No. 60/645,285, filed on Jan. 19, 2005, provisional application No. 60/749,317, filed on Dec. 9, 2005.

(51) Int. Cl.
*A61K 31/4436* (2006.01)
*C07D 417/12* (2006.01)

(52) U.S. Cl. ..................... 514/342; 546/268.7
(58) Field of Classification Search ............... 546/268.7; 514/342
See application file for complete search history.

(56) References Cited

U.S. PATENT DOCUMENTS

| | | |
|---|---|---|
| 3,118,888 A | 1/1964 | Giraldi et al. |
| 6,020,357 A | 2/2000 | Pinto et al. |
| 6,187,797 B1 | 2/2001 | Pruitt et al. |
| 6,586,453 B2 | 7/2003 | Dhanoa et al. |
| 7,388,021 B2 | 6/2008 | Chao et al. |
| 7,470,712 B2 | 12/2008 | Herpin et al. |
| 7,550,499 B2 | 6/2009 | Tuerdi et al. |
| 2006/0079563 A1 | 4/2006 | Das et al. |
| 2006/0293522 A1 | 12/2006 | Sutton |
| 2007/0004677 A1 | 1/2007 | Chao et al. |
| 2008/0221197 A1 | 9/2008 | Lam et al. |

FOREIGN PATENT DOCUMENTS

| | | |
|---|---|---|
| FR | 1342550 | 12/1962 |
| WO | WO99/24404 | 5/1999 |
| WO | WO00/39101 | 7/2000 |
| WO | WO02/064211 | 8/2002 |
| WO | WO03/080553 | 10/2003 |
| WO | WO2004/054617 | 7/2004 |
| WO | WO2004/060907 | 7/2004 |
| WO | WO2005/070920 | 8/2005 |

OTHER PUBLICATIONS

Indian Journal of Chemistry, Section B (Organic including Medicinal), vol. 22B(3), pp. 311-312 (1983).
Zhang, N. et al., "MED (MAPKK) Inhibitors. Part 2: Structure-Activity Relationships of 4-Anilino-3-cyano-6,7-dialkoxyquinolines", Bioorganic & Medicinal Chemistry Letters, vol. 11, pp. 1407-1410 (2001).
Abbracchio, M.P. et al., "Characterization of the UDP-glucose receptor (re-named here the P2Y$_{14}$ receptor) adds diversity to the P2Y receptor family", Trends in Pharmacological Sciences, vol. 24, No. 2, pp. 52-55 (2003).
Abbracchio, M.P. et al., "Purinoceptors: Are There Families of P2X and P2Y Purinoceptors?", Pharmac. Ther., vol. 64, pp. 445-475 (1994).
Baurand, A. et al., "The P2Y$_1$ Receptor as a Target for New Antithrombotic Drugs: A Review of the P2Y$_1$ Antagonist MRS-2179", Cardiovascular Drug Reviews, vol. 21, No. 1, pp. 61-76 (2003).
Bensemann, I. et al., "Creation of hydrogen bonded 1D networks by co-crystallization of N,N'-bis(2-pyridyl)aryldiamines with dicarboxylic acids", Org. Biomol. Chem., vol. 1, pp. 1425-1434 (2003).
Boeynaems, J.-M. et al., "Overview of P2Y Receptors as Therapeutic Targets", Drug Development Research, vol. 52, pp. 187-189 (2001).
Burnstock, G. et al., "P2 Purinergic Receptors: Modulation of Cell Function and Therapeutic Potential", The Journal of Pharmacology and Experimental Therapeutics, vol. 295, No. 3, pp. 862-869 (2000).
Daniel, J.L. et al., "Molecular Basis for ADP-induced Platelet Activation", The Journal of Biological Chemistry, vol. 273, No. 4, pp. 2024-2029 (1998).
Fabre, J.-E. et al., "Decreased platelet aggregation, increased bleeding time and resistance to thromboembolism in P2Y$_1$-deficient mice", Nature Medicine, vol. 5, No. 10, pp. 1199-1202 (1999).
Hechler, B. et al., "The P2Y$_1$ receptor, necessary but not sufficient to support full ADP-induced platelet aggregation, is not the target of the drug clopidogrel", British Journal of Haematology, vol. 103, pp. 858-866 (1998).
Ito, Y. et al., "Syntheses of Nitrogen-containing Heterocyclic Compounds. XXIX. An Improved Method for the Preparation of 10H-Pyrido[3,2-b]-[1,4]benzoxazine (1-Azaphenoxazine)", Chem. Pharm. Bull., vol. 26, No. 5, pp. 1375-1383 (1978).
Janssens, R. et al., "Cloning and Tissue Distribution of the Human P2Y$_1$ Receptor", Biochemical and Biophysical Research Communications, vol. 221, No. 3, pp. 588-593 (1996). Jin, J. et al., "Coactivation of two different G protein-coupled receptors is essential for ADP-induced platelet aggregation", Proc. Natl. Acad. Sci. USA, vol. 95, pp. 8070-8074 (1998).
Jin, J. et al., "Molecular Basis for ADP-induced Platelet Activation. II. The P2Y$_1$ Receptor Mediates ADP-induced Intracellular Calcium Mobilization and Shape Change in Platelets", The Journal of Biological Chemistry, vol. 273, No. 4, pp. 2030-2034 (1998).
Lenain, N. et al., "Inhibition of localized thrombosis in P2Y$_1$-deficient mice and rodents treated with MRS2179, a P2Y$_1$ receptor antagonist", Journal of Thrombosis and Haemostasis, vol. 1, pp. 1144-1149 (2002).
Léon, C. et al., "Key Role of the P2Y$_1$ Receptor in Tissue Factor-Induced Thrombin-Dependent Acute Thromboembolism: Studies in P2Y$_1$-Knockout Mice and Mice Treated With a P2Y$_1$ Antagonist", Circulation, vol. 103, pp. 718-723 (2001).

(Continued)

*Primary Examiner* — Patricia Morris
(74) *Attorney, Agent, or Firm* — Jing G. Sun

(57) ABSTRACT

The present invention provides novel heteroaryl compounds and analogues thereof, which are selective inhibitors of the human P2Y$_1$ receptor. The invention also provides for various pharmaceutical compositions of the same and methods for treating diseases responsive to modulation of P2Y$_1$ receptor activity.

10 Claims, No Drawings

OTHER PUBLICATIONS

Marcincal-Lefebvre, A. et al., "2-[2-(Phenylthio)phenylamino]nicotinic acids and 2-[4-(phenylthio)phenylamino]nicotinic acids. Synthesis and antiinflammatory activity", Annales Pharmaceutiques Francaises, vol. 38, No. 3, pp. 243-252 (1980) (English abstract).

Matsuo, M. et al., "New 2-Aryliminoimidazolidines. I. Synthesis and Antihypertensive Properties of 2-(2-Phenoxyphenylimino)imidazolidines and Related Compounds", Chem. Pharm. Bull., vol. 33, No. 10, pp. 4409-4421 (1985).

Nörenberg, W. et al., "Characterization and possible function of adenosine 5'-triphosphate receptors in activated rat microglia", Br. J. Pharmacol., vol. 111, pp. 942-950 (1994).

Roberts, M.E. et al., "On the Alkyl Derivatives of the Isomeric Ortho and Para-phenoxyphenyl Thiazolidones", The University of Kansas Science Bulletin, vol. 25, No. 11, pp. 213-227 (1938).

Rodig, O.R. et al., "Pyridine Chemistry. II. Further Studies on the Smiles Rearrangement of the 3-Amino-2,2'-dipyridyl Sulfide System. The Synthesis of Some 1,6-Diazaphenothiazines", Journal of Medicinal Chemistry, vol. 9, No. 1, pp. 116-120 (1966).

Salter, M.W. et al., "ATP Causes Release of Intracellular $Ca^{2+}$ via the Phospholipase $C\beta/IP_3$ Pathway in Astrocytes from the Dorsal Spinal Cord", The Journal of Neuroscience, vol. 15, No. 4, pp. 2961-2971 (1995).

Savi, P. et al., "Role of P2Y1 purinoceptor in ADP-induced platelet activation", vol. 422, pp. 291-295 (1998).

Tomita, M. at al., "Synthesis of the thiazole derivatives containing diphenyl ether nucleus", Yakugaku Zasshi, vol. 75, pp. 1077-1081 (1955) (English abstract).

Bensemann et al., "Creation of hydrogen bonded 1D networks by co-crystallization of N, $N^1$-bis(2-pyridyl)aryldiamines with dicarboxylic acids" The Royal Society of Chemistry 2003, 1, 1425-1434.

Bareich et al., "Simultaneous in Vitro Assay of the First Four Enzymes in the Fungal Aspartate Pathway Identifies a New Class of Aspartate Kinase Inhibitor" Chemistry & Biology vol. 10, 967-973, 2003.

Database Beilstein 1988, XP002386183.

Database Beilstein 1985, XP002386192.

Database Beilstein 1988, XP002386184.

Vippagunata et al., "Crystalline Solid" advanced Drug Delivery Reviews, vol. 48.

Guillory (in Brittain ed.,),"Polymorphism, etc.." NY: Marcel Dekker, Inc., vol. 1-2, pp. 183-226 (1999).

HETEROARYL COMPOUNDS AS P2Y$_1$ RECEPTOR INHIBITORS

CROSS-REFERENCE TO RELATED APPLICATIONS

This application is a divisional of U.S. patent application Ser. No. 11/333,050, filed Jan. 17, 2005, now allowed, which claims the priority benefit of U.S. Provisional Application No. 60/645,285, filed Jan. 19, 2005 and the priority benefit of U.S. Provisional Application No. 60/749,317, filed Dec. 9, 2005, all of which are expressly incorporated fully herein by reference.

FIELD OF THE INVENTION

The present invention provides novel heteroaryl compounds and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b and A3), which bind to and are activated by the nucleoside adenosine, and the P2 receptors, which comprise a second, more diverse class of receptors which are activated by a wide variety of nucleotides including ATP, ADP, UTP and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al. *Drug Development Research* 2000, 52, 187-9). In addition, an eighth receptor, P2Y$_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review see Burnstock, G. and Williams, M. *J. Pharm. Exp Ther.* 2000, 295, 862-9), including diabetes, cancer, CF, and treatment of ischemia-reperfusion injury (Abbracchio M. P., Burnstock G. *Pharmacol. Ther.* 1994, 64, 445-475). P2Y1 receptors, almost ubiquitous among human organs (Jassens R; Communi D.; Pirotton S. et al. *Biochem. Biophys. Res. Comm.* 1996, 221, 588-593) have been identified on microglia (Norenberg W. et al.; *Br. J. Pharmacol.* 1994, 111, 942-950) and on astrocytes (Salter M. W. and Hicks J. L. *J. Neurosc.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, J. et al. *Proc.* *Natl. Acad. Sci.* 1998, 95, 8070). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation (Jin, J. et al. *Proc. Natl. Acad. Sci.* 1998, 273, 2030-4). The first signal arises from ADP driven activation of the P2Y$_1$ receptor and can most easily be tracked by measuring the transitory increase in intracellular free Ca$^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS and A2P5P) (Daniel, J. L. et al. *J. Biol. Chem.* 1998, 273, 2024-9; Savi, P. et al. *FEBS Letters* 1998, 422, 291-5; Hechler, B. et al. *Br. J. Haematol.* 1998, 103, 858-66.) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al. *Circulation* 2001, 103, 718-23, in a model of thromboplastin induced thromboembolism using both a P2Y$_1$ knock-out mouse and the P2Y$_1$ antagonist MRS-2179 (Baurand, A. and Gachet, C. *Cardiovascular Drug Reviews* 2003, 21, 67-76). These results were subsequently extended to include the inhibition of both venous and arterial thrombosis in the rat (Lenain, N. er al. *J. Thromb. Haemost.* 2003, 1, 1144-9) and confirmed by a second laboratory using an independently derived P2Y$_1$ knock-out mouse (Fabre, J-E. et al. *Nature Medicine* 1999, 5, 1199-1202). Taken together, these data suggest that the discovery of novel P2Y$_1$ antagonists with improved pharmaceutical characteristics could have significant utility in the treatment of a variety of thromboembolic disorders.

SUMMARY OF THE INVENTION

The present invention provides novel heteroaryl compounds which are useful as selective inhibitors of the P2Y$_1$ receptor including stereoisomers, tautomers, pharmaceutically acceptable salts, solvates, or prodrugs thereof.

The present invention also provides processes and intermediates for making the compounds of the present invention or a stereoisomer, tautomer, pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a stereoisomer, tautomer, pharmaceutically acceptable salt, solvate, or prodrug form thereof.

The present invention also provides a method for modulation of platelet reactivity comprising administering to a host in need of such treatment a therapeutically effective amount of at least one of the compounds of the present invention or a stereoisomer, tautomer, pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a stereoisomer, tautomer, pharmaceutically acceptable salt, solvate, or prodrug form thereof.

The present invention also provides novel thiazole and oxazole derivatives for use in therapy for other disease states which are responsive to modulation of $P2Y_1$ activity.

The present invention also provides the use of novel thiazole and oxazole derivatives for the manufacture of a medicament for the treatment of a thromboembolic or other disorders.

These and other features of the invention will be set forth in the expanded form as the disclosure continues.

DETAILED DESCRIPTION OF PREFERRED EMBODIMENTS

In a first embodiment, the present invention provides, inter alia, compounds of Formula (Ia):

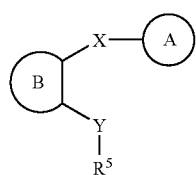

(Ia)

or a stereoisomer, tautomer, pharmaceutically acceptable salt, solvate, or prodrug thereof, wherein:

ring A is a 5- to 6-membered heteroaryl comprising: carbon atoms and 1-4 ring heteroatoms selected from N, $NR^{11}$, $S(O)_p$, and O, wherein said heteroaryl is substituted with 0-4 $R^1$;

ring B is phenyl substituted with 0-4 $R^7$, pyridyl substituted with 0-3 $R^7$, or thienyl substituted with 0-2 $R^7$;

X is NH or NMe;

Y is O or S;

$R^1$ is, independently at each occurrence, F, Cl, Br, I, $CF_3$, $-CF_2CF_3$, $OCF_3$, $-OCF_2CF_2H$, $-OCF_2CF_3$, $SiMe_3$, $-(CR^fR^f)_r-OR^c$, $SR^c$, CN, $NO_2$, $-(CR^fR^f)_r-NR^{12}R^{13}$, $-(CR^fR^f)_r-C(O)R^c$, $-(CR^fR^f)_r-CO_2R^c$, $-(CR^fR^f)_r-C(O)NR^{12}R^{13}$, $-C(O)NR^{14}(CR^fR^f)_nN^{12}R^{13}$, $-(CR^fR^f)_r-OC(O)NR^{12}R^{13}$, $-(CR^fR^f)_r-NR^{14}C(O)NR^{12}R^{13}$, $-(CR^fR^f)_r-NR^{14}C(O)R^d$, $-(CR^fR^f)_r-NR^{14}C(O)OR^h$, $-NR^{14}(CR^fR^f)_n-C(O)R^d$, $-NR^{14}CO(CR^fR^f)_nOR^c-(CH_2)_r-CR^{13}(=NOR^c)$, $-(CH_2)_r-C(NH_2)(=NOR^c)$, $-S(O)_pNR^{12}R^{13}$, $-(CR^fR^f)_r-NR^{14}S(O)_pNR^{12}R^{13}$, $-NR^{14}SO_2CF_3$, $-NR^{14}S(O)_pR^d$, $-S(O)_2CF_3$, $-S(O)R^d$, $-S(O)_2R^d$, $-OP(O)(OEt)_2$, $-O(CH_2)_2OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-13}$ carbocycle substituted with 0-5 $R^b$, or $-(CR^fR^f)_r-5-$ to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s are combined with the carbon atoms to which they attached, form a 5- to 7-membered carbocyclic or heterocyclic ring comprising: carbon atoms and 0-3 additional heteroatoms selected from N, $NR^{11}$, O, and $S(O)_p$, 0-2 carbonyls, and 0-2 double bond, wherein said carbocycle or heterocycle is substituted with 0-4 $R^b$;

$R^5$ is a $-(CR^fR^f)_n-C_{3-10}$ carbocycle substituted with 1-4 $R^{5a}$, or a $-(CR^fR^f)_n-5-$ to 10-membered heterocycle comprising: carbon atoms and 1-4 heteroatoms selected from N, $NR^{11}$, O, and $S(O)_p$, wherein said heterocycle is substituted with 0-4 $R^{5a}$;

$R^{5a}$ is, independently at each occurrence, F, Cl, Br, I, $-(CR^fR^i)_r-OR^c$, $SR^c$, CN, $NO_2$, $CF_3$, $-CF_2CF_3$, $OCF_3$, $-OCF_2CF_2H$, $-OCF_2CF_3$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $-Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-3 $R^e$, or $-(CR^fR^f)_r-5-$ to 10-membered heterocycle comprising: carbon atoms and 1-4 heteroatoms selected from N, $NR^{11}$, O, and $S(O)_p$, wherein said heterocycle is substituted with 0-3 $R^e$;

alternatively, two $R^{5a}$ groups, together with the atoms to which they are attached, form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 double bonds, wherein said carbocyclic or heterocyclic ring is substituted with 0-3 $R^e$;

$R^7$ is, independently at each occurrence, H, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-3 $R^b$, or $-(CR^fR^f)_r-5-$ to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s can form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-3 $R^{7c}$;

$R^{7b}$ is, independently at each occurrence, H, $C_{1-4}$ alkyl, $(C_{1-4}$ alkyl$)C(O)$—, phenyl-C(O)—, benzyl-C(O)—, benzyl-$S(O)_2$—, $(C_{1-4}$ alkyl$)NHC(O)$—, $(C_{1-4}$ alkyl$)_2NC(O)$—, phenyl-NHC(O)—, benzyl-NHC(O)—, $(C_{1-4}$ alkyl$)-S(O)_2$—, phenyl-$S(O)_2$—, phenyl substituted with 0-3 $R^b$, or benzyl substituted with 0-3 $R^b$;

$R^{7c}$ is, independently at each occurrence, H, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-6}$ alkyl substituted with 1-5 fluorine, $-(CR^fR^f)_rC(O)NR^{12}R^{13}$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $(C_{1-6}$ alkyl$)C(O)$—, $(C_{3-6}$ cycloalkyl$)C_{1-3}$ alkyl-C(O)—, $(C_{3-6}$ cycloalkyl$)C(O)$—, phenyl-C(O)—, benzyl-C(O)—, $(C_{1-6}$ alkyl$)NHC(O)$—, $(C_{1-6}$ alkyl$)_2NC(O)$—, phenyl-NHC(O)—, benzyl-NHC(O)—, (phenyl)$(C_{1-6}$ alkyl$)NC(O)$—, (benzyl)$(C_{1-6}$ alkyl$)NC(O)$—, $(C_{1-6}$ alkyl$)-S(O)_2$—, phenyl-$S(O)_2$—, benzyl-$S(O)_2$—, $-(CR^fR^f)_r-C_{3-10}$ carbocycle, or $-(CR^fR^f)_r-5-$ to 10-membered heterocycle comprising: carbon atoms and 1-4 heteroatoms selected from N, $NR^f$, O, and $S(O)_p$; wherein said phenyl, benzyl, carbocycle, and heterocycle are substituted with 0-3 $R^b$;

$R^{12}$ is, independently at each occurrence, H, $C_{1-6}$ alkyl substituted with 1-5 fluorine, $-(CR^fR^f)_rC(O)NR^fR^f$, $C_{1-6}$ alkyl, $(C_{1-6}$ alkyl)C(O)—, $(C_{1-4}$ alkyl)OC(O)—, $(C_{6-10}$ aryl)-$CH_2$—OC(O)—, $(C_{6-10}$ aryl)-$CH_2$—C(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, $(C_{1-6}$ alkyl)-NHC(O)—, $(C_{6-10}$ aryl)-NHC(O)—, (5- to 10-membered heteroaryl)-NHC(O)—, (5- to 10-membered heteroaryl)-$CH_2$—OC(O)—, (5- to 10-membered heteroaryl)-C(O)—, $(C_{6-10}$ aryl)-$(C_{0-4}$ alkyl)-C(O)—, $(C_{1-6}$ alkyl)-$S(O)_2$—, $(C_{6-10}$ aryl)-$S(O)_2$—, (5- to 10-membered heteroaryl)-$S(O)_2$—, or $(C_{6-10}$ aryl)-$(C_{1-4}$ alkyl)-$S(O)_2$—, —$(CR^fR^f)_n$—$(C_{6-10}$ aryl), —$(CR^fR^f)_n$-5- to 10-membered heterocycle; wherein said alkyl, phenyl and aryl are substituted with 0-2 $R^g$; said 5- to 10-membered heteroaryl is substituted with 0-2 $R^g$ and comprises: carbon atoms and 1-4 heteroatoms selected from N, $NR^f$, O, and $S(O)_p$; said 5- to 10-membered heterocycle is substituted with 0-2 $R^g$ and comprises: carbon atoms and 1-4 heteroatoms selected from N, $NR^f$, O, and $S(O)_p$;

$R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^f$, O, and $S(O)_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —$(CH_2)_r$—$C_{3-10}$ carbocycle substituted with 0-3 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, $NR^{12}R^{13}$, —$C(O)R^f$, —$C(O)OR^f$, —$C(O)NR^{12}R^{13}$, or —$S(O)_pR^f$;

$R^a$ is, independently at each occurrence, H, F, $OCF_3$, $CF_3$, —$(CR^fR^f)_rOR^c$, —$(CR^fR^f)_rSR^c$, CN, —$(CR^fR^f)_rNR^{12}R^{13}$, —$(CR^fR^f)_rC(O)R^c$, —$(CR^fR^f)_rC(O)OR^c$, —$(CR^fR^f)_rC(O)NR^{12}R^{13}$, —$(CR^fR^f)_rNR^{14}C(O)R^d$, —$(CR^fR^f)_rS(O)_pNR^{12}R^{13}$, —$(CR^fR^f)_rS(O)R^d$, —$(CR^fR^f)_rS(O)_2R^d$, $C_{1-4}$ alkyl substituted with 1-5 fluorine, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, —$(CH_2)_r$—$OR^c$, $SR^c$, CN, $NO_2$, $CF_3$, $OCF_3$, —$(CR^fR^f)_rNR^{12}R^{13}$, —$C(O)R^c$, —$(CH_2)_r$—$C(O)OR^c$, —$(CH_2)_r$—$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, —OP(O)(OEt)$_2$, $C_{1-8}$ alkyl substituted with 0-2 $R^e$, $C_{2-8}$ alkenyl substituted with 0-2 $R^e$, $C_{2-8}$ alkynyl substituted with 0-2 $R^e$, —$(CR^fR^f)_r$—$C_{3-8}$ cycloalkyl substituted with 0-2 $R^e$, —$(CR^fR^f)_r$—$C_{6-10}$ aryl substituted with 0-2 $R^e$, or —$(CR^fR^f)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —$C(O)R^f$, —$(CH_2)_r$—$C(O)OR^f$, —$NR^{14}C(O)R^f$, —$(CH_2)_r$—$C(O)NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$C_{1-4}$ alkyl, —$S(O)_p$-phenyl, —$(CF_2)_rCF_3$, Si($C_{1-4}$ alkyl)$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, $NR^f$, O, and $S(O)_p$, 0-1 carbonyl and 0-3 double bonds, wherein said carbocyclic or heterocyclic ring is substituted with 0-3 $R^g$;

$R^f$ is, independently at each occurrence, H, F, $C_{1-6}$ alkyl, or —$(CH_2)_n$-phenyl;

$R^g$ is, independently at each occurrence, H, =O, ORE, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, or —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^i$ is, independently at each occurrence, H, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

n, at each occurrence, is selected from 0, 1, 2, 3, and 4;

p, at each occurrence, is selected from 0, 1, and 2; and r, at each occurrence, is selected from 0, 1, 2, 3, and 4;

provided that:
i) when $R^5$ is pyridyl substituted with $NO_2$, then ring A is other than pyridyl substituted with $NO_2$;
ii) when Y is S, ring B is phenylene or phenylene substituted with Cl, $R^5$ is phenyl substituted with Cl, then ring A is other than pyridyl substituted with $CO_2H$;
iii) when Y is S, ring B is phenylene, $R^5$ is phenyl substituted with —NH-pyridyl, then ring A is other than pyridyl;
iv) when Y is O, ring B is phenylene substituted with Cl, $R^5$ is pyridyl, then ring A is other than trizolyl substituted with $CO_2H$; or
v) when Y is O, ring B is phenylene, $R^5$ is phenyl substituted with —NH-thiazolyl or —NH-(4-Me-thiazolyl), then ring A is other than thiazolyl or 4-Me-thiazolyl.

In a second embodiment, the present invention includes compounds of Formula (Ia), or a stereoisomer, tautomer, pharmaceutically acceptable salt, solvate, or prodrug thereof, wherein: ring B is pyridyl substituted with 0-3 $R^7$.

In another embodiment, the present invention includes compounds of Formula (Ia), or a stereoisomer, tautomer, pharmaceutically acceptable salt, solvate, or prodrug thereof, wherein: ring B is substituted with 0-3 $R^7$ and selected from:

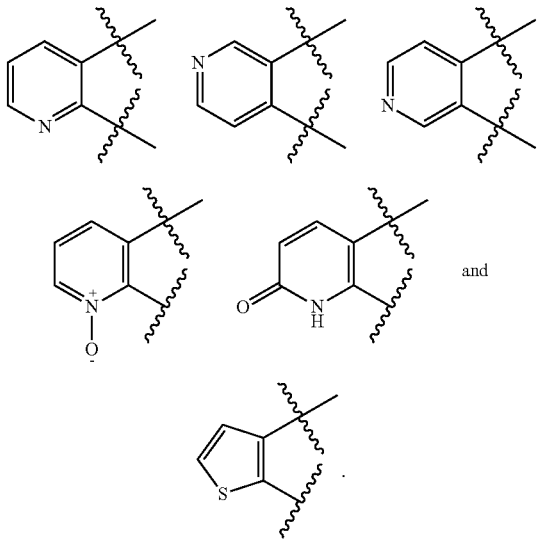

and

In another embodiment, the present invention includes compounds of Formula (Ia), or a stereoisomer, tautomer, pharmaceutically acceptable salt, solvate, or prodrug thereof, wherein: ring B is

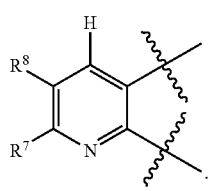

In a third embodiment, the present invention includes compounds of Formula (Ia), or a stereoisomer, tautomer, pharmaceutically acceptable salt, solvate, or prodrug thereof, wherein: ring A is substituted with 0-3 $R^1$ and selected from:

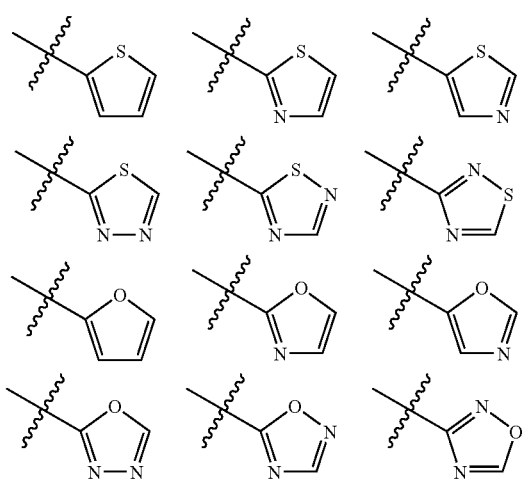

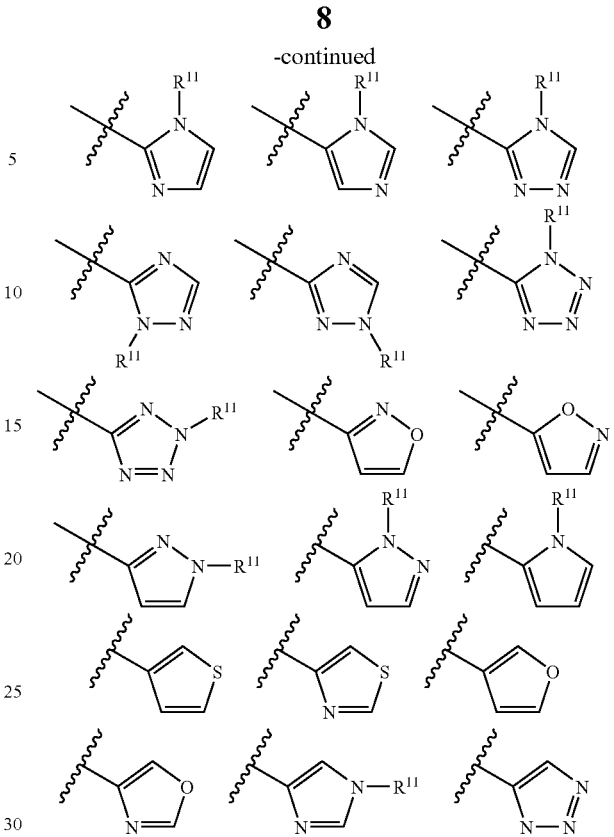

In another embodiment, the present invention includes compounds of Formula (Ia), or a stereoisomer, tautomer, pharmaceutically acceptable salt, solvate, or prodrug thereof, wherein: ring A is substituted with 0-3 $R^1$ and selected from:

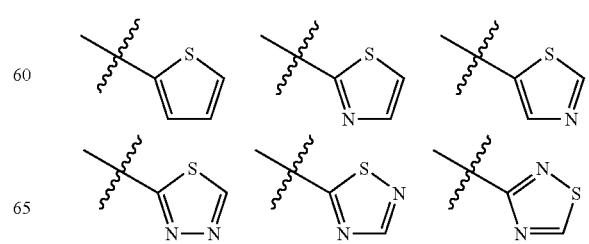

-continued

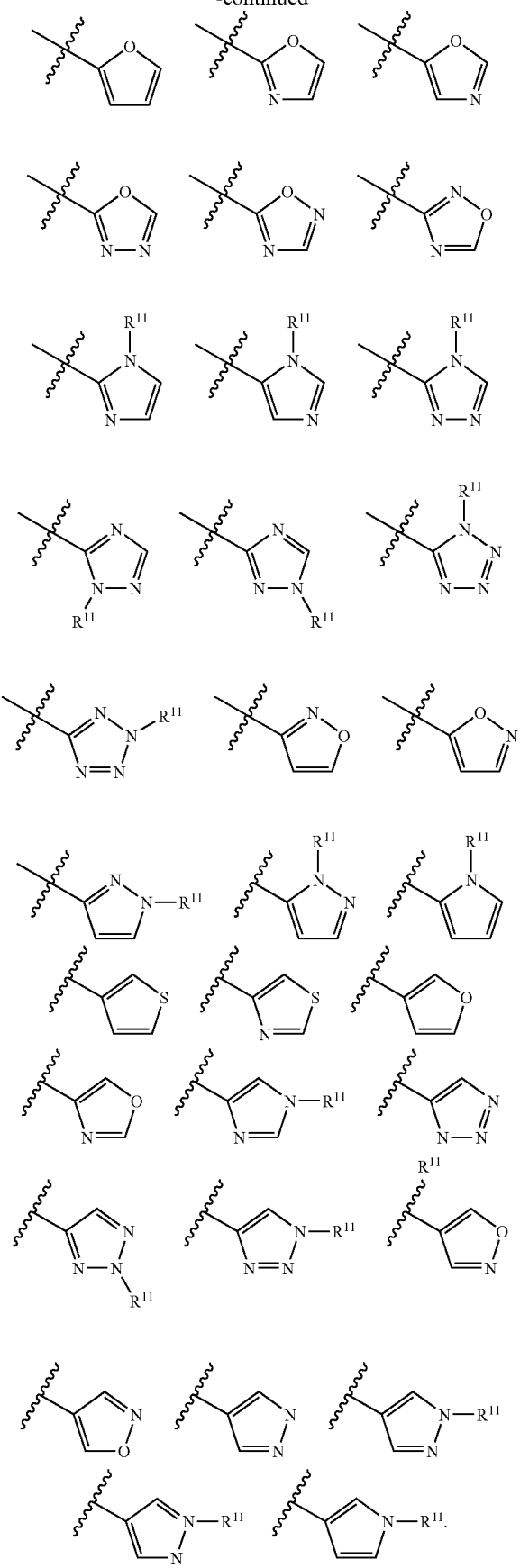

In a fourth embodiment, the present invention includes the compounds of Formula (Ia), or a stereoisomer, tautomer, pharmaceutically acceptable salt, solvate, or prodrug thereof, wherein:

ring B is

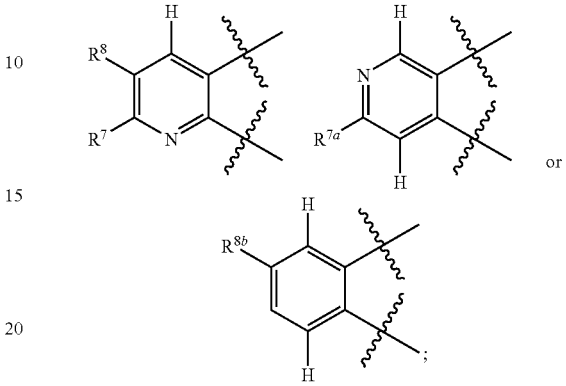

$R^7$ and $R^{7a}$ are H, Me, Cl, Br, CN, OMe, SMe, NHMe, $NH_2$, $NMe_2$, or —NH(4-OMe-Ph);

$R^8$ and $R^{8b}$ are H, Me, Cl, Br, CN, $NMe_2$, or —N(Me)(4-OMe-Ph);

X is NH; and

Y is O, S, or NH.

In a fifth embodiment, the present invention includes compounds of Formula (II):

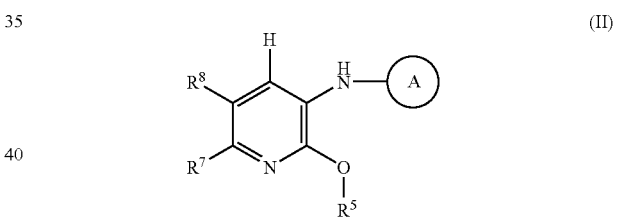

(II)

or a stereoisomer, tautomer, pharmaceutically acceptable salt, solvates, or prodrug thereof, wherein:

ring A is selected from:

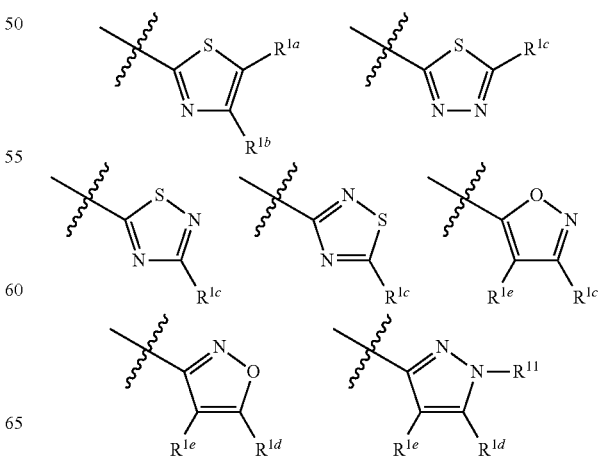

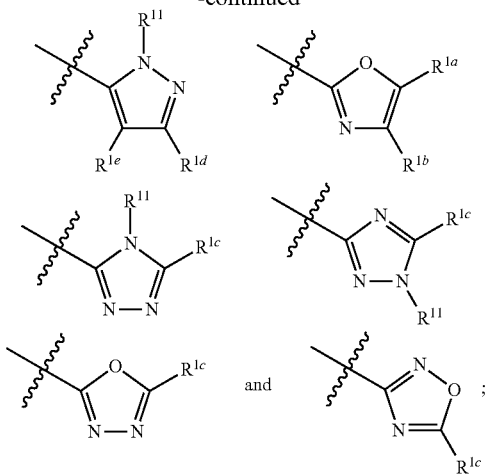

alternatively, ring A is substituted with 0-3 $R^1$ and is selected from:

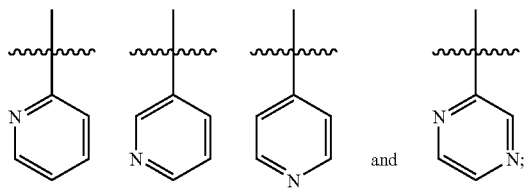

$R^1$, $R^{1a}$, $R^{1b}$, $R^{1c}$, $R^{1d}$, and $R^{1e}$ are, independently at each occurrence, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, Br, CN, $CF_3$, —$CF_2CF_3$, —$C(NH_2)$=$N(OH)$, $C(O)R^c$, —CH(=NOH), —C(O)$OR^c$, $NR^{12}R^{13}$, —C(O)$NR^{12}R^{13}$, —CON(Me)(CH$_2$)$_2$OH, —CO-morpholin-4-yl, —SO$_2$-morpholin-4-yl, —S(O)$_p$NR$^{12}$R$^{13}$, —(CH$_2$)$_r$—C$_{3-6}$ cycloalkyl substituted with 0-2 $R^b$, —(CH$_2$)$_r$-adamantyl substituted with 0-2 $R^b$, —(CH$_2$)$_r$-phenyl substituted with 0-4 $R^b$, —(CH$_2$)$_r$-naphthyl substituted with 0-4 $R^b$, —(CH$_2$)$_r$-3- to 10-membered heterocycle substituted with 0-4 $R^b$, wherein said heterocycle is selected from: aziridinyl, azetidinyl, pyrrolidinyl, furanyl, imidazolyl, oxadiazolyl, thienyl, pyrrolyl, isoxazolyl, triazolyl, tetrazolyl, pyridinyl, pyrazinyl, pyrimidinyl, piperidinyl, morpholinyl, piperazinyl, 1,3-benzodioxolyl, benzothienyl, isoindolinyl, 1,4-diazacycloheptanyl, tetrahydroisoquinolyl, and

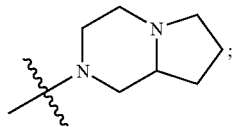

alternatively, $R^{1a}$ and $R^{1b}$ or $R^{1d}$ and $R^{1e}$ are combined with the carbon atoms to which they attached, form a 5- to 6-membered carbocycle or heterocycle comprising: carbon atoms and 0-3 additional heteroatoms selected from N, $NR^{11}$, O, and S(O)$_p$, 0-2 carbonyl, and 0-1 additional double bond, wherein said carbocycle and heterocycle are substituted with 0-3 $R^b$;

alternatively, two $R^1$s are combined with the carbon atoms to which they attached, form a 5- to 6-membered carbocycle or heterocycle comprising: carbon atoms and 0-3 additional heteroatoms selected from N, $NR^{11}$, O, and S(O)$_p$, 0-2 carbonyl, and 0-1 additional double bond, wherein said carbocycle and heterocycle are substituted with 0-3 $R^b$;

$R^5$ is phenyl substituted with 1-4 Rya;

$R^{5a}$ is, independently at each occurrence, F, Cl, Br, I, —(CR$^f$R$^i$)$_r$—OR$^c$, SR$^c$, CN, CF$_3$, —CF$_2$CF$_3$, OCF$_3$, —OCF$_2$CF$_2$H, —OCF$_2$CF$_3$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, —Si(Me)$_3$, Si(C$_{1-4}$ alkyl)$_3$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —(CR$^f$R$^f$)$_r$—$C_{3-10}$ carbocycle substituted with 0-3 $R^e$, or —(CR$^f$R$^f$)$_r$-5- to 10-membered heterocycle comprising: carbon atoms and 1-4 heteroatoms selected from N, $NR^{11}$, O, and S(O)$_p$, wherein said heterocycle is substituted with 0-3 $R^e$;

alternatively, two $R^{5a}$ groups attached to two adjacent carbon atoms, together with the carbon atoms to which they are attached, form a 5- to 7-membered carbocyclic or heterocyclic ring comprising: carbon atoms and 0-2 heteroatoms selected from N, $NR^{11}$, O, and S(O)$_p$, 0-1 carbonyl and 0-3 double bonds, wherein said carbocyclic or heterocyclic ring is substituted with 0-3 $R^e$;

$R^7$ is H, Br, CN, NH$_2$, NMe$_2$, or —NH(4-OMe-Ph);

$R^8$ is H, Br, CN, NMe$_2$, or —N(Me)(4-OMe-Ph);

$R^{11}$ is, independently at each occurrence, H, —COPh, —COBn, —SO$_2$Me, —SO$_2$Ph, —SO$_2$Bn, $C_{1-6}$ alkyl substituted with 1-5 fluorine, —(CR$^f$R$^f$)$_r$C(O)NR$^{12}$R$^{13}$, $C_{1-4}$ alkyl substituted with 0-2 $R^a$, —(CH$_2$)$_r$—C$_{3-6}$ cycloalkyl substituted with 0-2 $R^b$, —(CH$_2$)$_r$-phenyl substituted with 0-3 $R^b$, —CHMe-phenyl substituted with 0-3 $R^b$, or —(CH$_2$)$_r$-5- to 10-membered heterocycle substituted with 0-3 $R^b$; wherein said heterocycle is selected from: furanyl, thienyl, thiazolyl, pyridyl, and indolyl;

$R^{12}$ is, independently at each occurrence, H, $C_{1-6}$ alkyl substituted with 1-5 fluorine, —(CR$^f$R$^f$)$_r$C(O)NR$^f$R$^f$, $C_{1-6}$ alkyl, —(CH$_2$)$_r$—C$_{3-6}$ cycloalkyl, —(CH$_2$)$_n$-phenyl, —(CH$_2$)$_r$-5- to 6-membered heterocycle selected from pyrrolidinyl, furanyl, thienyl, pyrrolyl, isoxazolyl, triazolyl, tetrazolyl, pyridinyl, pyrazinyl, pyrimidinyl, piperidinyl, morpholinyl, and piperazinyl; wherein said alkyl and phenyl are substituted with 0-2 $R^g$; said 5- to 10-membered heterocycle is substituted with 0-2 $R^g$;

$R^{13}$ is, independently at each occurrence, H, $C_{1-6}$ alkyl, or —(CH$_2$)$_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, NR$^f$, O, and S(O)$_p$;

$R^{14}$ is, independently at each occurrence, H, $C_{1-6}$ alkyl, $C_{2-6}$ alkenyl, —(CH$_2$)$_r$-phenyl carbocycle substituted with 0-3 $R^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^g$;

$R^a$ is, independently at each occurrence, H, F, OCF$_3$, CF$_3$, —(CR$^f$R$^f$)$_r$OR$^c$, —(CR$^f$R$^f$)$_r$SR$^c$, CN, —(CR$^f$R$^f$)$_r$NR$^{12}$R$^{13}$, —(CR$^f$R$^f$)$_r$C(O)R$^c$, —(CR$^f$R$^f$)$_r$C(O)OR$^c$, —(CR$^f$R$^f$)$_r$C(O)NR$^{12}$R$^{13}$, —(CR$^f$R$^f$)$_r$NR$^{14}$C(O)R$^d$, —(CR$^f$R$^f$)$_r$S(O)$_p$NR$^{12}$R$^{13}$, —(CR$^f$R$^f$)$_r$S(O)R$^d$, —(CR$^f$R$^f$)$_r$S(O)$_2$R$^d$, $C_{1-4}$ alkyl substituted with 1-5 fluorine, —(CH$_2$)$_r$—C$_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^b$ is, independently at each occurrence, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, F, Cl, Br, $CF_3$, —$OCF_3$, —$(CH_2)_r$—$OR^c$, —$(CH_2)_r$—$C(O)OR^c$, —$(CR^fR^f)_r$ $NR^{12}R^{13}$, —$(CH_2)_r$—$C(O)NR^{12}R^{13}$, CN, —$OCH_2C(Me)_2$ $CH_2NMe_2$, $NO_2$, —$SO_2Me$, OBn, —$(CH_2)_r$—$C_{3-6}$ cycloalkyl, —$(CH_2)_r$-phenyl substituted with 0-2 $R^e$, —$(CH_2)_r$-naphthyl substituted with 0-3 $R^e$, —$(CH_2)_r$-5- to 10-membered heterocycle substituted with 0-4 $R^e$; wherein said heterocycle is selected from: thienyl, thiazolyl, imidazolyl, tetrazolyl, pyrrolidinyl, morpholinyl, piperidinyl, azepanyl, morpholinyl, piperazinyl, pyridinyl, tetrahydropyranyl, or tetrahydroisoquinolinyl;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —$C(O)$ $R^f$, —$(CH_2)_r$—$C(O)OR^f$, —$NR^{14}C(O)R^f$, —$(CH_2)_r$—$C(O)$ $NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$C_{1-4}$ alkyl, —$S(O)_p$-phenyl, —$(CF_2)_rCF_3$, $Si(C_{1-4}$ alkyl$)_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, $NR^f$, O, and $S(O)_p$, 0-1 carbonyl and 0-3 double bonds, wherein said carbocyclic or heterocyclic ring is substituted with 0-2 $R^g$;

$R^f$ is, independently at each occurrence, H, F, $C_{1-6}$ alkyl, or —$(CH_2)_n$-phenyl;

$R^g$ is, independently at each occurrence, H, =O, ORE, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^i$ is, independently at each occurrence, H or $C_{1-6}$ alkyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a sixth embodiment, the present invention includes compounds of Formula (II), or a stereoisomer, tautomer, pharmaceutically acceptable salt, solvate, or prodrug thereof, wherein:

ring A is

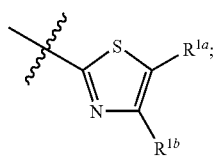

$R^{1a}$ and $R^{1b}$, independently at each occurrence, H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, Br, CN, $CF_3$, —$CF_2CF_3$, —$C(NH_2)$=$N(OH)$, $C(O)R^c$, —$C(O)OR^c$, $NR^{12}R^{13}$, —$C(O)NR^{12}R^{13}$, —$CON(Me)(CH_2)_2OH$, —$SO_2$-morpholin-4-yl, —$S(O)_pNR^{12}R^{13}$, —$CO$-(4-morpholinyl), —$(CH_2)_r$-phenyl substituted with 0-3 $R^b$; —$(CH_2)_r$-3- to 10-membered heterocycle substituted with 0-3 $R^b$; wherein said heterocycle is selected from: aziridinyl, pyrrolidinyl, furanyl, imidazolyl, oxadiazolyl, triazolyl, tetrazolyl, piperidinyl, morpholinyl, piperazinyl, pyridyl, pyrimidinyl, 1,3-benzodioxolyl, isoindolinyl, 1,4-diazacycloheptanyl, tetrahydroisoquinolinyl, or

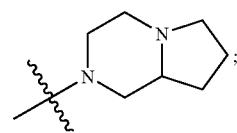

alternatively, ring A is

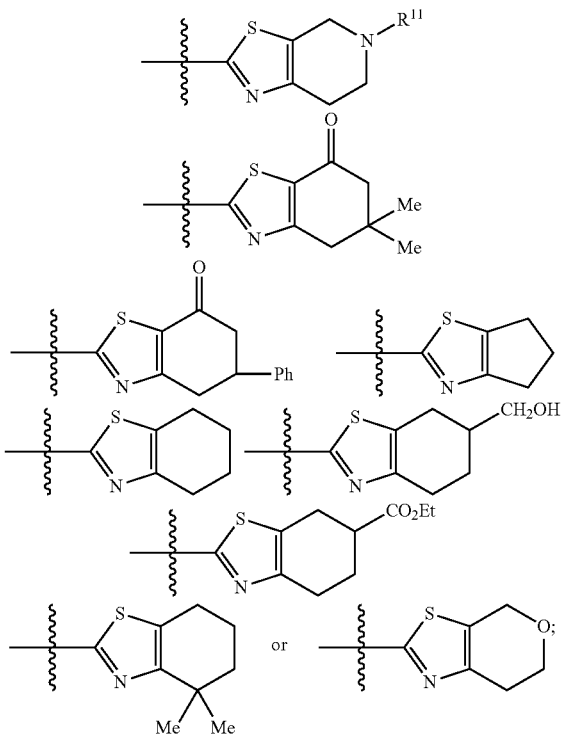

$R^{11}$ is H, $C_{1-6}$ alkyl substituted with 1-5 fluorine, —$CH_2CH_2O(C_{1-4}$ alkyl), —$(CR^fR^f)_rC(O)NR^{12}R^{13}$, $C_{1-6}$ alkyl, cyclopropylmethyl, cyclopentylmethyl, —$(CH_2)_2OH$, Bn, —COPh, —COBn, —$SO_2Me$, —$SO_2Ph$, —$SO_2Bn$, —$(CH_2)_r$-phenyl substituted with 0-2 $R^b$, or —$(CH_2)_r$-5- to 6-membered heterocycle substituted with 0-2 $R^b$, wherein said heterocycle is selected from: furanyl, thienyl, thiazolyl, and pyridyl;

$R^a$ is, independently at each occurrence, OH, OMe, —$C(O)ORS$, —$(CR^fR^f)_rNR^{12}R^{13}$, —$(CR^fR^f)_rC(O)$ $NR^{12}R^{13}$, $C_{1-4}$ alkyl substituted with 1-5 fluorine, or —CO (4-morpholinyl);

$R^b$ is, independently at each occurrence, $C_{1-6}$ alkyl, F, $CF_3$, —$OCF_3$, OH, —$CH_2OH$, —$CH_2CH_2OH$, —CH$_2$CH$_2$CH$_2$OH, OMe, —CH$_2$OMe, —OCH$_2$C(Me)$_2$ CH$_2$NMe$_2$, CO$_2$H, —CH$_2$CH$_2$CO$_2$H, CO$_2$Me, —CH$_2$CH$_2$CO$_2$Me, CO$_2$Et, CN, —CH$_2$NHMe, —CH$_2$NHEt, —CH$_2$NHBn, NMe$_2$, —CH$_2$NMe$_2$, —CH$_2$N(Me)Et, —CH$_2$N(Me)Bn, —CH$_2$CH$_2$CH$_2$N(Me)Et, NO$_2$, —SO$_2$Me, OBn, cyclopropylmethyl, tetrahydropyranyl, pyrrolidinyl, pyrrolidinylmethyl, or morpholinylethyl.

In a seventh embodiment, the present invention includes compounds of Formula (II), or a stereoisomer, tautomer, pharmaceutically acceptable salt, solvate, or prodrug thereof, wherein:

ring A is selected from:

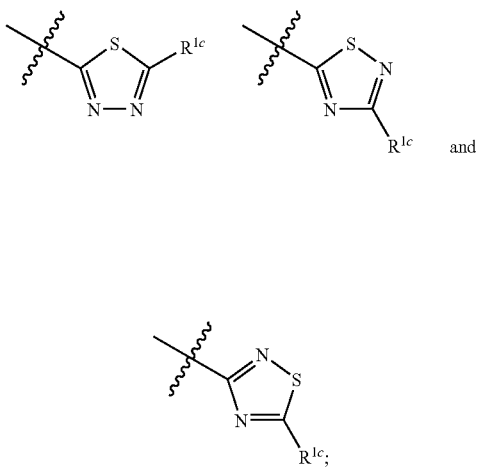

R$^{1c}$ is, independently at each occurrence, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, Br, CF$_3$, C(O)R$^c$, —C(O)OR$^c$, NR$^{12}$R$^{13}$, —C(O)NR$^{12}$R$^{13}$, —(CH$_2$)$_r$—C$_{3-6}$ cycloalkyl substituted with 0-2 R$^b$, —(CH$_2$)$_r$-adamantyl substituted with 0-2 R$^b$, —(CH$_2$)$_r$-phenyl substituted with 0-3 R$^b$, —(CH$_2$)$_r$-naphthyl substituted with 0-3 R$^b$, —C(Me)$_2$(CH$_2$)$_r$-piperazinyl substituted with 0-3 R$^b$, —C(Me)$_2$(CH$_2$)$_r$-CO-piperazinyl substituted with 0-3 R$^b$, —(CH$_2$)$_r$-5- to 10-membered heterocycle substituted with 0-3 R$^b$; wherein said heterocycle is selected from: azetidinyl, pyrrolidinyl, furanyl, thienyl, pyrrolyl, isoxazolyl, triazolyl, pyridinyl, pyrazinyl, piperidinyl, piperazinyl, benzothienyl, isoindolinyl, and tetrahydroisoquinolinyl;

R$^a$ is, independently at each occurrence, —O(CH$_2$)$_2$OMe, —C(O)OR$^c$, —(CR$^f$R$^f$)$_r$NR$^{12}$R$^{13}$, —(CR$^f$R$^f$)$_r$C(O)NR$^{12}$R$^{13}$, C$_{1-4}$ alkyl substituted with 1-5 fluorine, SPh, phenoxy substituted with 0-2 R$^e$, or benzoxy substituted with 0-2 R$^e$;

R$^b$ is, independently at each occurrence, C$_{1-6}$ alkyl, C$_{1-4}$ alkoxyl, F, Cl, CF$_3$, —OCF$_3$, OH, —CH$_2$OH, CN, —(CR$^f$R$^f$)$_r$NR$^{12}$R$^{13}$, —CH$_2$NMe$_2$, NO$_2$, —SO$_2$Me, —(CH$_2$)$_r$—C$_{3-6}$ cycloalkyl, CH(Ph)$_2$, —(CH$_2$)$_r$-phenyl substituted with 0-2 R$^e$, —(CH$_2$)$_r$-naphthyl substituted with 0-3 R$^e$, —(CH$_2$)$_r$-furyl substituted with 0-2 R$^e$, —(CH$_2$)$_r$-thienyl substituted with 0-2 R$^e$, —(CH$_2$)$_r$-thiazolyl substituted with 0-2 R$^e$, —(CH$_2$)$_r$-imidazolyl substituted with 0-2 R$^e$, piperazinyl substituted with 0-2 R$^e$, or —(CH$_2$)$_r$-pyridinyl substituted with 0-2 R$^e$; and R$^e$ is, independently at each occurrence, C$_{1-6}$ alkyl, F, Cl, CN, or Bn.

In an eighth embodiment, the present invention includes compounds of Formula (II), or a stereoisomer, tautomer, pharmaceutically acceptable salt, solvate, ring A is selected from:

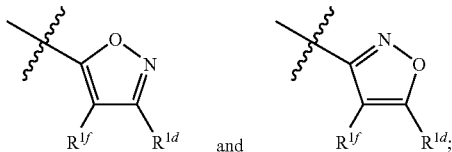

R$^{1d}$ and R$^{1f}$ are, independently at each occurrence, C$_{1-6}$ alkyl substituted with 0-2 R$^a$, —C(O)OR$^c$, —C(O)NR$^{12}$R$^{13}$, —(CH$_2$)$_r$-phenyl substituted with 0-3 R$^b$, —(CH$_2$)$_r$-naphthyl substituted with 0-3 R$^b$, —(CH$_2$)$_r$-5- to 10-membered heterocycle substituted with 0-3 R$^b$, wherein said heterocycle is selected from: thienyl, isoxazolyl, benzothienyl, and 1,3-benzodioxolyl;

R$^a$ is, independently at each occurrence, OMe or N(Me)Bn; and

R$^b$ is, independently at each occurrence, Me, F, Cl, Br, CH$_2$OH, CF$_3$, —CH$_2$NMe$_2$, —CH$_2$N(Me)Bn, CN, NO$_2$, —SO$_2$Me, 2-CH$_2$NH$_2$-Ph, —(CH$_2$)$_r$—C$_{3-6}$ cycloalkyl, —(CH$_2$)$_r$-phenyl, —(CH$_2$)$_r$-pyrrolidinyl, —(CH$_2$)$_r$-tetrazolyl, —(CH$_2$)$_r$-piperidinyl, —(CH$_2$)$_r$-azepanyl, —(CH$_2$)$_r$-morpholinyl, —(CH$_2$)$_r$-piperazinyl, —(CH$_2$)$_r$-(4-Bn-piperazinyl), or —(CH$_2$)$_r$-tetrahydroisoquinolinyl.

In a ninth embodiment, the present invention includes compounds of Formula (II), or a stereoisomer, tautomer, pharmaceutically acceptable salt, solvate, or prodrug thereof, wherein:

ring A is selected from:

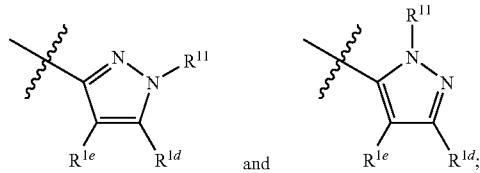

R$^{1d}$ and R$^{1e}$ are, independently at each occurrence, CN, —C(O)OR$^c$, NR$^{12}$R$^{13}$, or —C(O)NR$^{12}$R$^{13}$, C$_{1-6}$ alkyl substituted with 0-2 R$^a$, or —(CH$_2$)$_r$-phenyl substituted with 0-3 R$^b$;

R$^{11}$ is, independently at each occurrence, H, C$_{1-6}$ alkyl substituted with 1-5 fluorine, —(CR$^f$R$^f$)$_r$C(O)NR$^{12}$R$^{13}$, C$_{1-6}$ alkyl substituted with 0-2 R$^a$, C$_{2-6}$ alkenyl substituted with 0-2 R$^a$, —(CH$_2$)$_r$—C$_{3-6}$ cycloalkyl substituted with 0-2 R$^b$, —(CH$_2$)$_r$-phenyl substituted with 0-3 R$^b$, —CHMe-phenyl substituted with 0-3 R$^b$, or —(CH$_2$)$_r$-5- to 10-membered heterocycle substituted with 0-3 R$^b$, wherein said heterocycle is selected from: furanyl, thienyl, thiazolyl, pyridinyl, and indolyl;

R$^a$ is, independently at each occurrence, OR$^c$, SR$^c$, —C(O)OR$^c$, —(CR$^f$R$^f$)$_r$NR$^{12}$R$^{13}$, —(CR$^f$R$^f$)$_r$C(O)NR$^{12}$R$^{13}$, or C$_{1-4}$ alkyl substituted with 1-5 fluorine; and R$^b$ is, independently at each occurrence, C$_{1-4}$ alkyl, C$_{1-4}$ alkoxyl, F, Cl, Br, CF$_3$, —OCF$_3$, CN, —(CR$^f$R$^f$)$_r$NR$^{12}$R$^{13}$, —CH$_2$NMe$_2$, NO$_2$, or —SO$_2$Me.

In a tenth embodiment, the present invention provides compounds of Formula (IIa):

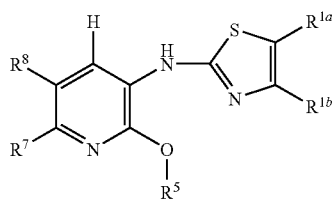

(IIa)

or a stereoisomer, tautomer, pharmaceutically acceptable salt, solvate, or prodrug thereof, wherein:

$R^{1a}$ is H, Me, Et, i-Pr, neopentyl, vinyl, 1-Me-vinyl, cyclopentyl, 1-cyclopentenyl, cyclohexyl, 1-cyclohexenyl, Br, $CF_3$, —$C(NH_2)$=$N(OH)$, —$CH_2OH$, —$(CH_2)_2OH$, —$CH_2OMe$, COMe, $CO_2H$, $CO_2Me$, $CO_2Et$, —$CH_2CO_2H$, —$CH_2CO_2Et$, CN, —N(Me)Et, —$N(CH_2CH_2OMe)_2$, —$N(Me)CH_2CH_2NMe_2$, —$N(Me)CH_2CH_2CH_2NMe_2$, —$CH_2NHEt$, —$CH_2NH(t\text{-}Bu)$, —$CH_2NH$-neopentyl, —$CH_2NHBn$, —$CH_2N(Me)Et$, —$CH_2N(Me)Pr$, —$CH_2N(Me)(i\text{-}Bu)$, —$CH_2N(Me)(t\text{-}Bu)$, —$CH_2N(Me)$cyclohexyl, —$CH_2N(Me)Ph$, —$CH_2N(Me)Bn$, —$CH_2N(i\text{-}Pr)Bn$, —$CH_2N(t\text{-}Bu)Bn$, —$CH_2N(Me)CH(Me)Ph$, —$CH_2N(Me)(CH_2)_2Ph$, —$CH_2N(Me)(CH_2)_3Ph$, —$CH_2N(Me)(CH_2$-pyridin-3-yl), —$CONH_2$, —CONHMe, —CONHEt, —CONHPr, —CONH-neopentyl, —CONHPh, —CONHBn, —$CONH(CH_2$-pyridin-2-yl), —$CONH(CH_2$-pyridin-3-yl), —$CONH(CH_2CH_2$-pyridin-3-yl), —$CH_2CONHBn$, —$CON(Me)_2$, —CON(Me)Et, —CON(Me)Pr, —CON(Me)(t-Bu), —CON(Me)Bn, —$CON(Me)(CH_2)_2OH$, —$CON(Me)(CH_2)_2Ph$, —$CON(Me)(CH_2)_3Ph$, —$CON(Me)(CH_2$-pyridin-3-yl), —$CH_2CON(Me)Et$, —$SO_2$-morpholin-4-yl, —$SO_2NHEt$, —$SO_2NHBn$, —$SO_2N(Me)Et$, —$SO_2N(Me)Bn$, —$SO_2N(Bn)_2$, Ph, 2-Me-Ph, 3-Me-Ph, 4-Me-Ph, 4-(i-Pr)-Ph, 4-(t-Bu)-Ph, 2-F-Ph, 3-$CF_3$-Ph, 4-$CF_3$-Ph, 2-OH-Ph, 3-OH-Ph, 4-OH-Ph, 4-$CH_2OH$-Ph, 3-(—$CH_2CH_2CH_2OH$)-Ph, 4-(—$CH_2CH_2CH_2OH$)-Ph, 3-OMe-Ph, 4-OMe-Ph, 3-$OCF_3$-Ph, 4-$OCF_3$-Ph, 2-$CH_2OMe$-Ph, 3-$NMe_2$-Ph, 4-$NMe_2$-Ph, 2-(—$CH_2NHMe$)-Ph, 3-(—$CH_2NHMe$)-Ph, 4-(—$CH_2NHMe$)-Ph, 2-(—$CH_2NHBn$)-Ph, 3-(—$CH_2NHBn$)-Ph, 4-(—$CH_2NHBn$)-Ph, 2-(—$CH_2NMe_2$)-Ph, 3-(—$CH_2NMe_2$)-Ph, 4-(—$CH_2NMe_2$)-Ph, 2-(—$CH_2N(Me)Bn$)-Ph, 3-(—$CH_2N(Me)Bn$)-Ph, 4-(—$CH_2N(Me)Bn$)-Ph, 3-(—$CH_2CH_2CH_2N(Me)Et$)-Ph, 4-(—$CH_2CH_2CH_2N(Me)Et$)-Ph, 3-$CO_2H$-Ph, 4-$CO_2H$-Ph, 3-$CO_2Me$-Ph, 4-$CO_2Me$-Ph, 3-(—$CH_2CH_2CO_2H$)-Ph, 4-(—$CH_2CH_2CO_2H$)-Ph, 3-(—$CH_2CH_2CO_2Me$)-Ph, 2-CN-Ph, 3-CN-Ph, 4-CN-Ph, 4-$SO_2Me$-Ph, 2-OBn-Ph, 3-OBn-Ph, 4-OBn-Ph, 3-(—$OCH_2C(Me)_2CH_2NMe_2$)-Ph, 4-(—$OCH_2C(Me)_2CH_2NMe_2$)-Ph, 2,4-diF-Ph, 3,5-diF-Ph, 2-F-4-Me-Ph, 2-F-4-OMe-Ph, 3-F-4-OMe-Ph, 2-(—$CH_2NMe_2$)-4-OMe-Ph, 3-(—$CH_2NHMe$)-4-OMe-Ph, 2-(—$CH_2NHBn$)-4-OMe-Ph, 2-(—$CH_2N(Me)Bn$)-4-OMe-Ph, 3,4,5-triOMe-Ph, pyrrolidin-1-yl, 2-($CH_2OMe$)-pyrrolidin-1-yl, 3-(—N(Me)COMe)-pyrrolidin-1-yl, furan-3-yl, imidazol-1-yl, 3-Me-1,2,4-oxadiazol-5-yl, 5-Me-1,2,4-oxadiazol-3-yl, 3-Ph-1,2,4-oxadiazol-5-yl, 1H-tetrazol-5-yl, 1H-1,2,4-triazol-3-yl, 1-(i-Pr)-1,2,4-triazol-3-yl, piperidin-1-yl, 4-OH-piperidin-1-yl, 3-OMe-piperidin-1-yl, 4-$CH_2OH$-piperidin-1-yl, 2-(—$CH_2CH_2OH$)-piperidin-1-yl, 4-(—$CH_2CH_2OH$)-piperidin-1-yl, 2-(—$CH_2NMe_2$)-piperidin-1-yl, 2-$CO_2Et$-piperidin-1-yl, 3-$CO_2Et$-piperidin-1-yl, 4-$CO_2Et$-piperidin-1-yl, 3-$CONH_2$-piperidin-1-yl, 4-$CONH_2$-piperidin-1-yl, 3-CON(Et)-2-piperidin-1-yl, —N(Me)(1-Me-piperidin-4-yl), 4-(pyrrolidin-1-yl)-piperidin-1-yl, piperazin-1-yl, 4-Me-piperazin-1-yl, 4-Et-piperazin-1-yl, 4-i-Pr-piperazin-1-yl, 4-(—$CH_2CH_2OH$)-piperazin-1-yl, 4-(—$CH_2CH_2OCH_2CH_2OH$)-piperazin-1-yl, 4-COMe-piperazin-1-yl, 4-$CO_2Et$-piperazin-1-yl, 4-Bn-piperazin-1-yl, pyridin-3-yl, pyridin-4-yl, —N(Me)(1-Me-pyrrolidin-3-yl), —N(Me)-$CH_2$-pyridin-3-yl, —N(Me)-$CH_2$-pyridin-4-yl, morpholin-4-yl, —$CH_2$-morpholin-4-yl, —CO-morpholin-4-yl, 2-OMe-pyrimidin-5-yl, 1,3-benzodioxol-4-yl,

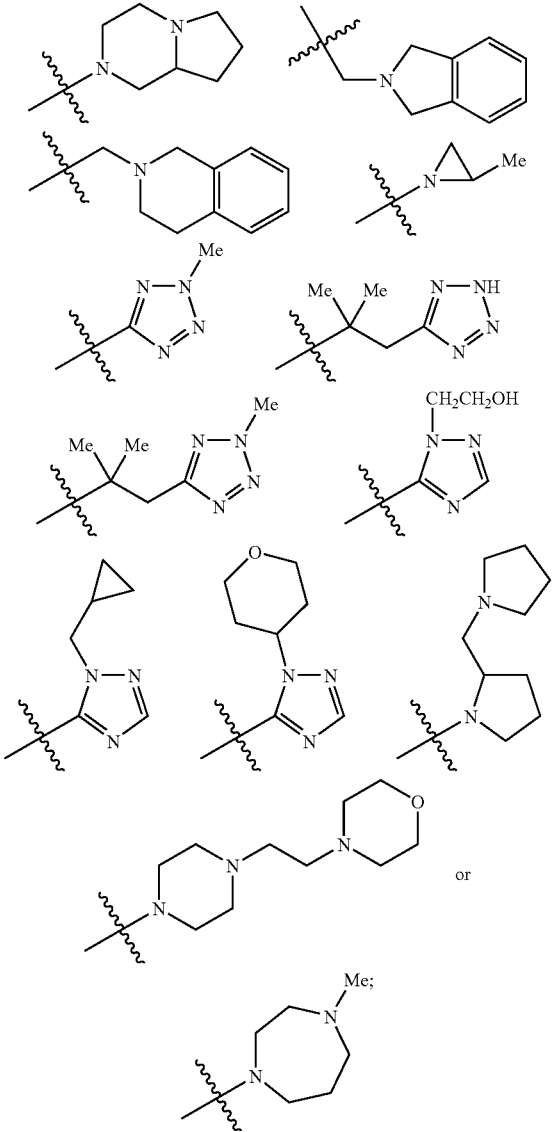

or $R^{1b}$ is H, Me, Et, i-Pr, i-Bu, t-Bu, neopentyl, cyclopropyl, cyclobutyl, $CH_2OH$, —$C(Me)_2CH_2OH$, —$C(Me)_2(CH_2)_2OH$, —$CH_2OMe$, —$CH_2OEt$, $CH_2O(i\text{-}Bu)$, —$CH_2O(CH_2)_2OMe$, $CO_2Et$, —$CH_2CO_2(i\text{-}Pr)$, —$(CH_2)_2CO_2Me$, —$(CH_2)_2CO_2Et$, —$C(Me)_2CH_2CO$-morpholin-4-yl, —$C(Me)_2CO_2H$, —$C(Me)_2CO_2Me$, —$C(Me)_2CH_2CO_2H$, —$C(Me)_2CH_2CO_2Et$, —$C(Me)_2(CH_2)_2CO_2H$, —$C(Me)_2(CH_2)_3CO_2Et$, CN, —$C(Me)_2CH_2CN$, $CF_3$, —$CH_2CF_3$, —$CF_2CF_3$, —$CH(i\text{-}Bu)NH_2$, —$CH_2NMe_2$, —$C(Me)_2CH_2N(Me)Et$, —$C(Me)_2(CH_2)_2N(Me)Et$, —$C(Me)_2(CH_2)_2N(Me)(i\text{-}Bu)$, —CH₂OCH₂CH₂NEt₂, —CONHMe, —CONHEt, —CONHPr, —CONH(t-Bu), —CONH-neopentyl, —CONHPh, —CONHBn, —CONMe₂, —CON(Me)(t-Bu), —CON(Me)Bn, —C(Me)₂CON(Me)Et, —C(Me)₂CH₂CONH₂, —C(Me)₂CH₂CONHEt, —C(Me)₂CH₂CONHBn, —C(Me)₂CH₂CON(Me)Et, —C(Me)₂CH₂CON(Me)(i-Bu), —C(Me)₂CH₂CON(Me)Bn, —CH(i-Bu)NHCO₂(t-Bu), Ph, 4-Me-Ph, 3-F-Ph, 2-CH₂OH-Ph, 3-CH₂OH-Ph, 4-CH₂OH-Ph, 2-OMe-Ph, 3-OMe-Ph, 4-OMe-Ph, 2-(CH₂NHEt)-Ph, 2-(CH₂NHBn)-Ph, 2-(CH₂NMe₂)-Ph, 2-(CH₂N(Me)Et)-Ph, 2-(CH₂N(Me)Bn)-Ph, 3-(CH₂N(Me)Bn)-Ph, 4-(CH₂N(Me)Bn)-Ph, 2-CO₂Et-Ph, 4-CF₃-Ph, 4-OCF₃-Ph, 4-CN-Ph, 2-NO₂-Ph, 3-NO₂-Ph, 4-NO₂-Ph, —C(Me)₂(CH₂)₂(Pyrrolidin-1-yl), —CH₂OCH₂(1-Me-piperidin-3-yl), —CH₂OCH₂(1-Me-piperidin-4-yl), alternatively,

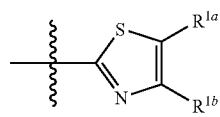

is

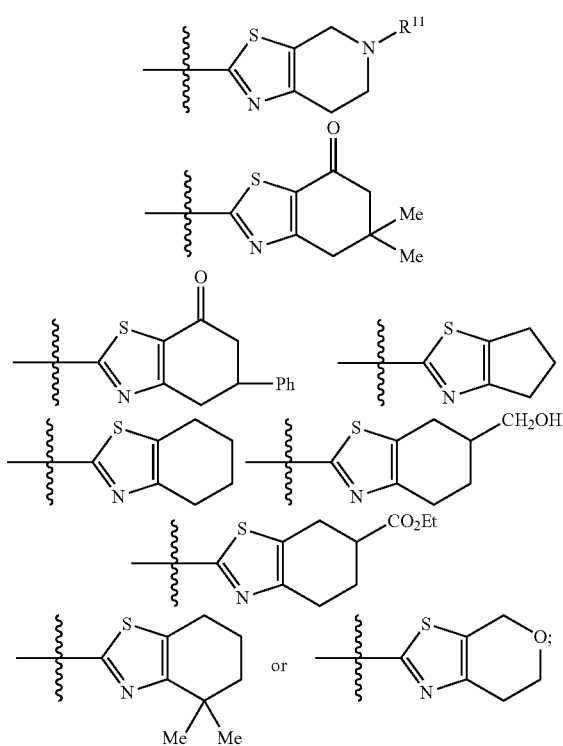

$R^5$ is 2-i-Pr-Ph, 2-t-Bu-Ph, 2-OCF₃-Ph, 2-CO₂Me-Ph,

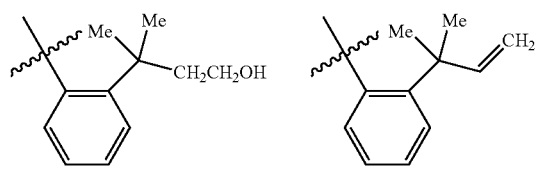

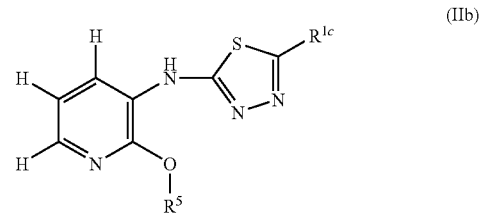

$R^7$ is H, Br, CN, NH₂, NHMe, NMe₂, or —NH(4-OMe-Ph);

$R^8$ is H, Br, CN, NHMe, NMe₂, or N(Me)(4-OMe-Ph); and $R^8$ is H, Pr, i-Pr, Bu, i-Bu, isopentyl, —CH₂CH(Me)Et, —CH₂CH(Et)₂, —CH₂CH₂CMe₃, cyclopropylmethyl, cyclopentylmethyl, —(CH₂)₂OH, Bn, —COMe, —COPh, —COBn, —SO₂Me, —SO₂Ph, —SO₂Bn, Bn, 2-Me-Bn, 3-Me-Bn, 3-OH-Bn, 4-OH-Bn, 2-OMe-Bn, 3-OMe-Bn, 4-OMe-Bn, 2-F-Bn, 3-OCF₃-Bn, 3-CN-Bn, 4-CN-Bn, phenethyl, 2-furanylmethyl, 3-furanylmethyl, 3-pyridylmethyl, or 4-pyridylmethyl.

In an eleventh embodiment, the present invention includes compounds of Formula (IIa), or a stereoisomer, tautomer, pharmaceutically acceptable salt, solvate, or prodrug thereof, wherein:

$R^6$ is 2-t-Bu-Ph;
$R^7$ is H; and
$R^8$ is H.

In a twelfth embodiment, the present invention provides compounds of Formula (IIb):

(IIb)

or a stereoisomer, tautomer, pharmaceutically acceptable salt, solvate, or prodrug thereof, wherein:

$R^{1c}$ is H, i-Pr, t-Bu, neopentyl, cyclopropyl, 1-Ph-cyclopropyl, cyclobutyl, cyclopentyl, cyclohexyl, 4-NHBn-cyclohexyl, 4-N(Me)Bn-cyclohexyl, —CH₂OBn, —CH₂—O—(CH₂)₂OMe, CO₂H, CO₂Et, —C(Me)₂(CH₂)₂CO₂Me, —CH₂N(Me)Bn, —(CH₂)₃N(Me)Bn, —C(Me)₂(CH₂)₃N(Me)Bn, —CON(Me)Bn, —C(Me)₂CH₂CON(Me)Bn, —C(Me)₂(CH₂)₂CON(Me)Bn, Ph, phenethyl, 3-Me-Ph, 4-Me-Ph, 4-t-Bu-Ph, 3-OH-Ph, 2-OMe-Ph, 4-OMe-Ph, 4-F-Ph, 2-Cl-Ph, 3-Cl-Ph, 4-CF₃-Ph, 3-OCF₃-Ph, 4-OCF₃-Ph, 4-CN-Ph, 3-NMe₂-Ph, 4-NMe₂-Ph, 2-CH₂NMe₂-Ph, 3-CH₂NMe₂-Ph, 4-CH₂NMe₂-Ph, 4-NO₂-Ph, 4-Ph-Ph, 3,5-diCl-Ph, 4-(imidazol-1-yl)-Ph, 3-(4-Bn-piperazin-1-yl)-Ph, 4-(4-Bn-piperazin-1-yl)-Ph, 4-F-Bn, 4-OMe-Bn, 4-NMe₂-

Bn, naphth-2-yl, 1-Bn-pyrrolidin-3-yl, thien-2-yl, —CH$_2$-thien-2-yl, 1-Me-pyrrol-2-yl, 2,5-diMe-furan-3-yl, isoxazol-5-yl, pyridin-2-yl, pyridin-3-yl, pyridin-4-yl, 1-neohexyl-4-Me-piperidin-4-yl, 1-(CH$_2$-cyclohexyl)-4-Me-piperidin-4-yl, 2-Ph-piperidin-4-yl, 1-Me-2-Ph-piperidin-4-yl, 1-Bn-piperidin-3-yl, 1-Bn-piperidin-4-yl, 1-Bn-4-Me-piperidin-4-yl, 1-(2-Cl-Bn)-piperidin-4-yl, 1-(2-Cl-Bn)-4-Me-piperidin-4-yl, 1-(2-CN-Bn)-4-Me-piperidin-4-yl, 1-(3-CN-Bn)-4-Me-piperidin-4-yl, 1-(4-CN-Bn)-4-Me-piperidin-4-yl, 1-(2,4-diF-Bn)-4-Me-piperidin-4-yl, 1-(2,5-diF-Bn)-4-Me-piperidin-4-yl, 1-(2,6-diCl-Bn)-4-Me-piperidin-4-yl, 1-(CH$_2$-naphth-1-yl)-4-Me-piperidin-4-yl, 1-(CH$_2$-furan-3-yl)-4-Me-piperidin-4-yl, 1-(CH$_2$-thien-2-yl)-4-Me-piperidin-4-yl, 1-(CH$_2$-thiazol-2-yl)-4-Me-piperidyin-4-yl, 1-(CH$_2$-pyrid-2-yl)-4-Me-piperid-4-yl, 1-(CH$_2$-pyrid-3-yl)-4-Me-piperid-4-yl, 1-(1-Bn-piperid-4-yl)-piperid-4-yl, —CH$_2$-(4-Bn-piperazin-1-yl), —(CH$_2$)$_3$-(4-Bn-piperazin-1-yl), —C(Me)$_2$(CH$_2$)$_3$-(4-Bn-piperazin-1-yl), —C(Me)$_2$(CH$_2$)$_2$CO(4-Bn-piperazin-1-yl),

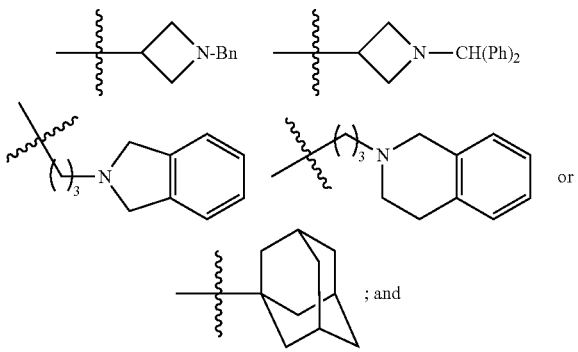

R$^5$ is 2-t-Bu-Ph, 2-Br-Ph, 2-CO$_2$Me-Ph, 3-CO$_2$Et-Ph,

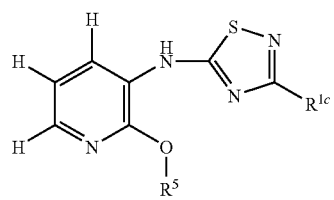

In a thirteenth embodiment, the present invention provides compounds of Formula (IIc):

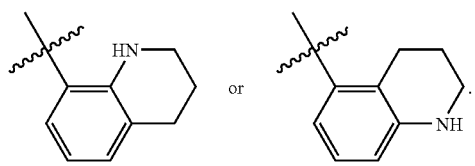

(IIc)

or a stereoisomer, tautomer, pharmaceutically acceptable salt, solvate, or prodrug thereof, wherein:

R$^{1c}$ is Me, i-Pr, t-Bu, cyclopropyl, Br, CF$_3$, —CH$_2$OPh, —CH$_2$O(4-t-Bu-Ph), —CH$_2$O(2-Cl-Ph), —CH$_2$O(4-Cl-Ph), —CH$_2$SPh, —CH$_2$N(Me)Bn, Ph, 4-Me-Ph, 4-t-Bu-Ph, 3-OH-Ph, 4-OMe-Ph, 2-F-Ph, 3-F-Ph, 4-Cl-Ph, 3-CF$_3$-Ph, 4-CF$_3$-Ph, 3-NO$_2$-Ph, 4-SO$_2$Me-Ph, 3-Cl-4-F-Ph, 3,4-diOMe-Ph, 3,5-diOMe-Ph, 3,5-diCl-Ph, 2,6-diCl-Bn, pyridin-2-yl, pyridin-3-yl, pyridin-4-yl, 2,6-diCl-pyridin-4-yl, furan-3-yl, thien-2-yl, pyrazin-2-yl, —CH$_2$-1-(1,2,4-triazol-1-yl), 1-Bn-piperidin-4-yl, —CH$_2$-piperidin-1-yl, —CH$_2$-4-Bn-piperazin-1-yl, benzo[b]thien-3-yl, or

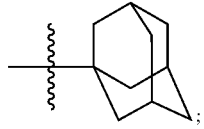

and

R$^5$ is 2-t-Bu-Ph, 2-Br-Ph, 2-CO$_2$Me-Ph, 3-CO$_2$Et-Ph,

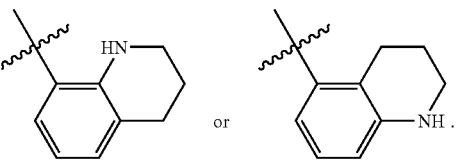

In a fourteenth embodiment, the present invention provides compounds of Formula (IId$_1$) or Formula (IId$_2$):

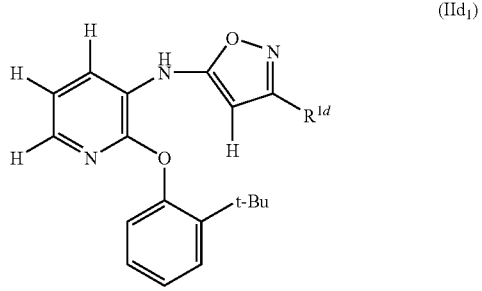

(IId$_1$)

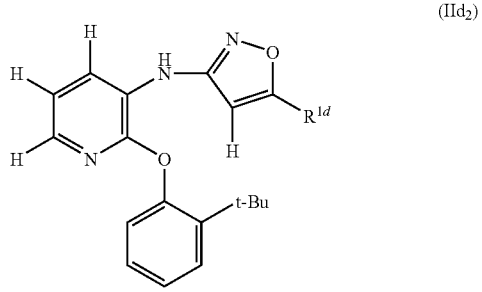

(IId$_2$)

or a stereoisomer, tautomer, pharmaceutically acceptable salt, solvate, or prodrug thereof, wherein:

R$^{1d}$ is, independently at each occurrence, —CH(OMe)$_2$, —CH$_2$N(Me)Bn, CO$_2$Et, —CON(Me)Bn, Ph, 2-F-Ph, 3-F-Ph, 2-Cl-Ph, 3-Cl-Ph, 3-CH$_2$OH-Ph, 3-CH$_2$NMe$_2$-Ph, 4-CF$_3$-Ph, 3-CN-Ph, 4-CN-Ph, 3-NO$_2$-Ph, 4-NO$_2$-Ph, 4-SO$_2$Me-Ph, 4-cyclohexyl-Ph, 4-Ph-Ph, 3-CH$_2$N(Me)Bn-Ph, 3-(CH$_2$-piperidin-1-yl)-Ph, 3-(CH$_2$-morpholin-4-yl)-Ph, 3-(CH$_2$-piperazin-1-yl)-Ph, 3-(CH$_2$-(4-Me-piperazin-1-yl))-Ph, 2,4-diMe-Ph, 3-Me-4-Cl-Ph, 3,4-diCl-Ph, 2-F-4-Br-Ph, 3-NO$_2$-4-Cl-Ph, 2-F-4-(2-CH$_2$NMe$_2$-Ph)-Ph, 2-F-4-(pyrrolidin-1-yl)-Ph, 4-(1H-tetrazol-5-yl)-Ph, 2-F-4-(piperidin-1-yl)-Ph, 2-F-4-(1-azepanyl)-Ph, 2-F-4-(4-Bn-piperazin-1-yl)-Ph, 2-F-4-Cl-5-Me-Ph, naphth-2-yl, 3-Ph-isoxazol-5-yl, 3-Ph-5-Me-isoxazol-4-yl, 5-Ph-thien-2-yl, pyridin-3-yl, pyridin-4-yl, benzo[b]thien-3-yl, 1,3-benzodioxol-4-yl, or 3-(CH$_2$-1,2,3,4-tetrahydroisoquinolin-2-yl)-Ph.

In a fifteenth embodiment, the present invention provides compounds of Formula (IIe$_1$) or Formula (IIe$_2$):

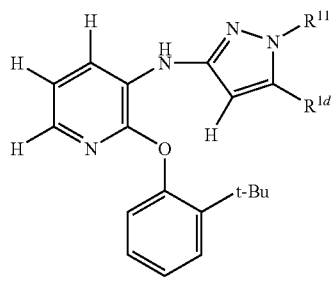

(IIe$_1$)

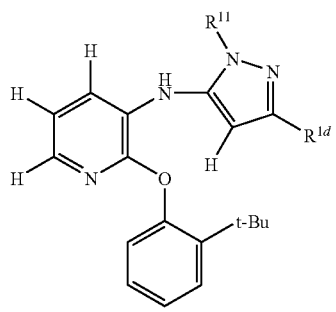

(IIe$_2$)

or a stereoisomer, tautomer, pharmaceutically acceptable salt, solvate, or prodrug thereof, wherein:

R$^{1h}$ is, independently at each occurrence, CN, CO$_2$Et, CONMe$_2$, Ph, 2-F-Ph, or 4-CF$_3$-Ph; and R$^{11}$ is, independently at each occurrence, H, Me, n-Bu, neohexyl, —CH$_2$CH═C(Me)$_2$, —(CH$_2$)$_2$OMe, —(CH$_2$)$_2$SMe, —(CH$_2$)$_2$SEt, —(CH$_2$)$_2$S(i-Pr), —(CH$_2$)$_3$SMe, —(CH$_2$)$_3$N(Me)$_2$, —(CH$_2$)$_2$O(CH$_2$)$_2$Cl, —(CH$_2$)$_2$O(4-Cl-Ph), —CH$_2$-cyclopropyl, Ph, Bn, 2-Cl-Bn, 3-Cl-Bn, 2-Br-Bn, 4-Br-Bn, 4-CF$_3$-Bn, 4-SMe-Bn, 2-F-6-Cl-Bn, 2-Cl-4-F-Bn, 2-F-4-Br-Bn, 3,5-diCl-Bn, —CHMe-Ph, phenethyl, 4-Cl-phenethyl, —CH$_2$-thien-2-yl, —(CH$_2$)$_2$-thien-2-yl, —(CH$_2$)$_2$-thien-3-yl, —(CH$_2$)$_2$-(4-Me-thiazol-5-yl), —CHMe-furan-2-yl, —(CH$_2$)$_2$-pyridin-2-yl, —(CH$_2$)$_2$-pyridin-4-yl, or —(CH$_2$)$_2$-indol-3-yl.

In a sixteenth embodiment, the present invention includes compounds of Formula (II), or a stereoisomer, tautomer, pharmaceutically acceptable salt, solvate, or prodrug thereof, wherein:

R$^5$ is a phenyl substituted with 1-2 Rya;

R$^{5a}$ is, independently at each occurrence, F, Cl, Br, I, CN, —C(Me)$_2$CN, CF$_3$, —CF$_2$CF$_3$, OCF$_3$, —OCF$_2$CF$_2$H, —OCF$_2$CF$_3$, C$_{1-8}$ alkyl, C$_{2-8}$ alkenyl, OH, C$_{1-4}$ alkyloxy, SMe, S(i-Pr), —C(Me)$_2$OMe, —C(Me)$_2$OEt, —C(Me)$_2$OPr, —CHMeO(CH$_2$)$_2$OMe, —C(Me)$_2$OBu, —C(Me)$_2$O(CH$_2$)$_2$OMe, —C(Me)(OMe)CH$_2$OMe, —C(Me)$_2$O(CH$_2$)$_2$N(i-Bu)$_2$, —C(Me)$_2$O(CH$_2$)$_2$S(i-Bu), —C(Me)$_2$O(CH$_2$)$_2$S(O)(i-Bu), —C(Me)$_2$O(CH$_2$)$_2$S(furan-2-ylmethyl), —C(Me)$_2$O(CH$_2$)$_2$S(Pyridin-2-yl), —C(Me)$_2$O(CH$_2$)$_2$S(O)$_2$ (pyridin-2-yl), —C(Me)$_2$CH$_2$OSi(Me)$_2$(t-Bu), —C(Me)$_2$O(CH$_2$)$_2$Si(Me)$_2$(t-Bu), —C(Et)$_2$OH, —C(Pr)$_2$OH, —C(CH$_2$CH═CH$_2$)$_2$OH, —C(CH$_2$CH═CH$_2$)$_2$OMe, —C(Et)$_2$OMe, —C(Et)$_2$OEt, —C(Et)$_2$OPr, COMe, COPh, CO$_2$Me, CO$_2$Et, —NH(i-Bu), —CH═CHCO$_2$(t-Bu), —OCH$_2$CO$_2$(t-Bu), C$_{3-7}$ cycloalkyl, C$_{3-7}$ cycloalkenyl, Ph, Bn, naphthyl, 1-pyrrolidinyl, 5-isoxazolyl, N-morpholinyl, 1-piperidinyl, —SiMe$_3$,

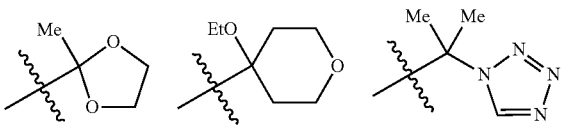

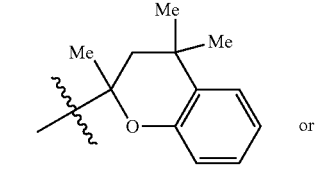

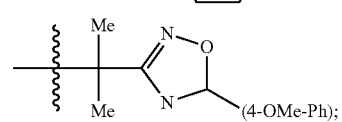

or

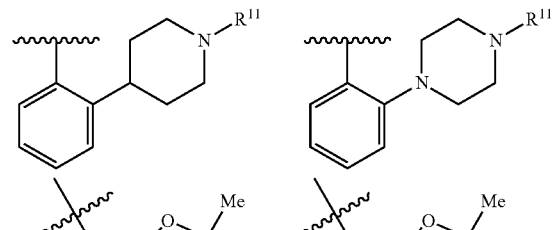

(4-OMe-Ph);

alternatively, R$^5$ is:

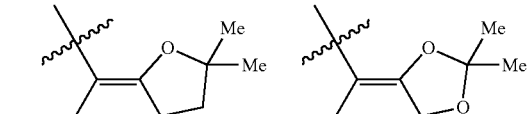

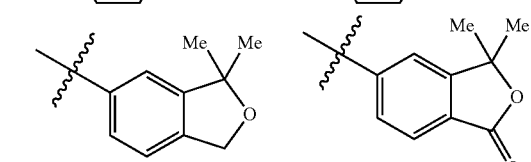

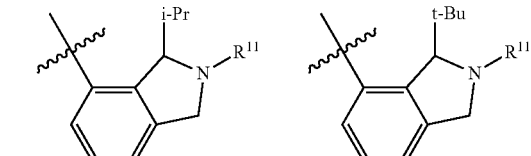

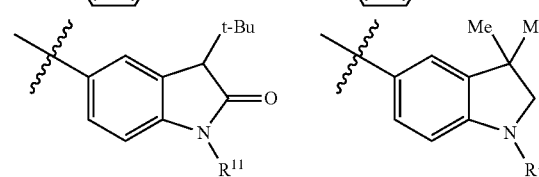

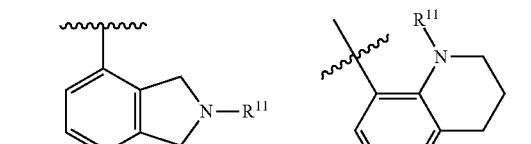

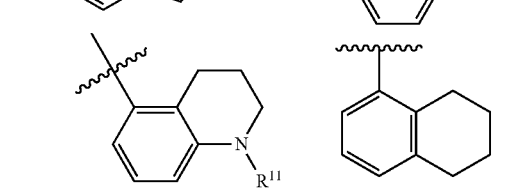

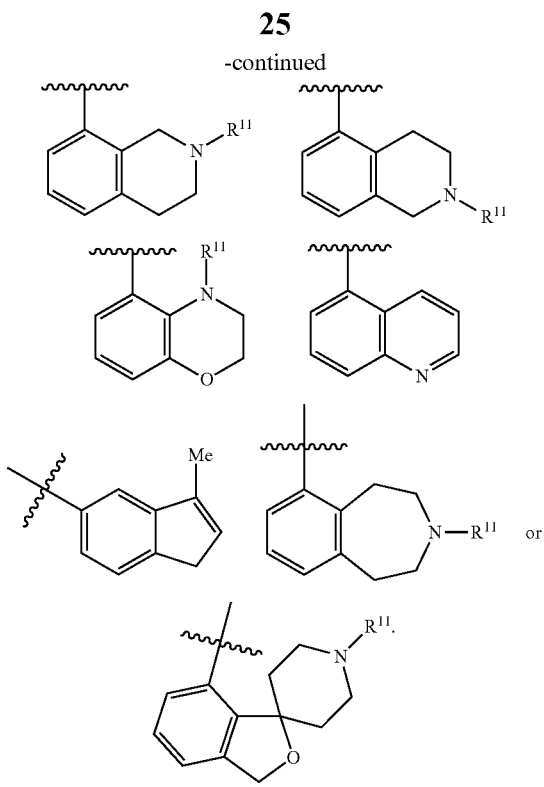
In a seventeenth embodiment, the present invention includes compounds of Formula (II), or a stereoisomer, tautomer, pharmaceutically acceptable salt, solvate, or prodrug thereof, wherein:
$R^5$ is 2-i-Pr-Ph, 2-t-Bu-Ph, 2-Br-Ph, 2-OCF$_3$-Ph, 2-CO$_2$Me-Ph, 3-CO$_2$Et-Ph,
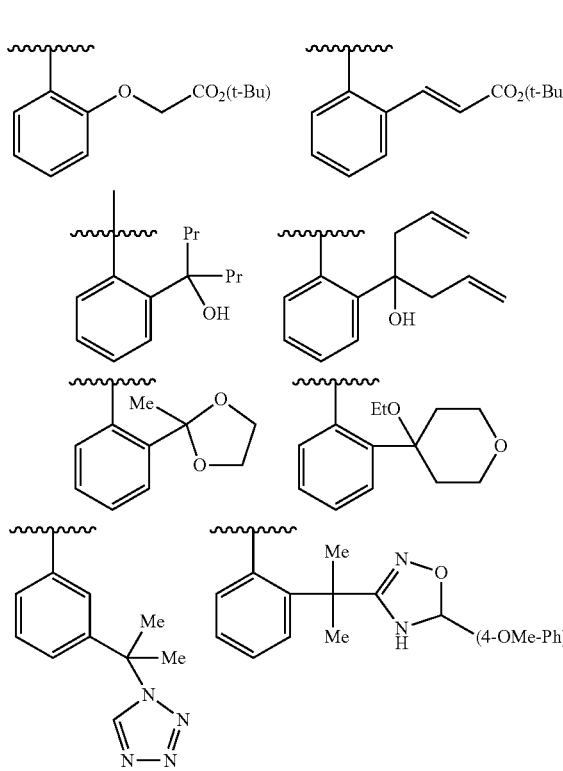
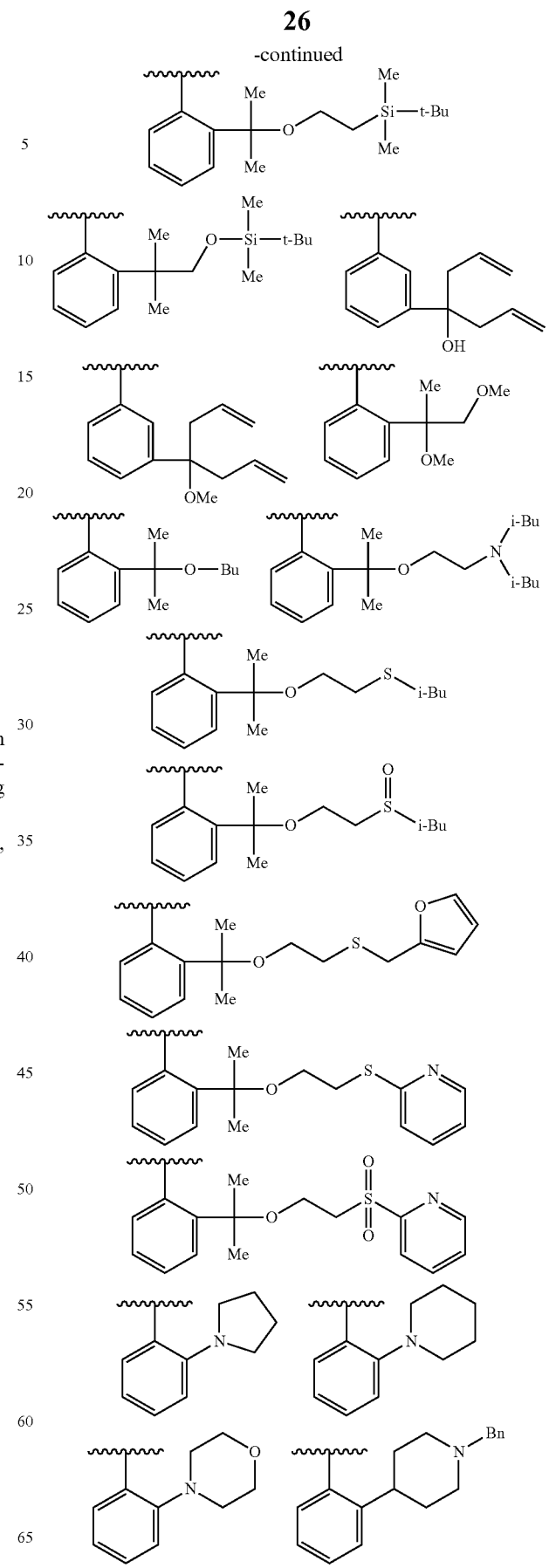

27
-continued
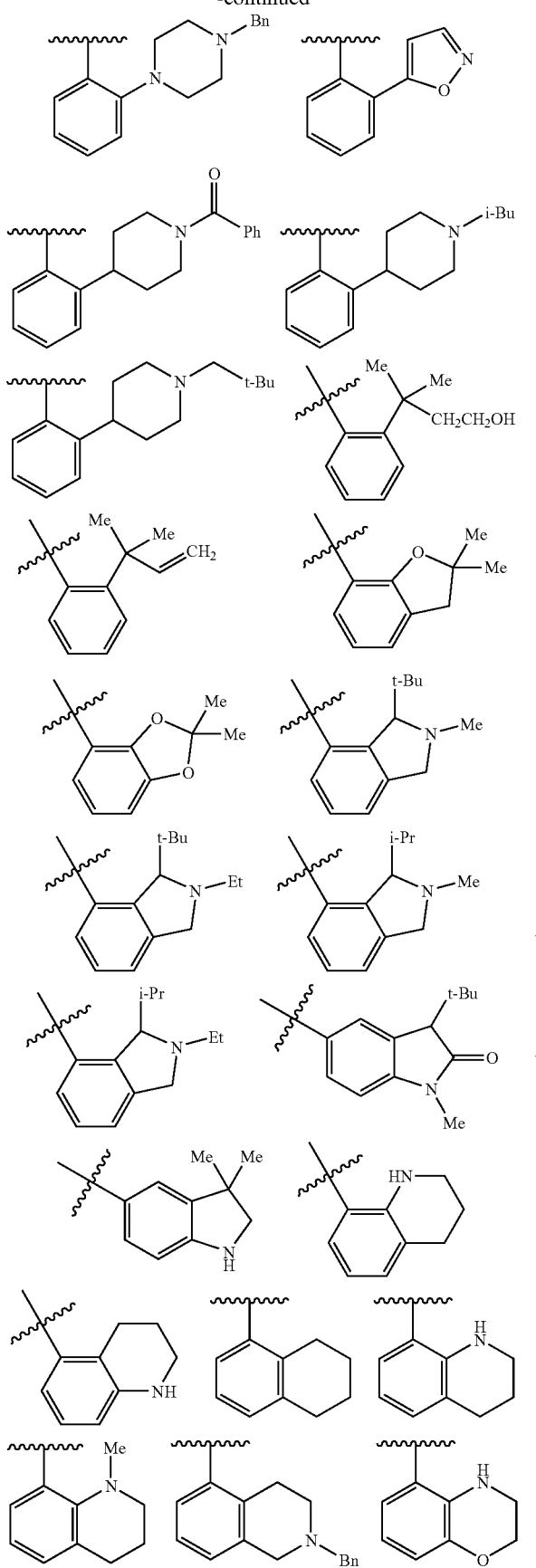
28
-continued
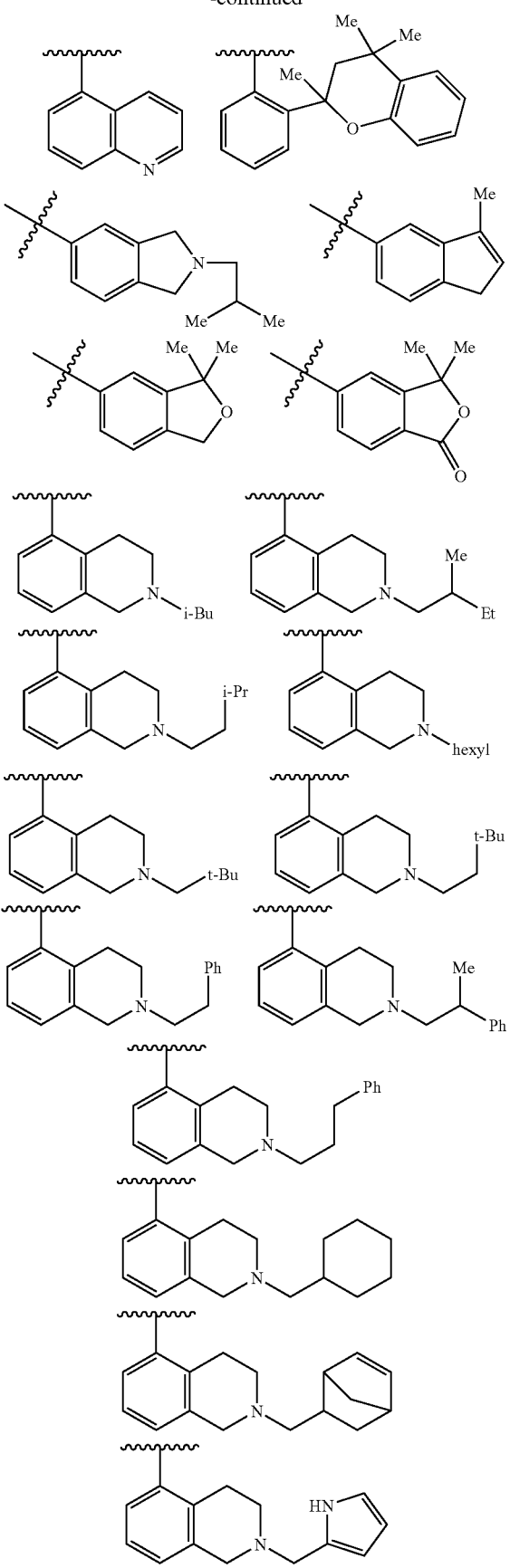

-continued

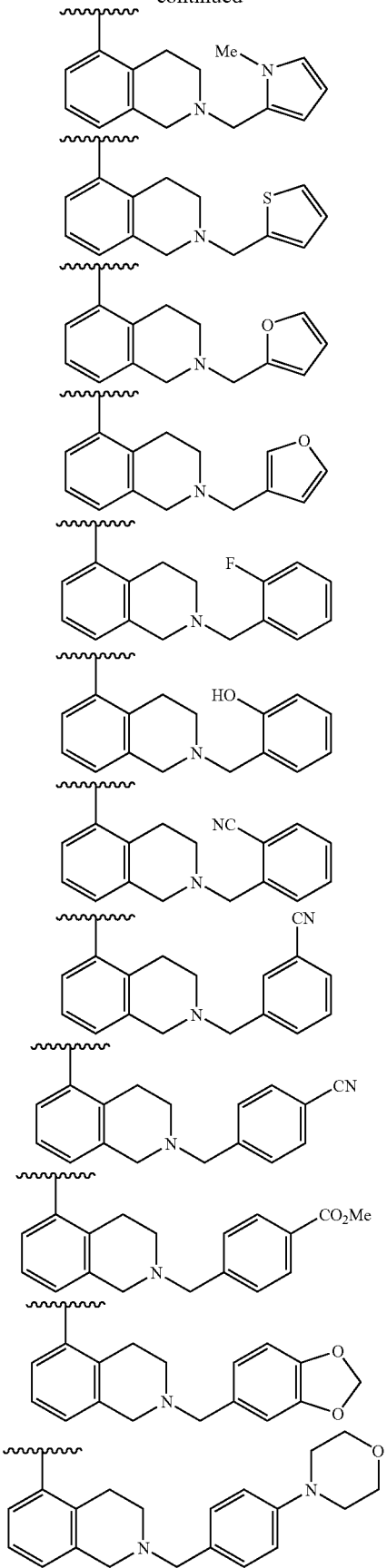

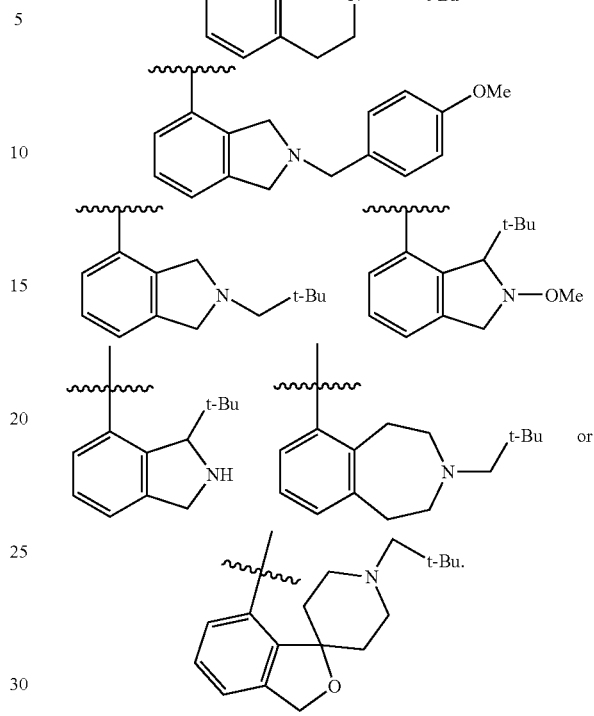

In an eighteenth embodiment, the present invention provides a compound selected from the exemplified examples or a stereoisomer, tautomer, pharmaceutically acceptable salt, solvate, or prodrug thereof.

In another embodiment, the present invention includes compounds of Formula (II):

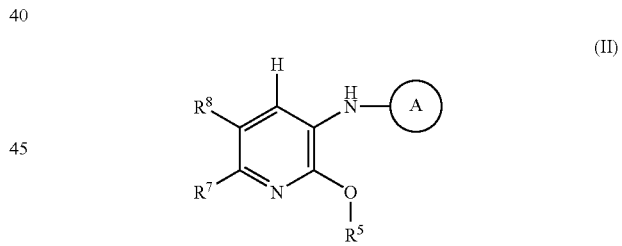

(II)

or a stereoisomer or pharmaceutically acceptable salts, solvates, or prodrugs thereof, wherein:
ring A is selected from:

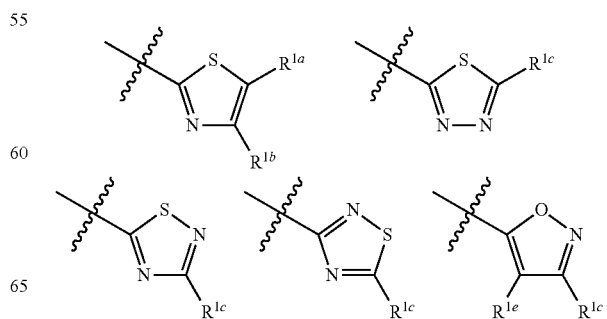

-continued

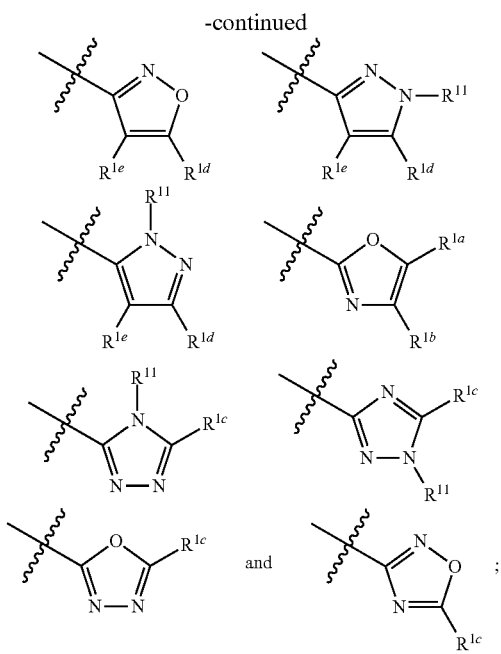

alternatively, ring A is substituted with 0-3 R¹ and selected from:

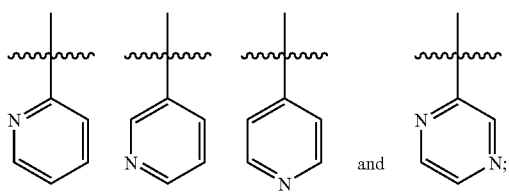

$R^1$, $R^{1a}$, $R^{1b}$, $R^{1c}$, $R^{1d}$, and $R^{1e}$ are, independently at each occurrence, $C_{1-6}$ alkyl substituted with 0-2 $R^a$, Br, CN, $CF_3$, —$CF_2CF_3$, COH, —CH(=NOH), —C(O)OR$^c$, NR$^{12}$R$^{13}$, —C(O)NR$^{12}$R$^{13}$, —CON(Me)(CH$_2$)$_2$OH, —CO-morpholin-4-yl, —SO$_2$-morpholin-4-yl, —S(O)$_p$NR$^{12}$R$^{13}$, —(CH$_2$)$_r$-C$_{3-6}$ cycloalkyl substituted with 0-2 R$^b$, —(CH$_2$)$_r$-adamantyl substituted with 0-2 R$^b$, —(CH$_2$)$_r$-phenyl substituted with 0-4 R$^b$, —(CH$_2$)$_r$-naphthyl substituted with 0-4 R$^b$, —(CH$_2$)$_r$-5- to 10-membered heterocycle substituted with 0-4 R$^b$ and selected from: azetidinyl, pyrrolidinyl, furanyl, thienyl, pyrrolyl, isoxazolyl, triazolyl, tetrazolyl, pyridinyl, pyrazinyl, pyrimidinyl, piperidinyl, morpholinyl, piperazinyl, 1,3-benzodioxolyl, benzothienyl, isoindolinyl, tetrahydroisoquinolyl, and

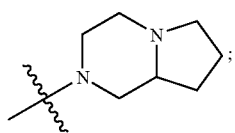

alternatively, two R¹s on two adjacent carbon atoms are combined with the carbon atoms to which they attached, form a 5- to 6-membered carbocycle or heterocycle comprising: carbon atoms and 0-3 additional heteroatoms selected from N, NR$^{11}$—, O, and S(O)$_p$, 0-2 carbonyl, and 0-1 additional double bond, wherein said carbocycle or heterocycle is substituted with 0-3 R$^b$;

$R^5$ is 2-i-Pr-Ph, 2-t-Bu-Ph, 2-Br-Ph, 2-OCF$_3$-Ph, 3-CO$_2$Et-Ph,

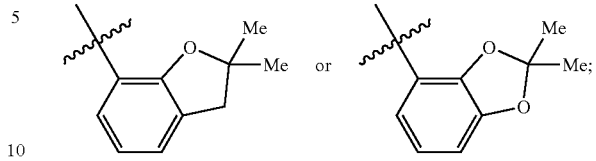

$R^7$ is H, Br, CN, NH$_2$, NMe$_2$, or —NH(4-OMe-Ph);
$R^8$ is H, Br, CN, NMe$_2$, or —N(Me)(4-OMe-Ph);
$R^{11}$ is, independently at each occurrence, H, —COPh, —COBn, —SO$_2$Me, —SO$_2$Ph, —SO$_2$Bn, C$_{1-4}$ alkyl substituted with 0-2 R$^a$, —(CH$_2$)$_r$-phenyl substituted with 0-3 R$^b$, —CHMe-phenyl substituted with 0-3 R$^b$, or —(CH$_2$)$_r$-5- to 10-membered heterocycle substituted with 0-3 R$^b$ and selected from: furanyl, thienyl, thiazolyl, pyridinyl, and indolyl;
$R^{12}$ is, independently at each occurrence, H, C$_{1-6}$ alkyl, —(CH$_2$)$_r$—C$_{3-6}$ cycloalkyl, —(CH$_2$)$_n$-phenyl, —(CH$_2$)$_r$-5- to 6-membered heterocycle selected from pyrrolidinyl, furanyl, thienyl, pyrrolyl, isoxazolyl, triazolyl, tetrazolyl, pyridinyl, pyrazinyl, pyrimidinyl, piperidinyl, morpholinyl, and piperazinyl;
$R^{13}$ is, independently at each occurrence, H, C$_{1-6}$ alkyl, or —(CH$_2$)$_n$-phenyl;
$R^a$ is, independently at each occurrence, OH, OR$^c$, SR$^c$, —C(O)OR$^c$, NR$^{12}$R$^{13}$, —C(O)NR$^{12}$R$^{13}$, or —CO-4-morpholin-4-yl;
$R^b$ is, independently at each occurrence, C$_{1-6}$ alkyl, C$_{1-4}$ alkoxyl, F, Cl, Br, CF$_3$, —OCF$_3$, —CH$_2$OH, OH, OMe, —CH$_2$OMe, —(CH$_2$)$_r$—C(O)OR$^c$, —(CH$_2$)$_r$—NR$^{12}$R$^{13}$, —(CH$_2$)$_r$—C(O)NR$^{12}$R$^{13}$, CN, —OCH$_2$C(Me)$_2$CH$_2$NMe$_2$, NO$_2$, —SO$_2$Me, OBn, —(CH$_2$)$_r$—C$_{3-6}$ cycloalkyl, —(CH$_2$)$_r$- phenyl substituted with 0-2 R$^e$, —(CH$_2$)$_r$-naphthyl substituted with 0-3 R$^e$, —(CH$_2$)$_r$-5- to 10-membered heterocycle substituted with 0-4 R$^e$ and selected from: thienyl, thiazolyl, imidazolyl, tetrazolyl, pyrrolidinyl, piperidinyl, azepanyl, morpholinyl, piperazinyl, pyridinyl or tetrahydroisoquinolinyl;
$R^c$ is, independently at each occurrence, H, C$_{1-6}$ alkyl substituted with 0-2 R$^e$, or —(CH$_2$)$_r$-phenyl substituted with 0-2 R$^e$;
$R^e$ is, independently at each occurrence, C$_{1-4}$ alkyl, OMe, F, Cl, —CH$_2$NH$_2$, CN, Ph, or Bn;
n, at each occurrence, is selected from 0, 1, 2, 3, and 4;
p, at each occurrence, is selected from 0, 1, and 2; and
r, at each occurrence, is selected from 0, 1, 2, 3, and 4.

In another embodiment, the present invention includes compounds of Formula (II), wherein:
ring A is

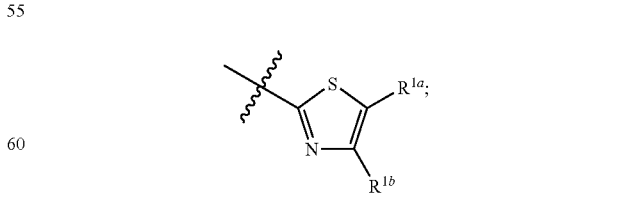

$R^{1a}$ and $R^{1b}$, independently at each occurrence, H, C$_{1-6}$ alkyl substituted with 0-2 R$^a$, Br, CN, CF$_3$, —CF$_2$CF$_3$, —C(O)OR$^c$, —C(O)NR$^{12}$R$^{13}$, —CON(Me)(CH$_2$)$_2$OH, —SO$_2$-morpholin-4-yl, —S(O)$_p$NR$^{12}$R$^{13}$, —CO-(4-morpholinyl), —(CH₂)ᵣ-phenyl substituted with 0-3 $R^b$; —(CH₂)ᵣ-5- to 10-membered heterocycle substituted with 0-3 $R^b$ and selected from: pyrrolidinyl, furanyl, triazolyl, tetrazolyl, piperidinyl, morpholinyl, piperazinyl, pyridyl, pyrimidinyl, 1,3-benzodioxolyl, isoindolinyl, tetrahydroisoquinolinyl, and

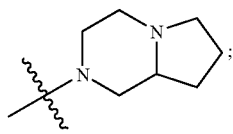

alternatively, ring A is

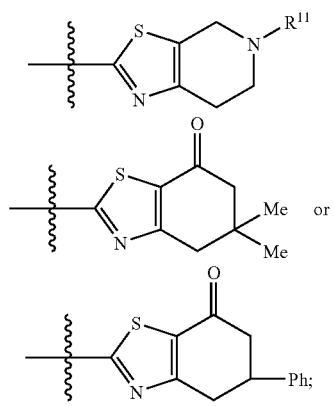

$R^{11}$ is H, $C_{1-4}$ alkyl, —(CH₂)₂OH, Bn, —COPh, —COBn, —SO₂Me, —SO₂Ph, or —SO₂Bn;

$R^a$ is, independently at each occurrence, OH, OMe, —C(O)OR$^c$, NR$^{12}$R$^{13}$, —C(O)NR$^{12}$R$^{13}$, or —CO(4-morpholinyl); and $R^b$ is, independently at each occurrence, $C_{1-4}$ alkyl, F, CF₃, —OCF₃, —CH₂OH, OH, OMe, —CH₂OMe, —OCH₂C(Me)₂CH₂NMe₂, CO₂Me, CO₂Et, CN, —CH₂NHMe, —CH₂NHEt, —CH₂NHBn, —CH₂NMe₂, —CH₂N(Me)Et, —CH₂N(Me)Bn, NO₂, —SO₂Me, or OBn.

In another embodiment, the present invention includes the compounds of Formula (IIa), wherein:

$R^{1a}$ is H, Me, Br, —CH₂OH, —(CH₂)₂OH, —CH₂OMe, CO₂H, CO₂Me, CO₂Et, —CH₂CO₂H, —CH₂CO₂Et, CN, —CH₂NHEt, —CH₂NH(t-Bu), —CH₂NH-neopentyl, —CH₂NHBn, —CH₂N(Me)Et, —CH₂N(Me)Pr, —CH₂N(Me)(t-Bu), —CH₂N(Me)cyclohexyl, —CH₂N(Me)Ph, —CH₂N(Me)Bn, —CH₂N(i-Pr)Bn, —CH₂N(t-Bu)Bn, —CH₂N(Me)CH(Me)Ph, —CH₂N(Me)(CH₂)₂Ph, —CH₂N(Me)(CH₂)₃Ph, —CH₂N(Me)(CH₂-pyridin-3-yl), —CONH₂, —CONHMe, —CONHEt, —CONHPr, —CONH-neopentyl, —CONHPh, —CONHBn, —CONH(CH₂-pyridin-2-yl), —CONH(CH₂-pyridin-3-yl), —CONH(CH₂CH₂-pyridin-3-yl), —CH₂CONHBn, —CON(Me)₂, —CON(Me)Et, —CON(Me)Pr, —CON(Me)(t-Bu), —CON(Me)Bn, —CON(Me)(CH₂)₂OH, —CON(Me)(CH₂)₂Ph, —CON(Me)(CH₂)₃Ph, —CON(Me)(CH₂-pyridin-3-yl), —CH₂CON(Me)Et, —SO₂-morpholin-4-yl, —SO₂NHEt, —SO₂NHBn, —SO₂N(Me)Et, —SO₂N(Me)Bn, —SO₂N(Bn)₂, Ph, 2-Me-Ph, 3-Me-Ph, 4-Me-Ph, 3-CF₃-Ph, 4-CF₃-Ph, 4-CH₂OH-Ph, 3-OH-Ph, 4-OH-Ph, 3-OMe-Ph, 4-OMe-Ph, 3-OCF₃-Ph, 4-OCF₃-Ph, 2-CH₂OMe-Ph, 2-(—CH₂NMe₂)-Ph, 2-(—CH₂NHMe)-Ph, 3-(—CH₂NHMe)-Ph, 4-(—CH₂NHMe)-Ph, 2-(—CH₂NHBn)-Ph, 3-(—CH₂NHBn)-Ph, 4-(—CH₂NHBn)-Ph, 3-(—CH₂NMe₂)-Ph, 4-(—CH₂NMe₂)-Ph, 2-(—CH₂N(Me)Bn)-Ph, 3-(—CH₂N(Me)Bn)-Ph, 4-(—CH₂N(Me)Bn)-Ph, 3-CO₂Me-Ph, 4-CO₂Me-Ph, 2-CN-Ph, 3-CN-Ph, 4-CN-Ph, 4-SO₂Me-Ph, 3-OBn-Ph, 4-OBn-Ph, 3-(—OCH₂C(Me)₂CH₂NMe₂)-Ph, 4-(—OCH₂C(Me)₂CH₂NMe₂)-Ph, 2,4-diF-Ph, 3,5-diF-Ph, 3-F-4-OMe-Ph, 2-(—CH₂NMe₂)-4-OMe-Ph, 3-(—CH₂NHMe)-4-OMe-Ph, 2-(—CH₂NHBn)-4-OMe-Ph, 2-(—CH₂N(Me)Bn)-4-OMe-Ph, 3,4,5-triOMe-Ph, pyrrolidin-1-yl, furan-3-yl, 1H-tetrazol-5-yl, 1H-1,2,4-triazol-3-yl, piperidin-1-yl, —N(Me)(1-Me-piperidin-4-yl), 4-(pyrrolidin-1-yl)-piperidin-1-yl, piperazin-1-yl, 4-Me-piperazin-1-yl, 4-Et-piperazin-1-yl, 4-i-Pr-piperazin-1-yl, 4-Bn-piperazin-1-yl, pyridin-4-yl, —N(Me)-CH₂-pyridin-3-yl, —N(Me)-CH₂-pyridin-4-yl, —CH₂-morpholin-4-yl, —CO-morpholin-4-yl, 2-OMe-pyrimidin-5-yl, 1,3-benzodioxol-4-yl,

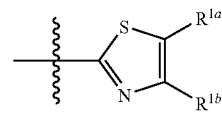

$R^{1b}$ is H, Me, Et, t-Bu, —C(Me)₂(CH₂)₂OH, CO₂Et, —CH₂CO₂(i-Pr), —C(Me)₂CH₂CO-morpholin-4-yl, —C(Me)₂CH₂CO₂Et, CN, CF₃, —CF₂CF₃, —CH(i-Bu)NH₂, —CONHEt, —CONHPr, —CONH(t-Bu), —CONH-neopentyl, —CONHPh, —CONHBn, —CON(Me)(t-Bu), —CON(Me)Bn, —C(Me)₂CH₂CONHBn, —C(Me)₂CH₂CON(Me)Et, —C(Me)₂CH₂CON(Me)Bn, —CH(i-Bu)NHCO₂(t-Bu), Ph, 4-Me-Ph, 3-F-Ph, 2-CH₂OH-Ph, 3-CH₂OH-Ph, 4-CH₂OH-Ph, 2-OMe-Ph, 3-OMe-Ph, 4-OMe-Ph, 2-(CH₂NHEt)-Ph, 2-(CH₂NHBn)-Ph, 2-(CH₂NMe₂)-Ph, 2-(CH₂N(Me)Et)-Ph, 2-(CH₂N(Me)Bn)-Ph, 3-(CH₂N(Me)Bn)-Ph, 4-(CH₂N(Me)Bn)-Ph, 2-CO₂Et-Ph, 4-CF₃-Ph, 4-OCF₃-Ph, 4-CN-Ph, 2-NO₂-Ph, 3-NO₂-Ph, or 4-NO₂-Ph;

alternatively,

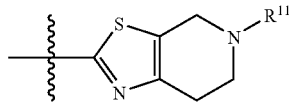

is

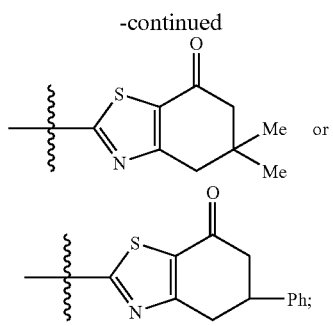

$R^5$ is 2-i-Pr-Ph, 2-t-Bu-Ph, or 2-OCF$_3$-Ph,

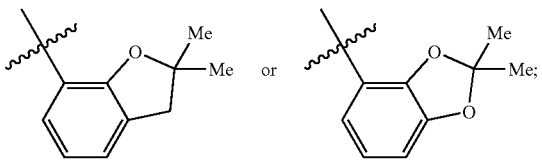

$R^7$ is H, Br, CN, NH$_2$, NMe$_2$, or —NH(4-OMe-Ph);
$R^8$ is H, Br, CN, NMe$_2$, or —N(Me)(4-OMe-Ph); and
$R^{11}$ is H, Pr, i-Bu, —(CH$_2$)$_2$OH, Bn, —COMe, —COPh, —COBn, —SO$_2$Me, —SO$_2$Ph, or —SO$_2$Bn.

In another embodiment, the present invention includes the compounds of Formula (Ia), wherein:
$R^5$ is 2-i-Pr-Ph, 2-t-Bu-Ph, 2-Br-Ph, 2-OCF$_3$-Ph, 2-CO$_2$Me-Ph, 3-CO$_2$Et-Ph,

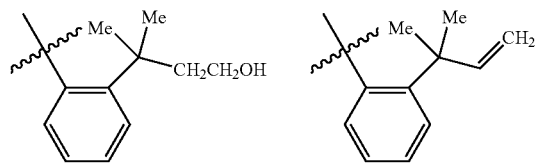

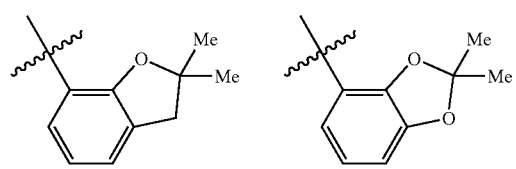

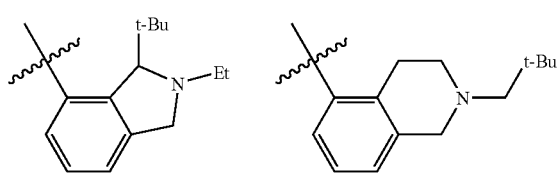

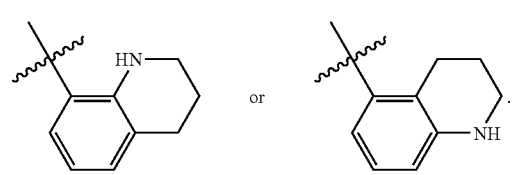

In another embodiment, the present invention includes the compounds of Formula (Ia), wherein:
ring A is substituted with 0-3 $R^1$ and selected from:

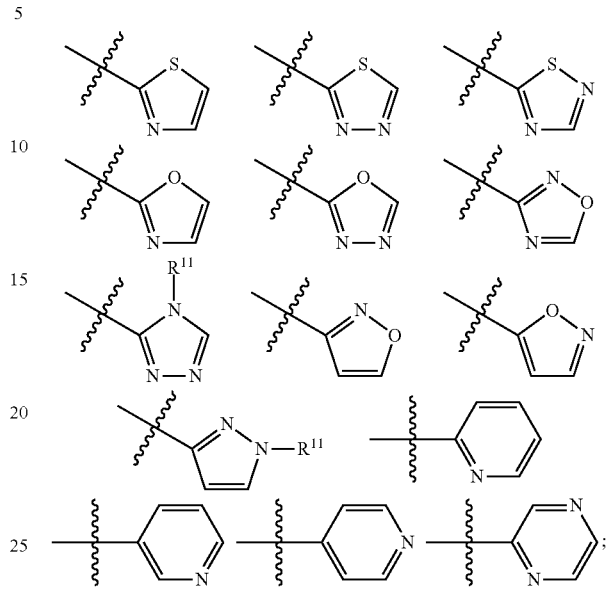

ring B is

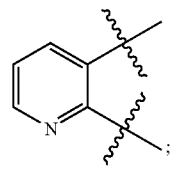

$R^1$ is, independently at each occurrence, Me, Pr, i-Pr, t-Bu, —CH$_2$OH, —C(Me)$_2$(CH$_2$)$_2$OH, —CH$_2$OMe, —CO$_2$H, —CH$_2$CO$_2$H, —CO$_2$Me, —CO$_2$Et, —CH$_2$CO$_2$Et, —CH$_2$CO$_2$(i-Pr), —C(Me)$_2$CH$_2$CO$_2$Et, —C(Me)$_2$(CH$_2$)$_2$CO$_2$Et, —CF$_3$, —CF$_2$CF$_3$, CN, cyclopropyl, 1-Ph-cyclopropyl, 4-NHBn-cyclohexyl, 4-N(Me)Bn-cyclohexyl, Ph, Bn, 2-F-Ph, 3-F-Ph, 2-Cl-Ph, 4-Cl-Ph, 2-Me-Ph, 3-Me-Ph, 4-Me-Ph, 4-t-Bu-Ph, 2-OMe-Ph, 3-OMe-Ph, 4-OMe-Ph, 3-CF$_3$-Ph, 4-CF$_3$-Ph, 4-OCF$_3$-Ph, 4-CN-Ph, 2-NO$_2$-Ph, 3-NO$_2$-Ph, 4-NO$_2$-Ph, 4-SO$_2$Me-Ph, 2-F-4-Br-Ph, 3-Cl-4-F-Ph, 3,4-diOMe-Ph, 3,5-diOMe-Ph, 2,6-diCl-Ph, 2-F-4-(2-CH$_2$NH$_2$-Ph)-Ph, 2,6-diCl-Bn, —CH$_2$OPh, —CH$_2$O(4-t-Bu-Ph), —CH$_2$O(2-Cl-Ph), —CH$_2$O(4-Cl-Ph), —CH(t-Bu)NH$_2$, —CH$_2$NHEt, —CH$_2$NH-neopentyl, —CH$_2$NHPh, —CH$_2$NHBn, —CH$_2$N(Me)Et, —CH$_2$N(Me)Pr, —CH$_2$N(Me)(t-Bu), —CH$_2$N(Me)Ph, —CH$_2$N(Me)-cyclohexyl, —CH$_2$N(Me)Bn, —CH$_2$N(i-Pr)Bn, —CH$_2$N(t-Bu)Bn, —CH$_2$N(Me)CH(Me)Ph, —CH$_2$N(Me)(CH$_2$)$_2$Ph, —CH$_2$N(Me)(CH$_2$)$_3$Ph, —CH$_2$N(Me)CH$_2$(3-pyridyl), —CH(t-Bu)NHCO$_2$(t-Bu), —CONHPr, —CONH(t-Bu), —CONH-neopentyl, —CONHPh, —CONHBn, —CON(Me)$_2$, —CON(Me)Et, —CON(Me)Pr, —CON(Me)(t-Bu), —CON(Me)Ph, —CON(Me)Bn, —CON(Me)(CH$_2$)$_2$Ph, —CON(Me)(CH$_2$)$_3$Ph, —CH$_2$CONHBn, —C(Me)$_2$CH$_2$CONHBn, —C(Me)$_2$CH$_2$CON(Me)Et, —C(Me)$_2$CH$_2$CON(Me)Ph, —C(Me)$_2$(CH$_2$)$_2$CON(Me)Bn, —CON(Me)CH$_2$(3-pyridyl), 3-furyl, 2-thienyl, 2-pyridyl, 3-pyridyl, 4-pyridyl, 2,6-diCl-4-pyridyl, 2-pyrazinyl, —CH$_2$—(N-morpholinyl), —CO—(N-morpholinyl), —C(Me)₂CH₂CO—(N-morpholinyl), 1-Bn-4-Me-4-piperidyl, —NH-(1-(4-t-Bu-Ph)-4-piperidyl), —(CH₂)₃-(4-Bn-piperazinyl), —C(Me)₂(CH₂)₂—CO-(4-Bn-piperazinyl), 3-benzothienyl,

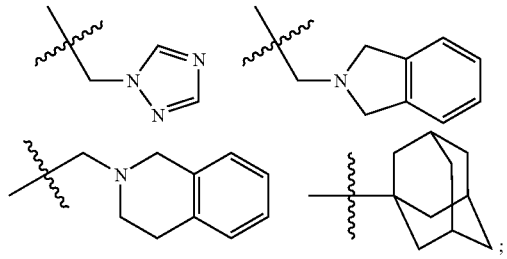

alternatively, ring A is substituted with 0-3 R$^b$ and selected from:

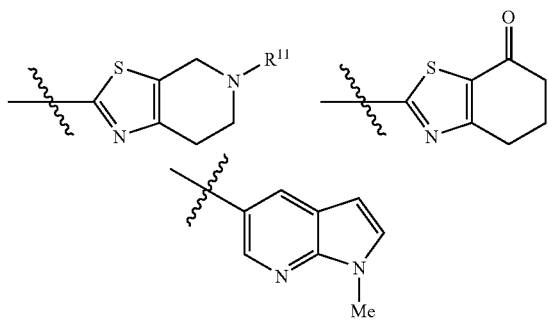

R$^5$ is 2-t-Bu-Ph,
R$^{11}$ is H, Ph, Bn, —COPh, —COBn, —SO₂Me, —SO₂Ph, or —SO₂Bn;
R$^b$ is Me or Ph;
X is NH; and
Y is O.

In another embodiment, the present invention includes, inter alia, a method for treating a thromboembolic disorder, comprising: administering to a patient in need thereof a therapeutically effective amount of a compound of Formula (I):

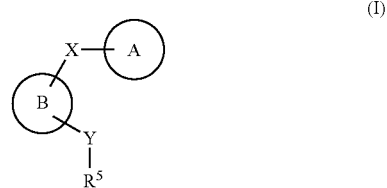

or a stereoisomer, tautomer, pharmaceutically acceptable salt, solvate, or prodrug thereof, wherein:

ring A is 5- to 6-membered heteroaryl comprising: carbon atoms and 1-4 ring heteroatoms selected from O, N, NR$^{11}$, and S(O)$_p$, wherein said heteroaryl is substituted with 0-4 R$^7$;

ring B is phenyl substituted with 0-4 R$^7$, or a 5- to 6-membered heteroaryl comprising: carbon atoms and 1-4 ring heteroatoms selected from N, NR$^{11}$, S(O)$_p$, and O, wherein said heteroaryl is substituted with 0-4 R$^7$;

X is —(CR$^{16}$R$^{17}$)$_s$—, —(CR$^{16}$R$^{17}$)$_r$CR═CR(CR$^{16}$R$^{17}$)$_r$—, —(CR$^{16}$R$^{17}$)$_r$C≡C(CR$^{16}$R$^{17}$)$_r$—, —(CR$^{16}$R$^{17}$)$_r$O(CR$^{16}$R$^{17}$)$_r$—, —(CR$^{16}$R$^{17}$)$_r$NR$^{14}$(CR$^{16}$R$^{17}$)$_r$—, —(CR$^{16}$R$^{17}$)$_r$C(O)(CR$^{16}$R$^{17}$)$_r$—, —(CR$^{16}$R$^{17}$)$_r$C(O)O(CR$^{16}$R$^{17}$)$_r$—, —(CR$^{16}$R$^{17}$)$_r$OC(O)(CR$^{16}$R$^{17}$)$_r$—, —(CR$^{16}$R$^{17}$)$_r$C(O)NR$^{14}$(CR$^{16}$R$^{17}$)$_r$—, —(CR$^{16}$R$^{17}$)$_r$S(CR$^{16}$R$^{17}$)$_r$—, —(CR$^{16}$R$^{17}$)$_r$S(O)(CR$^{16}$R$^{17}$)$_s$—, —(CR$^{16}$R$^{17}$)$_r$S(O)₂(CR$^{16}$R$^{17}$)$_r$—, —(CR$^{16}$R$^{17}$)$_r$SO₂NR$^{14}$(CR$^{16}$R$^{17}$)$_r$—, or —(CR$^{16}$R$^{17}$)$_r$NR$^{14}$SO₂(CR$^{16}$R$^{17}$)$_r$—;

Y is NR$^{15}$, O, or S;

R$^1$ is, independently at each occurrence, F, Cl, Br, I, CF₃, —CF₂CF₃, OCF₃, —OCF₂CF₂H, —OCF₂CF₃, SiMe₃, —(CR$^f$R$^f$)$_r$—OR$^c$, SR$^c$, CN, NO₂, —(CR$^f$R$^f$)$_r$—NR$^{12}$R$^{13}$, —(CR$^f$R$^f$)$_r$—C(O)R$^c$, —(CR$^f$R$^f$)$_r$—CO₂R$^c$, —(CR$^f$R$^f$)$_r$—C(O)NR$^{12}$R$^{13}$, —C(O)NR$^{14}$(CR$^f$R$^f$)$_n$N$^{12}$R$^{13}$, —(CR$^f$R$^f$)$_r$—OC(O)NR$^{12}$R$^{13}$, —(CR$^f$R$^f$)$_r$—NR$^{14}$C(O)NR$^{12}$R$^{13}$, —(CR$^f$R$^f$)$_r$—NR$^{14}$C(O)R$^d$, —(CR$^f$R$^f$)$_r$—NR$^{14}$C(O)OR$^h$, —NR$^{14}$(CR$^f$R$^f$)$_n$C(O)R$^d$, —NR$^{14}$CO(CR$^f$R$^f$)$_n$OR$^c$, —(CH₂)$_r$—CR$^{13}$(═NOR$^c$), —(CH₂)$_r$—C(NH₂)(═NOR$^c$), —S(O)$_p$NR$^{12}$R$^{13}$, —(CR$^f$R$^f$)$_r$—NR$^{14}$S(O)$_p$NR$^{12}$R$^{13}$, —NR$^{14}$SO₂CF₃, —NR$^{14}$S(O)$_p$R$^d$, —S(O)₂CF₃, —S(O)R$^d$, —S(O)₂R$^d$, —OP(O)(OEt)₂, —O(CH₂)₂OP(O)(OEt)₂, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R$^1$s are combined with the carbon atoms to which they attached, form a 5- to 7-membered carbocycle or heterocycle comprising: carbon atoms and 0-3 additional heteroatoms selected from N, NR$^{11}$, O, and S(O)$_p$, 0-2 carbonyls, and 0-2 double bond, wherein said carbocycle or heterocycle is substituted with 0-4 R$^b$;

R$^5$ is a —(CR$^f$R$^f$)$_n$—C$_{3-10}$ carbocycle substituted with 0-5 R$^{5a}$, or a —(CR$^f$R$^f$)$_n$-5- to 10-membered heterocycle comprising: carbon atoms and 1-4 heteroatoms selected from N, NR$^{11}$, O, and S(O)$_p$, wherein said heterocycle is substituted with 0-5 R$^{5a}$;

R$^{5a}$ is, independently at each occurrence, F, Cl, Br, I, —(CR$^f$R$^i$)$_r$—OR$^c$, SR$^c$, CN, NO₂, CF₃, —CF₂CF₃, OCF₃, —OCF₂CF₂H, —OCF₂CF₃, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)₂R$^d$, —Si(Me)₃, Si(C$_{1-4}$ alkyl)₃, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-3 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-3 R$^e$;

alternatively, two R$^{5a}$ groups, together with the atoms to which they are attached, form a 5- to 7-membered carbocyclic or heterocyclic ring comprising: carbon atoms and 0-2 heteroatoms selected from N, NR$^{11}$, O, and S(O)$_p$, 0-1 carbonyl and 0-3 double bonds, wherein said carbocyclic or heterocyclic ring is substituted with 0-3 R$^e$;

R$^7$ is, independently at each occurrence, H, F, Cl, Br, I, OCF₃, CF₃, OR$^c$, SR$^c$, CN, NO₂, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)₂R$^d$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-3 R$^b$, or —(CR$^f$R$^f$)$_r$-5- to 10-membered heterocycle comprising: carbon atoms and 1-4 heteroatoms selected from N, NR$^{7b}$, O, and S(O)$_p$, wherein said heterocycle is substituted with 0-3 R$^b$;

alternatively, two R$^7$s form a 5- to 7-membered carbocyclic or heterocyclic ring comprising: carbon atoms and 0-3 ring heteroatoms selected from O, N, NR$^{7b}$, and S(O)$_p$, wherein said carbocyclic or heterocyclic ring is substituted with 0-3 R$^{7c}$;

R$^{7b}$ is, independently at each occurrence, H, C$_{1-4}$ alkyl, (C$_{1-4}$ alkyl)C(O)—, phenyl-C(O)—, benzyl-C(O)—, benzyl-S(O)$_2$—, (C$_{1-4}$ alkyl)NHC(O)—, (C$_{1-4}$ alkyl)$_2$NC(O)—, phenyl-NHC(O)—, benzyl-NHC(O)—, (C$_{1-4}$ alkyl)-S(O)$_2$—, phenyl-S(O)$_2$—, phenyl substituted with 0-3 R$^b$, or benzyl substituted with 0-3 R$^b$;

R$^{7c}$ is, independently at each occurrence, H, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ alkyl, phenyl substituted with 0-3 R$^b$, or benzyl substituted with 0-3 R$^b$;

R$^{11}$ is, independently at each occurrence, H, C$_{1-6}$ alkyl substituted with 1-5 fluorine, —(CR$^f$R$^f$)$_r$C(O)NR$^{12}$R$^{13}$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, (C$_{1-6}$ alkyl)C(O)—, (C$_{3-6}$ cycloalkyl)C$_{1-3}$ alkyl-C(O)—, (C$_{3-6}$ cycloalkyl)C(O)—, phenyl-C(O)—, benzyl-C(O)—, (C$_{1-6}$ alkyl)NHC(O)—, (C$_{1-6}$ alkyl)$_2$NC(O)—, phenyl-NHC(O)—, benzyl-NHC(O)—, (phenyl)(C$_{1-6}$ alkyl)NC(O)—, (benzyl)(C$_{1-6}$ alkyl)NC(O)—, (C$_{1-6}$ alkyl)-S(O)$_2$—, phenyl-S(O)$_2$—, benzyl-S(O)$_2$—, —(CR$^f$R$^f$)$_r$—C$_{3-10}$ carbocycle, or —(CR$^f$R$^f$)$_r$-5- to 10-membered heterocycle comprising: carbon atoms and 1-4 heteroatoms selected from N, NR$^f$, O, and S(O)$_p$; wherein said phenyl, benzyl, carbocycle, and heterocycle are substituted with 0-3 R$^b$;

R$^{12}$ is, independently at each occurrence, H, C$_{1-6}$ alkyl substituted with 1-5 fluorine, —CH$_2$O(C$_{1-4}$ alkyl), —(CR$^f$R$^f$)$_r$C(O)NR$^f$R$^f$, C$_{1-6}$ alkyl, (C$_{1-6}$ alkyl)C(O)—, (C$_{1-4}$ alkyl)OC(O)—, (C$_{6-10}$ aryl)-CH$_2$—OC(O)—, (C$_{6-10}$ aryl)-CH$_2$—C(O)—, (C$_{1-4}$ alkyl)-C(O)O—(C$_{1-4}$ alkyl)-OC(O)—, (C$_{6-10}$ aryl)-C(O)O—(C$_{1-4}$ alkyl)-OC(O)—, (C$_{1-6}$ alkyl)-NHC(O)—, (C$_{6-10}$ aryl)-NHC(O)—, (5- to 10-membered heteroaryl)-NHC(O)—, (5- to 10-membered heteroaryl)-CH$_2$—OC(O)—, (5- to 10-membered heteroaryl)-C(O)—, (C$_{6-10}$ aryl)-(C$_{0-4}$ alkyl)-C(O)—, (C$_{1-6}$ alkyl)-S(O)$_2$—, (C$_{6-10}$ aryl)-S(O)$_2$—, (5- to 10-membered heteroaryl)-S(O)$_2$—, or (C$_{6-10}$ aryl)-(C$_{1-4}$ alkyl)-S(O)$_2$—, —(CR$^f$R$^f$)$_n$—(C$_{6-10}$ aryl), —(CR$^f$R$^f$)$_n$-5- to 10-membered heterocycle; wherein said alkyl, phenyl and aryl are substituted with 0-2 R$^g$; said 5- to 10-membered heteroaryl is substituted with 0-2 R$^g$ and comprises: carbon atoms and 1-4 heteroatoms selected from N, NR$^f$, O, and S(O)$_p$; said 5- to 10-membered heterocycle is substituted with 0-2 R$^g$ and comprises: carbon atoms and 1-4 heteroatoms selected from N, NR$^f$, O, and S(O)$_p$;

R$^{13}$ is, independently at each occurrence, H, C$_{1-6}$ alkyl, or —(CH$_2$)$_n$-phenyl;

alternatively, R$^{12}$ and R$^{13}$, when attached to the same nitrogen, combine to form a 5- to 10-membered heterocyclic ring comprising: carbon atoms and 1-2 additional heteroatoms selected from N, NR$^f$, O, and S(O)$_p$;

R$^{14}$ is, independently at each occurrence, H, C$_{1-6}$ alkyl substituted with 0-2 R$^{14a}$, C$_{2-6}$ alkenyl substituted with 0-2 R$^{14a}$, C$_{2-6}$ alkynyl substituted with 0-2 R$^{14a}$, —(CH$_2$)$_r$—C$_{3-10}$ carbocycle substituted with 0-3 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^g$;

R$^{14a}$ is, independently at each occurrence, H, C$_{1-4}$ alkyl, OR$^f$, Cl, F, Br, I, =O, CF$_3$, CN, NO$_2$, NR$^{12}$R$^{13}$, —C(O)R$^f$, —C(O)OR$^f$, —C(O)NR$^{12}$R$^{13}$, or —S(O)$_p$R$^f$;

R$^{15}$ is H, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, (C$_{1-6}$ alkyl)C(O)—, (C$_{3-6}$ cycloalkyl)C$_{1-3}$ alkyl-C(O)—, (C$_{3-6}$ cycloalkyl)C(O)—, phenyl-C(O)—, benzyl-C(O)—, benzyl-S(O)$_2$—, (C$_{1-6}$ alkyl)NHC(O)—, (C$_{1-6}$ alkyl)$_2$NC(O)—, phenyl-NHC(O)—, benzyl-NHC(O)—, (phenyl)(C$_{1-6}$ alkyl)NC(O)—, (benzyl)(C$_{1-6}$ alkyl)NC(O)—, (C$_{1-6}$ alkyl)-S(O)$_2$—, phenyl-S(O)$_2$—, —(CH$_2$)$_r$—C$_{3-10}$ carbocycle substituted with 0-3 R$^b$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^b$;

R$^{16}$ is, independently at each occurrence, H, F, Cl, Br, I, OCF$_3$, CF$_3$, —(CH$_2$)$_r$—OR$^c$, SR$^c$, CN, NO$_2$, —(CH$_2$)$_r$—NR$^{12}$R$^{13}$, —(CH$_2$)$_r$—C(O)R$^c$, —(CH$_2$)$_r$—CO$_2$R$^c$, —(CH$_2$)$_r$—C(O)NR$^{12}$R$^{13}$, —(CH$_2$)$_r$—OC(O)NR$^{12}$R$^{13}$, —(CH$_2$)$_r$—NR$^{14}$C(O)R$^d$, —S(O)$_p$NR$^{12}$R$^{13}$, —NR$^{14}$S(O)$_p$NR$^{12}$R$^{13}$, —NR$^{14}$SO$_2$CF$_3$, —NR$^{14}$SO$_2$R$^d$, —S(O)$_2$CF$_3$, —S(O)R$^d$, —S(O)$_2$R$^d$, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —(CH$_2$)$_r$—C$_{3-10}$ carbocycle substituted with 0-5 R$^b$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-5 R$^b$;

R$^{17}$ is, independently at each occurrence, H, OH, C$_{1-6}$ alkyl, or —(CH$_2$)$_n$-phenyl;

R$^a$ is, independently at each occurrence, H, F, OCF$_3$, CF$_3$, —(CR$^f$R$^f$)$_r$OR$^c$, —(CR$^f$R$^f$)$_r$SR$^c$, CN, —(CR$^f$R$^f$)$_r$NR$^{12}$R$^{13}$, —(CR$^f$R$^f$)$_r$C(O)R$^c$, —(CR$^f$R$^f$)$_r$C(O)OR$^c$, —(CR$^f$R$^f$)$_r$C(O)NR$^{12}$R$^{13}$, —(CR$^f$R$^f$)$_r$NR$^{14}$C(O)R$^d$, —(CR$^f$R$^f$)$_r$S(O)$_p$NR$^{12}$R$^{13}$, —(CR$^f$R$^f$)$_r$S(O)R$^d$, —(CR$^f$R$^f$)$_r$S(O)$_2$R$^d$, C$_{1-4}$ alkyl substituted with 1-5 fluorine, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^b$ is, independently at each occurrence, H, =O, F, Cl, Br, I, —(CH$_2$)$_r$—OR$^c$, SR$^c$, CN, NO$_2$, CF$_3$, OCF$_3$, —(CR$^f$R$^f$)$_r$NR$^{12}$R$^{13}$, —C(O)R$^c$, —(CH$_2$)$_r$—C(O)OR$^c$, —(CH$_2$)$_r$—C(O)NR$^{12}$R$^{13}$, —NR$^{14}$C(O)R$^d$, —S(O)$_p$NR$_{12}$R$^{13}$, —S(O)R$^d$, —S(O)$_2$R$^d$, C$_{1-4}$ haloalkyl, C$_{1-4}$ haloalkyloxy-, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^c$ is, independently at each occurrence, H, —OP(O)(OEt)$_2$, C$_{1-8}$ alkyl substituted with 0-2 R$^e$, C$_{2-8}$ alkenyl substituted with 0-2 R$^e$, C$_{2-8}$ alkynyl substituted with 0-2 R$^e$, —(CR$^f$R$^f$)$_r$—C$_{3-8}$ cycloalkyl substituted with 0-2 R$^e$, —(CR$^f$R$^f$)$_r$—C$_{6-10}$ aryl substituted with 0-2 R$^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^d$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —$(CF_2)_rCF_3$, $Si(C_{1-4}$ alkyl$)_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, $NR^f$, O, and $S(O)_p$, 0-1 carbonyl and 0-3 double bonds, wherein said carbocyclic or heterocyclic ring is substituted with 0-3 $R^g$;

$R^f$ is, independently at each occurrence, H, F, $C_{1-6}$ alkyl, or —$(CH_2)_n$-phenyl;

$R^g$ is, independently at each occurrence, H, =O, $ORE$, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, or —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^i$ is, independently at each occurrence, H, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

n, at each occurrence, is selected from 0, 1, 2, 3, and 4;
p, at each occurrence, is selected from 0, 1, and 2;
r, at each occurrence, is selected from 0, 1, 2, 3, and 4;
s, at each occurrence, is selected from 0, 1, 2, 3, 4, 5, and 6; and
t, at each occurrence, is selected from 1, 2, 3, and 4;
provided that when Y is S, $R^5$ is Ph or 6-$NO_2$-pyridyl, ring A is other than 2-imidazolinyl or 6-$NO_2$-pyridyl.

In another embodiment, the present invention includes, inter alia, a method for treating a thromboembolic disorder, comprising: administering to a patient in need thereof a therapeutically effective amount of a compound of Formula (Ia):

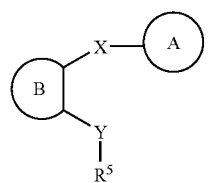

(Ia)

or a stereoisomer, tautomer, pharmaceutically acceptable salt, solvate, or prodrug thereof, wherein:

ring A is a 5- to 6-membered heteroaryl comprising: carbon atoms and 1-4 ring heteroatoms selected from N, $NR^{11}$, $S(O)_p$, and O, wherein said heteroaryl is substituted with 0-4 $R^1$;

ring B is phenyl substituted with 0-4 $R^7$, pyridyl substituted with 0-3 $R^7$, or thienyl substituted with 0-2 $R^7$;

X is NH or NMe;
Y is O or S;

$R^1$ is, independently at each occurrence, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$C(O)NR^{14}(CR^fR^f)_nN^{12}R^{13}$, —$(CR^fR^f)_r$—$OC(O)NR^{12}R^{13}$, —$(CR^fR^f)_r$—$NR^{14}C(O)NR^{12}R^{13}$, —$(CR^fR^f)_r$—$NR^{14}C(O)R^d$, —$(CR^fR^f)_r$—$NR^{14}C(O)OR^h$, —$NR^{14}(CR^fR^f)_nC(O)R^d$, —$NR^{14}CO(CR^fR^f)_nOR^c$, —$(CH_2)_r$—$CR^{13}(=NOR^c)$, —$(CH_2)_r$—$C(NH_2)(=NOR^c)$, —$S(O)_pNR^{12}R^{13}$, —$(CR^fR^f)_r$—$NR^{14}S(O)_pNR^{12}R^{13}$, —$NR^{14}SO_2CF_3$, —$NR^{14}S(O)_pR^d$, —$S(O)_2CF_3$, —$S(O)R^d$, —$S(O)_2R^d$, —$OP(O)(OEt)_2$, —$O(CH_2)_2OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s are combined with the carbon atoms to which they attached, form a 5- to 7-membered carbocycle or heterocycle comprising: carbon atoms and 0-3 additional heteroatoms selected from N, $NR^{11}$, O, and $S(O)_p$, 0-2 carbonyls, and 0-2 double bond, wherein said carbocycle or heterocycle is substituted with 0-4 $R^b$;

$R^5$ is a —$(CR^fR^f)_n$—$C_{3-10}$ carbocycle substituted with 0-4 $R^{ya}$, or a —$(CR^fR^f)_n$-5- to 10-membered heterocycle comprising: carbon atoms and 1-4 heteroatoms selected from N, $NR^{11}$, O, and $S(O)_p$, wherein said heterocycle is substituted with 0-4 $R^{5a}$; provided that $R^5$ is other than unsubstituted phenyl;

$R^{5a}$ is, independently at each occurrence, F, Cl, Br, I, —$(CR^iR^i)_r$—$OR^c$, $SR^c$, CN, $NO_2$, $CF_3$, —$CF_2CF_3$, $OCF_3$, —$OCF_2CF_2H$, —$OCF_2CF_3$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, —$Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-3 $R^e$;

alternatively, two $R^{5a}$ groups, together with the atoms to which they are attached, form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 double bonds, wherein said carbocyclic or heterocyclic ring is substituted with 0-3 $R^e$;

$R^7$ is, independently at each occurrence, H, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^b$, or —$(CR^fR^f)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-3 $R^{7c}$;

$R^{7b}$ is, independently at each occurrence, H, $C_{1-4}$ alkyl, $(C_{1-4}$ alkyl)C(O)—, phenyl-C(O)—, benzyl-C(O)—, benzyl-S(O)$_2$—, $(C_{1-4}$ alkyl)NHC(O)—, $(C_{1-4}$ alkyl)$_2$NC(O)—, phenyl-NHC(O)—, benzyl-NHC(O)—, $(C_{1-4}$ alkyl)-S(O)$_2$—, phenyl-S(O)$_2$—, phenyl substituted with 0-3 $R^b$, or benzyl substituted with 0-3 $R^b$;

$R^{7c}$ is, independently at each occurrence, H, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, $C_{1-4}$ alkyl, phenyl substituted with 0-3 $R^b$, or benzyl substituted with 0-3 $R^b$;

$R^{11}$ is, independently at each occurrence, H, $C_{1-6}$ alkyl substituted with 1-5 fluorine, —(CR$^f$R$^f$)$_r$C(O)NR$^{12}$R$^{13}$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, $(C_{1-6}$ alkyl)NHC(O)—, $(C_{1-6}$ alkyl)$_2$NC(O)—, phenyl-NHC(O)—, benzyl-NHC(O)—, (phenyl)$(C_{1-6}$ alkyl)NC(O)—, (benzyl)$(C_{1-6}$ alkyl)NC(O)—, $(C_{1-6}$ alkyl)-S(O)$_2$—, phenyl-S(O)$_2$—, benzyl-S(O)$_2$—, —(CR$^f$R$^f$)$_r$—$C_{3-10}$ carbocycle, or —(CR$^f$R$^f$)$_r$-5- to 10-membered heterocycle comprising: carbon atoms and 1-4 heteroatoms selected from N, NR$^f$, O, and S(O)$_p$; wherein said phenyl, benzyl, carbocycle, and heterocycle are substituted with 0-3 $R^b$;

$R^{12}$ is, independently at each occurrence, H, $C_{1-6}$ alkyl substituted with 1-5 fluorine, —CH$_2$O$(C_{1-4}$ alkyl), —(CR$^f$R$^f$)$_r$C(O)NR$^f$R$^f$, $C_{1-6}$ alkyl, $(C_{1-6}$ alkyl)C(O)—, $(C_{1-4}$ alkyl)OC(O)—, $(C_{6-10}$ aryl)-CH$_2$—OC(O)—, $(C_{6-10}$ aryl)-CH$_2$—C(O)—, $(C_{1-4}$ alkyl)-C(O)O—$(C_{1-4}$ alkyl)-OC(O)—, $(C_{6-10}$ aryl)-C(O)O—$(C_{1-4}$ alkyl)-OC(O)—, $(C_{1-6}$ alkyl)-NHC(O)—, $(C_{6-10}$ aryl)-NHC(O)—, (5- to 10-membered heteroaryl)-NHC(O)—, (5- to 10-membered heteroaryl)-CH$_2$—OC(O)—, (5- to 10-membered heteroaryl)-C(O)—, $(C_{6-10}$ aryl)-$(C_{0-4}$ alkyl)-C(O)—, $(C_{1-6}$ alkyl)-S(O)$_2$—, $(C_{6-10}$ aryl)-S(O)$_2$—, (5- to 10-membered heteroaryl)-S(O)$_2$—, or $(C_{6-10}$ aryl)-$(C_{1-4}$ alkyl)-S(O)$_2$—, —(CR$^f$R$^f$)$_n$—$(C_{6-10}$ aryl), —(CR$^f$R$^f$)$_n$-5- to 10-membered heterocycle; wherein said alkyl, phenyl and aryl are substituted with 0-2 $R^g$; said 5- to 10-membered heteroaryl is substituted with 0-2 $R^g$ and comprises: carbon atoms and 1-4 heteroatoms selected from N, NR$^f$, O, and S(O)$_p$; said 5- to 10-membered heterocycle is substituted with 0-2 $R^g$ and comprises: carbon atoms and 1-4 heteroatoms selected from N, NR$^f$, O, and S(O)$_p$;

$R^{13}$ is, independently at each occurrence, H, $C_{1-6}$ alkyl, or —(CH$_2$)$_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, NR$^f$, O, and S(O)$_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —(CH$_2$)$_r$—$C_{3-10}$ carbocycle substituted with 0-3 $R^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^g$;

$R^{14a}$ is, independently at each occurrence, H, $C_{1-4}$ alkyl, OR$^f$, Cl, F, Br, I, ═O, CF$_3$, CN, NO$_2$, NR$^{12}$R$^{13}$, —C(O)R$^f$, —C(O)OR$^f$, —C(O)NR$^{12}$R$^{13}$, or —S(O)$_p$R$^f$;

$R^a$ is, independently at each occurrence, H, F, OCF$_3$, CF$_3$, —(CR$^f$R$^f$)$_r$OR$^c$, —(CR$^f$R$^f$)$_r$SR$^c$, CN, —(CR$^f$R$^f$)$_r$NR$^{12}$R$^{13}$, —(CR$^f$R$^f$)$_r$C(O)R$^c$, —(CR$^f$R$^f$)$_r$C(O)OR$^c$, —(CR$^f$R$^f$)$_r$C(O)NR$^{12}$R$^{13}$, —(CR$^f$R$^f$)$_r$NR$^{14c}$(O)R$^d$, —(CR$^f$R$^f$)$_r$S(O)$_p$NR$^{12}$R$^{13}$, —(CR$^f$R$^f$)$_r$S(O)R$^d$, —(CR$^f$R$^f$)$_r$S(O)$_2$R$^d$, $C_{1-4}$ alkyl substituted with 1-5 fluorine, —(CH$_2$)$_r$—$C_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^b$ is, independently at each occurrence, H, ═O, F, Cl, Br, I, —(CH$_2$)$_r$—OR$^c$, SR$^c$, CN, NO$_2$, CF$_3$, OCF$_3$, —(CR$^f$R$^f$)$_r$NR$^{12}$R$^{13}$, —C(O)R$^c$, —(CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, $C_{1-4}$ haloalkyl, $C_{1-4}$ haloalkyloxy-, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —(CH$_2$)$_r$—$C_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^c$ is, independently at each occurrence, H, —OP(O)(OEt)$_2$, $C_{1-8}$ alkyl substituted with 0-2 $R^e$, $C_{2-8}$ alkenyl substituted with 0-2 $R^e$, $C_{2-8}$ alkynyl substituted with 0-2 $R^e$, —(CR$^f$R$^f$)$_r$—$C_{3-8}$ cycloalkyl substituted with 0-2 $R^e$, —(CR$^f$R$^f$)$_r$—$C_{6-10}$ aryl substituted with 0-2 $R^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-2 $R^e$;

$R^d$ is, independently at each occurrence, CF$_3$, OH, $C_{1-4}$ alkoxy, $C_{1-6}$ alkyl, —(CH$_2$)$_r$—$C_{3-10}$ carbocycle substituted with 0-2 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^e$;

$R^e$ is, independently at each occurrence, H, ═O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—$C_{1-4}$ alkyl, —NR$^{14}$SO$_2$CF$_3$, —NR$^{14}$SO$_2$-phenyl, —S(O)$_2$CF$_3$, —S(O)$_p$—$C_{1-4}$ alkyl, —S(O)$_p$-phenyl, —(CF$_2$)$_r$CF$_3$, Si$(C_{1-4}$ alkyl)$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —(CH$_2$)$_r$—$C_{3-8}$ cycloalkyl substituted with 0-2 $R^g$, —(CH$_2$)$_r$—$C_{6-10}$ aryl substituted with 0-2 $R^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^g$;

alternatively, two $R^e$ groups, together with the atoms to which they are attached, form a 5- to 7-membered carbocyclic or heterocyclic ring comprising: carbon atoms and 0-2 heteroatoms selected from N, NR$^f$, O, and S(O)$_p$, 0-1 carbonyl and 0-3 double bonds, wherein said carbocyclic or heterocyclic ring is substituted with 0-3 $R^g$;

$R^f$ is, independently at each occurrence, H, F, $C_{1-6}$ alkyl, or —(CH$_2$)$_n$-phenyl;

$R^g$ is, independently at each occurrence, H, ═O, ORE, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—$C_{1-4}$ alkyl, —NR$^f$SO$_2$CF$_3$, —NR$^f$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, or —(CH$_2$)$_n$-phenyl substituted with 0-2 $R^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 $R^g$;

$R^i$ is, independently at each occurrence, H, $C_{1-6}$ alkyl substituted with 0-2 $R^g$, —(CH$_2$)$_n$-phenyl substituted with 0-2 $R^g$, or —(CH$_2$)$_n$-5- to 10-membered heterocycle comprising:

carbon atoms and 1-4 heteroatoms selected from N, NR$^f$, O, and S(O)$_p$, wherein said heterocycle is substituted with 0-2 R$^g$;

n, at each occurrence, is selected from 0, 1, 2, 3, and 4;
p, at each occurrence, is selected from 0, 1, and 2; and
r, at each occurrence, is selected from 0, 1, 2, 3, and 4;

In another embodiment, the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment, the present invention provides a pharmaceutical composition comprising additional therapeutic agent(s) selected from potassium channel openers, potassium channel blockers, calcium channel blockers, sodium hydrogen exchanger inhibitors, antiarrhythmic agents, anti-atherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition comprising additional therapeutic agent(s) are selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition comprising additional therapeutic agent(s) an antihypertensive agent selected from ACE inhibitors, AT-1 receptor antagonists, ET receptor antagonists, dual ET/AII receptor antagonists, and vasopepsidase inhibitors, or an antithrombotic agent selected from an anti-platelet agent selected from GPIIb/IIIa blockers, P2Y$_1$ and P2Y$_{12}$ antagonists, thromboxane receptor antagonists, and aspirin, or a combination thereof.

In another embodiment, the present invention provides a method for modulation of platelet reactivity comprising administering to a patient in need of such treatment a therapeutically effective amount of at least one of the compounds of the present invention or a a stereoisomer, tautomer, pharmaceutically acceptable salt, solvate, or prodrug thereof.

In another embodiment, the present invention provides a method for treating thromboembolic disorders comprising: administering to a patient in need of such treatment a therapeutically effective amount of at least one of the compounds of the present invention or a a stereoisomer, tautomer, pharmaceutically acceptable salt, solvate, or prodrug thereof.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a method for treating a thromboembolic disorder, wherein the additional therapeutic agent(s) are selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, a combination thereof.

In another embodiment, the present invention provides a method for treating a thromboembolic disorder, wherein the additional therapeutic agent(s) are selected from an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_1$ and $P2Y_{12}$ antagonists, thromboxane receptor antagonists, and aspirin, a combination thereof.

In another embodiment, the present invention provides a method for treating a thromboembolic disorder, wherein the additional therapeutic agent(s) are an anti-platelet agent or a combination thereof.

In another embodiment, the present invention provides a method for treating a thromboembolic disorder, wherein the additional therapeutic agent(s) are the anti-platelet agent(s) clopidogrel and/or aspirin.

In another embodiment, the present invention provides a novel method, comprising: administering a compound of the present invention in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative. In cases wherein there are quarternary carbon atoms on compounds of the present invention, these can be replaced by silicone atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 R', then said group may optionally be substituted with up to three $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_{6-10}$ aryl" or "aromatic residue", is intended to mean an aromatic moiety containing, if specified, the specified number of carbon atoms; for example phenyl or naphthyl. Unless otherwise specified, "aryl", "$C_{6-10}$ aryl" or "aromatic residue" may be unsubstituted or substituted with 0 to 3 groups selected from H, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —SO$_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

As used herein, the term "aromatic heterocyclic system" or "heteroaryl" is intended to mean monocyclic and polycyclic aromatic hydrocarbon that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridinyl, pyrimidinyl, pyrazinyl, pyridazinyl, triazinyl, furanyl, quinolyl, isoquinolyl, thienyl, imidazolyl, thiazolyl, indolyl, pyrryl, oxazolyl, benzofuranyl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydro-benzofuranyl, chromanyl, 1,2,3,4-tetrahydro-quinoxaline, and 1,2,3,4-tetrahydro-quinazoline.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17-th ed., Mack Publishing Company, Easton, Pa., 1985, p. 1418, the disclosure of which is hereby incorporated by reference.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkylbenzyl, 4-methoxybenzyl, indanyl, phthalyl, methoxymethyl, $C_{1-6}$ alkanoyloxy-$C_{1-6}$ alkyl, e.g. acetoxymethyl, pivaloyloxymethyl or propionyloxymethyl, $C_{1-6}$-alkoxycarbonyloxy-$C_{1-6}$-alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit P2Y$_1$. "Therapeutically effective amount" is also intended to include an amount of the combination of compounds claimed that is effective to inhibit P2Y$_1$. The combination of compounds is preferably a synergistic combination. Synergy, as described, for example, by Chou and Talalay, *Adv. Enzyme Regul.* 1984, 22, 27-55, occurs when the effect (in this case, inhibition of P2Y$_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17-th ed., 1985, which is incorporated herein by reference in its entirety.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

| | |
|---|---|
| Me | methyl |
| Et | ethyl |
| MeOH | methanol |
| EtOH | ethanol |
| i-PrOH | isopropanol |
| Ph | phenyl |
| Bn | benzyl |
| t-Bu | tertiary butyl |
| AcOH | acetic acid |
| EtOAc | ethyl acetate |
| 2MeS-ADP | 2 methylthio adenosine diphosphate |
| cDNA | complimentary DNA |
| DBAD | Di-tert-butylazodicarboxylate |
| DEAD | Diethylazodicarboxyalte |
| DIPEA | N,N,-diisopropylethylamine |
| DMEM | Dulbecco's modified Eagle media |
| DMF | dimethyl formamide |
| DMSO | dimethyl sulfoxide |
| DCE | 1,2 dichloroethane |
| DCM | dichloromethane |
| DCC | dicyclohexylcarbodiimide |
| DIC or DIPCDI | diisopropylcarbodiimide |
| DIEA | diethylpropyl amine |
| EDC (or EDC•HCl) or EDCI (or EDCI•HCl) or EDAC | 3-ethyl-3'-(dimethylamino)propyl-carbodiimide hydrochloride (or 1-(3-dimethylaminopropyl)-3-ethylcarbodiimide hydrochloride) |
| EDTA | ethylenediaminetetraacetic acid |
| FBS | Fetal Bovine Serum |
| HEPES | 4-(2-hydroxyethyl)piperaxine-1-ethanesulfonic acid |
| HOBt | 1-Hydroxybenzotriaole hydrate |
| iPr$_2$NEt | N,N,-diisopropylethylamine |
| LDA | Lithium diisopropylamide |
| LiHMDS | Lithium bis(trimethylsilyl amide) |
| MCPBA | meta-chloroperbenzoic acid |
| D-PBS | Dulbecco's Phosphate Buffered Saline |
| Pd/C | palladium on carbon |
| PCy$_3$ | Tricyclohexyl phosphine |
| SCX | Strong Cation Exchanger |
| TBTU | O-Benzotriazol-1-yl-N,N•N',N'-tetra-methyluronium tetrafluoroborate |
| TFA | trifluoroacetic acid |
| THF | tetrahydrofuran |
| TRIS | tris (hydroxymethyl) aminomethane |

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Alternatively, flash chromatography was carried out on an ISCO CombiFlash™ System Sq16x using prepacked SiO$_2$ cartridges eluted with gradients of hexanes and ethyl acetate.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing many alternatives to one skilled in the art is Greene and Wuts (*Protective Groups In Organic Synthesis*, Wiley and Sons, 1991). All references cited herein are hereby incorporated in their entirety herein by reference.

Scheme 1 describes the preparation of compounds of the invention from functionalized intermediates of formula 1.1 wherein X, for example, is a nucleophilic nitrogen or oxygen species. Coupling of intermediates of formula 1.1 with intermediates of formula 1.2 wherein G, for example, is a halide or tosylate can be accomplished thermally by methods known to one skilled in the art of organic synthesis at temperatures between –78° C. and 250° C. in a variety of solvents such as, for example, tetrahydrofuran, ethanol, dichloroethane, dichloromethane, toluene, dimethylformamide or dioxane provides compounds of the invention of formula 1.3. Alternately, coupling of intermediates of formula 1.1 with intermediates of formula 1.2 wherein G, for example, is a halide, tosylate, boronic acid, boronate ester, or trialkylstanane can be accomplished using metal catalyzed couplings known to one skilled in the art of organic synthesis or described herein at temperatures between –78° C. and 250° C. in a variety of solvents such as, for example, tetrahydrofuran, ethanol, dichloroethane, dichloromethane, toluene, dimethylformamide or dioxane provides compounds of the invention of formula 1.3. A variety of examples of such metal catalyzed couplings are provided the following articles and book: Muci, A. R.; Buchwald, S. L. *Top. Curr. Chem.* 2002, 219, 131. and Hartwig, J. F. In Modern Amination Methods; Ricci, A., Ed., Wiley-VCH: Weinheim, Germany, 2000. The metal catalyst is usually palladium or nickel complexed with ligands such as a diphosphine or a ferrocene.

In similar fashion as described above, intermediates of formula 1.4 and formula 1.5 can be coupled to provide compounds of the invention of formula 1.3.

Intermediates of formula 1.1, 1.2, 1.4 and 1.5 are commercially available or can readily be prepared from commercially available materials by methods known to one skilled in the art of organic synthesis or can be prepared from commercially available materials through schemes and examples provided herein.

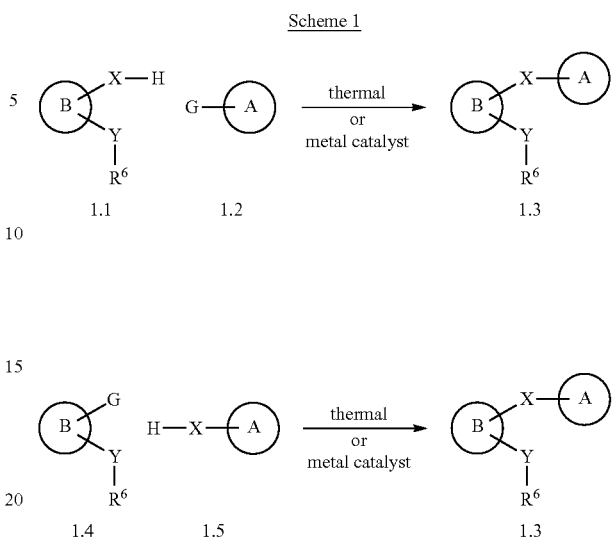

for example G = halide, OTf, B(OH)$_2$, B(O-alkyl)$_2$, Sn(alkyl)$_3$

Scheme 2 describes the preparation of compounds of the invention from functionalized intermediates of formula 2.1 wherein Y, for example, is a nucleophilic nitrogen, sulfur or oxygen species. Coupling of intermediates of formula 2.1 with intermediates of formula 2.2 wherein G, for example, is a halide or tosylate can be accomplished thermally by methods known to one skilled in the art of organic synthesis at temperatures between –78° C. and 250° C. in a variety of solvents such as, for example, tetrahydrofuran, ethanol, dichloroethane, dichloromethane, toluene, dimethylformamide or dioxane provides compounds of the invention of formula 2.3. Alternately, coupling of intermediates of formula 2.1 with intermediates of formula 2.2 wherein G, for example, is a halide, tosylate, boronic acid, boronate ester, or trialkylstanane can be accomplished using metal catalyzed couplings known to one skilled in the art of organic synthesis or described herein at temperatures between –78° C. and 250° C. in a variety of solvents such as, for example, tetrahydrofuran, ethanol, dichloroethane, dichloromethane, toluene, dimethylformamide or dioxane provides compounds of the invention of formula 2.3. A variety of examples of such metal catalyzed couplings are provided the following articles and book: Muci, A. R.; Buchwald, S. L. *Top. Curr. Chem.* 2002, 219, 131. and Hartwig, J. F. In Modern Amination Methods; Ricci, A., Ed., Wiley-VCH: Weinheim, Germany, 2000. The metal catalyst is usually palladium or nickel complexed with ligands such as a diphosphine or a ferrocene.

In similar fashion as described above, intermediates of formula 2.4 and formula 2.5 can be coupled to provide compounds of the invention of formula 2.3. Intermediates of formula 2.1, 2.2, 2.4 and 2.5 are commercially available or can readily be prepared from commercially available materials by methods known to one skilled in the art of organic synthesis or can be prepared from commercially available materials through schemes and examples provided herein.

Scheme 2

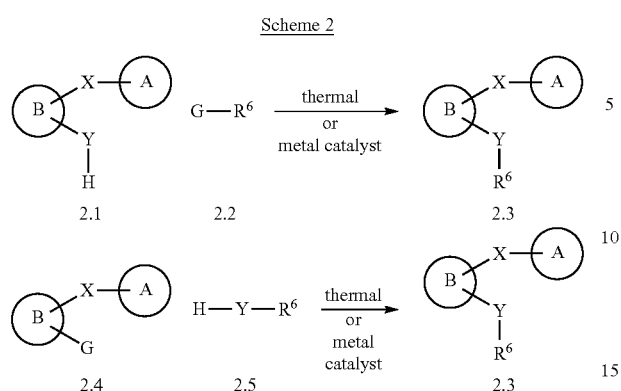

for example G = halide, OTf, B(OH)$_2$, B(O-alkyl)$_2$, Sn(alkyl)$_3$

Scheme 3 describes the preparation of compounds of the invention from functionalized intermediates of formula 3.1 wherein Z is a nitrogen or sulfur. Treatment of intermediate 3.1 with reagents such as, for example, α-haloketones or α-haloaldehydes, or equivalent reagents, in a solvent such as, for example, ethanol with or without a base such as, for example, 2,6-lutidine or NaOAc at temperatures between 0° C. to 110° C. provides compounds of the invention of formula 3.3. (Similar chemistry for Z=sulfur described in: Udapudi, V. T. et al. Indian Journal of Chemistry, Section B: Organic Chemistry Including Medicinal Chemistry 1986, 25B(12), 1269-72. Singh, S. P.; et. al. Indian Journal of Chemistry, Section B: Organic Chemistry Including Medicinal Chemistry 1985, 24B(1), 119-23.)

Scheme 3

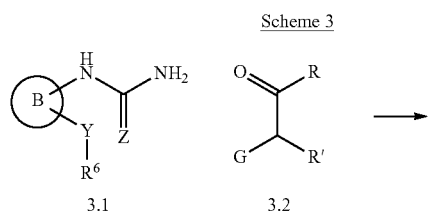

for example Z = S or NH, and G = halide, OTf, OMs

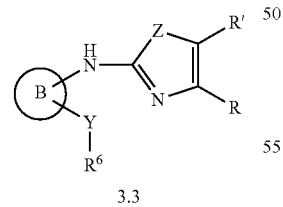

Scheme 4 describes the preparation of compounds of the invention from functionalized intermediates of formula 4.1. Treatment of intermediate 4.1 with reagents such as, for example, α-azidoketones or α-azidoaldehydes, or equivalent reagent, and triphenylphosphine, or equivalent reagent, in a solvents such as, for example, toluene or DMF at temperatures between 0° C. to 150° C. provides compounds of the invention of formula 4.3. α-Azidoketones and α-azidoaldehydes can be prepared by methods known to one skilled in the art of synthetic chemistry from the corresponding commercially available α-haloketones or α-haloaldehydes, or equivalent reagents.

Scheme 4

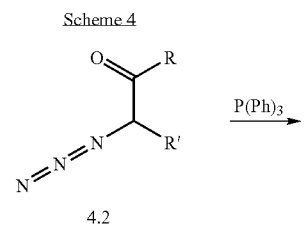

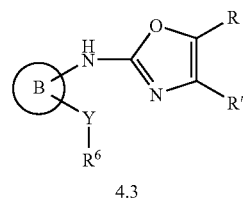

Scheme 5 describes the preparation of compounds of the invention from functionalized intermediates of formula 5.1. Treatment of intermediate 5.1 with amidines of formula 5.2 in a solvent such as, for example, dimethylformamide at temperatures between 70° C. to 120° C. provide intermediates formula 5.3. Treatment of intermediates of formula 5.3 with DEAD (M. Furukawa et al., *Synthesis,* 1990, 1020-1023), or an equivalent reagent, in a solvent such as, for example, ethanol or acetonitrile at temperatures between 0° C. to 70° C. provide compounds of the invention of formula 5.4. Amidines 5.2 are commercially available or can be prepared by methods known to one skilled in the art of synthetic chemistry (such as described in M. Anbazhagan, D. W. Boykin, C. E. Stephens, *Synthesis,* 2003, 2467-2469.)

Scheme 5

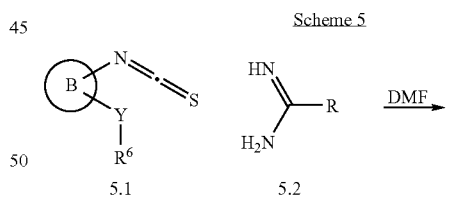

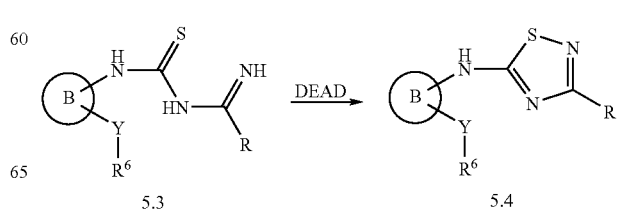

Scheme 6 describes the preparation of compounds of the invention from functionalized intermediates of formula 6.1. Treatment of thioisocyanate intermediate 6.1 with acylhydrazides of formula 6.2 in a solvent such as, for example, dichloromethane at temperatures between 0° C. to 50° C. provide intermediates formula 6.3. Treatment of intermediates of formula 6.3 with an acid such as, for example, neat sulfuric acid or an equivalent reagent, at temperatures between 0° C. to 20° C. provide compounds of the invention of formula 6.4. Acylhydrazides of formula 6.2 are commercially available or can be prepared from carboxylic acids, acyl chlorides or equivalent reagents by methods known to one skilled in the art of synthetic chemistry.

Alternately compounds of the invention of formula 6.4 can be prepared by treatment of intermediate 6.1 with tert-butyl carbazate 6.6, or an equivalent reagent, in a solvent such as, for example, dichloromethane at temperature between 0° C. to 50° C. Subsequent removal of the tert-butoxycarbonyl with an acid such as, for example, TFA in a solvent such as, for example, dichloromethane provides intermediates of formula 6.7. Treatment of intermediates of formula 6.7 with an acyl chloride, or similar suitably activated acylating reagent, in a solvent such as, for example, tetrahydrofuran at temperatures between 0° C. to 50° C. provides intermediates of the formula 6.3. Treatment of intermediates of formula 6.3 with an acid such as, for example, neat sulfuric acid or an equivalent reagent such as trifloroacetic acid, at temperatures between 0° C. to 20° C. provide compounds of the invention of formula 6.4.

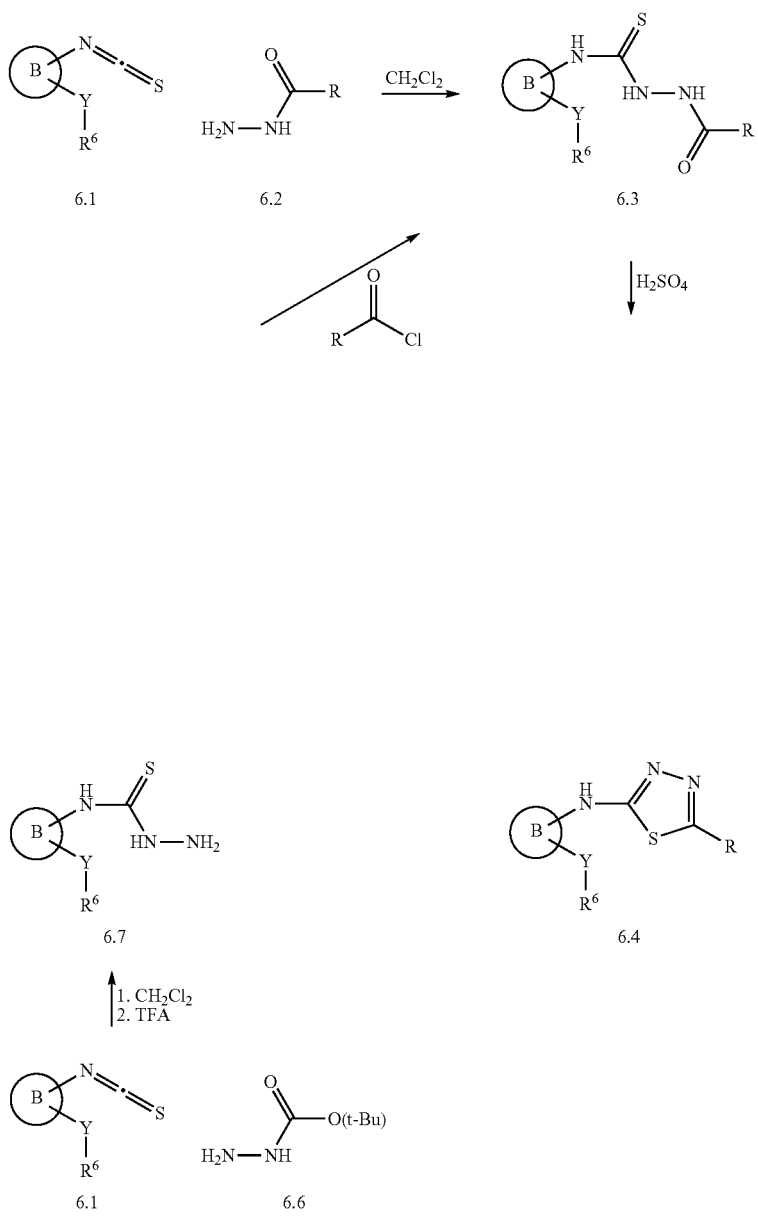

Scheme 6

Scheme 7 describes the preparation of compounds of the invention from functionalized intermediates of formula 7.1. Treatment of isocyanate intermediate 7.1 with acylhydrazides of formula 7.2 in a solvent such as, for example, tetrahydrofuran at temperatures between 20° C. to 65° C. provide intermediates formula 7.3. Treatment of intermediates of formula 7.3 with triphenylphosphine, or an equivalent reagent, in a solvent such as, for example, hexachloroethane, with a base such as, for example, triethylamine, at temperatures between 0° C. to 50° C. provide compounds of the invention of formula 7.4. Acylhydrazides of formula 7.2 are commercially available or can be prepared from carboxylic acids, acyl chlorides or equivalent reagents by methods known to one skilled in the art of synthetic chemistry.

Scheme 8 describes the preparation of compounds of the invention from functionalized intermediates of formula 8.1. Treatment of intermediates of formula 8.1 with acyl isothiocyanates of formula 8.2 in a solvent such as, for example, tetrahydrofuran at temperatures between −78° C. to 70° C. provides intermediates of formula 8.3. Treatment of intermediates of formula 8.4 with a base such as, for example, sodium hydride followed by treatment with an alkylating agent such as, for example, methyliodide in a solvent such as, for example, THF at temperatures between −78° C. to 70° C. provides intermediates of formula 8.4. Treatment of intermediates of formula 8.4 with hydroxylamine in a solvent such as, for example, THF at temperatures between −78° C. to 20° C. provides compounds of the invention of formula 8.5 (T. G. M. Dhar et al. Bioorg. Med. Chem. Lett. 2002, 12, 3125). Acyl-isothiocyanates of formula 8.2 are commercially available or can be prepared from carboxylic acids, acyl chlorides or equivalent reagents by methods known to one skilled in the art of synthetic chemistry.

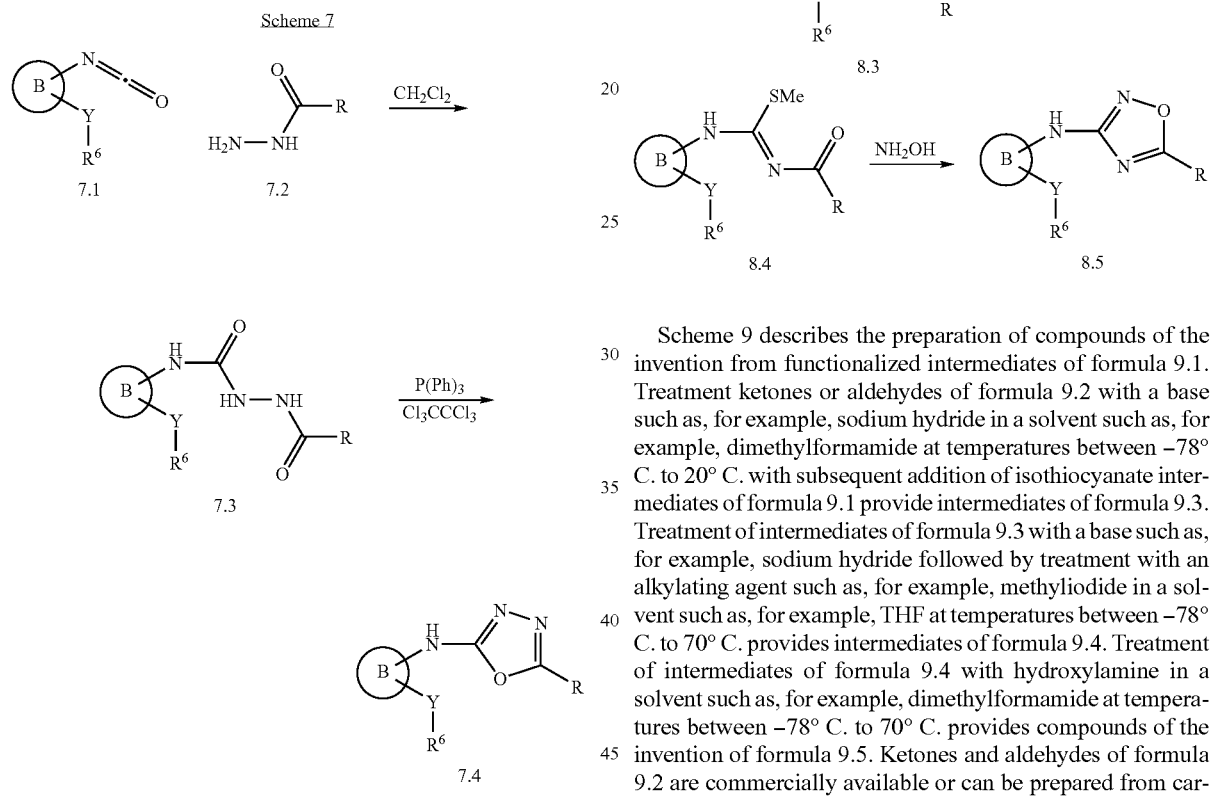

Scheme 9 describes the preparation of compounds of the invention from functionalized intermediates of formula 9.1. Treatment ketones or aldehydes of formula 9.2 with a base such as, for example, sodium hydride in a solvent such as, for example, dimethylformamide at temperatures between −78° C. to 20° C. with subsequent addition of isothiocyanate intermediates of formula 9.1 provide intermediates of formula 9.3. Treatment of intermediates of formula 9.3 with a base such as, for example, sodium hydride followed by treatment with an alkylating agent such as, for example, methyliodide in a solvent such as, for example, THF at temperatures between −78° C. to 70° C. provides intermediates of formula 9.4. Treatment of intermediates of formula 9.4 with hydroxylamine in a solvent such as, for example, dimethylformamide at temperatures between −78° C. to 70° C. provides compounds of the invention of formula 9.5. Ketones and aldehydes of formula 9.2 are commercially available or can be prepared from carboxylic acids, acyl chlorides, alcohols or equivalent reagents by methods known to one skilled in the art of synthetic chemistry.

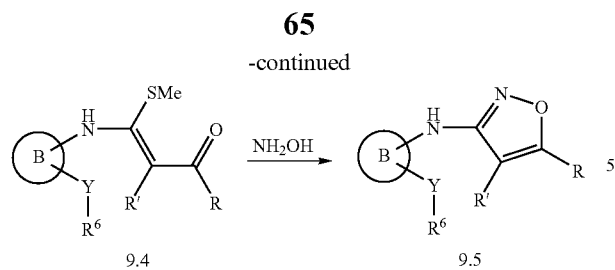

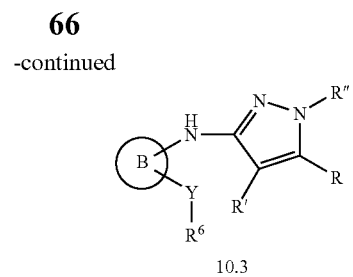

Scheme 10 describes the preparation of additional compounds of the invention from functionalized intermediates of formula 10.1 (intermediate 9.3 as described previously). Treatment of intermediates of formula 10.1 with hydrazine, or an equivalent reagent, in the presence of an acid such as, for example, acetic acid in a solvent such as, for example, ethanol, at temperatures between 20° C. to 70° C. provides compounds of the invention of formula 10.2. Treatment of 10.2 with a base such as, for example, LDA or NaH followed by addition of an alkylating reagent in a solvent such as, for example, tetrahydrofuran, dioxane or dimethylformamide provide compounds of the invention of formula 10.3 and 10.4.

Alternately treatment of intermediate 10.1 with reagents such as, for example, alkyl, aryl or heteroaryl substituted hydrazines in the presence of an acid such as, for example, acetic acid in a solvent such as, for example, ethanol provides compounds of the invention of formula 10.3.

Examples of R or R' side-chains in Schemes 3 to 10 above are given in Scheme 10A below. Form a masked aldehyde or ketone precursor, the conversion to the amines requires either a reductive amination or a SN2 displacement on an activated chloride:

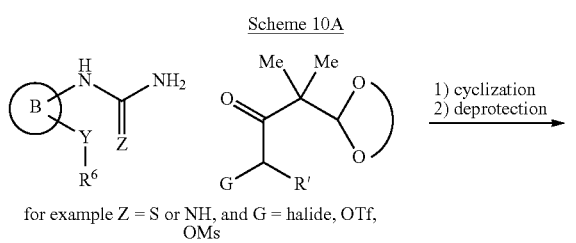

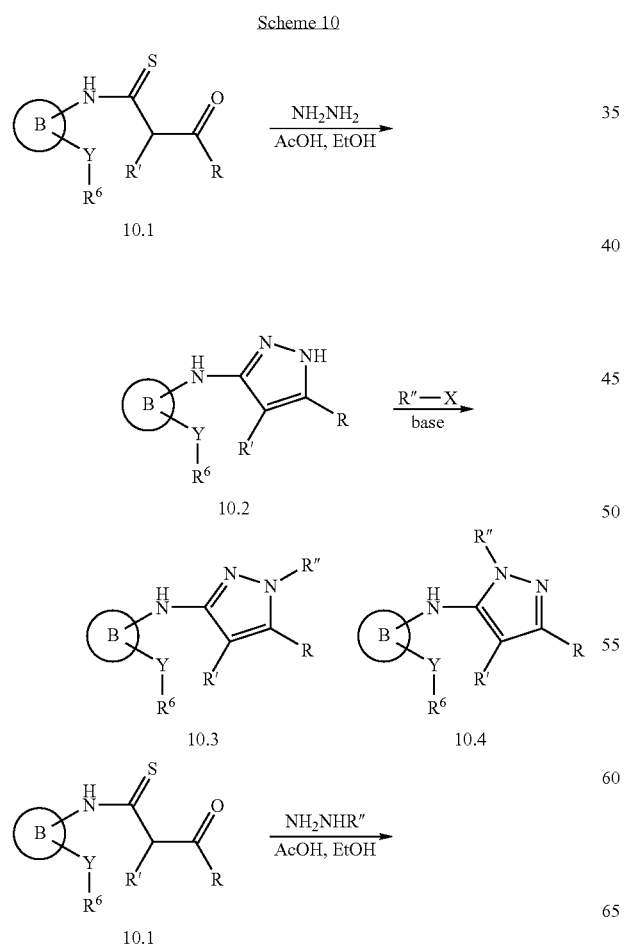

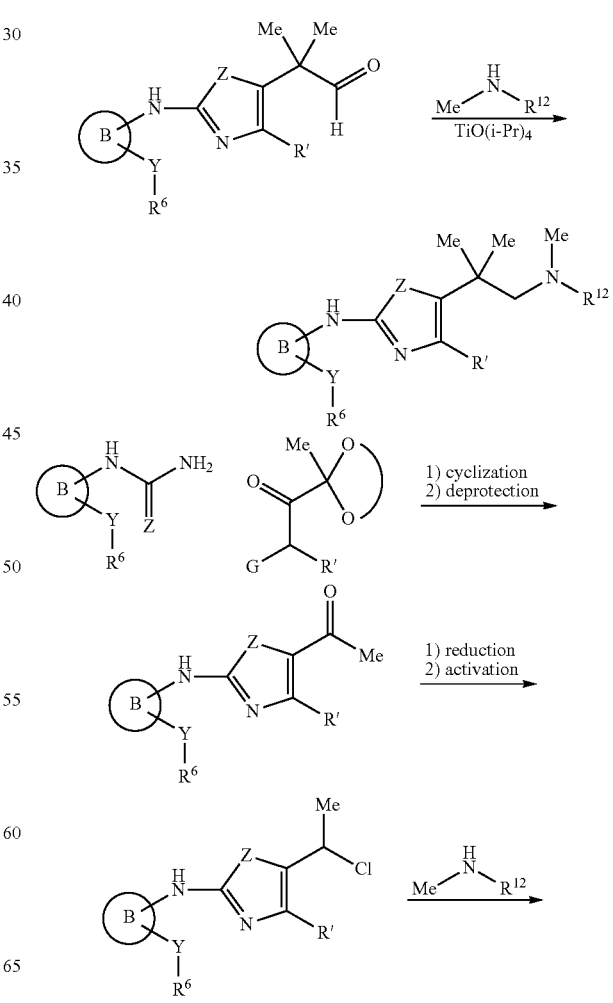

-continued

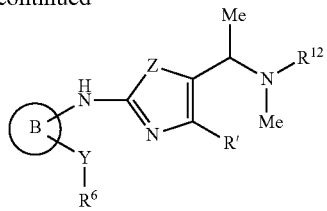

Scheme 11 outlines a preparation of the key isothiocyanate intermediate 11.2. Anilines 11.1 (prepared according to Schemes 5-6), can be treated with a thiophosgene equivalent in an organic solvent such as dichloromethane, dichloroethane or toluene, to produce the corresponding isothiocyanate. Thiophosgene equivalents include thiocarbonic acid O,O-dipyridin-2-yl ester1,1'-thiocarbonyldi-2,2'-pyridone, carbon disulfide, thiocarbonyl-diimidazole, and thiophosgene.

Scheme 11

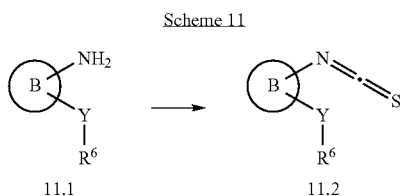

Scheme 12 outlines one possible preparation of amino derivatives 12.4, by aromatic nucleophilic substitution followed by reduction. Nitroaryl derivatives or nitroheteroaryl derivatives 12.1, substituted in the ortho position with a halogen (such as chlorine, fluorine or bromine), are commercially available or can readily be prepared by one skilled in the art of organic synthesis. They can be reacted with nucleophiles such as substituted alcohols, substituted amines, or substituted thiols to provide the corresponding ether, amine or thioether respectively. Typically, a nucleophile and a halonitro derivative are reacted in an organic solvent such as THF, DMF, toluene, dioxane or n-butanol, in presence of a base such as potassium carbonate, cesium carbonate, triethylamine, or DIEA. The temperature of the reaction is usually between room temperature and reflux. Occasionally, microwave irradiation can be used to accelerate the rate of reaction. The diaryl ethers are preferably synthesized by reacting an ortho chloro-nitroaryl derivative with a substituted phenol and cesium carbonate at 80° C. in DMF. The diaryl amines are preferably synthesized by reacting an ortho chloro-nitroaryl derivative with a substituted aniline and triethylamine in butanol at 210° C. using microwave irradiation.

Following aromatic nucleophilic substitution, the resulting nitro derivative 12.3 can be reduced to the corresponding aniline. Typical reducing conditions include hydrogenation in the presence of a metal catalyst such as palladium or platinum. Reduction of 12.3 or analogs may also be accomplished by treatment with reducing agents such as $SnCl_2$, or zinc powder with ammonium chloride. The nascent amine 12.4 can be converted to a halide 12.5 by treatment of 12.4 with a reagent such as, for example, sodium nitrite in the presence of an acid such as, for example, HCl in a solvent such as, for example, water at temperatures between 0° C. to 60° C. Treatment of the halide 12.5 with a reagent such as, for example, n-BuLi in a solvent such as, for example, THF at a temperature between −78° C. to −43° C. followed by treatment with a reagent such as, for example, triisopropyloxyborane leads to the formation of an intermediate aryl or heteroaryl boronic ester which can be converted to the corresponding boronic acid 12.6 with a mild basic aqueous hydrolysis.

All of the following references are incorporated herein by reference. For additional preparations of starting materials and intermediates used herein, see U.S. patent application publications US20050203146 and US2005/0261244, and U.S. application Ser. No. 11/126,915.

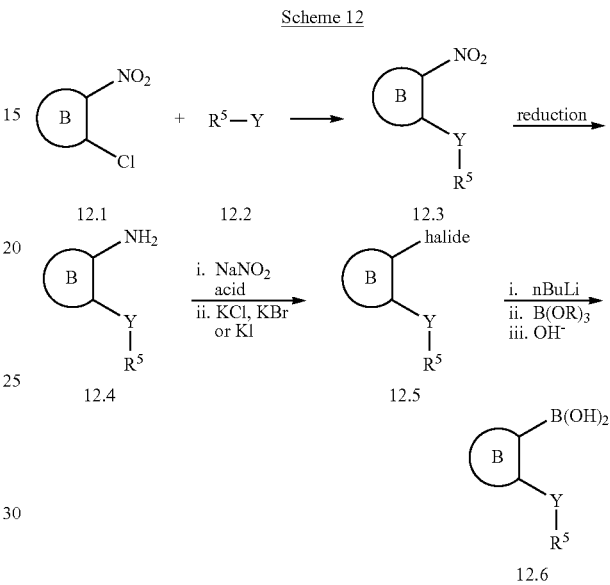

INTERMEDIATES

Intermediate 1

2-(2-tert-Butylphenoxy)-3-aminopyridine

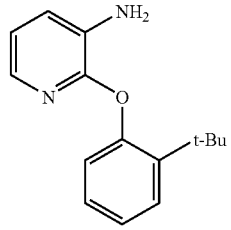

Intermediate 1a. 2-(2-tert-Butylphenoxy)-3-nitropyridine: A solution of 2-chloro-3-nitropyridine (21.1 g, 133 mmol) in DMF (100 mL) was treated with 2-tert-butylphenol (23.5 mL, 153 mmol) and cesium carbonate (130 g, 398 mmol). The mixture was heated at 80° C. for 30 h. The reaction was cooled to rt and the mixture was poured into water (1 L) with stirring. The resulting yellow precipitate was filtered, washed with water, and recrystallized from ethanol to afford Intermediate 1a (32.8 g, 90% yield) as beige crystals; HPLC purity: 92%, 3.66 min (Method A); $^1$H NMR (400 MHz, $CD_3OD$) δ ppm 1.34 (s, 9 H), 6.93 (m, 1 H), 7.22 (m, 3 H), 7.47 (m, 1 H), 8.31 (dd, J=4.82, 1.75 Hz, 1 H), 8.46 (dd, J=7.89, 1.75 Hz, 1 H).

Intermediate 1: Intermediate 1a (7.2 g, 27 mmol) was dissolved in a 1:1 mixture of methanol and ethyl acetate (160 mL). Palladium on charcoal (10%, 360 mg, 0.33 mmol) was added and the mixture was stirred overnight under hydrogen atmosphere (40 psi). The reaction mixture was filtered over Celite® and concentrated to afford Intermediate 1 (7.2 g, 100% yield) as a white powder; HPLC purity: 100%, 2.87 min (Method A); [M+H]$^+$=243.3.

Intermediate 2

2-(3-Isopropylphenoxy)-3-aminopyridine

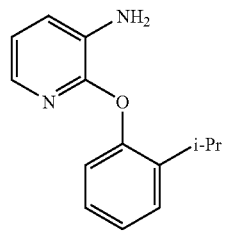

Intermediate 2a. 2-(3-Isopropylphenoxy)-3-nitropyridine: To a solution of meta-isopropylphenol (214 mg, 1.57 mmol) in dry DMF (3 mL) was added cesium carbonate (587 mg, 1.8 mmol) followed by 2-chloro-3-nitropyridine (237 mg, 1.5 mmol). The mixture was heated at 180° C. for 700 s in a Personal Chemistry microwave. The mixture was diluted with water (3 mL) and extracted with ethyl acetate (2×4 mL). The combined organic layers were washed with 5% aqueous LiCl solution (2×1.5 mL), saturated Na$_2$CO$_3$ (2×1.5 mL), water (1×1.5 mL), and then dried over Na$_2$SO$_4$. The solvent was removed in vacuo to yield Intermediate 2a (338 mg, 87% yield) as a dark brown oil; HPLC purity: 90%, 2.89 min (Method B).

Intermediate 2. Intermediate 2a: (338 mg, 1.3 mmol) was dissolved in 1:1 methanol/ethyl acetate (5 mL) and a small spatula of 10% Pd/C was added. The mixture was hydrogenated at 40 psi for 3.5 h. The catalyst was removed by filtering through a pad of Celite®. Solvent removal afforded Intermediate 2 (267 mg, 90% yield) as a brown oil; HPLC purity: 81%, 2.89 min (Method B); [M+H]$^+$=229.52.

Intermediate 3

2-(2-tert-Butylphenoxy)-3-aminothiophene

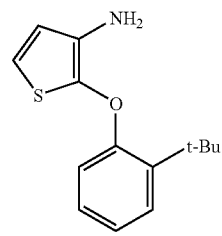

Intermediate 3a. 2-(2-tert-butylphenoxy)-3-nitrothiophene: To a solution of 2-chloro-3-nitrothiophene (1.13 g, 6.93 mmol) in NMP (10 ml) in a pressure vessel was added 2-tert-butylphenol (1.04 g, 6.93 mmol) and K$_2$CO$_3$ (1.0 g, 10.1 mmol). The reaction was flushed with nitrogen, sealed and then heated to 105° C. for 48 h. The reaction was cooled to rt, diluted with EtOAc (~150 mL) and washed twice with saturated aqueous NaCl (2×~150 mL). The aqueous washes were then back extracted with EtOAc. The combined organics were dried over MgSO$_4$, filtered and concentrated.

Intermediate 3: The residue from Intermediate 3a was taken up in THF (50 ml) in a pressure vessel to which was added Raney Ni in water (~300 mg) and a stir bar. The reaction was degassed under mild vacuum and then placed under hydrogen gas (60-65 psi) and then stirred under hydrogen for ~3 h. The reaction vessel was then charged again with hydrogen gas (back to 60-65 psi) and the reaction was stirred overnight. The catalyst was removed by filtration through Celite®, taking care not to allow the cake to dry and the solid catalyst to ignite. The Celite® pad was washed with THF until no UV activity was observed in the eluent. Purification by flash chromatography (110 g ISCO silica cartridge, 0 to 15% EtOAc in hexanes over 40 min., hold at 15% EtOAc in hexanes for 10 min., 50 ml/min) provided Intermediate 3 (2.0 g). (M+H)$^+$=248.3.

Intermediate 4

2-(2-tert-Butylphenoxy)benzenamine

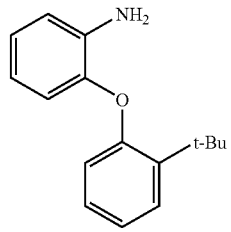

Intermediate 4a. 1-tert-butyl-2-(2-nitrophenoxy)benzene: A mixture of 2-chloronitrobenzene (9.5 g, 60 mmol), 2-t-butyl phenol (9.04 g, 60.2 mmol) and potassium carbonate (10.6 g) in DMF was heated at 130° C. for 6 days. The reaction was cooled to rt and partitioned between diethyl ether (400 mL) and water (500 mL). The organic layer was separated and the aqueous layer was extracted with ether (3×100 mL). The combined organic layers were dried over magnesium sulfate, filtered and evaporated to give Intermediate 4a (20 g). (M+H)$^+$=216.23.

Intermediate 4: To a solution of Intermediate 4a (~20 g, crude) in MeOH/THF (1:1, 200 mL) was added 10% Pd/C (2 g). The mixture was hydrogenated under 75 psi overnight. The mixture was filtered through Celite® cake and the filtrate was evaporated to give the crude product as a black oil. Purification by flash chromatography (0-30% EtOAc/hexane) provided Intermediate 4 (11 g) as a brown solid.

Intermediates 5-9 listed in Table 1 were prepared following the procedures described for Intermediate 1.

TABLE 1

| Intermediate | Structure | (M + H)$^+$ |
|---|---|---|
| 5 | 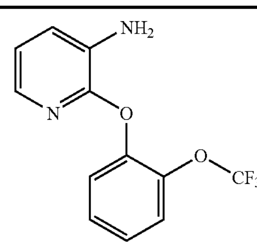 | 271 |

TABLE 1-continued

| Intermediate | Structure | (M + H)+ |
|---|---|---|
| 6 | ![structure] 3-amino-2-(2,2-dimethylbenzo[d][1,3]dioxol-4-yloxy)pyridine | 259 |
| 7 | ![structure] with 2,2-dimethyl-2,3-dihydrobenzofuran | 257 |
| 8 | ![structure] with 2-bromophenoxy | 265 |
| 9 | ![structure] with ethyl 3-phenoxybenzoate | 259 |

Intermediate 10

3,3-spiro-(4-(1-neopentylpiperidine))-1,3-dihydroisobenzofuran-4-ol

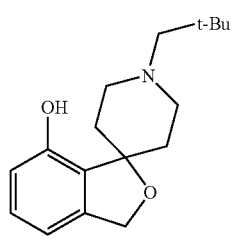

Intermediate 10a. (2-iodo-3-(methoxymethoxy)phenyl)methanol: (3-(Methoxymethoxy)phenyl)methanol (*Tetrahedron*, 2003, 59, 3201-3217) (12 g, 71.4 mmol) in benzene (400 mL) was stirred at 0° C. Butyllithium (1.6 M in hexanes, 89.2 mL, 142.8 mmol) was added and the mixture was warmed to rt and stirred for 2 h. Diiodoethane (20.12 g, 71.4 mmol) in 50 mL of benzene was added and stirring was continued for a period of 2 h. A saturated solution of ammonium chloride was added and the solution was extracted twice using ethyl acetate. The organic phases were combined, dried using $MgSO_4$ and evaporated in vacuo. The crude material was purified using flash chromatography (15 to 40% ethyl acetate/hexanes) to yield the desired material (5.74 g).

Intermediate 10b. 4-(methoxymethoxy)-3,3-spiro-(4-(1-neopentylpiperidine))-1,3-dihydroisobenzofuran: (2-Iodo-3-(methoxymethoxy)phenyl)methanol (2 g, 6.8 mmol) was diluted in THF (40 mL) at rt and isopropylmagnesiumbromide (9.6 mL, 2.12 M/$Et_2O$, 20.4 mmol) was added. The reaction mixture was stirred for 2 h and cooled down to −78° C. 1-Pivaloylpiperidin-4-one (2.5 g, 13.6 mmol) was added and mixture was slowly warmed to rt and stirred for a period of 2 h. Methanesulfonylchloride (1.6 mL, 20.4 mmol) was added and mixture was refluxed for a period of 2 h. The mixture was cooled down, a saturated solution of ammonium chloride was added, and mixture was extracted twice using ethylacetate. The organic phase was dried ($MgSO_4$) and evaporated in vacuo. The crude product was diluted in THF (40 mL) and lithium aluminum hydride (516 mg, 13.6 mmol) was added at rt and stirred for 18 h. Sodium sulfate decahydrate was added and mixture was stirred for 2 h. The reaction mixture was filtered over celite and evaporated in vacuo. The crude product was purified on preparative HPLC to give the desired material (170 mg). $(M+H)^+=320$.

Intermediate 10: 4-(Methoxymethoxy)-3,3-spiro-(4-(1-neopentylpiperidine))-1,3-dihydroisobenzofuran (170 mg, 0.53 mmol) was diluted in $CH_2Cl_2$ (5 mL), cooled at −78° C. Iodotrimethylsilane (145 µL, 1.06 mmol) was added, the reaction mixture was warmed to rt and stirred for a period of 2 h. A 1 M sodium thiosulfate solution was added and organic phase was separated, dried using $MgSO_4$, and evaporated in vacuo. The mixture was directly purified on preparative HPLC to give the desired material (39 mg). $(M+H)^+=276$.

Intermediate 11

3-neopentyl-2,3,4,5-tetrahydro-1H-benzo[d]azepin-6-ol

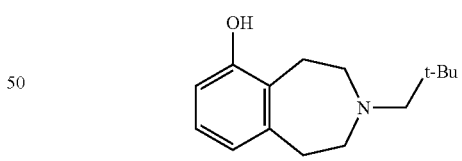

A mixture of 2,3,4,5-tetrahydro-1H-benzo[d]azepin-6-ol (see Demarinis et al. *J. Med. Chem.* 1984, 27, 918-921) (60 mg, 0.37 mmol), trimethylacetaldehyde (400 µL, 3.7 mmol), trimethyl orthoformate (390 µL, 3.7 mmol) and glacial acetic acid (40 µL) in 1-methyl-2-pyrrolidinone (2.5 mL) was stirred at rt for 2.5 h. Sodium triacetoxyborohydride (388 mg, 1.8 mmol) was then added and the mixture was stirred at room temperature for 16 h. The mixture was then loaded on top of a silica gel-SCX (sulfonic acid) column and eluted first with methanol, then with 2 M ammonia in methanol. The latter fraction was evaporated and the resulting 3-neopentyl-2,3,4,5-tetrahydro-1H-benzo[d]azepin-6-ol was used in the next step without further purification. $(M+H)^+=234.0$.

EXAMPLES

The following Examples have been prepared, isolated and characterized using the methods disclosed herein. The following Examples demonstrate a partial scope of the invention and are not meant to be limiting of the scope of the invention.

Example 1

2-(2-tert-Butylphenoxy)-N-(5-phenyl-1,3,4-thiadiazol-2-yl)pyridin-3-amine

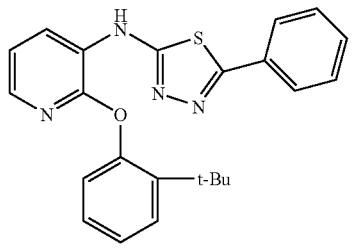

Example 1a 2-(2-tert-Butylphenoxy)-3-isothiocyanatopyridine

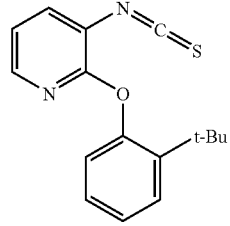

A mixture of 2-(2-tert-Butylphenoxy)-3-aminopyridine (Example 203b) (5.21 g, 21.5 mmol) and 1,1'-thiocarbonyldi-2(1H)-pyridone (5 g, 21.5 mmol) in DCM (100 mL) was stirred at rt for 18 h. The mixture was evaporated and the solid was dissolved in hexanes/DCM (50 mL, 9/1). The residual solid was removed by filtration and the solution was evaporated to provide the title compound as a brown solid. $(M+H)^+ = 285$.

Example 1b 4-(2-(2-tert-Butylphenoxy)pyridin-3-yl)thiosemicarbazide

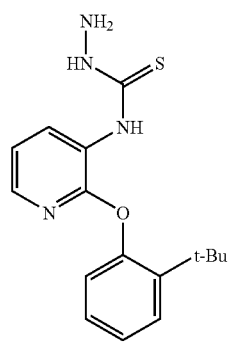

A mixture of Example 1a (1 g, 3.51 mmol) and tert-butyl-carbazate (465 mg, 3.51 mmol) in DCM (10 mL) was stirred at rt for 2 h. Trifluoroacetic acid (2 mL) was added and mixture was stirred for 2 h. The solvent was removed and the residue was dissolved in EtOAc (15 mL), washed with saturated sodium bicarbonate solution, dried (anh. MgSO$_4$), filtered and evaporated to give the title compound (1.32 g) as a brown solid. $(M+H)^+ = 317$.

Example 1

A mixture of Example 1b (100 mg, 0.32 mmol), benzoyl chloride (45 mg, 0.32 mmol) in DCM (2 mL) was stirred at rt for 18 h. Trifluoroacetic acid (2 mL) was then added and mixture was stirred for 6 h. The solvent was removed and residue was purified by preparative HPLC to give the title compound (6 mg, TFA salt) as a white powder. $(M+H)^+ = 403$; $^1$H NMR (400 MHz, DMSO d$_6$) δ ppm 1.30 (s, 9 H), 6.93 (dd, J=7.83, 1.26 Hz, 1 H), 7.10-7.17 (m, 2 H), 7.23 (td, J=7.83, 1.77, 1H), 7.41 (dd, J=8.08, 1.77 Hz, 1 H), 7.48-7.54 (m, 3 H), 7.77 (dd, J=4.80, 1.77 Hz, 1H), 7.84-7.88 (m, 2 H), 8.84 (d, J=9.35 Hz, 1 H), 10.47 (s, 1 H).

Examples 2-55 listed in Table 2 were prepared following the procedure described for Example 1.

TABLE 2

| Example | R$^{1c}$ | (M + H)$^+$ |
|---------|----------|-------------|
| 1 | Ph | 403 |
| 2 | 4-CF$_3$-Ph | 471 |
| 3 | 4-t-Bu-Ph | 459 |
| 4 | 4-Me-Ph | 417 |
| 5 | neopentyl | 397 |
| 6 | 4-OCF$_3$-Ph | 487 |
| 7 | 4-F-Ph | 421 |
| 8 | 4-Ph-Ph | 479 |
| 9 | 3-Cl-Ph | 438 |
| 10 | 3-OCF$_3$-Ph | 487 |
| 11 | naphth-2-yl | 453 |
| 12 | 3-Me-Ph | 417 |
| 13 | 2-Cl-Ph | 438 |
| 14 | cyclohexyl | 409 |
| 15 | pyridin-2-yl | 404 |
| 16 | adamantyl | 461 |
| 17 | 4-CN-Ph | 428 |
| 18 | 4-OMe-Ph | 433 |
| 19 | 1-Me-pyrrol-2-yl | 406 |
| 20 | 3,5-diCl-Ph | 472 |
| 21 | 4-NMe$_2$-Ph | 446 |
| 22 | 2,5-diMe-furan-3-yl | 421 |
| 23 | 2-OMe-Ph | 433 |
| 24 | 4-(4-Bn-piperazin-1-yl)-Ph | 577 |
| 25 | 4-NO$_2$-Ph | 448 |
| 26 | cyclopentyl | 395 |

TABLE 2-continued

[Structure: pyridine with NH-thiadiazole-R^1c, 2-O-(2-t-Bu-phenyl)]

| Example | R^1c | (M + H)^+ |
|---------|------|-----------|
| 27 | thien-2-yl | 409 |
| 28 | 3-NMe₂-Ph | 446 |
| 29 | 3-(4-Bn-piperazin-1-yl)-Ph | 577 |
| 30 | 1-Bn-piperidin-4-yl | 500 |
| 31 | 1-Bn-piperidin-3-yl | 500 |
| 32 | —CH₂OBn | 447 |
| 33 | phenethyl | 431 |
| 34 | 1-Ph-cyclopropyl | 443 |
| 35 | t-Bu | 383 |
| 36 | 4-F-Bn | 435 |
| 37 | cyclobutyl | 381 |
| 38 | 4-NMe₂-Bn | 460 |
| 39 | pyridin-4-yl | 404 |
| 40 | 3-(N-(CHPh₂)-azetidin-3-yl) | 548 |
| 41 | 1-Bn-pyrrolidin-3-yl | 486 |
| 42 | pyridin-3-yl | 404 |
| 43 | —CH₂-thien-2-yl | 423 |
| 44 | 4-OMe-Bn | 447 |
| 45 | i-Pr | 369 |
| 46 | isoxazol-5-yl | 394 |
| 47 | 4-CH₂NMe₂-Ph | 460 |
| 48 | cyclopropyl | 367 |
| 49 | 4-(imidazol-1-yl)-Ph | 469 |
| 50 | 1-Bn-azetidin-3-yl | 472 |
| 51 | 3-CH₂NMe₂-Ph | 460 |
| 52 | 1-(1-Bn-piperidin-4-yl)-piperidin-4-yl | 583 |
| 53 | H | 327 |
| 54 | 2-Ph-piperidin-4-yl | 486 |
| 55 | —CH₂O(CH₂)₂OMe | 415 |
| 93 | —CON(Me)Bn | 474 |
| 96 | —C(Me)₂(CH₂)₂CO₂Me | 455 |
| 97 | —C(Me)₂(CH₂)₂CON(Me)Bn | 544 |
| 98 | —C(Me)₂(CH₂)₂CO(4-Bn-piperazin-1-yl) | 599 |
| 99 | —C(Me)₂CH₂CON(Me)Bn | 530 |
| 100 | —C(Me)₂(CH₂)₃N(Me)Bn | 530 |
| 101 | —C(Me)₂(CH₂)₃(4-Bn-piperazin-1-yl) | 585 |
| 102 | —(CH₂)₃N(Me)(Bn) | 488 |
| 103 | —(CH₂)₃(1,2,3,4-tetrahydroisoquinolin-2-yl) | 500 |
| 104 | —(CH₂)₃-isoindolin-2-yl | 486 |
| 105 | —(CH₂)₃(4-Bn-piperazin-1-yl) | 543 |
| 106 | 1-Bn-4-Me-piperidin-4-yl | 460 |
| 107 | 1-(2-Cl-Bn)-4-Me-piperidin-4-yl | 549 |
| 108 | 1-(2,5-diF-Bn)-4-Me-piperidin-4-yl | 550 |
| 109 | 1-(2,4-diF-Bn)-4-Me-piperidin-4-yl | 550 |
| 110 | 1-(2,6-diF-Bn)-4-Me-piperidin-4-yl | 583 |
| 111 | 1-(CH₂-thien-2-yl)-4-Me-piperidin-4-yl | 520 |
| 112 | 1-(CH₂-cyclohexyl)-4-Me-piperidin-4-yl | 520 |
| 113 | 1-(CH₂-naphth-1-yl)-4-Me-piperidin-4-yl | 564 |
| 114 | 1-(3-CN-Bn)-4-Me-piperidin-4-yl | 539 |
| 115 | 1-(2-CN-Bn)-4-Me-piperidin-4-yl | 539 |
| 116 | 1-(4-CN-Bn)-4-Me-piperidin-4-yl | 539 |
| 117 | 1-(CH₂-thiazol-2-yl)-4-Me-piperidin-4-yl | 521 |
| 118 | 1-(CH₂-furan-3-yl)-4-Me-piperidin-4-yl | 504 |

TABLE 2-continued

[Structure: pyridine with NH-thiadiazole-R^1c, 2-O-(2-t-Bu-phenyl)]

| Example | R^1c | (M + H)^+ |
|---------|------|-----------|
| 119 | trans-4-(NHBn)-cyclohexyl | 514 |
| 120 | 1-neohexyl-4-Me-piperidin-4-yl | 508 |
| 121 | cis-4-(NHBn)-cyclohexyl | 514 |
| 122 | 1-Me-2-Ph-piperidin-4-yl | 500 |
| 123 | 1-(CH₂-pyridin-2-yl)-4-Me-piperidin-4-yl | 515 |
| 124 | 1-(CH₂-pyridin-3-yl)-4-Me-piperidin-4-yl | 515 |
| 125 | 4-(N(Me)Bn)-cyclohexyl | 527.74 |

Example 56

2-(2-tert-Butylphenoxy)-N-(3-phenyl-1,2,4-thiadiazol-5-yl)pyridin-3-amine

[Structure of Example 56 compound]

A mixture of 2-(2-tert-butylphenoxy)-3-isothiocyanatopyridine (Example 1a) (100 mg, 0.35 mmol), diisopropylethylamine (186 μL, 1.05 mmol) and benzamidine hydrochloride (55 mg, 0.35 mmol) in DMF (2 mL) was stirred at rt for 18 h. Diethylazodicarboxylate (110 μL, 0.7 mmol) was added and mixture was stirred for 4 h. The reaction mixture was purified by preparative HPLC to give the title compound (110 mg, TFA salt) as a white solid. (M+H)$^+$=403. $^1$H NMR (400 MHz, DMSO d$_6$) δ ppm 1.31 (s, 9 H), 6.94 (dd, J=7.83, 1.26 Hz, 1 H), 7.16 (dd, J=7.58, 1.26 Hz, 1 H), 7.20-7.27 (m, 2 H), 7.44 (dd, J=8.09, 1.77, 1H), 7.48-7.56 (m, 3 H), 7.79 (dd, J=4.80, 1.51 Hz, 1H), 8.20 (dd, J=7.83, 1.52 Hz, 2 H), 9.04 (dd, J=7.83, 1.52 Hz, 1 H), 10.93 (s, 1 H).

Examples 57-92 listed in Table 3 were prepared following the procedure described for Example 56.

TABLE 3

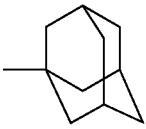

| Example | $R^{1c}$ | $(M + H)^+$ |
|---|---|---|
| 56 | Ph | 403 |
| 57 | t-Bu | 383 |
| 58 | 2,6-diCl-pyridin-4-yl | 473 |
| 59 | 3,5-diCl-Ph | 472 |
| 60 | (1-adamantyl) | 461 |
| 61 | —CH$_2$O(4-t-Bu-Ph) | 489 |
| 62 | 2,6-diCl-Bn | 486 |
| 63 | 3-F-Ph | 421 |
| 64 | 3-CF$_3$-Ph | 471 |
| 65 | CF$_3$ | 395 |
| 66 | i-Pr | 369 |
| 67 | 3-Cl-4-F-Ph | 456 |
| 68 | —CH$_2$O(4-Cl-Ph) | 468 |
| 69 | 4-Cl-Ph | 437 |
| 70 | cyclopropyl | 367 |
| 71 | 3,5-diOMe-Ph | 463 |
| 72 | —CH$_2$OPh | 433 |
| 73 | thien-2-yl | 409 |
| 74 | benzo[b]thien-3-yl | 459 |
| 75 | 2-F-Ph | 421 |
| 76 | —CH$_2$O(2-Cl-Ph) | 468 |
| 77 | furan-3-yl | 393 |
| 78 | 4-CF$_3$-Ph | 471 |
| 79 | 4-Me-Ph | 417 |
| 80 | 3-NO$_2$-Ph | 448 |
| 81 | 4-t-Bu-Ph | 459 |
| 82 | 4-OMe-Ph | 433 |
| 83 | pyridin-4-yl | 404 |
| 84 | pyridin-3-yl | 404 |
| 85 | 3,4-diOMe-Ph | 463 |
| 86 | Me | 341 |
| 87 | 4-SO$_2$Me-Ph | 481 |
| 88 | pyridin-2-yl | 404 |
| 89 | pyrazin-2-yl | 405 |
| 92 | —CH$_2$-1,2,4-triazol-1-yl | 408 |
| 94 | —CH$_2$N(Me)Bn | 460 |
| 95 | —CH$_2$-piperidin-1-yl | 424 |
| 126 | 1-Bn-piperidin-4-yl | 500 |

Example 93

N-Benzyl-5-(2-(2-tert-butylphenoxy)pyridin-3-ylamino)-N-methyl-1,3,4-thiadiazole-2-carboxamide

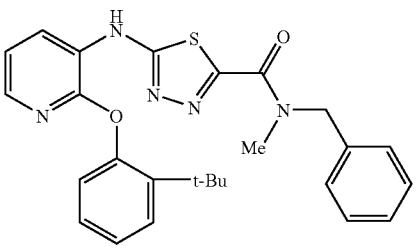

Example 93a 5-(2-(2-tert-Butylphenoxy)pyridin-3-ylamino)-1,3,4-thiadiazole-2-carboxylic acid

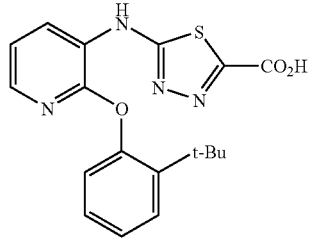

A mixture of 4-(2-(2-tert-butylphenoxy)pyridin-3-yl)thiosemicarbazide (Example 1b) (640 mg, 2.02 mmol) and ethyl chlorooxoacetate (226 μL, 2.02 mmol) in DCM (10 mL) was stirred at rt for 18 h. The mixture was evaporated and the solid was dissolved in sulfuric acid (8 mL) and stirred for 3 h. The reaction mixture was cooled to 0° C. and water (50 mL) was added. The solid formed was isolated by filtration. (M+H)$^+$= 399. The resulting crude solid and lithium hydroxide hydrate (424 mg, 10.1 mmol) were added to THF (10 mL) and water (10 mL) and stirred at rt for 3 h. Saturated ammonium chloride was added and the solution was extracted twice using ethyl acetate. The organic phase was dried (MgSO$_4$), filtered and evaporated to give Example 93a (120 mg) as a brown solid. (M+H)$^+$=327.

Example 93

A mixture of Example 93a (100 mg, 0.27 mmol), TBTU (87 mg, 0.41 mmol) and N-benzylmethylamine (104 μL, 0.81 mmol) in DMF (2 mL) was stirred at rt for 18 h. The reaction mixture was purified by preparative HPLC to give Example 93 (18 mg, TFA salt) as a white powder. (M+H)$^+$=474; $^1$H NMR (400 MHz, DMSO d$_6$) δ ppm 1.30 (s, 9 H), 2.94 (s, 1.5H), 3.41 (s, 1.5H), 4.70 (s, 1H), 5.25 (s, 1H), 6.94 (td, J=7.83, 1.26 Hz, 1 H), 7.09-7.20 (m, 2 H), 7.24 (td, J=7.32, 1.77, 1H), 7.27-7.46 (m, 6H), 7.76 (dd, J=6.07, 1.76 Hz, 1 H), 8.78 (ddd, J=8.09, 7.83, 1.27 Hz, 1H), 10.62 (d, J=4.30 Hz, 1 H).

Example 94

N-(3-((Benzyl(methyl)amino)methyl)-1,2,4-thiadiazol-5-yl)-2-(2-tert-butylphenoxy)pyridin-3-amine

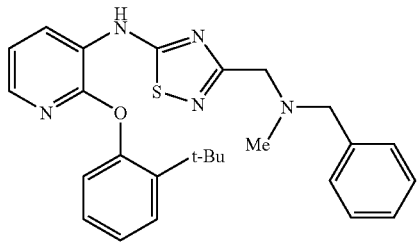

A mixture of N-benzylmethylamine (68 µL, 0.53 mmol), diisopropylethylamine (187 µL, 1.06 mmol) and chloroacetamidine hydrochloride (68 mg, 0.53 mmol) in DMF (5 mL) was stirred at rt for 18 h. 2-(2-tert-butylphenoxy)-3-isothiocyanatopyridine (Example 1a) (150 mg, 0.53 mmol) was then added and mixture was stirred for 3 h at 80° C. The reaction mixture was cooled to rt and diethylazodicarboxylate (168 µL, 1.06 mmol) was added and mixture was stirred for 2 h. The reaction mixture was purified by preparative HPLC to give Example 94 (2 mg, 2TFA salt) as a white. (M+H)⁺=460. ¹H NMR (400 MHz, DMSO d₆) δ ppm 1.30 (s, 9 H), 2.26 (s, 3H), 3.64 (s, 2H), 3.67 (s, 2H), 6.92 (dd, J=7.83, 1.26 Hz, 1H), 7.12-7.39 (m, 9 H), 7.42 (dd, J=7.83, 1.52, 1H), 7.76 (dd, J=5.05, 1.26, 1H), 8.89 (d, J=7.58 Hz, 1H), 10.82 (s, 1 H).

Example 95 listed in Table 3 were prepared following the procedure described for Example 94.

Example 96

Methyl 4-(5-(2-(2-tert-butylphenoxy)pyridin-3-ylamino)-1,3,4-thiadiazol-2-yl)-4-methylpentanoate

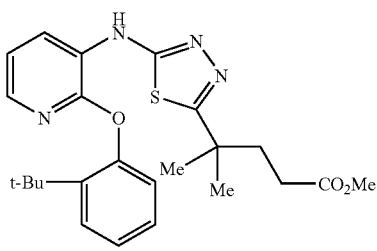

A mixture of 5-methoxy-2,2-dimethyl-5-oxopentanoic acid (500 mg, 2.87 mmol), oxalyl chloride (250 µL, 2.87 mmol) and DMF (1 drop) in DCM (10 mL) was stirred at rt for 2 h. 4-(2-(2-tert-butylphenoxy)pyridin-3-yl)thiosemicarbazide (Example 1b) (908 mg, 2.87 mmol) was added and mixture was stirred for 2 h at 20° C. The reaction mixture was evaporated, diluted in concentrated sulfuric acid and stirred at rt for 2 h. The reaction mixture was cooled to 0° C. and water was added. The solid formed was isolated by filtration, diluted in ethyl acetate and washed with saturated sodium bicarbonate. The organic phase was separated, dried (MgSO₄), filtered and evaporated. The crude material was purified by flash chromatography on silica gel (50% EtOAc/Hexanes) to give Example 96 (600 mg) as a white solid. (M+H)⁺=455. ¹H NMR (400 MHz, DMSO d₆) δ ppm 1.29 (s, 9 H), 1.70-1.85 (m, 3H), 2.05-2.15 (m, 3H), (m, 2H), 3.05-3.20 (m, 2H), 3.60-3.70 (m, 2H), 4.50 (s, 3H), 6.91 (dd, J=7.83, 1.26 Hz, 1 H), 7.17 (t, J=5.81, 2H), 7.24 (td, J=7.58, 1.52, 1H), 7.44 (dd, J=7.83, 1.52, 1H), 7.81 (dd, J=4.80, 1.52, 1H), 8.83 (dd, J=8.08, 1.52 Hz, 1H), 11.06 (s, 1 H).

Example 97

N-Benzyl-4-(5-(2-(2-tert-butylphenoxy)pyridin-3-ylamino)-1,3,4-thiadiazol-2-yl)-N,4-dimethylpentanamide

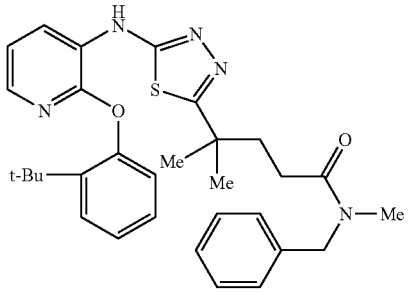

Example 97a 4-(5-(2-(2-tert-Butylphenoxy)pyridin-3-ylamino)-1,3,4-thiadiazol-2-yl)-4-methylpentanoic acid

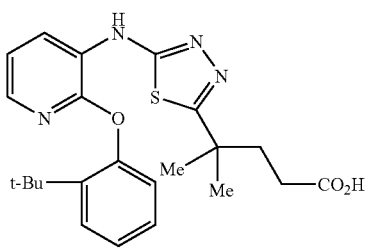

A mixture of methyl 4-(5-(2-(2-tert-butylphenoxy)pyridin-3-ylamino)-1,3,4-thiadiazol-2-yl)-4-methylpentanoate (Example 96) (450 mg, 1.0 mmol), lithium hydroxide hydrate (125 mg, 3 mmol) in THF (10 mL) and water (2 mL) was stirred at rt for 2 h. A solution of saturated ammonium chloride was added and mixture was extracted twice using ethyl acetate. The organic phase was separated, dried (MgSO₄), filtered and evaporated. The crude material was purified by preparative HPLC to give the title compound (430 mg, TFA salt) as a white solid. (M+H)⁺=441.

Example 97

A mixture of Example 97a (175 mg, 0.40 mmol), TBTU (193 mg, 0.6 mmol) and N-benzylmethylamine (52 µL, 0.4 mmol) in DMF (4 mL) was stirred at rt for 2 h. The reaction mixture was purified by preparative HPLC to give Example 97 (40 mg, TFA salt) as a white powder. (M+H)⁺=544; ¹H NMR (400 MHz, DMSO d$_6$) δ ppm 1.29 (s, 9 H), 1.30 (s, 3H), 1.38 (s, 3H), 1.90-2.00 (m, 2H), 2.20-2.35 (m, 2H), 2.85 (s, 3H), 4.46 (s, 2H), 6.90 (dd, J=7.83, 1.52 Hz, 1 H), 7.05-7.35 (m, 7 H), 7.41 (dt, J=7.83, 2.02, 1H), 7.68 (dd, J=4.80, 1.76 Hz, 1 H), 8.76 (t, J=6.32 Hz, 1H), 10.19 (s, 1 H).

Examples 98 and 99 listed in Table 2 were prepared following the procedure described for Example 97.

Example 100

N-(5-(5-(Benzyl(methyl)amino)-2-methylpentan-2-yl)-1,3,4-thiadiazol-2-yl)-2-(2-tert-butylphenoxy)pyridin-3-amine

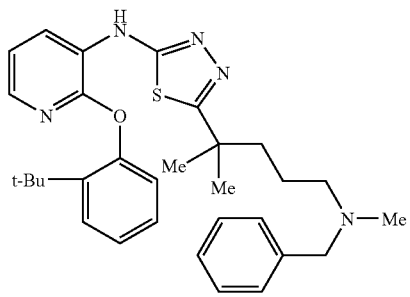

A mixture of N-benzyl-4-(5-(2-(2-tert-butylphenoxy)pyridin-3-ylamino)-1,3,4-thiadiazol-2-yl)-N,4-dimethylpentanamide (Example 97) (38 mg, 0.058 mmol), diisobutyl aluminumhydride (290 μL, 1.0 M/hexanes, 0.29 mmol) in THF (2 mL) was stirred at rt for 2 h. A solution of 1.0 M sodium potassium tartrate was added and mixture was extracted twice using ethyl acetate. The organic phase was separated, dried (MgSO$_4$), filtered and evaporated. The crude material was purified by preparative HPLC to give Example 100 (11 mg, TFA salt) as a white solid. (M+H)$^+$=530. $^1$H NMR (400 MHz, DMSO d$_6$) δ ppm 1.29 (s, 9H), 1.37 (s, 6H), 1.55-1.70 (m, 4H), 2.60-2.70 (m, 2H), 2.95 (m, 1H), 3.06 (m, 1H), 4.20 (dd, J=12.89, 6.06 Hz, 1 H), 4.38 (dd, J=12.38, 3.79 Hz, 1 H), 6.90 (dd, J=6.57, 1.26 Hz, 1H), 7.12 (dd, J=5.05, 8.08 Hz, 1 H), 7.15 (dd, J=7.58, 1.52 Hz, 1 H), 7.21 (dd, J=7.83, 1.77 Hz, 1 H), 7.43 (dd, J=7.83, 1.52 Hz, 1 H), 7.40-7.50 (m, 4H), 7.70 (dd, J=4.80, 1.77, 1H), 8.80 (dd, J=7.83, 1.26 Hz, 1 H), 9.32 (m, 1H), 10.25 (s, 1 H).

Example 101 listed in Table 2 was prepared following the procedure described for Example 100.

Example 102

N-(5-(3-(Benzyl(methyl)amino)propyl)-1,3,4-thiadiazol-2-yl)-2-(2-tert-butylphenoxy)pyridin-3-amine

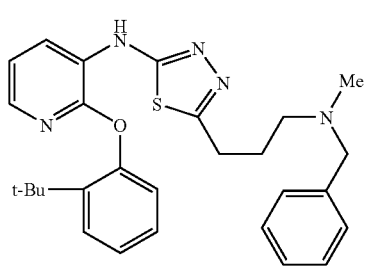

Example 102a

N-(5-(3-Bromopropyl)-1,3,4-thiadiazol-2-yl)-2-(2-tert-butylphenoxy)pyridin-3-amine

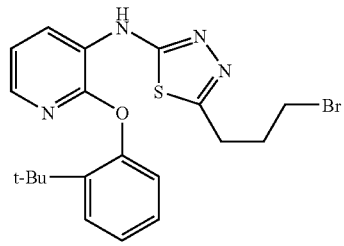

Example 102a was synthesized following the procedure for Example 1 using 4-(2-(2-tert-butylphenoxy)pyridin-3-yl)thiosemicarbazide (Example 1b) with 4-bromobutanoyl chloride.

Example 102

A mixture of Example 102a (100 mg, 0.22 mmol), N-benzylmethylamine (115 μL, 0.89 mmol) in DMF (4 mL) was heated at 120° C. for 5 min in a microwave oven (personal chemistry). The crude material was purified by preparative HPLC to give Example 102 (22 mg, 2 TFA salt) as a white solid. (M+H)$^+$=488. $^1$H NMR (400 MHz, DMSO d$_6$) δ ppm 1.30 (s, 9 H), 2.05-2.25 (m, 2H), 2.70 (d, J=4.80 Hz, 3H), 3.00 (t, J=6.80 Hz, 2H), 3.05-3.30 (m, 2H), 4.24 (dd, J=12.88, 6.32 Hz, 1 H), 4.42 (dd, J=12.38, 4.04 Hz, 1 H), 6.92 (dd, J=9.10, 1.01 Hz, 1 H), 7.12 (dd, J=8.09, 4.80 Hz, 1 H), 7.15 (dd, J=7.83, 6.32 Hz, 1 H), 7.22 (dt, J=7.58, 1.51 Hz, 1 H) 7.40-7.55 (m, 5H), 7.69 (dd, J=4.80, 1.52, 1H), 8.78 (d, J=9.10 Hz, 1 H), 9.54 (m, 1H), 10.25 (s, 1 H).

Examples 103-105 listed in Table 2 were prepared following the procedure described for Example 102.

Example 106

N-(5-(1-Benzyl-4-methylpiperidin-4-yl)-1,3,4-thiadiazol-2-yl)-2-(2-tert-butylphenoxy)pyridin-3-amine

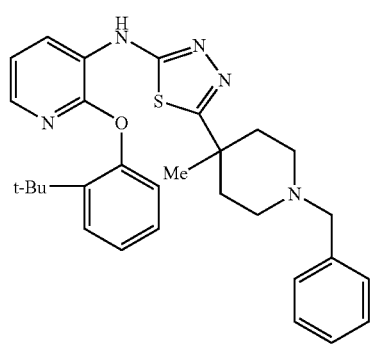

Example 106a 2-(2-tert-Butylphenoxy)-N-(5-(4-methylpiperidin-4-yl)-1,3,4-thiadiazol-2-yl)pyridin-3-amine

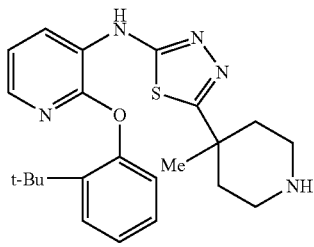

A mixture of 1-(tert-butoxycarbonyl)-4-methylpiperidine-4-carboxylic acid (1.15 g, 4.74 mmol), oxalylchloride (4.13 µL, 4.74 mmol), diisopropylethylamine (1.67 mL, 9.48 mmol) and DMF (1 drop) in DCM (10 mL) was stirred at rt for 30 min. 4-(2-(2-tert-butylphenoxy)pyridin-3-yl)thiosemicarbazide (Example 1b) (1.5 g, 4.74 mmol) was then added and mixture was stirred for 30 min at 20° C. The reaction mixture was evaporated, diluted in concentrated sulfuric acid and stirred at rt for 30 min. The reaction mixture was cooled to 0° C. and water was added. The reaction mixture was diluted in ethyl acetate and washed with saturated sodium bicarbonate. The organic phase was separated, dried (MgSO$_4$), filtered and evaporated. The crude material was purified by preparative HPLC to give Example 106a (350 mg) as a white solid. (M+H)$^+$=424.

Example 106

A mixture of Example 106a (15 mg, 0.35 mmol), benzaldehyde (3.5 µL, 0.35 mmol), acetic acid (50 µL), trimethylorthoformate (0.5 mL), and DMF (0.5 mL) was stirred at rt for 18 h. Sodium borohydride (4 mg, 1.05 mmol) was added and mixture was stirred for 2 h. The reaction mixture was purified by preparative HPLC to give Example 106 (8 mg, 2 TFA salt) as a white. (M+H)$^+$=460. $^1$H NMR (400 MHz, DMSO d$_6$) δ ppm (rotomere mixture) 1.30-1.4 (m, 9 H), 1.85-2.45 (s, 5H), 3.00-3.15 (m, 4H), 3.25-3.40 (m, 4H), 4.30 (d, J=5.30 Hz, 0.6 H), 4.41 (d, J=5.30 Hz, 1.4 H), 6.90 (d, J=7.83 Hz, 1 H), 7.10-7.35 (m, 3 H), 7.40-7.55 (m, 5H), 7.65-7.70 (m, 1H), 7.74 (d, J=8.09, 0.3H), 7.84 (d, J=8.9 Hz, 0.7H), 9.27 (s, 0.7H), 9.36 (s, 0.3H), 10.28 (s, 0.3), 10.41 (s, 0.7 H).

Examples 107-125 listed in Table 2 were prepared following the procedure described for Example 106.

Example 126

N-(3-(1-Benzylpiperidin-4-yl)-1,2,4-thiadiazol-5-yl)-2-(2-tert-butylphenoxy)pyridin-3-amine

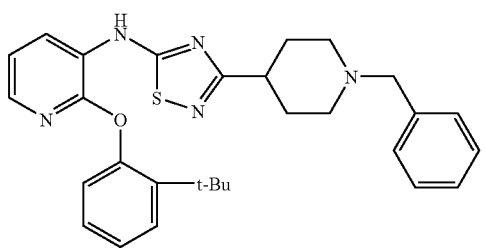

Example 126a

1-Benzylpiperidine-4-carboxamidine

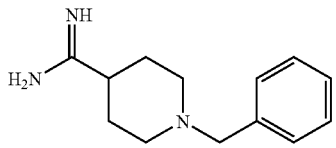

A mixture of ammonium chloride (216 mg, 4.04 mmol), trimethylaluminium (2.02 mL, 2.0M/toluene, 4.04 mmol), in toluene (5 mL) was stirred at rt for 30 min. Ethyl 1-benzylpiperidine-4-carboxylate (500 mg, 2.02 mmol) was added and mixture was stirred for 18 h at 80° C. The reaction mixture was cooled down and 1N sodium potassium tartrate solution was added. The reaction mixture was extracted with ethyl acetate, the organic phase was separated, dried (MgSO$_4$), filtered and evaporated. The crude material was purified by preparative HPLC to give Example 126a (120 mg) as a white solid. (M+H)$^+$=218.

Example 126

A mixture of Example 126a (120 mg, 0.55 mmol), 2-(2-tert-butylphenoxy)-3-isothiocyanatopyridine (Example 1a) (157 mg, 0.55 mmol), in DMF (5 mL) was stirred at rt for 2 h. Diethylazodicarboxylate (87 µL, 0.55 mmol) was added and mixture was stirred for 1 h. The reaction mixture was purified by preparative HPLC to give Example 126 (9 mg, 2 TFA salt) as a white solid. (M+H)$^+$=500. $^1$H NMR (400 MHz, MeOD d$_4$) δ ppm 1.35 (s, 9 H), 2.00-2.50 (m, 5H), 3.10-3.25 (m, 2H), 3.62 (d, J=12.38 Hz, 2H), 6.88 (d, J=9.34 Hz, 1 H), 7.09 (dd, J=8.08, 5.05, 1H), 7.15-7.25 (m, 3 H), 7.45-7.55 (m, 5H), 7.72 (dd, J=5.05, 1.52 Hz, 1H), 8.85 (dd, J=8.08, 1.77 Hz, 1H).

Example 127

2-(2-tert-Butylphenoxy)-N-(5-(4-(trifluoromethyl)phenyl)isoxazol-3-yl)pyridin-3-amine

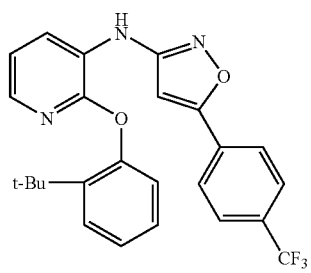

Example 127a (Z)-3-(2-(2-tert-Butylphenoxy)pyridin-3-ylamino)-3-(methylthio)-1-(4-(trifluoromethyl)phenyl)prop-2-en-1-one

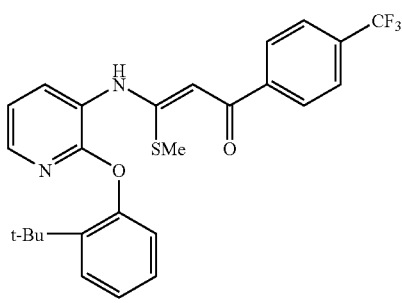

To a solution of 1-(4-(trifluoromethyl)phenyl)ethanone (2 g, 10.63 mmol) in DMF (45 mL) at 0° C. was added portionwise the sodium hydride (60% dispersion in mineral oil, 425 mg, 10.63 mmol). After 30 min, 2-(2-tert-butylphenoxy)-3-isothiocyanatopyridine (Example 1a) (3.02 g, 10.63 mmol) was added and the mixture was allowed to warm to 23° C. After 16 h, iodomethane (0.73 mL, 11.69 mmol) was added and the mixture was stirred for 24 h. Ethyl acetate (100 mL) and water (100 mL) were added and the layers were separated. The organic layer was washed with brine (100 mL), dried over $Na_2SO_4$ and concentrated in vacuo. The crude material was purified by flash chromatography (silica, 10-40% EtOAc/hexane gradient) providing 2.1 g (45%) of Example 127a as an orange solid. $(M+H)^+=487$. $^1H$ NMR (400 MHz, DMSO-$d_6$) δ ppm 13.49 (s, 1H), 8.13 (d, 2H, J=8.1 Hz), 8.02 (t, 1H, J=1.8 Hz), 8.01 (s, 1H), 7.82 (d, 2H, J=8.3 Hz), 7.38 (dd, 1H, J=7.8, 1.5 Hz), 7.25-7.12 (m, 3H), 6.98 (dd, 1H, J=8.1, 1.3 Hz), 6.14 (s, 1H), 2.60 (s, 3H), 1.26 (s, 9H).

Example 127

In a 10 mL resealable tube, hydroxylamine (50% solution in water, 50 µL, 0.823 mmol) and 1 drop of acetic acid were added to Example 127a (100 mg, 0.206 mmol) in ethyl alcohol (1 mL). The tube was sealed with a Teflon® cap and the mixture was heated at 85° C. for 6 h. The residue was purified by preparative HPLC to yield 15 mg (16%, TFA salt) of Example 127. $(M+H)^+=454$. $^1H$ NMR (400 MHz, DMSO-$d_6$) δ ppm 9.91 (s, 1H), 8.06 (d, 2H, J=8.1 Hz), 7.93 (dd, 1H, J=7.9, 1.5 Hz), 7.86 (d, 2H, J=8.3 Hz), 7.77 (dd, 1H, J=4.8, 1.3 Hz), 7.40, (dd, 1H, J=8.1, 1.8 Hz), 7.22, (td, 1H, J=7.5, 1.5 Hz), 7.16-7.11 (m, 2H), 6.94 (dd, 1H, J=8.1, 1.2 Hz), 6.31 (s, 1H), 1.28 (s, 9H).

Examples 128-131 listed in Table 4 were prepared following the procedure described for Example 127.

TABLE 4

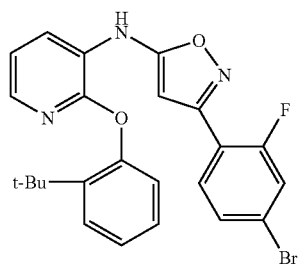

| Example | $R^{1d}$ | $(M + H)^+$ |
|---|---|---|
| 127 | 4-CF$_3$-Ph | 454 |
| 128 | Ph | 386 |
| 129 | pyridin-3-yl | 387 |
| 130 | pyridin-4-yl | 387 |
| 131 | —CH(OMe)$_2$ | 384 |

Example 132

N-(3-(4-Bromo-2-fluorophenyl)isoxazol-5-yl)-2-(2-tert-butylphenoxy)pyridin-3-amine

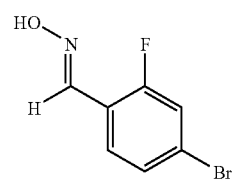

Example 132a (E)-4-Bromo-2-fluorobenzaldehyde oxime

To a solution of 4-bromo-2-fluorobenzaldehyde (6 g, 29.6 mmol) in ethyl alcohol (50 mL) at 23° C. was added hydroxylamine hydrochloride (3.75 M, 9.5 mL, 35.5 mmol) followed by aqueous solution of sodium acetate (1.50 M, 15.8 mL, 23.6 mmol). After 5 h, the reaction mixture was concentrated in vacuo. The residual solid was washed with water (50 mL), filtered, toluene was added and the suspension was concentrated in vacuo affording 5.43 g (84%) of Example 132a as a white solid. $(M+H)^-=217$. $^1H$ NMR (400 MHz, DMSO-$d_6$) δ ppm 11.81 (s, 1H), 8.16 (s, 1H), 7.84 (dd, 1H, J=6.4, 2.5 Hz), 7.65-7.55 (m, 1H), 7.28 (dd, 1H, J=10.1, 9.0 Hz).

Example 132b (Z)-4-Bromo-2-fluorobenzoyl chloride oxime

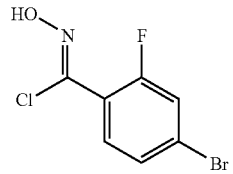

To a solution of Example 132a (5.43 g, 24.9 mmol) in chloroform (62 mL) at 0° C. was added N-chlorosuccinimide (3.66 g, 27.4 mmol) followed by the pyridine (20 μL, 0.24 mmol) and the mixture was allowed to reach 23° C. After 4 h, the reaction mixture poured into a mixture of water and ethyl acetate, layers were separated. The organic layer was washed with water (twice), brine, dried over $Na_2SO_4$ and concentrated in vacuo affording 6.28 g (100%) of Example 132b as a beige solid. $^1$H NMR (400 MHz, DMSO-$d_6$) δ ppm 12.79 (s, 1H), 7.82 (dd, 1H, J=6.3 2.5 Hz), 7.77-7.73 (m, 1H), 7.36 (dd, 1H, J=10.3, 8.9 Hz).

Example 132c 3-(4-Bromo-2-fluorophenyl)-5-chloroisoxazole

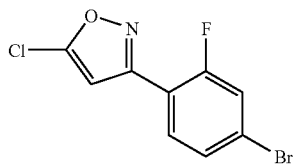

To a solution of Example 132b (6.28 g, 24.9 mmol) in 1,1-dichloroethylene (39 mL) at 23° C. was added dropwise a solution of triethylamine (8.7 mL, 62.2 mmol) in 1,1-dichloroethylene (39 mL). After 4 h, the reaction mixture was poured into a mixture of water and ethyl acetate and the layers were separated. The organic layer was washed with water (twice), dried over $Na_2SO_4$ and concentrated in vacuo. The crude material was purified by flash chromatography (silica gel, 5% EtOAc/hexanes) providing 2.69 g (39%) of Example 132c as a white solid. $^1$H NMR (400 MHz, DMSO-$d_6$) δ ppm 8.02 (dd, 1H, J=6.3, 2.5 Hz), 7.83-7.79 (m, 1H), 7.44 (dd, 1H, J=10.6, 8.8 Hz), 7.26 (d, 1H, J=2.3 Hz).

Example 132

To a solution of 2-(2-tert-Butylphenoxy)-3-aminopyridine (Intermediate 1) (4.38 g, 18.08 mmol) in THF (30 mL) at 0° C. was added dropwise a solution of n-butyllithium (11.3 mL, 18.08 mmol) in hexanes. After 20 min, Example 132c (2.5 g, 9.04 mmol) was added, the mixture was allowed to reach 23° C. and stirred at 23° C. for 60 h. The reaction mixture was quenched with a saturated s solution of ammonium chloride (30 mL) and extracted with ethyl acetate (3×50 mL). The combined organic layers were washed with water (150 mL), brine (150 mL), dried over $Na_2SO_4$ and concentrated in vacuo. The crude material was purified by flash chromatography (silica gel, 10% EtOAc/hexanes) providing 1.97 g (45%) of Example 132. (M+H)$^+$=482. $^1$H NMR (400 MHz, DMSO-$d_6$) δ ppm 9.92 (s, 1H), 8.00 (dd, 1H, J=6.3, 2.5 Hz), 7.92 (dd, 1H, J=7.8, 1.8 Hz), 7.77 (dd, 1H, J=4.8, 1.6 Hz), 7.77-7.72 (m, 1H), 7.42-7.37 (m, 2H), 7.22, (td, 1H, J=7.3, 1.5 Hz), 7.15-7.11 (m, 2H), 6.93 (dd, 1H, J=8.1, 1.3 Hz), 6.10 (s, 1H), 1.28 (s, 9H).

Examples 133-134 listed in Table 5 were prepared following the procedure described for Example 132.

TABLE 5

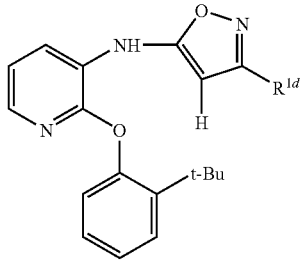

| Example | $R^{1d}$ | (M + H)$^+$ |
|---|---|---|
| 132 | 2-F-4-Br-Ph | 482 |
| 133 | Ph | 386 |
| 134 | 3-CH$_2$OH-Ph | 416 |
| 135 | 2-F-4-(piperidin-1-yl)-Ph | 487 |
| 136 | 2-F-4-(azepan-1-yl)-Ph | 501 |
| 137 | 2-F-4-(pyrrolidin-1-yl)-Ph | 473 |
| 138 | 2-F-4-(2-CH$_2$NMe$_2$-Ph)-Ph | 537 |
| 139 | 2-F-4-(4-Bn-piperazin-1-yl)-Ph | 577 |
| 140 | CO$_2$Et | 382 |
| 141 | 3-NO$_2$-Ph | 431 |
| 142 | 4-SO$_2$Me-Ph | 464 |
| 143 | 2-Cl-Ph | 420 |
| 144 | 2,4-diMe-Ph | 414 |
| 145 | benzo[b]thien-3-yl | 442 |
| 146 | 3-Ph-isoxazol-5-yl | 453 |
| 147 | 3-CN-Ph | 411 |
| 148 | 3-Me-4-Cl-Ph | 434 |
| 149 | 3-NO$_2$-4-Cl-Ph | 465 |
| 150 | naphth-2-yl | 436 |
| 151 | 3,4-diCl-Ph | 455 |
| 152 | 4-NO$_2$-Ph | 431 |
| 153 | 4-CN-Ph | 411 |
| 154 | 4-Ph-Ph | 462 |
| 155 | 3-F-Ph | 404 |
| 156 | 2-F-4-Cl-5-Me-Ph | 452 |
| 157 | 2-F-Ph | 404 |
| 158 | 4-cyclohexyl-Ph | 468 |
| 159 | 3-Ph-5-Me-isoxazol-4-yl | 467 |
| 160 | 5-Ph-thien-2-yl | 468 |
| 161 | 1,3-benzodioxol-4-yl | 430 |
| 162 | 3-CH$_2$N(Me)Bn-Ph | 519 |
| 163 | 3-(CH$_2$-piperidin-1-yl)-Ph | 483 |
| 164 | 3-(CH$_2$-morpholin-4-yl)-Ph | 485 |
| 165 | 3-(CH$_2$-1,2,3,4-tetrahydroisoquinolin-2-yl)-Ph | 531 |
| 166 | 3-(CH$_2$-4-Me-piperazin-1-yl)-Ph | 498 |
| 167 | 3-CH$_2$NMe$_2$-Ph | 443 |
| 168 | 3-(CH$_2$-piperazin-1-yl)-Ph | 484 |
| 169 | CON(Me)Bn | 457 |
| 170 | —CH$_2$N(Me)Bn | 443 |
| 171 | 4-(1H-tetrazol-5-yl)-Ph | 454 |

Example 135

2-(2-tert-Butylphenoxy)-N-(3-(2-fluoro-4-(piperidin-1-yl)phenyl)isoxazol-5-yl)pyridin-3-amine

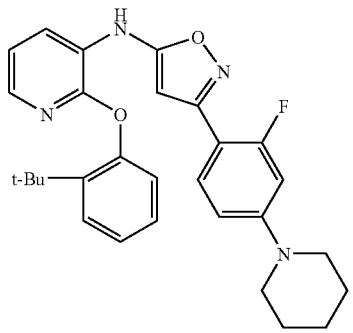

A 15-mL oven-dried resealable flask capped with a rubber septum was evacuated and backfilled with argon. The flask was charged with N-(3-(4-bromo-2-fluorophenyl)isoxazol-5-yl)-2-(2-tert-butylphenoxy)pyridin-3-amine (Example 132) (35 mg, 0.073 mmol), sodium tert-butoxide (10 mg, 0.102 mmol), Pd$_2$(dba)$_3$ (3 mg, 0.003 mmol), (o-biphenyl)PCy$_2$ (2.1 mg, 5.24 mmol) and evacuated and backfilled with Argon. Toluene (0.72 mL) and piperidine (8.6 µL, 0.087 mmol) were added and argon was bubbled through the mixture for 20 min. The septum was replaced with a Teflon® screwcap, the flask was sealed and the mixture was heated at 80° C. for 16 h. The mixture was cooled to rt, filtered through Celite® and concentrated in vacuo. The residue was purified by preparative HPLC to yield 10 mg (30%, TFA salt) of Example 135. (M+H)$^+$=487. $^1$H NMR (400 MHz, DMSO-d$_6$) δ ppm 9.85 (s, 1H), 7.90 (dd, 1H, J=7.8, 1.7 Hz), 7.76 (dd, 1H, J=4.8, 1.5 Hz), 7.40 (dd, 1H, J=8.1, 1.8 Hz), 7.26-7.34 (m, 1H), 7.22, (td, 1H, J=7.6, 1.7 Hz), 7.10-7.16 (m, 3H), 6.93 (dd, 1H, J=8.1, 1.6 Hz), 6.03 (d, 1H, J=3.0 Hz), 3.22 (m, 4H), 1.69 (m, 4H), 1.56 (m, 2H), 1.28 (s, 9H).

Examples 136-139 listed in Table 5 were prepared following the procedure described for Example 135.

Example 140

Ethyl 5-(2-(2-tert-butylphenoxy)pyridin-3-ylamino)isoxazole-3-carboxylate

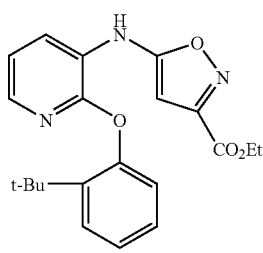

Example 140a 2-(2-tert-Butylphenoxy)-3-isocyanopyridine

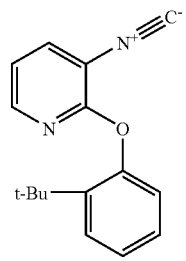

Example 140a was prepared according to the procedure described by Barton et al. (*Tetrahedron*, 1988, 44, 3501-3512) using 2-(2-tert-butylphenoxy)pyridin-3-amine (Intermediate 1) (1 g, 4.12 mmol) affording 696 mg (67%) of the title compound. (M+H)$^+$=253.

Example 140b

Ethyl 3-Bromo-2-(hydroxyimino)propanoate

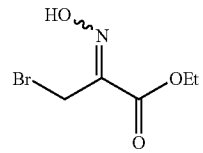

Example 140b was prepared according to the procedure described by Boger et al. in *J. Am. Chem. Soc*, 1991, 113(5), 1713-1729.

Example 140

To a solution of Example 140b (55 mg, 0.26 mmol) in DCM (1.3 mL) was added a solution of Example 140a (1M in DCM, 524 µL, 0.52 mmol) and sodium carbonate (56 mg, 0.52 mmol). The mixture was stirred for 16 h, then filtered and concentrated in vacuo. The residue was purified by preparative HPLC to yield 20 mg (20% TFA salt) of Example 140. (M+H)$^+$=382. $^1$H NMR (400 MHz, DMSO-d$_6$) δ ppm 7.89 (dd, 1H, J=7.8, 1.5 Hz), 7.78 (dd, 1H, J=4.8, 1.5 Hz), 7.39 (dd, 1H, J=8.1, 1.8 Hz), 7.22, (td, 1H, J=7.6, 1.8 Hz), 7.10-7.15 (m, 2H), 6.93 (dd, 1H, J=8.1, 1.6 Hz), 5.92 (d, 1H, J=3.7 Hz), 4.32 (q, 2H, J=7.0 Hz), 1.29 (t, 3H, J=7.3 Hz), 1.26 (s, 9H).

Examples 141-161 listed in Table 5 were prepared following the procedure described for Example 140.

Example 162

N-(3-(3-((Benzyl(methyl)amino)methyl)phenyl)isoxazol-5-yl)-2-(2-tert-butylphenoxy)pyridin-3-amine

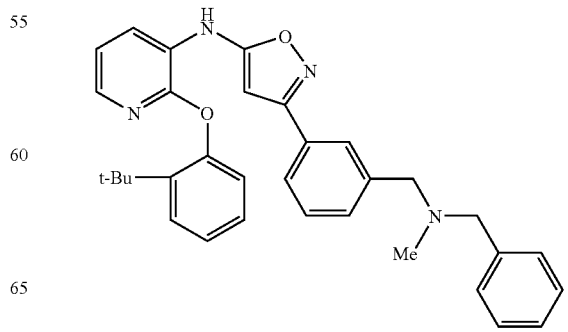

Example 162a 3-(5-(2-(2-tert-Butylphenoxy)pyridin-3-ylamino)isoxazol-3-yl)benzaldehyde

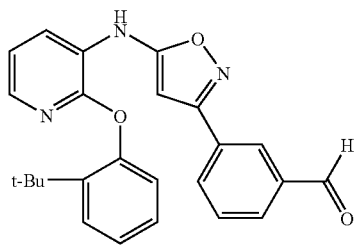

To a solution of (3-(5-(2-(2-tert-butylphenoxy)pyridin-3-ylamino)isoxazol-3-yl)phenyl)methanol (378 mg, 0.91 mmol) in DCM (10 mL) was added Dess-Martin periodinane (424 mg, 1.00 mmol). The mixture was stirred at 23° C. for 15 min, then concentrated in vacuo. Ethyl acetate was added, washed with a saturated aqueous bicarbonate solution, 10% aqueous solution of sodium thiosulfate, water and brine, dried over Na$_2$SO$_4$ and concentrated in vacuo. The crude material was purified by flash chromatography (silica gel, 30-50% EtOAc/hexane gradient) providing 328 mg (87%) of Example 162a. (M+H)$^+$=414.

Example 162

To a solution of Example 162a (20 mg, 0.048 mmol) in DMF (0.5 mL) was added N-methyl(phenyl)methanamine (17 mg, 0.14 mmol), acetic acid (12.5 µL) and trimethylorthoformate (0.5 mL). The reaction mixture was shaken for 16 h then, sodium borohydride (5.5 mg, 0.14 mmol) was added and after 3 h, then a 50% aqueous solution of methanol was added and the mixture was concentrated in vacuo. The residue was purified by preparative HPLC.) to yield 6.6 mg (18% TFA salt) of Example 162. (M+H)$^+$=519.

Examples 163-168 listed in Table 5 were prepared following the procedure described for Example 162.

Example 169

N-Benzyl-5-(2-(2-tert-butylphenoxy)pyridin-3-ylamino)-N-methylisoxazole-3-carboxamide

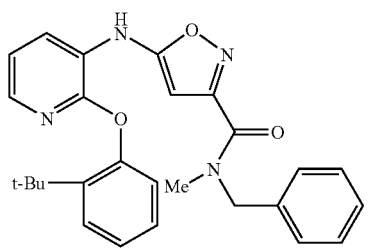

Under Argon atmosphere, in a resealable tube equipped with a septum, a trimethylaluminium solution (2M in toluene, 157 µL, 0.31 mmol) was added to methylbenzylamine (40 µL, 0.31 mmol) in toluene at 0° C. The mixture was allowed to reach r.t. and after 1 h, ethyl 5-(2-(2-tert-butylphenoxy)pyridin-3-ylamino)isoxazole-3-carboxylate (60 mg, 0.16 mmol) was added, the septum was replaced by a Teflon® cap, sealed and heated at reflux for 2 h. The mixture was cooled to r.t, neutralized with 1N HCl solution, extracted with ethyl acetate. The combined organic layers were washed with water, brine, dried over Na$_2$SO$_4$ and concentrated in vacuo. The residue was purified by preparative HPLC to yield 35 mg (48% of the TFA salt) of Example 169. (M+H)$^+$=457. $^1$H NMR (400 MHz, DMSO-d$_6$) δ ppm 9.95 (s, 1H, rotamer A), 9.93 (s, 1H, rotamer B), 7.90-7.85 (m, 2H, rotamers), 7.77-7.75 (m, 2H, rotamers), 7.40-7.19 (m, 12H, rotamers), 7.15-7.07 (m, 4H, rotamers), 6.94-6.91 (m, 2H, rotamers), 5.85 (s, 1H, rotamer A), 5.80 (s, 1H, rotamer B), 4.67 (s, 2H, rotamer A), 4.66 (s, 2H, rotamer B), 3.00 (s, 3H, rotamer B), 2.85 (s, 3H, rotamer A), 1.27 (s, 9H, rotamer A), 1.27 (s, 9H, rotamer B).

Example 170

N-(3-((Benzyl(methyl)amino)methyl)isoxazol-5-yl)-2-(2-tert-butylphenoxy)pyridin-3-amine

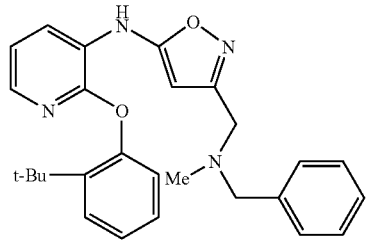

To a solution of N-benzyl-5-(2-(2-tert-butylphenoxy)pyridin-3-ylamino)-N-methylisoxazole-3-carboxamide (Example 169) (18.7 mg of TFA salt, 0.033 mmol) in THF (1 mL) was added lithium aluminium hydride (2 mg, 0.053 mmol) and the mixture was stirred at rt for 16 h. The mixture was quenched with Rochelle's salt solution and extracted with ethyl acetate. Combined organic layers were washed with water, brine, dried over Na$_2$SO$_4$ and concentrated in vacuo. The residue was purified by preparative HPLC to yield 6 mg (41% of the TFA salt) of Example 170. (M+H)$^+$=443. $^1$H NMR (400 MHz, DMSO-d$_6$) δ ppm 10.34 (broad s, 1H, rotamer A), 10.00 (broad s, 1H, rotamer B), 7.88 (dd, 1H, J=7.8, 1.5 Hz), 7.78 (dd, 1H, J=4.8, 1.5 Hz), 7.55-7.45 (broad m, 5H), 7.39 (dd, 1H, J=8.1, 1.8 Hz), 7.22, (td, 1H, J=7.6, 1.8 Hz), 7.16-7.09 (m, 2H), 6.93 (dd, 1H, J=8.1, 1.6 Hz), 5.83 (s, 1H), 4.50-4.25 (broad m, 4H), 2.68 (broad s, 3H), 1.27 (s, 9H).

Example 171

N-(3-(4-(1H-Tetrazol-5-yl)phenyl)isoxazol-5-yl)-2-(2-tert-butylphenoxy)pyridin-3-amine

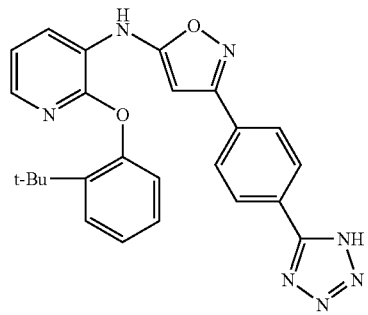

To a solution of 4-(5-(2-(2-tert-butylphenoxy)pyridin-3-ylamino)isoxazol-3-yl)benzonitrile (Example 153) (120 mg, 0.29 mmol) in DMF (1.3 mL) was added sodium azide (21 mg, 0.32 mmol) and ammonium chloride (17 mg, 0.32 mmol) and the mixture was stirred at 100° C. for 4 days. The residue was purified by preparative HPLC to yield 0.92 mg (0.6% of the TFA salt) of Example 171. (M+H)$^+$=454.

Example 172

1-Benzyl-3-(2-(2-tent-butylphenoxy)pyridin-3-ylamino)-1H-pyrazole-5-carbonitrile

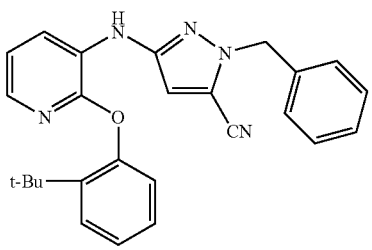

Example 172a 1,1-Dimethoxy-4,4-bis(methylthio)but-3-en-2-one

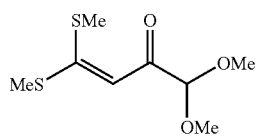

Example 172a was prepared following the procedure described by Mahata et al. in *Tetrahedron*, 2003, 59, 2631-3639.

Example 172b (Z)-4-(2-(2-tert-Butylphenoxy)pyridin-3-ylamino)-1,1-dimethoxy-4-(methylthio)but-3-en-2-one

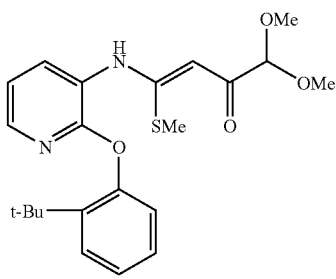

Example 172b was prepared, following the procedure described for Example 132, using 2-(2-tert-butylphenoxy)pyridin-3-amine (Intermediate 1) (4.30 g, 17.8 mmol), Example 172a (3.29 g, 14.8 mmol), n-butyllithium (765 µL, 5.48 mmol) and THF (105 mL) as a tan solid (4.04 g, 66%). (M+H)$^+$=417.

Example 172c 2-(2-tert-Butylphenoxy)-N-(5-(dimethoxymethyl)-1H-pyrazol-3-yl)pyridin-3-amine

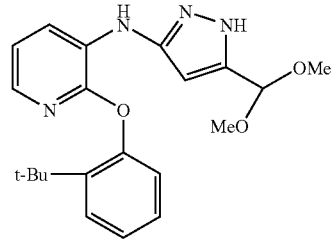

To a solution of Example 172b (2.5 g, 6.0 mmol) in ethanol (12 mL) was added hydrazine hydrate (280 µL, 9.0 mmol). The mixture was heated at reflux for 2 h, allowed to cool down, concentrated in vacuo. Dichloromethane was then added and the mixture was washed with water, dried over Na$_2$SO$_4$ and concentrated in vacuo. The residue was purified by flash chromatography (silica gel, 40% EtOAc/hexanes) to provide 2.07 g (90%) of Example 172c. (M+H)$^+$=383.

Example 172d

N-(1-(4-Methoxybenzyl)-5-(dimethoxymethyl)-1H-pyrazol-3-yl)-2-(2-tert-butylphenoxy)pyridin-3-amine

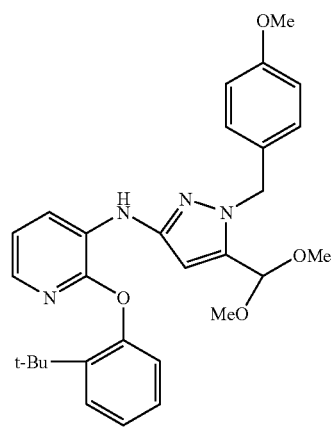

To a solution of Example 172c (1.31 g, 3.42 mmol) in THF (17 mL) was added 4-methoxybenzylalcohol (854 µL, 6.85 mmol), tributylphosphine (1.71 mL, 6.85 mL) and 1,1'-azobisdimethylformamide (1.18 g, 6.85 mmol). The mixture was stirred at 23° C. for 28 h, filtered, washed with THF and the filtrate was concentrated in vacuo. The residue was purified by flash chromatography (silica gel, 25-40% EtOAc/hexanes) to provide 792 mg (46%) of Example 172d. (M+H)⁺=503.

Example 172e 1-(4-Methoxybenzyl)-3-(2-(2-tert-butylphenoxy)pyridin-3-ylamino)-1H-pyrazole-5-carbaldehyde

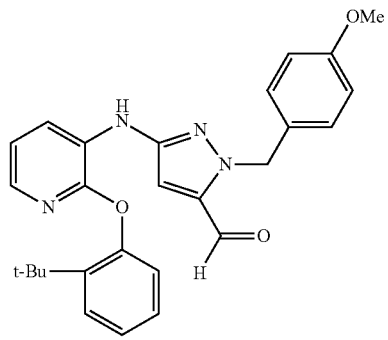

To a solution of Example 172d (782 mg, 1.55 mmol) in THF (8 mL) was added a 50% aqueous solution of acetic acid (20 mL). After 24 h, the mixture was neutralized carefully with an aqueous solution of sodium bicarbonate, extracted with chloroform (3×). The combined organic layers were washed with water, dried over Na₂SO₄ and concentrated in vacuo to give 657 mg (92%) of Example 172e. (M+H)⁺=457.

Example 172f 1-(4-Methoxybenzyl)-3-(2-(2-tert-butylphenoxy)pyridin-3-ylamino)-1H-pyrazole-5-carbaldehyde oxime

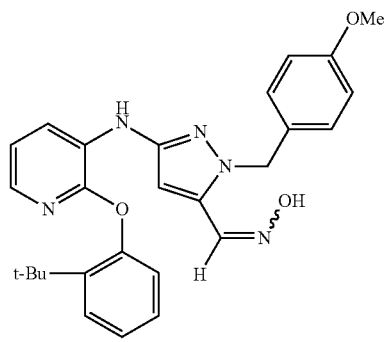

To a solution of Example 172e (492 mg, 1.08 mmol) in ethanol (2.15 mL) was added hydroxylamine hydrochloride (150 mg, 2.16 mmol). The mixture was stirred at 23° C. for 21 h, then concentrated in vacuo, water was added and the separated aqueous layer was extracted with ethyl acetate (3×). The combined organic layers were washed with a saturated aqueous solution of sodium bicarbonate, water, dried over Na₂SO₄ and concentrated in vacuo to afford 500 mg (99%) of Example 172f. (M+H)⁺=472.

Example 172g 1-(4-Methoxybenzyl)-3-(2-(2-tert-butylphenoxy)pyridin-3-ylamino)-1H-pyrazole-5-carbonitrile

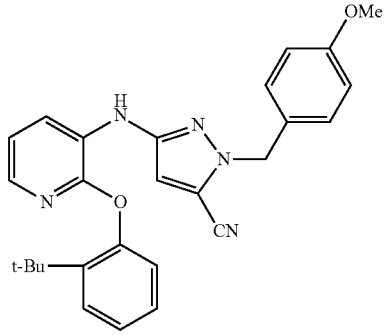

To a solution of Example 172f (500 mg, 1.06 mmol) in diethyl ether (5.3 mL) was added thionyl chloride (155 µL, 2.12 mmol) at 0° C. The mixture was allowed to reach 23° C. and stirred for 2 h, water was added and the separated aqueous layer was extracted with ethyl acetate (3×). The combined organic layers were washed with water, brine, dried over Na₂SO₄ and concentrated in vacuo. The residue was purified by flash chromatography (silica gel, 15-30% EtOAc/hexane) to provide 334 mg (70%) of Example 172g. (M+H)⁺=454.

Example 172h 3-(2-(2-tert-Butylphenoxy)pyridin-3-ylamino)-1H-pyrazole-5-carbonitrile

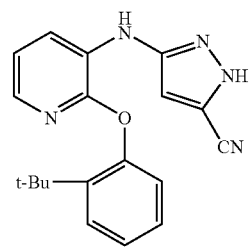

Example 172g (238 mg, 0.52 mmol) was placed in a microwave vessel and trifluoroacetic acid (5 mL) was added. The mixture was heated for 5 min. at 100° C., then cooled to 23° C. and concentrated in vacuo. Ethyl acetate was added, washed with a saturated aqueous solution of sodium bicarbonate, dried over Na₂SO₄ and concentrated in vacuo. The residue was purified by flash chromatography (silica gel, 20% EtOAc/hexanes) to afford 160 mg (93%) of Example 172h. (M+H)⁺=334.

Example 172

To a solution of Example 172h (20 mg, 0.076 mmol) in THF (1 mL) was added benzylalcohol (12 µL, 0.120 mmol), tributylphosphine (30 mL, 0.12 mmol) and 1,1'-azobisdimethylformamide (21 mg, 0.12 mmol). The mixture was stirred at 23° C. for 21 h, filtered, washed with THF and the filtrate was concentrated in vacuo. The residue was purified by preparative HPLC to yield 3 mg (12% TFA salt) of Example 172. (M+H)$^+$=424. $^1$H NMR (400 MHz, DMSO-d$_6$) δ ppm 8.74 (s, 1H), 8.34 (dd, 1H, J=7.8, 1.8 Hz), 7.50 (dd, 1H, J=4.8, 1.5 Hz), 7.41-7.38 (m, 3H), 7.33 (tt, 1H, J=7.3, 2.6 Hz), 7.27 (dd, 2H, J=8.4, 1.6 Hz), 7.21 (td, 1H, J=7.5, 1.5 Hz), 7.13 (td, 1H, J=7.3, 1.5 Hz), 7.00 (dd, 1H, J=7.8, 4.8 Hz), 6.88 (dd, 1H, J=8.1, 1.5 Hz), 6.84 (s, 1H), 1.30 (s, 9H).

Examples 173-188 listed in Table 6 were prepared following the procedure described for Example 172.

TABLE 6

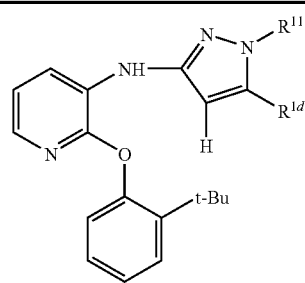

| Example | R$^{11}$ | R$^{1d}$ | (M + H)$^+$ |
|---|---|---|---|
| 172 | Bn | CN | 424 |
| 173 | phenethyl | CN | 438 |
| 174 | —(CH$_2$)$_2$-indol-3-yl | CN | 477 |
| 175 | —(CH$_2$)$_2$-thien-2-yl | CN | 444 |
| 176 | —(CH$_2$)$_2$-pyridin-2-yl | CN | 439 |
| 177 | —(CH$_2$)$_2$-pyridin-4-yl | CN | 439 |
| 178 | —(CH$_2$)$_2$-(4-Me-thiazol-5-yl) | CN | 459 |
| 179 | —(CH$_2$)$_2$SMe | CN | 408 |
| 180 | —(CH$_2$)$_2$OMe | CN | 392 |
| 181 | neohexyl | CN | 418 |
| 182 | —CH$_2$CH=C(Me)$_2$ | CN | 402 |
| 183 | —CH$_2$-cyclopropyl | CN | 388 |
| 184 | n-Bu | CN | 390 |
| 185 | 4-CF$_3$-Bn | CN | 492 |
| 186 | Bn | Ph | 475 |
| 187 | —(CH$_2$)$_3$N(Me)$_2$ | 2-F-Ph | 488 |
| 188 | phenethyl | 2-F-Ph | 507 |
| 189 | Me | Ph | 399 |
| 191 | Me | 2-F-Ph | 417 |
| 192 | Me | 4-CF$_3$-Ph | 467 |
| 194 | H | Ph | 385 |
| 197 | Me | CN | 348 |
| 198 | Et | Ph | 413 |
| 199 | phenethyl | CONMe$_2$ | 484 |
| 202b | Ph | CN | 410 |
| 477 | —CH$_2$-thien-2-yl | CN | 430 |
| 478 | 2-F-6-Cl-Bn | CN | 477 |
| 479 | —CHMe-furan-2-yl | CN | 428 |
| 480 | 2-Cl-Bn | CN | 459 |
| 481 | 2-Cl-4-F-Bn | CN | 477 |
| 482 | 2-Br-Bn | CN | 503 |
| 483 | —CHMe-Ph | CN | 438 |
| 484 | —(CH$_2$)$_2$S(i-Pr) | CN | 436 |
| 485 | —(CH$_2$)$_2$SEt | CN | 422 |
| 486 | —(CH$_2$)$_2$SMe | CN | 422 |
| 487 | 3-Cl-Bn | CN | 459 |
| 488 | 4-SMe-Bn | CN | 470 |
| 489 | 4-Cl-phenethyl | CN | 473 |
| 490 | —(CH$_2$)$_2$O(4-Cl-Ph) | CN | 489 |
| 491 | 3,5-diCl-Bn | CN | 493 |
| 492 | 4-Br-Bn | CN | 503 |
| 493 | —(CH$_2$)$_2$O(CH$_2$)$_2$Cl | CN | 441 |
| 494 | 2-F-4-Br-Bn | CN | 521 |
| 495 | —(CH$_2$)$_2$-thien-3-yl | CN | 444 |

Examples 189 & 190

Example 189

2-(2-tert-butylphenoxy)-N-(1-methyl-5-phenyl-1H-pyrazol-3-yl)pyridin-3-amine

Example 190

2-(2-tert-butylphenoxy)-N-(1-methyl-3-phenyl-1H-pyrazol-5-yl)pyridin-3-amine

Example 189

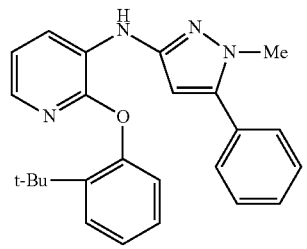

Example 190

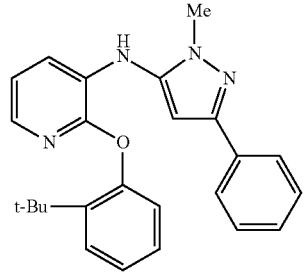

Example 189a

N-(2-(2-tert-Butylphenoxy)pyridin-3-yl)-3-oxo-3-phenylpropanethioamide

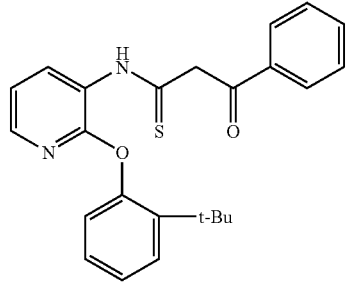

To a solution of acetophenone (123 μL, 1.05 mmol) in THF (4.4 mL) at −78° C. was added the solution of LiHMDS (1M/THF, 1.14 mL, 1.30 mmol). After 30 min, 2-(2-tert-butylphenoxy)-3-isothiocyanatopyridine (Example 1a) (250 mg, 1.00 mmol) was added and the mixture was allowed to reach 23° C. After 17 h, ethyl acetate (100 mL) and an aqueous solution of saturated ammonium chloride (100 mL) were added and the layers were separated. The separated organic layer was washed with water (100 mL), brine (100 mL), dried over Na$_2$SO$_4$ and concentrated in vacuo. The crude material was purified by trituration in mixture of 10% EtOAc/hexanes to provide 180 mg (51%) of Example 189a. (M+H)$^+$=405.

Examples 189 & 190

Examples 189 and 190 were prepared following the procedure described for Example 127 using Example 189a (22.2 mg, 0.06 mmol) and methylhydrazine (12 µL, 0.22 mmol). Example 189 and 190 were separated by preparative HPLC (solvent A: 10% acetonitrile-90% water+0.1% TFA; solvent B: 90% acetonitrile-10% water+0.1% TFA, with 20% B to 100% in 7 min gradient. Column: YMC Pack C-18 20×100 mm. Flow rate=20 mL/min.) to yield 10 mg (35%, TFA salt) of Example 190 and 9 mg (32%, TFA salt) of Example 189. Example 190: (M+H)$^+$=399. $^1$H NMR (400 MHz, DMSO-d$_6$) δ ppm 7.87 (s, 1H), 7.80 (dd, 2H, J=7.1, 1.2 Hz), 7.50 (dd, 1H, J=4.8, 1.5 Hz), 7.42-7.36 (m, 3H), 7.28 (tt, 1H, J=7.3), 7.23, (td, 1H, J=7.3, 1.8 Hz), 7.15-7.11 (m, 2H), 6.96-6.92 (m, 2H), 6.65 (s, 1H), 3.71 (s, 3H), 1.34 (s, 9H). Example 189: (M+H)$^+$= 399. $^1$H NMR (400 MHz, DMSO-d$_6$) δ ppm 8.49 (dd, 1H, J=7.8, 1.5 Hz), 8.23 (s, 1H), 7.54-7.48 (m, 3H), 7.46-7.40 (m, 3H), 7.21 (td, 1H, J=7.6, 1.3 Hz), 7.13 (td, 1H, J=7.9, 1.3 Hz), 6.99 (dd, 1H, J=8.1, 4.8 Hz), 6.89 (dd, 1H, J=8.1, 1.2 Hz), 6.19 (s, 1H), 3.77 (s, 3H), 1.33 (s, 9H).

Examples 191-192 and 194 listed in Table 6 and Examples 193 and 195-196 listed in Table 7 were prepared using the appropriate commercially available substituted benzophenone following the procedures described for Examples 189 and 190.

TABLE 7

| Example | R$^{11}$ | R$^{1d}$ | (M + H)$^+$ |
|---|---|---|---|
| 190 | Me | Ph | 399 |
| 193 | H | 2-F-Ph | |
| 195 | Me | 2-F-Ph | 417 |
| 196 | Me | 4-CF$_3$-Ph | 467 |
| 202a | Ph | CN | 410 |

Example 197

3-(2-(2-tert-Butylphenoxy)pyridin-3-ylamino)-1-methyl-1H-pyrazole-5-carbonitrile

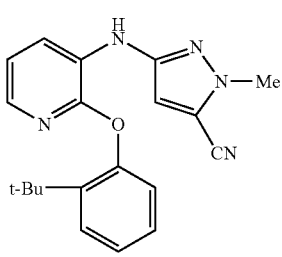

To a solution of 3-(2-(2-tert-butylphenoxy)pyridin-3-ylamino)-1H-pyrazole-5-carbonitrile (Example 172h) (47 mg, 0.141 mmol) in THF (1.4 mL) at 0° C. was added sodium hydride (60%, 5.6 mg, 0.141 mmol). After 5 min, iodomethane (9 µL, 0.141 mmol) was added, the mixture was allowed to reach 23° C. and stirred for 20 h. Saturated NH$_4$Cl was added and the separated aqueous layer was extracted with ethyl acetate (2×). The combined organic layers were washed with water, brine, dried over Na$_2$SO$_4$ and concentrated in vacuo. The residue was purified preparative HPLC to yield 5 mg (10%, TFA salt) of Example 197. (M+H)$^+$=348. $^1$H NMR (400 MHz, DMSO-d$_6$) δ ppm 8.11 (s, 1H), 7.58 (dd, 1H, J=4.8, 1.5 Hz), 7.39 (dd, 1H, J=8.1, 1.5 Hz), 7.24-7.17 (m, 3H), 7.12 (td, 1H, J=7.6, 1.5 Hz), 6.95 (dd, 1H, J=6.4, 4.8 Hz), 6.94 (dd, 1H, J=7.8, 1.3 Hz), 6.82 (s, 1H), 3.77 (s, 3H), 1.30 (s, 9H).

Example 198 listed in Table 6 was prepared following the procedure described for Example 197.

Example 199

3-(2-(2-tert-Butylphenoxy)pyridin-3-ylamino)-N,N-dimethyl-1-phenethyl-1H-pyrazole-5-carboxamide

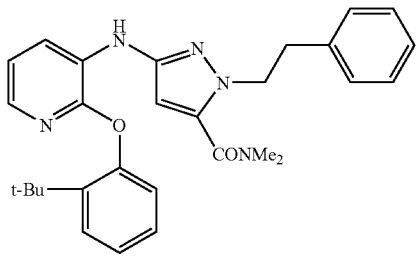

Example 199a 3-(2-(2-tert-Butylphenoxy)pyridin-3-ylamino)-1-phenethyl-1H-pyrazole-5-carboxylic acid

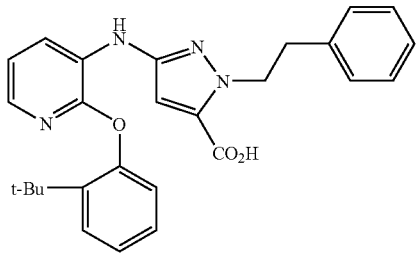

To 3-(2-(2-tert-butylphenoxy)pyridin-3-ylamino)-1-phenethyl-1H-pyrazole-5-carbonitrile (Example 177) (75.6 mg, 0.17 mmol) in methanol (7.2 mL) was added a 1N NaOH solution (2.76 mL, 2.76 mmol) and the mixture was heated at reflux for 5 h. The mixture was concentrated in vacuo, acidified using 1N HCl (until pH=1) then extracted with ethyl acetate (three times). The combined organic layers were washed with water, brine, dried over Na$_2$SO$_4$ and concentrated in vacuo to afford 14.2 mg (18%) of Example 199a. (M+H)$^+$=457.

Example 199

To Example 199a (5.7 mg, 0.012 mmol) in 1 mL of N,N-dimethylformamide, was added 1-ethyl-3-(3-dimethylaminopropyl) carbodiimide (20 mg, 0.104 mmol), 1-hydroxybenzotriazole hydrate (15 mg, 0.104 mmol), N,N-dimethylamine (2M in THF, 52 μL, 0.104 mmol) and Hunig's base (36 μL, 0.208 mmol). The mixture was stirred for 18 h at 23° C. and water (50 mL) was added. The aqueous layer was extracted with ethyl acetate (3×50 mL) and the combined organic layers were washed with an aqueous saturated solution of sodium bicarbonate (50 mL), water (50 mL), brine (50 mL) and dried (anh. Na$_2$SO$_4$), filtered and concentrated in vacuo. The residue was purified preparative HPLC to yield 3 mg (42%, TFA salt) of Example 199. (M+H)$^+$=484. $^1$H NMR (400 MHz, DMSO-d$_6$) δ ppm 8.32 (dd, 1H, J=8.1, 1.8 Hz), 8.29 (s, 1H), 7.45 (dd, 1H, J=4.8, 1.5 Hz), 7.40 (dd, 1H, J=7.8, 1.5 Hz), 7.27-7.17 (m, 5H), 7.14-7.10 (m, 3H), 6.98 (dd, 1H, J=7.8, 4.8 Hz), 6.87 (dd, 1H, J=8.1, 1.5 Hz), 6.12 (s, 1H), 4.39 (t, 2H, J=6.5 Hz), 3.05 (t, 2H, J=6.8 Hz), 2.86 (s, 3H), 2.71 (s, 3H), 1.30 (s, 9H).

Example 202a 2 5-(2-(2-tert-Butylphenoxy)pyridin-3-ylamino)-1-phenyl-1H-pyrazole-3-carbonitrile Example 202b 3-(2-(2-tert-Butylphenoxy)pyridin-3-ylamino)-1-phenyl-1H-pyrazole-5-carbonitrile Example 202a

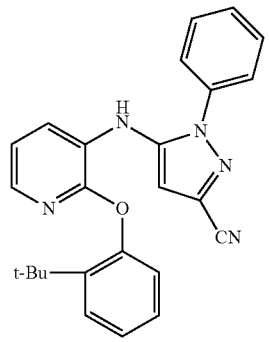

Example 202b

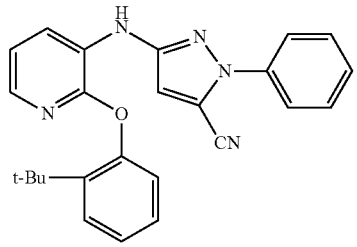

A 15-mL oven-dried re-sealable flask capped with a rubber septum was evacuated and backfilled with argon. The flask was charged with 3-(2-(2-tert-butylphenoxy)pyridin-3-ylamino)-1H-pyrazole-5-carbonitrile (Example 172h) (20 mg, 0.076 mmol), phenyl boronic acid (14.5 mg, 0.120 mmol), Cu(OAc)$_2$ (16.3 mg, 0.089 mmol), pyridine (10 μL, 0.120 mmol) and molecular sieves 4 Å (44 mg) and evacuated and backfilled with Argon. Dichloromethane (1.0 mL) was then added and the septum was replaced with a Teflon® screwcap, the flask was sealed and the mixture was stirred for 15 h. The mixture was filtered through Celite® and concentrated in vacuo. The residue was purified by preparative HPLC (solvent A: 10% acetonitrile-90% water+0.1% TFA; solvent B: 90% acetonitrile-10% water+0.1% TFA, with 20% B to 100% in 7 min. gradient. Column: YMC Pack C-18 20×100 mm. Flow rate=20 mL/min to yield 7.3 mg (14%, TFA salt) of Example 202a and 6.8 mg (14%, TFA salt) of Example 202b. Example 202a: (M+H)$^+$=410. $^1$H NMR (400 MHz, DMSO-d$_6$) δ ppm 8.16 (s, 1H), 7.64 (dd, 2H, J=7.1, 1.5 Hz), 7.51-7.41 (m, 4H), 7.36 (dd, 1H, J=7.8, 1.5 Hz), 7.20 (td, 1H, J=7.6, 1.5 Hz), 7.13-7.06 (m, 2H), 7.06 (s, 1H), 6.87 (dd, 1H, J=7.9, 7.5 Hz), 6.83 (dd, 1H, J=7.8, 1.3 Hz), 1.24 (s, 9H). Example 202b: (M+H)$^+$=410. $^1$H NMR (400 MHz, DMSO-d$_6$) δ ppm 8.98 (s, 1H), 8.49 (dd, 1H, J=7.9, 1.6 Hz) 7.77 (d, 2H, J=7.6 Hz), 7.61 (t, 2H, J=8.4 Hz), 7.55 (dd, 1H, J=4.6, 1.3 Hz), 7.49 (t, 1H, J=7.3 Hz), 7.42 (dd, 1H, J=7.8, 1.5 Hz), 7.23 (td, 1H, J=7.3, 1.5 Hz), 7.14 (td, 1H, J=7.3, 1.2 Hz), 7.12 (s, 1H), 7.04 (dd, 1H, J=7.9, 5.0 Hz), 6.92 (dd, 1H, J=8.1, 1.3 Hz), 1.31 (s, 9H).

Example 203

2-(2-tert-Butylphenoxy)-N-(5-phenyl-1,3,4-oxadiazol-2-yl)pyridin-3-amine

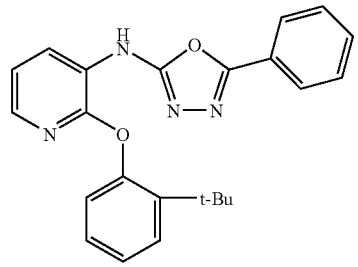

Example 203a 4-(2-(2-tert-Butylphenoxy)pyridin-3-yl)-1-phenylsemicarbazide

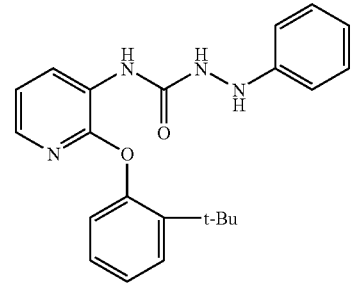

A mixture of 2-(2-tert-butylphenoxy)-3-aminopyridine (Intermediate 1) (358 mg, 1.48 mmol), 1,1-carbonylimidazole (239 mg, 1.48 mmol) and benzoic hydrazide (200 mg, 1.48 mmol) in THF (10 mL) was stirred at room temperature for 72 h. Saturated ammonium chloride (15 mL) was added and the mixture was extracted with ethyl acetate (3×25 mL). The combined organic layers were dried (anhydrous sodium sulfate), filtered and evaporated to yield an oily residue which was purified by reverse phase preparative HPLC to afford Example 203a (75 mg). (M+H)+=405.

Example 203

Hexachloroethane (25 mg, 0.1 mmol) was added to a mixture of Example 203a (34 mg, 0.08 mmol), triphenylphosphine (37 mg, 0.14 mmol) and N,N-diisopropylethylamine (73 μL, 0.42 mmol) in acetonitrile (1 mL) and the mixture was stirred at rt for 1.5 h. The solvent was removed and the residue was dissolved in ethyl acetate, washed with water, dried (anhydrous sodium sulfate), filtered and evaporated. The residue was purified by reverse phase preparative HPLC. (M+H)+=387; mono-TFA salt: $^1$H NMR (400 MHz, DMSO-$d_6$) δ ppm 1.31 (s, 9 H), 6.91 (dd, J=8.0, 1.3 Hz, 1 H), 7.15-7.23 (m, 3 H), 7.42 (dd, J=7.8, 1.8 Hz, 1 H), 7.58 (m, 3 H), 7.81 (dd, J=4.8, 1.5 Hz, 1 H), 7.91 (m, 2 H), 8.50 (dd, J=7.8, 1.5 Hz, 1 H), 10.52 (s, 1 H).

Example 204

2-(2-tert-Butylphenoxy)-N-(5-phenyl-1,2,4-oxadiazol-3-yl)pyridin-3-amine

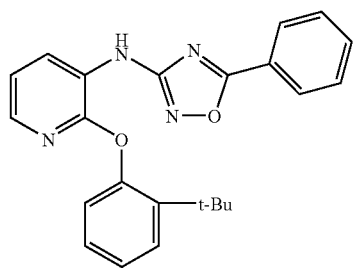

Example 204a

1-Benzoyl-3-[2-(2-tert-butyl-phenoxy)-pyridin-3-yl]-thiourea

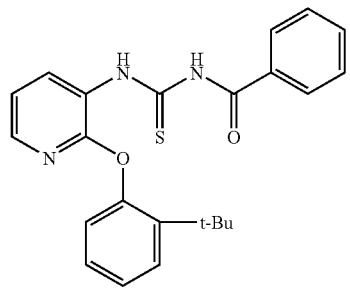

A mixture of 2-(2-tert-Butylphenoxy)-3-aminopyridine (Intermediate 1) (200 mg, 0.82 mmol) and benzoyl isothiocyanate (133 μL, 0.99 mmol, 1.2 eq) in DCM (10 mL) was heated at reflux for 1 h. The mixture was cooled to rt and evaporated to give the crude product. Purification by flash chromatography (silica, 0-50% EtOAc/hexane gradient) provided Example 204a as a white fluffy powder. (M+H)+=406.29.

Example 204

Sodium hydride (16 mg, 60% oil dispersion, 0.39 mmol) was added to a mixture of Example 204a (160 mg, 0.39 mmol) in THF (2.0 mL) and the mixture was stirred at rt for 5 min. Iodomethane (27 μL, 0.44 mmol) was added and the mixture was stirred at rt for 3 h. The solvent was removed and the residue was dissolved in ethanol. Hydroxylamine hydrochloride (27 mg, 0.39 mmol) was added and the mixture was heated at 75° C. for 16 h. The mixture was then allowed to cool and saturated ammonium chloride (30 mL) was added and the mixture was extracted with ethyl acetate (3×25 mL). The combined organic layers were dried (anhydrous sodium sulfate), filtered and evaporated to yield an oily residue which was purified by reverse preparative HPLC. (M+H)+=387; mono-TFA salt: $^1$H NMR (400 MHz, DMSO-$d_6$) δ ppm 1.31 (s, 9 H), 6.90 (dd, J=8.0, 1.3 Hz, 1 H), 7.13-7.22 (m, 3 H), 7.40 (dd, J=7.8, 1.8 Hz, 1 H), 7.63-7.75 (m, 2 H), 7.76 (dd, J=4.8, 1.8 Hz, 1 H), 8.09 (m, 2 H), 8.24 (dd, J=7.8, 1.5 Hz, 1 H), 9.58 (s, 1 H).

Example 208

5-((Benzylmethyl)amino)methyl)-N-(2-(2-tert-butylphenoxy)pyridin-3-yl)pyridine-2-amine

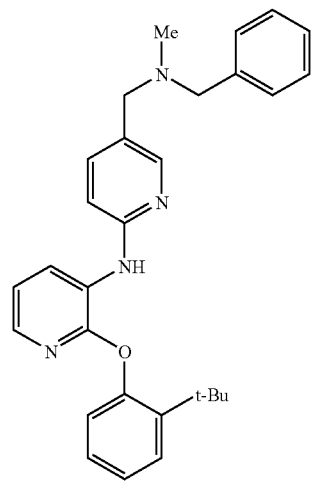

Example 208a

N-((6-Bromopyridin-3-yl)-N-methyl(phenyl)methanamine

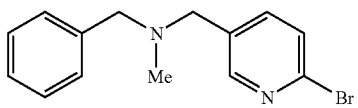

To a solution of 6-bromonicotinaldehyde (930 mg, 5.0 mmol) and N-(6-bromopyridin-3-yl)-N-methyl(phenyl) methanamine (727 mg, 6.0 mmol) in dry THF (10 mL) was added NaBH(OAc)$_3$ (1.59 g, 7.5 mmol) followed by AcOH (300 mg, 5.0 mmol). The reaction was stirred at 25° C. for 16 h and poured into std NaHCO$_3$ aqueous solution. The solution was extracted with AcOEt. The organic phase was dried (MgSO$_4$) and concentrated to give crude product. Purification by flash chromatography (silica gel, 1:1 EtOAc/hexane) provided Example 208a (1.16 g, 80%) as light brown oil.

Example 208b

N-Benzyl-6-chloro-N-methylnicotinamide

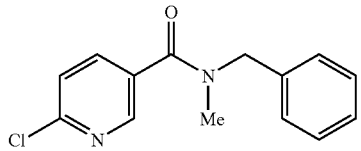

A solution of N-methyl(phenyl)metanamine (424 mg, 3.5 mmol) and Et$_3$N (0.98 mL, 7.0 mmol) in CH$_2$Cl$_2$ (10 mL) was slowly treated with a suspension of 6-chloronicotinoyl chloride (528 mg, 3.0 mmol) in CH$_2$Cl$_2$ (10 mL). The reaction was stirred at 23° C. for 1 h and washed with H$_2$O. The organic phase was dried (MgSO$_4$) and concentrated to give crude material. Purification by flash chromatography (silica, 1:1 EtOAc/hexane) provided Example 208b (450 mg, 32%) as thick colorless oil.

Example 208

To a solution of 2-(2-tert-butylphenoxy)pyridin-3-amine (Intermediate 1) (100 mg, 0.413 mmol) and Example 208a (145 mg, 0.50 mmol) in oxygen-free toluene (2 mL) was added Nolan catalyst (25 mg) followed by sodium tert-butoxyde (39 mg, 0.41 mmol). The reaction was stirred at 85° C. for 20 h and partitioned between H$_2$O and AcOEt. The organic phase was dried (MgSO$_4$) and concentrated to give crude material. Purification by flash chromatography (silica gel, 5-10% CH$_3$CN/CH$_2$Cl$_2$ gradient) provided Example 208 (88 mg, 47%) as a thick oil. (M+H)$^+$=452; $^1$H NMR (400 MHz, DMSO-d$_6$) δ ppm 1.27 (s, 9 H), 2.05 (s, 3 H), 3.41 (s, 2 H), 3.47 (s, 2H), 6.93 (dd, J=7.9, 1.3 Hz, 1H), 7.03 (dd, J=7.9, 5.0 Hz, 1H), 7.11 (s, 2H), 7.13 (s, 2H), 7.16-7.27 (m, 2H), 7.32 (s, 2H), 7.33 (s, 2H), 7.37 (dd, J=7.8, 1.5 Hz, 1 H), 7.57 (dd, J=8.7, 2.3 Hz, 1 H), 7.62 (dd, J=4.8, 1.8 Hz, 1H), 8.07 (d, J=2.0 Hz, 1H), 8.62 (s, 1 H), 8.68 (dd, J=7.9, 1.8 Hz, 1 H).

Examples 209-211 listed in Table 8 were prepared following the procedure described for Example 208.

TABLE 8

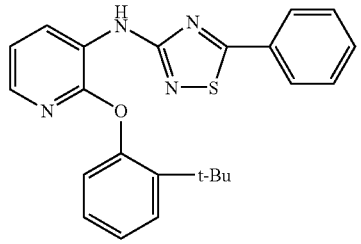

| Example | R$^1$ | (M + H)$^+$ |
|---|---|---|
| 208 | —CH$_2$N(Me)Bn | 387 |
| 209 | —CH$_2$N(Me)(CH$_2$)$_2$Ph | 467 |
| 210 | —CH$_2$-(4-Bn-piperidin-1-yl) | 507 |

TABLE 8-continued

| Example | R$^1$ | (M + H)$^+$ |
|---|---|---|
| 211 | CON(Me)(Bn) | 466 |
| 215 | CO$_2$Me | 378 |

Example 212

2-(2-tert-Butylphenoxy)-N-(5-phenyl-1,2,4-thiadiazol-3-yl)pyridine-3-amine

A solution of 2-(2-tert-butylphenoxy)-3-iodopyridine (Example 206a) (145 mg, 0.413 mmol) and 5-phenyl-1,2,4-thiadiazol-3-amine (88 mg, 0.50 mmol) (F. Kurzer, *J. Chem. Soc.*, 1956, 4524) in oxygen free toluene (2 ml) was treated with tris(dibenzylideneacetone)dipalladium (5.2 mg, 0.0056 mmol), 1,1-bis(diphenylphosphino)-ferrocene (5.0 mg, 0.009 mmol) and sodium tert-butoxyde (40 mg, 0.42 mmol). The reaction was heated at 120° C. for 16 h, cooled at 23° C., diluted with AcOEt and washed with H$_2$O. The organic solution was dried (MgSO$_4$) and concentrated to a crude material. Purification by flash chromatography (silica gel, CH$_2$Cl$_2$) provided Example 212 (138 mg, 83%). (M+H)$^+$=402; $^1$H NMR (400 MHz, CDCl$_3$) δ ppm 1.46 (s, 9 H), 6.97 (dd, J=8.1, 1.5 Hz, 1 H), 7.07 (dd, J=7.9, 5.0 Hz, 1 H), 7.20 (dt, J=7.4, 1.5 Hz, 1 H), 7.26 (dd, J=7.8, 2.0 Hz, 1 H), 7.48-7.61 (m, 4 H), 7.82 (dd, J=6.6, 1.6 Hz, 1 H), 7.94-8.0 (m, 2 H), 8.18 (bs, 1 H), 8.95 (dd, J=8.1, 1.7 Hz, 1 H).

Example 213

N-(2-(2-tert-butylphenoxy)pyridin-3-yl)pyrimidin-4-amine

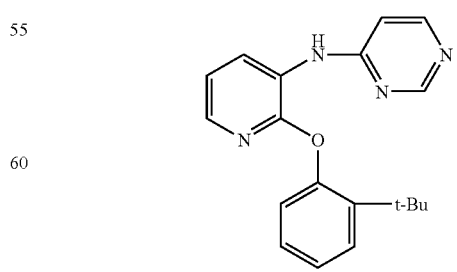

Example 213 was prepared following the procedure described for Example 212.

Example 214

N[3]-(2-(2-tert-Butylphenoxy)pyridin-3-yl)-N[4]-(4-trifluoromethoxy)phenyl)-1,2,5-thiadiazole-5-oxide-3,4-diamine

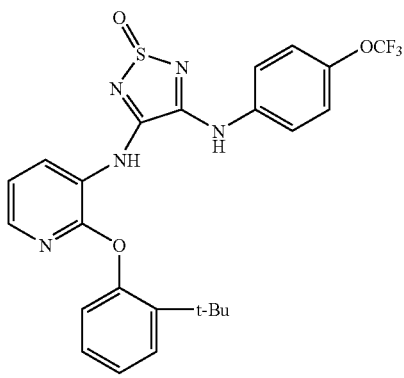

Example 214a

N[3]-((4-Trifluoromethoxy)phenyl)-1,2,5-thiadiazole-S-oxide-3,4-diamine

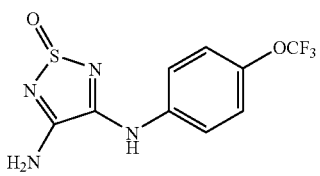

A cold (0° C.) solution of 2-(2-tert-butylphenoxy)pyridin-3-amine (Intermediate 1) (354 mg, 2.0 mmol) in CHCl$_3$ (3 mL) was treated dropwise with Al(CH$_3$)$_3$ (2 M in hexanes, 2.3 mL, 4.6 mmol) and stirred for 3 h. A solution of 1,2,5-thiadiazole-5-oxide-3,4-diamine (486 mg, 3.0 mmol) in CHCl$_3$ (6 mL) was added and the mixture was stirred at (0° C.) for 4 h. The mixture was treated with NH$_4$Cl std solution, diluted with AcOEt, stirred for 1 h and filtered on Celite® pad. The organic phase was separated, dried (MgSO$_4$) and concentrated to a crude material. Purification by flash chromatography (silica, 5 to 10% AcOEt in CH$_2$Cl$_2$) provided Example 214a (265 mg, 43%) as a crystalline material, m.p. 186° C.; (M+H)$^+$=307; $^1$H NMR (400 MHz, CD$_3$OD) δ ppm 4.26 (s, 3 H), 7.34 (d, J=8.4 Hz, 2 H), 7.95-8.05 (m, 2 H).

Example 214

To a cold (0° C.) solution of 2-(2-tert-butylphenoxy)pyridin-3-amine (Intermediate 1) (48.4 mg, 0.20 mmol) in CH$_2$Cl$_2$ (1.5 mL) kept under an argon atmosphere was added dropwise (5 min) Al(CH$_3$)$_3$ (2 M in hexanes, 0.40 mL, 0.80 mmol). The mixture was stirred for 1.5 h, treated with Example 214a (30.7 mg, 0.10 mmol) and stirred at 23° C. for 2 h. Excess of Al(CH$_3$)$_3$ was destroyed by adding NH4Cl std solution. The mixture was diluted with CH$_2$Cl$_2$ (3 mL) and stirred for 0.25 h. The organic phase was separated, dried (MgSO$_4$) and concentrated to a crude material. Purification by preparative HLPC (YMC-Pack ODS-A 100×20 mm I.D. S-5 μm, 12 nm, CH$_3$CN:H$_2$O:NH$_4$OAc (5M)=1.3:3.7:0.01 to 9:1:0.01; flow=20 mL/min; grad. time=7 min) provided Example 214 (10 mg, 19%); (M+H)$^+$=517; $^1$H NMR (400 MHz, CD$_3$OD) δ ppm 1.36 (s, 9 H), 7.06 (dd, J=8.1, 1.3 Hz, 1 H), 7.18-7.25 (m, 2 H), 7.29 (dt, J=7.5, 1.5 Hz, 1 H), 7.37 (d, J=8.6 Hz, 2 H), 7.50 (dd, J=7.9, 1.4 Hz, 2 H), 7.86-7.99 (m, 3 H), 7.94 (dd, J=5.0, 1.6 Hz), 8.65 (m, 1 H).

Example 215

Methyl 6-(2-(2-tert-butylphenoxy)pyridin-3-ylamino)nicotinate

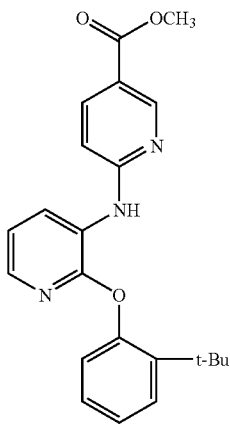

To a solution of 2-(2-tert-butylphenoxy)pyridin-3-amine (Intermediate 1) (100 mg, 0.413 mmol) and methyl 6-chloronicotinate (355 mg, 2.07 mmol) in oxygen-free THF (2 mL) was added Nolan catalyst (10 mg) followed by sodium tert-butoxyde (39 mg, 0.41 mmol). The reaction was stirred at refluxed for 3 h and partitioned between H$_2$O and AcOEt. The organic phase was dried (MgSO$_4$) and concentrated to give crude material. Purification by flash chromatography (silica gel, 15% AcOEt/hexanes the CH$_2$Cl$_2$) provided Example 215 (18 mg, 12%). (M+H)$^+$=378.1817; $^1$H NMR (400 MHz, CDCl$_3$) δ ppm 1.38 (s, 9 H), 3.93 (s, 3 H), 6.75 (d, J=8.0 Hz, 1 H), 6.95 (dd, J=7.9, 1.3 Hz, 1 H), 7.05 (dd, J=8.1, 5.0 Hz, 1 H), 7.16 (dt, J=7.8, 1.5 Hz, 1 H), 7.23 (dd, J=7.9, 1.8 Hz, 1 H), 7.43 (bs, 1 H), 7.46 (dd, J=7.8, 1.8 Hz, 1 H), 7.81 (dd, J=4.8, 1.8 Hz, 1 H), 8.13 (dd, J=8.6, 2.2 Hz, 1 H), 8.80 (dd, J=7.8, 1.8 Hz, 1 H), 8.93 (d, J=1.8, 1 H).

Example 216

N-(2-(2-tert-Butylphenoxy)pyridine-3-yl)pyrazin-2-amine

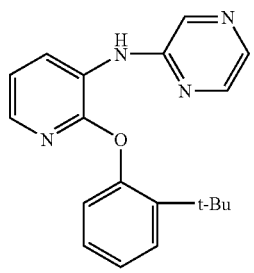

A solution of 2-(2-tert-butylphenoxy)pyridin-3-amine (342 mg, 1.41 mmol) in dry THF (5 mL) was cooled at 0° C. and treated successively with n-BuLi (1.6M, 0.89 mL, 1.42 mmol) and chloropyrazine (90 mg, 0.79 mmol). After stirring at 23° C. for 24 h, the reaction was diluted with AcOEt. The organic solution was washed with H₂O, dried (MgSO₄) and concentrated to give crude material. Purification by flash chromatography (silica, CH₂Cl₂) provided Example 216 (40 mg, 16%) as a yellow foam. (M+H)⁺=320; ¹H NMR (400 MHz, CDCl₃) δ ppm 1.43 (s, 9 H), 7.00 (dd, J=7.8, 1.3 Hz, 1 H), 7.04 (dd, J=8.1, 5.0 Hz, 1 H), 7.37 (dt, J=7.3, 1.3 Hz, 1 H), 7.25 (dd, J=7.9, 1.8 Hz, 1 H), 7.29 (bs, 1 H), 7.50 (dd, J=8.1, 1.8 Hz, 1H), 7.82 (dd, J=5.1, 1.8 Hz, 1 H), 8.11 (bs, 1 H), 8.24 (bs, 1 H), 8.84 (dd, J=8.1, 1.8 Hz, 1 H).

Example 217

[2-(2-tert-Butyl-phenoxy)-pyridin-3-yl]-(4-phenyl-thiazol-2-yl)-amine

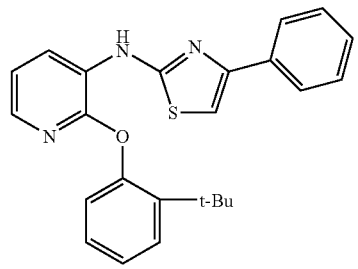

Example 217a

1-Benzoyl-3-[2-(2-tert-butyl-phenoxy)-pyridin-3-yl]-thiourea

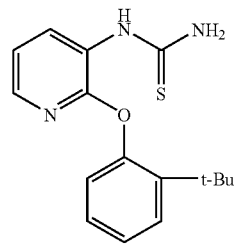

A mixture of 2-(2-tert-Butylphenoxy)-3-aminopyridine (200 mg, 0.82 mmol) and benzoyl isothiocyanate (133 μL, 0.99 mmol, 1.2 eq) in DCM (10 mL) was heated at reflux for 1 h. The mixture was cooled to rt and evaporated to give the crude product. Purification by flash chromatography (silica, 0-50% EtOAc/hexane gradient) provided Example 217a as a white fluffy powder. (M+H)⁺=406.29.

Example 217b

[2-(2-tent-Butyl-phenoxy)-pyridin-3-yl]-thiourea

A mixture of Example 217a (100 mg, 0.24 mmol) and 2 N LiOH solution (240 μL, 0.48 mmol, 2 eq) in a 1:1 mixture of MeOH and THF (2 mL) was stirred at 50° C. for 1 h. The solvent was removed. The residue was dissolved in EtOAc (15 mL), washed with water and brine, dried (MgSO₄), filtered and evaporated to give the crude product. Purification by flash chromatography (0-50% EtOAc/hexane) gave Example 217b (62 mg) as a white solid. (M+H)⁺=302.25.

Example 217

A mixture of Example 217b (13 mg, 0.043 mmol), 2-bromoacetophenone (9 mg, 0.045 mmol) in ethanol (1.5 ml) was heated at 100° C. for 1 h. The solvent was removed and residue was purified by flash chromatography (12 g ISCO silica column, 0-50% EtOAc/hexane gradient) to give Example 217 (10.1 mg) as a white powder. Rf (30% EtOAc/hexane) 0.70; (M+H)⁺=402.35; ¹H NMR (400 MHz, CDCl₃) δ ppm 1.41 (s, 9 H), 6.94 (s, 1 H), 6.95 (dd, J=7.91, 1.32 Hz, 1H), 7.07 (dd, J=7.91, 4.83, 1H), 7.16-7.26 (m, 2 H), 7.34 (t, J=7.25 Hz, 1 H), 7.42-7.49 (m, 3 H), 7.73 (s, 1 H), 7.78 (dd, J=5.05, 1.54 Hz, 1H), 7.89-7.92 (m, 2 H), 8.80 (dd, J=7.91, 1.76 Hz, 1 H).

Examples 218-250 listed in Table 9 were prepared following the procedure described for Example 217.

TABLE 9

| Example | $R^{1a}$ | $R^{1b}$ | $(M + H)^+$ |
|---|---|---|---|
| 217 | H | Ph | 402.4 |
| 218 | H | 4-Me-Ph | 416.4 |
| 219 | H | 4-OCF$_3$-Ph | 486.3 |
| 220 | H | 4-CN-Ph | 427.3 |
| 221 | H | 4-OMe-Ph | 432.3 |
| 222 | H | 4-CF$_3$-Ph | 470.1 |
| 223 | H | Et | 354.3 |
| 224 | Me | Ph | 416.4 |
| 225 | Me | Me | 354.3 |
| 226 | H | t-Bu | 382.3 |
| 227 | CO$_2$Et | Me | 412.2 |
| 228 | CO$_2$Et | H | 398.2 |
| 229 | H | 4-NO$_2$-Ph | 447.2 |
| 230 | H | 3-NO$_2$-Ph | 447.3 |
| 231 | H | 2-NO$_2$-Ph | 447.2 |
| 232 | H | 3-OMe-Ph | 432.4 |
| 233 | H | 2-OMe-Ph | 432.3 |
| 234 | H | 3-F-Ph | 420.4 |
| 235 | H | H | 326.4 |
| 236 | H | CO$_2$Et | 398.3 |
| 237 | CO$_2$Me | t-Bu | 440.3 |
| 238 | CO$_2$Et | CF$_3$ | 466.2 |
| 239 | CN | Ph | 427.3 |
| 240 | —CH$_2$CO$_2$H | Ph | 460.3 |
| 241 | —CH$_2$CO$_2$Et | Ph | 488.3 |
| 242 | H | —C(Me)$_2$CH$_2$CO$_2$Et | 454.3 |
| 243 | H | —C(NHCO$_2$(t-Bu))(i-Bu)— | 511.3 |
| 244 | H | —CH$_2$CO$_2$(i-Pr) | 426.3 |
| 245 | H | CF$_2$CF$_3$ | 444.3 |
| 246 | H | CF$_3$ | 394.3 |
| 247 | H | 2-CO$_2$Et-Ph | 474.3 |
| 248 | Ph | H | 402.4 |
| 249 | —CH$_2$OMe | H | 370.3 |
| 250 | H | —C(NH$_2$)(i-Bu)— | 411.3 |
| 251 | —CH$_2$OH | H | 356.3 |
| 252 | —CH$_2$OH | t-Bu | 412.3 |
| 253 | —CH$_2$OH | CF$_3$ | 424.2 |
| 254 | CON(Me)(Bn) | H | 473.3 |
| 255 | CONMe$_2$ | H | 397.3 |
| 256 | —CO-morpholin-4-yl | H | 439.2 |
| 257 | CONHPh | H | 445.3 |
| 258 | CONH-neopentyl | H | 439.3 |
| 259 | CON(Me)Pr | H | 425.3 |
| 260 | CONHPr | H | 411.3 |
| 261 | CON(Me)Et | H | 411.3 |
| 262 | CONH(t-Bu) | H | 425.3 |
| 263 | CON(Me)-phenethyl | H | 487.3 |
| 264 | CON(Me)(CH$_2$)$_3$Ph | H | 501.3 |
| 265 | CON(Me)(CH$_2$-pyridin-3-yl) | H | 474.3 |
| 266 | CON(Me)Et | CF$_3$ | 479.3 |

TABLE 9-continued

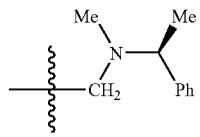

| Example | R¹ᵃ | R¹ᵇ | (M + H)⁺ |
|---|---|---|---|
| 267 | CON(Me)Bn | CF₃ | 541.2 |
| 268 | CONHPh | CF₃ | 513.2 |
| 269 | CONH₂ | CF₃ | 437.4 |
| 270 | —CH₂CON(Me)Et | Ph | 501.3 |
| 271 | —CH₂CONHBn | Ph | 549.3 |
| 272 | —CH₂N(Me)Bn | H | 359.3 |
| 273 | —CH₂NH-neopentyl | H | 425.0 |
| 274 | —CH₂NHBn | H | 445.3 |
| 275 | —CH₂N(Me)Et | H | 397.3 |
| 276 | —CH₂N(Me)(t-Bu) | H | 425.3 |
| 277 | —CH₂N(Me)-cyclohexyl | H | 451.3 |
| 278 | —CH₂N(Me)-phenethyl | H | 473.3 |
| 279 | —CH₂N(Me)(CH₂)₃Ph | H | 487.3 |
| 280 | 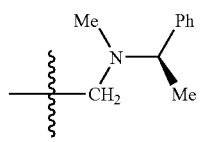 | H | 473.3 |
| 281 | —CH₂N(t-Bu)Bn | H | 501.3 |
| 282 | —CH₂N(i-Pr)Bn | H | 487.3 |
| 283 | —CH₂N(Me)-pyridin-3-yl | H | 460.3 |
| 284 | —CH₂N(Me)Et | t-Bu | 453.4 |
| 285 | —CH₂NHEt | t-Bu | 439.3 |
| 286 | —CH₂N(Me)Bn | t-Bu | 515.3 |
| 287 | —CH₂NHBn | t-Bu | 501.3 |
| 288 | —CH₂N(Me)-phenethyl | t-Bu | 529.3 |
| 289 | —CH₂N(t-Bu)Bn | t-Bu | ND |
| 290 | —CH₂N(i-Pr)Bn | t-Bu | ND |
| 291 | —CH₂N(Me)(CH₂)₃Ph | t-Bu | ND |
| 292 | —CH₂-isoindolin-2-yl | H | 457.3 |
| 293 | —CH₂-(1,2,3,4-tetrahydro-isoquinolin-2-yl) | H | 471.3 |
| 294 | 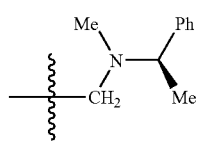 | H | 473.3 |
| 295 | —CH₂N(Me)Ph | H | 445.3 |
| 296 | —CH₂-isoindolin-2-yl | t-Bu | 513.3 |
| 297 | —CH₂-(1,2,3,4-tetrahydro-isoquinolin-2-yl) | t-Bu | 527.3 |
| 298 | 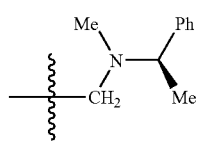 | t-Bu | 529.3 |
| 299 | —CH₂N(Me)Ph | t-Bu | ND |
| 300 | —CH₂N(Me)Et | t-Bu | 467.3 |
| 301 | —CH₂-morpholin-4-yl | t-Bu | 481.3 |
| 302 | —CH₂N(Me)Et | CF₃ | 465.3 |
| 303 | —CH₂N(Me)Bn | CF₃ | 527.2 |

TABLE 9-continued

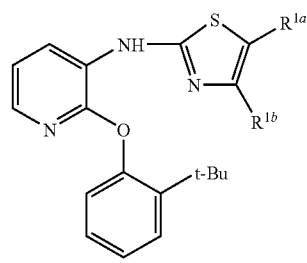

| Example | R1a | R1b | (M + H)+ |
|---|---|---|---|
| 304 | —CH$_2$-isoindolin-2-yl | CF$_3$ | 525.2 |
| 305 | —CH$_2$NHEt | CF$_3$ | 451.3 |
| 306 | H | CONHPr | 411.3 |
| 307 | H | CON(Me)Pr | 425.3 |
| 308 | H | CONHBn | 459.2 |
| 309 | H | CON(Me)Bn | 473.3 |
| 310 | H | CONHPh | 445.2 |
| 311 | H | CONH(t-Bu) | 425.3 |
| 312 | H | CON(Me)Bn | |
| 313 | H | CONH-neopentyl | 439.3 |
| 314 | H | CON(Me)(t-Bu) | 439.3 |
| 323 | 4-CF$_3$-Ph | CF$_3$ | 538.3 |
| 324 | 3-Me-Ph | CF$_3$ | 484.3 |
| 325 | 4-Me-Ph | CF$_3$ | 484.3 |
| 326 | 2-Me-Ph | CF$_3$ | 484.3 |
| 327 | 3-CN-Ph | CF$_3$ | 495.3 |
| 328 | pyridin-4-yl | CF$_3$ | 471.3 |
| 329 | 3-OMe-Ph | CF$_3$ | 500.3 |
| 330 | 4-OMe-Ph | CF$_3$ | 484.3 |
| 331 | 4-SO$_2$Me-Ph | CF$_3$ | 548.2 |
| 332 | 4-CH$_2$OH-Ph | CF$_3$ | 500.3 |
| 333 | 3-OH-Ph | CF$_3$ | 486.3 |
| 334 | Br | CF$_2$CF$_3$ | 522.2 |
| 335 | Ph | CF$_3$ | 370.3 |
| 336 | 4-CN-Ph | CF$_3$ | 495.3 |
| 337 | 3,5-diF-Ph | CF$_3$ | 506.3 |
| 338 | 2-CN-Ph | CF$_3$ | 495.3 |
| 339 | 2,4-diF-Ph | CF$_3$ | 506.3 |
| 340 | 4-CO$_2$Me-Ph | CF$_3$ | 528.3 |
| 341 | 3-CO$_2$Me-Ph | CF$_3$ | 528.3 |
| 342 | 3-OCF$_3$-Ph | CF$_3$ | 554.3 |
| 343 | Ph | CF$_2$CF$_3$ | 520.3 |
| 344 | 4-Me-Ph | CF$_2$CF$_3$ | 534.3 |
| 345 | 3-CF$_3$-Ph | CF$_3$ | 538.3 |
| 346 | 4-OCF$_3$-Ph | CF$_3$ | 554.2 |
| 347 | 3-CF$_3$-Ph | CF$_2$CF$_3$ | 588.2 |
| 348 | 4-OCF$_3$-Ph | CF$_2$CF$_3$ | 604.2 |
| 349 | 3-Me-Ph | CF$_2$CF$_3$ | 534.3 |
| 350 | 3-CN-Ph | CF$_2$CF$_3$ | 545.3 |
| 351 | 4-CN-Ph | CF$_2$CF$_3$ | 545.3 |
| 352 | 3-OMe-Ph | CF$_2$CF$_3$ | 550.3 |
| 353 | 4-OMe-Ph | CF$_2$CF$_3$ | 550.3 |
| 354 | furan-3-yl | CF$_3$ | 460.3 |
| 355 | 4-OBn-Ph | CF$_3$ | 576.3 |
| 356 | 3-F-4-OMe-Ph | CF$_3$ | 518.3 |
| 357 | 3,4,5-triOMe-Ph | CF$_3$ | 560.3 |
| 358 | 1,3-benzodioxol-4-yl | CF$_3$ | 514.3 |
| 359 | 3-OBn-Ph | CF$_3$ | 576.3 |
| 360 | 2-OMe-pyrimidin-5-yl | CF$_3$ | 619.3 |
| 361 | morpholin-4-yl | CF$_3$ | 406.3 |
| 362 | piperidin-1-yl | CF$_3$ | 477.3 |
| 363 | —N(Me)-CH$_2$-pyridin-4-yl | CF$_3$ | 514.3 |
| 364 | —N(Me)-CH$_2$-pyridin-3-yl | CF$_3$ | 514.3 |
| 365 | —N(Me)(1-Me-piperidin-4-yl) | CF$_3$ | 520.3 |
| 366 | pyrrolidin-1-yl | CF$_3$ | 463.3 |
| 367 | 4-Et-piperazin-1-yl | CF$_3$ | 506.3 |
| 368 | piperazin-1-yl | CF$_3$ | 478.3 |

TABLE 9-continued

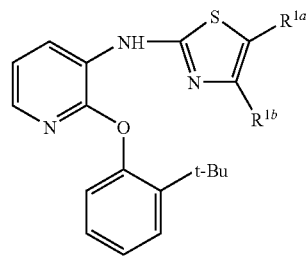

| Example | R$^{1a}$ | R$^{1b}$ | (M + H)$^+$ |
|---|---|---|---|
| 369 | 4-Me-piperazin-1-yl | CF$_3$ | 492.3 |
| 370 | 4-(pyrrolidin-1-yl)-piperidin-1-yl | CF$_3$ | 546.3 |
| 371 | 4-Bn-piperazin-1-yl | CF$_3$ | 568.3 |
| 372 | 4-i-Pr-piperazin-1-yl | CF$_3$ | 520.3 |
| 373 | | CF$_3$ | 518.3 |
| 374 | 3-(—CH$_2$NMe$_2$)-Ph | CF$_3$ | 527.3 |
| 375 | 3-(—CH$_2$N(Me)Bn)-Ph | CF$_3$ | 603.3 |
| 376 | 3-(—CH$_2$NHBn)-Ph | CF$_3$ | 589.3 |
| 377 | 3-(—CH$_2$NHMe)-Ph | CF$_3$ | 513.3 |
| 378 | 4-(—CH$_2$NMe$_2$)-Ph | CF$_3$ | 527.3 |
| 379 | 4-(—CH$_2$NHMe)-Ph | CF$_3$ | 513.3 |
| 380 | 4-(—CH$_2$N(Me)Bn)-Ph | CF$_3$ | 603.3 |
| 381 | 4-(—CH$_2$NHBn)-Ph | CF$_3$ | 589.3 |
| 382 | 2-(—CH$_2$NMe$_2$)-Ph | CF$_3$ | 527.3 |
| 383 | 2-(—CH$_2$NHMe)-Ph | CF$_3$ | 513.3 |
| 384 | 2-(—CH$_2$N(Me)Bn)-Ph | CF$_3$ | 603.3 |
| 385 | 2-(—CH$_2$NHBn)-Ph | CF$_3$ | 589.3 |
| 386 | 3-(—CH$_2$NHMe)-4-OMe-Ph | CF$_3$ | 543.3 |
| 387 | 2-(—CH$_2$NMe$_2$)-4-OMe-Ph | CF$_3$ | 557.3 |
| 388 | 2-(—CH$_2$NHBn)-4-OMe-Ph | CF$_3$ | 619.3 |
| 389 | 2-(—CH$_2$N(Me)Bn)-4-OMe-Ph | CF$_3$ | 633.3 |
| 390 | H | —C(Me)$_2$CH$_2$CON(Me)Et | 467.4 |
| 391 | H | —C(Me)$_2$CH$_2$CONHBn | 515.3 |
| 392 | H | —C(Me)$_2$CH$_2$CON(Me)Bn | 529.3 |
| 393 | H | —C(Me)$_2$CH$_2$CO-morpholi-4-yl | 495.3 |
| 394 | H | 2-(—CH$_2$N(Me)Et)-Ph | 473.4 |
| 395 | H | 3-CH$_2$OH-Ph | 432.4 |
| 396 | H | 4-CH$_2$OH-Ph | 432.4 |
| 397 | —(CH$_2$)$_2$OH | Ph | 446.3 |
| 398 | H | 2-(—CH$_2$NHEt)-Ph | 459.4 |
| 399 | H | 2-(—CH$_2$NHBn)-Ph | 521.4 |
| 400 | H | 2-(—CH$_2$N(Me)Bn)-Ph | 535.4 |
| 401 | H | 3-(—CH$_2$NMe$_2$)-Ph | 459.4 |
| 402 | H | 3-(—CH$_2$N(Me)Bn)-Ph | 535.3 |
| 403 | H | 4-(—CH$_2$N(Me)Bn)-Ph | 535.3 |
| 404 | CN | CF$_3$ | 419.3 |
| 405 | CN | H | |
| 406 | H | CN | |
| 407 | 1H-tetrazol-5-yl | H | 394.3 |
| 432 | 1H-1,2,4-triazol-3-yl | CF$_3$ | 461.3 |
| 433 | CN | CF$_3$ | 407.3 |
| 434 | CN | t-Bu | 407.3 |
| 435 | CO$_2$Et | Ph | 474.3 |
| 441 | —SO$_2$N(Me)Bn | Me | 523.3 |
| 442 | —SO$_2$N(Bn)$_2$ | Me | 599.3 |
| 443 | —SO$_2$N(Me)Et | Me | 461.3 |
| 444 | —SO$_2$NHBn | Me | 509.3 |
| 445 | —SO$_2$-morpholin-4-yl | Me | 489.3 |
| 446 | —SO$_2$NHEt | Me | 447.3 |

Example 251

(2-(2-(2-tert-Butylphenoxy)pyridin-3-ylamino)thiazol-5-yl)methanol

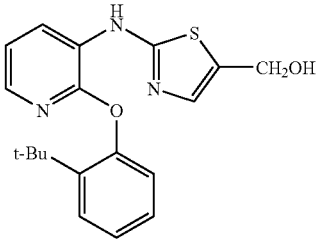

Example 251a 2-(2-(2-tert-Butylphenoxy)pyridin-3-ylamino)thiazole-5-carboxylic acid

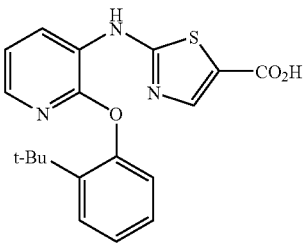

A mixture of Example 228 (1.63 g, 4.1 mmol), 1 N NaOH solution (16.4 mL, 16.4 mmol) in MeOH) 50 mL was heated at reflux for 6 h. The solvent was removed and the residue was acidified to PH=2~3. The solid was collected by filtration, washed with water and dried to give Example 251a (1.30 g) as a white powder. $(M+H)^+=370.2$.

Example 251

To a solution of Example 251a (200 mg, 0.54 mmol) in THF (2 mL) at rt was added borane-THF complex (1.0 M, 1.1 mL, 1.1 mmol). The mixture was stirred at rt overnight. LC-MS showed no completion. Another 1.1 mL of borane-THF solution was added and stirred at rt for additional 6 h. The reaction was quenched with water (5 mL) and extracted with EtOAc (2×15 mL). The combined organic layers were washed with saturated sodium bicarbonate solution and brine, dried over magnesium sulfate, filtered and evaporated to give the crude product. Purification by flash chromatography (12 g ISCO column, 0-50% EtOAc/hexane) gave Example 251 (20 mg) as a colorless film. $(M+H)^+=356.3$.

Example 252

(4-tert-Butyl-2-(2-(2-tert-butylphenoxy)pyridin-3-ylamino)thiazol-5-yl)methanol

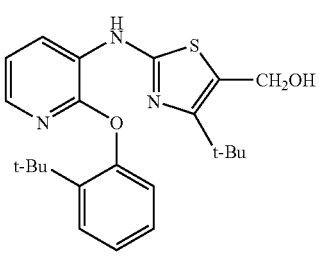

Example 252 was prepared from Example 237 according to a similar procedure described for Example 251 as a white foam. $(M+H)^+=412.3$

Example 253

(2-(2-(2-tent-Butylphenoxy)pyridin-3-ylamino)-4-(trifluoromethyl)thiazol-5-yl)methanol

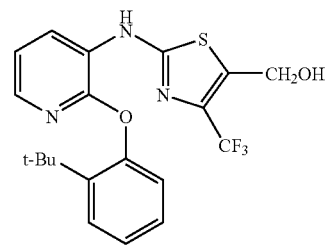

Example 253 was prepared from Example 238 according to a similar procedure described for Example 251 as a white foam. $(M+H)^+=424.2$

Example 254

N-Benzyl-2-(2-(2-tert-butylphenoxy)pyridin-3-ylamino)-N-methylthiazole-5-carboxamide

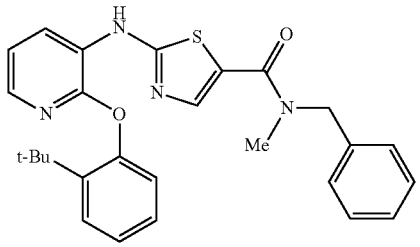

A mixture of compound 2-(2-(2-tert-butylphenoxy)pyridin-3-ylamino)thiazole-5-carboxylic acid (Example 251a, 30 mg, 0.081 mmol), N-benzylmethylamine (13 μL, 0.097 mmol), EDC (18 mg, 0.097 mmol) and HOBt (2 mg, 0.016 mmol) in DCM (1 mL) was stirred at rt overnight. The mixture was evaporated and purified by reverse phase prep HPLC to give Example 254 (15 mg) as a white foam. $(M+H)^+=473.25$.

Examples 255-271 listed in Table 9 were prepared following the procedure described for Example 254.

Example 272

N-(5-((Benzyl(methyl)amino)methyl)thiazol-2-yl)-2-(2-tert-butylphenoxy)pyridin-3-amine

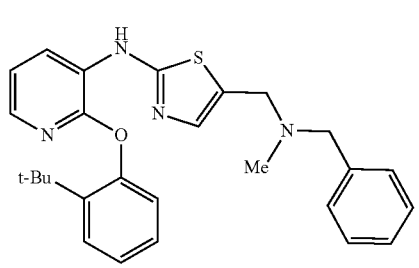

Example 272a 2-(2-tert-Butylphenoxy)-N-(5-(chloromethyl)thiazol-2-yl)pyridin-3-amine

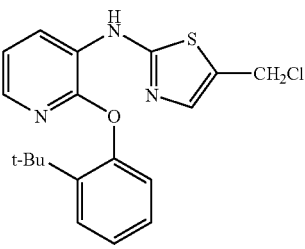

To a solution of (2-(2-(2-tert-butylphenoxy)pyridin-3-ylamino)-thiazol-5-yl)methanol (Example 251, 55 mg, 0.15 mmol) in DCM (3 mL) was added thionyl chloride (45 μL, 0.60 mmol) at 0° C. The mixture was stirred at 0° C. for 1 h. The mixture was evaporated to give Example 272a (65 mg) as a white solid.

Example 272

A mixture of Example 272a (30 mg, 0.080 mmol) and N-benzylmethylamine (13 μL, 0.097 mmol) in THF (2 mL) was stirred at rt overnight. The mixture was evaporated and purified by reverse phase prep HPLC to give Example 272 (21 mg) as a colorless film. $(M+H)^+=359.31$.

Examples 273-305 listed in Table 9 were prepared following the procedure described for Example 272.

Examples 306-313 listed in Table 9 were prepared following a similar procedure from ethyl 2-(2-(2-tert-butylphenoxy)pyridin-3-ylamino)thiazole-4-carboxylate (Example 236) described for Example 254.

Example 315

5-Benzyl-N-(2-(2-tert-butylphenoxy)pyridin-3-yl)-4,5,6,7-tetrahydrothiazolo[5,4-c]pyridin-2-amine

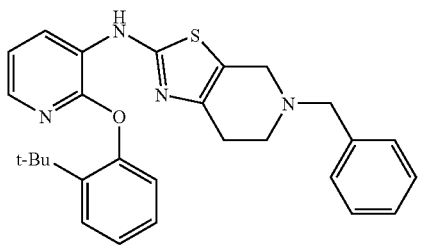

Example 315a

Benzyl 3-bromo-4-oxocyclohexanecarboxylate

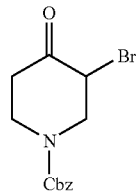

To a solution of benzyl 4-oxo-1-piperidine-carboxylate (1.0 g, 4.28 mmol) in diethyl ether (20 mL) at rt was added bromine dropwise. The resulting mixture was stirred at rt for 1 h. The mixture was diluted with EtOAc (30 mL), washed with water and brine, dried over MgSO$_4$ and filtered. The filtrate was evaporated to give the crude product which was purified by flash chromatography (40 g ISCO column, 0-30% EtOAc/hexane gradient) provided Example 315a (800 mg) as a colorless oil.

Example 315b

Benzyl 2-(2-(2-tert-butylphenoxy)pyridin-3-ylamino)-6,7-dihydrothiazolo[5,4-c]pyridine-5(4H)-carboxylate

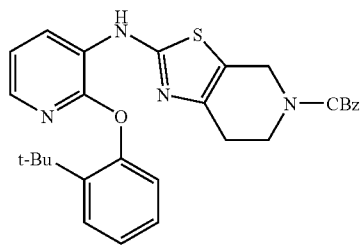

A mixture of 1-(2-(2-tert-butylphenoxy)pyridin-3-yl)thiourea (Example 217b) (100 mg, 0.33 mmol) and Example 315a in ethanol was heated at 95° C. for 2 h. The solvent was removed and the residue was purified by flash chromatography (12 g ISCO column, 0-20% EtOAc/hexane gradient) provided Example 315b (64 mg) as a colorless film. $(M+H)^+=515.3$.

Example 315c

N-(2-(2-tert-Butylphenoxy)pyridin-3-yl)-4,5,6,7-tetrahydrothiazolo[5,4-c]pyridin-2-amine

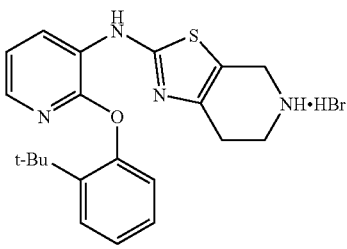

Example 315b (550 mg, 1.07 mmol) was treated with 30% HBr solution at rt for 30 min to give a clear orange solution. The mixture was diluted with diethyl ether (100 mL). The solid was collected by filtration and washed with ether to give Example 315c (440 mg). (M+H)⁺=381.3.

Example 315

A mixture of Example 315c (32 mg, 0.084 mmol), benzyl bromide (12 μL, 0.10 mmol), DIPEA (44 μL, 0.25 mmol) in DCM (2 mL) was stirred at rt overnight. The mixture was evaporated and the residue was purified by reverse phase preparative HPLC to give Example 315 (10 mg, TFA salt) as a white foam. (M+H)⁺=471.3.

Examples 316-317 listed in Table 10 were prepared following the procedure described for Example 315. Examples 318-322 listed in Table 10 were prepared by treating Example 315c with corresponding carbonyl chlorides or sulfonyl chlorides and DIPEA in DCM.

TABLE 10

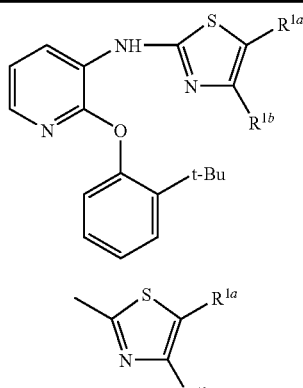

| Example | $R^{1b}$ | (M + H)⁺ |
|---|---|---|
| 315 | N-Bn | 471.3 |
| 316 | N-Pr | 201.0 |
| 317 | N-i-Bu | 289.2 |
| 318 | N-COPh | 1426.29 |
| 319 | N-COBn | 1652.39 |
| 320 | N-SO₂Me | 1072.18 |
| 321 | N-SO₂Ph | 150.08 |
| 322 | N-SO₂Bn | 297.62 |
| 436 | (2,2-dimethyl ketone thiazole) | 422.3 |
| 438 | (6-phenyl ketone thiazole) | 470.3 |

Example 323

2-(2-tert-Butylphenoxy)-N-(4-(trifluoromethyl)-5-(4-(trifluoromethyl)phenyl)thiazol-2-yl)pyridin-3-amine

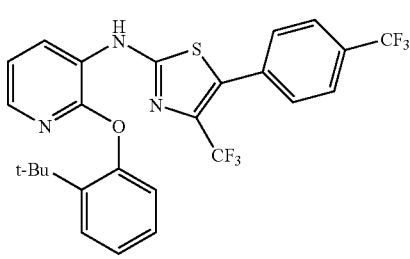

Example 323a

N-(5-Bromo-4-(trifluoromethyl)thiazol-2-yl)-2-(2-tert-butylphenoxy)pyridin-3-amine

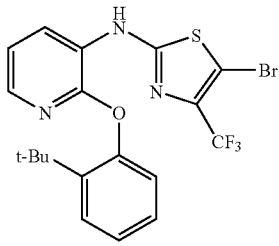

To a solution of 2-(2-tert-butylphenoxy)-N-(4-(trifluoromethyl)thiazol-2-yl)pyridin-3-amine (Example 246) (1.05 g, 2.67 mmol) in AcOH/THF (1:1, 30 mL) at rt was added NBS (475 mg, 2.67 mmol) portionwise. The resulting mixture was stirred at rt for 2 h. The mixture was diluted with EtOAc (200 mL), washed with 1 N NaOH, water and brine, dried over magnesium sulfate, filtered and evaporated to give the crude product. Purification by flash chromatography (40 g ISCO column, 0-20% EtOAc hexane gradient) provided Example 323a (1.08 g). $(M+H)^+=472.3$.

Example 323

To a solution of Example 323a (32 mg, 0.068 mmol) in toluene/methanol (2:1, 400 µL) was added 4-(trifluoromethyl)phenyl boronic acid (26 mg, 0.14 mmol), 2 M $Na_2CO_3$ solution (136 µL, 0.27 mmol). The mixture was bubbled with nitrogen, added catalyst $Pd(PPh_3)_4$ (7 mg) and heated at 85° C. overnight. The mixture was diluted with EtOAc, washed with brine, dried over magnesium sulfate, filtered and evaporated to give the crude product. Purification by reverse phase preparative HPLC provided Example 323 (19 mg). $(M+H)^+=538.3$.

Examples 324-360 listed in Table 9 were prepared following a similar procedure described for example 323.

Example 361

2-(2-tert-Butylphenoxy)-N-(5-morpholino-4-(trifluoromethyl)thiazol-2-yl)pyridin-3-amine

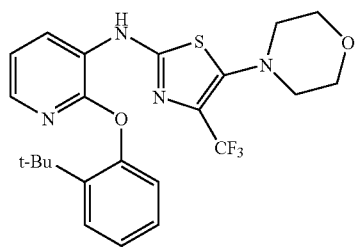

A mixture of N-(5-bromo-4-(trifluoromethyl)thiazol-2-yl)-2-(2-tert-butylphenoxy)-pyridin-3-amine (Example 323a) (20 mg, 0.042 mmol) and morpholine (200 µL) was heated at 100° C. overnight. The reaction was concentrated and the residue was purified by reverse phase preparative HPLC to give Example 361 (12 mg) as a white foam. $(M+H)^+=406.29$.

Examples 362-373 listed in Table 9 were prepared following the procedure described for Example 361.

Example 374

2-(2-tert-Butylphenoxy)-N-(5-(3-((dimethylamino)methyl)phenyl)-4-(trifluoromethyl)thiazol-2-yl)pyridin-3-amine

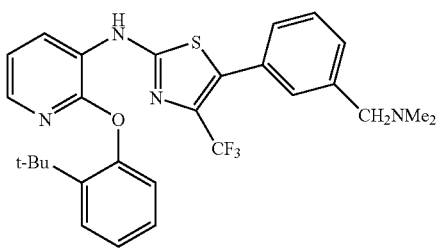

Example 374a 3-(2-(2-(2-tert-Butylphenoxy)pyridin-3-ylamino)-4-(trifluoromethyl)thiazol-5-yl)benzaldehyde

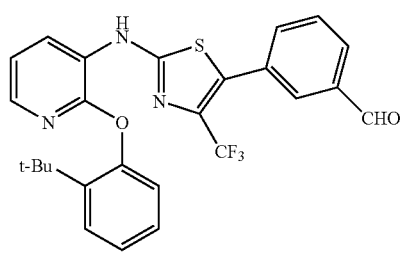

Example 374a was synthesized from N-(5-bromo-4-(trifluoromethyl)thiazol-2-yl)-2-(2-tert-butylphenoxy)pyridin-3-amine (Example 323a) and 3-formylphenyl boronic acid according to a similar procedure described for Example 107. Example 374a was obtained as a white foam. $(M+H)^+=498.3$.

Example 374

To a solution of Example 374a (30 mg, 0.060 mmol) in MeOH (1.0 mL) was added (2.0 M in THF, 1.0 mL), HOAc (10 µL, 0.18 mmol), $ZnCl_2$ (8 mg, 0.12 mmol) and $NaBH_3CN$ (8 mg, 0.13 mmol). The mixture was stirred at rt overnight. The reaction was concentrated and the residue was purified by reverse phase preparative HPLC to give Example 361 (25 mg) as a colorless film. $(M+H)^+$ 527.3.

Examples 375-389 listed in Table 9 were prepared according a similar procedure described for Example 374.

Example 390

3-(2-(2-(2-tert-Butylphenoxy)pyridin-3-ylamino)thiazol-4-yl)-N-ethyl-N,3-dimethylbutanamide

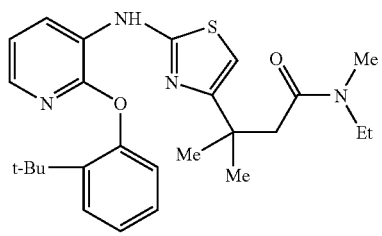

Example 390a 3-(2-(2-(2-tert-Butylphenoxy)pyridin-3-ylamino) thiazol-4-yl)-3-methylbutanoic acid

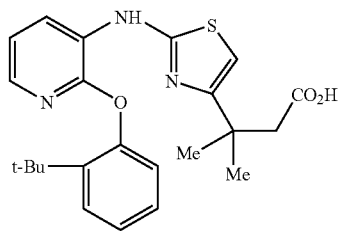

A mixture of Example 242 (420 mg, 0.92 mmol) and 1 N NaOH solution (5 mL) in THF/MeOH (1:3) was stirred at 70° C. for 4 h. The reaction was cooled to rt, acidified to PH=2~3, extracted with EtOAc (3×30 mL). The organic layers were combined and evaporated to give the crude product. Purification by flash chromatography (12 g ISCO column, 0-100% EtOAc/hexane) give the title product (170 mg). $(M+H)^+=426.4$.

Example 390

A mixture of Example 390a (25 mg, 0.059 mmol), N-ethyl methyl amine (50 µL, 0.59 mmol), EDC (17 mg, 0.088 mmol) and HOBt (2 mg) was stirred at rt overnight. The reaction was evaporated and purified by reverse preparative HPLC to give Example 390 (5 mg) as a white solid. $(M+H)^+=467.4$.

Examples 391-393 listed in Table 9 were prepared according a similar procedure described for Example 390.

Example 394

2-(2-tert-Butylphenoxy)-N-(4-(2-((ethyl(methyl) amino)methyl)phenyl)thiazol-2-yl)pyridin-3-amine

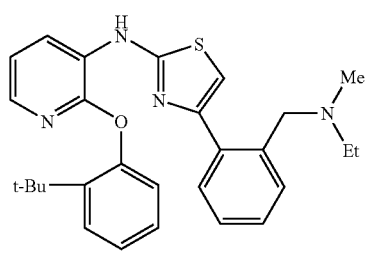

Example 394a (2-(2-(2-(2-tent-Butylphenoxy)pyridin-3-ylamino) thiazol-4-yl)phenyl)methanol

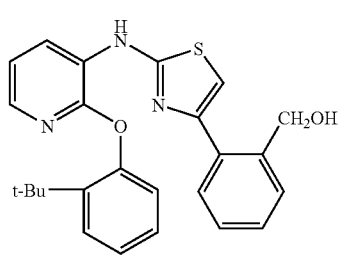

To a solution of ethyl 2-(2-(2-(2-tert-butylphenoxy)pyridin-3-ylamino)thiazol-4-yl)benzoate (Example 247, 210 mg, 0.44 mmol) in THF (3.0 mL) at rt was added Super-Hydride ((1.0 M/THF, 2.2 mL, 2.2 mmol). The reaction was stirred at rt overnight, quenched with the addition of water and extracted with EtOAc. The combined organic layers were dried (MgSO$_4$), filtered and evaporated to give the crude product. Purification by flash chromatography (12 g ISCO column, 0-50% EtOAc/hexane) provided Example 394a (137 mg) as a white foam. $(M+H)^+=432.3$.

Example 394b

N-(4-(2-(Bromomethyl)phenyl)thiazol-2-yl)-2-(2-tent-butylphenoxy)pyridin-3-amine

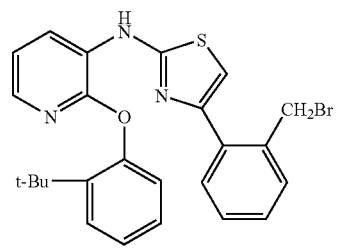

To a solution of Example 394a (124 mg, 0.29 mmol) in DCM (3 mL) was added a solution of PBr$_3$ (1.0 M/DCM). The mixture was stirred at rt for 1 h. The reaction was poured over ice/water (10 mL) and the mixture was extracted with EtOAc (3×15 mL). The combined organic layers were washed with saturated NaHCO$_3$ solution, brine, dried (MgSO$_4$), filtered and evaporated to give Example 394b (129 mg) as a white foam. $(M+H)^+=495.2$.

Example 394

A mixture of Example 394b (20 mg, 0.04 mmol), N-ethyl methylamine (20 µL) in THF was stirred at rt overnight. The reaction was evaporated and the residue was purified by reverse preparative HPLC to give Example 394 (8 mg) as a white solid. $(M+H)^+=473.4$.

Example 395-403 listed in Table 9 was prepared according to a similar procedure described for Example 394.

Example 404

2-(2-(2-tert-Butylphenoxy)pyridin-3-ylamino)-4-(trifluoromethyl)thiazole-5-carbonitrile

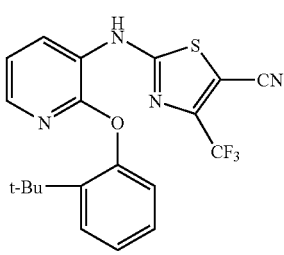

To a solution of 2-(2-(2-tert-butylphenoxy)-pyridin-3-ylamino)-4-(trifluoromethyl)-thiazole-5-carboxamide (Example 269, 89 mg, 0.20 mmol) in THF (1 mL) at 0° C. was added pyridine (99 μL, 1.2 mmol) followed by the addition of TFAA (113 μL, 0.8 mmol). The mixture was stirred at rt for 1 h. The mixture was diluted with EtOAc (20 mL), washed with 1 N HCl (10 mL) and brine (10 mL), dried (MgSO$_4$), filtered and evaporated to give to give the crude product. Purification by flash chromatography (12 g ISCO column, 0-30% EtOAc/hexane) provided Example 404 (137 mg) as a white solid. (M+H)$^+$=419.3.

Examples 405-406 listed in Table 9 was prepared according to a similar procedure described for Example 404.

Example 407

N-(5-(1H-Tetrazol-5-yl)thiazol-2-yl)-2-(2-tert-butylphenoxy)pyridin-3-amine

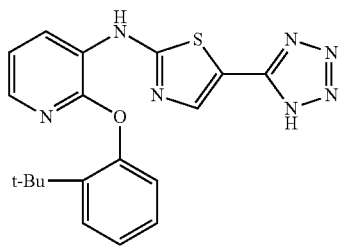

A mixture of 2-(2-(2-tert-butylphenoxy)pyridin-3-ylamino)-4-(trifluoromethyl)thiazole-5-carbonitrile (Example 404, 40 mg, 0.114 mmol), ammonium chloride (6.4 mg, 0.12 mmol), sodium azide (8 mg, 0.12 mmol) in DMF (200 μL) was heated at 90-95° C. overnight. The mixture was quenched with ice-water, acidified to pH=2 using 1 N HCl solution, extracted with DCM (3×15 mL). The combined organic layers were dried (MgSO$_4$), filtered and evaporated to give to give the crude product. Purification by flash chromatography (12 g ISCO column, 0-10% EtOAc/hexane) provided Example 407 (25 mg) as a white solid. (M+H)$^+$=394.3.

Example 408

4-tent-Butyl-N-(2-(2-tert-butylphenoxy)phenyl)thiazol-2-amine

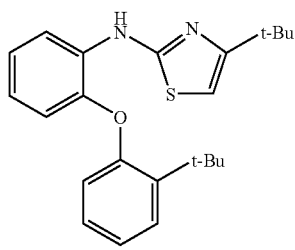

Example 408a 1-(2-(2-tert-Butylphenoxy)phenyl)thiourea

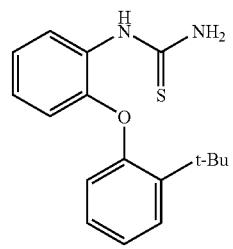

Example 408a was prepared from compound Intermediate 4 following a similar procedure described for [2-(2-tert-Butyl-phenoxy)-pyridin-3-yl]-thiourea (Example 217b).

Example 408

Example 408 was prepared from Example 408a following a similar procedure described for Example 217.

Examples 409-419 listed in Table 11 were prepared following a similar procedure described for Example 408.

TABLE 11

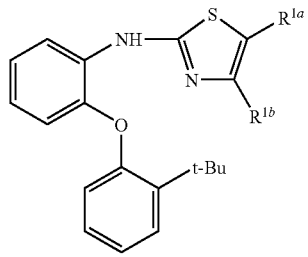

| Example | R$^{1a}$ | R$^{1b}$ | (M + H)$^+$ |
|---|---|---|---|
| 408 | H | t-Bu | |
| 409 | H | Ph | 401.3 |
| 410 | H | Et | 353.3 |
| 411 | Me | Ph | 415.3 |
| 412 | H | H | 325.3 |
| 413 | CO$_2$Et | Me | 411.3 |
| 414 | CO$_2$H | H | 369.3 |
| 415 | CO$_2$Et | H | 397.2 |
| 416 | H | Me | 339.8 |
| 417 | H | CO$_2$Et | 397.3 |
| 418 | CONHMe | H | 382.3 |
| 419 | CONMe$_2$ | H | 396.3 |

Example 420

2-(2-tert-Butyl-phenoxy)-pyridin-3-yl]-(5-phenyl-oxazol-2-yl)-amine

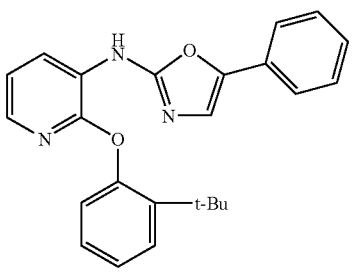

Example 420a

2-Azido-1-phenyl-ethanone

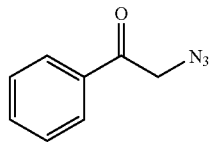

Sodium azide (68 mg, 1.05 mmol) was added to a solution of 2-bromoacetophenone (200 mg, 1.0 mmol) in a 3:1 mixture of acetone and water (12 mL). The mixture was stirred at rt overnight. The solvent was removed and the residue was diluted with EtOAc (20 mL) and washed with brine. The organic layer was dried (MgSO$_4$), filtered and evaporated to give the crude product. Purification by flash chromatography (silica, 0-20% EtOAc/hexane gradient) provided Example 420a (118 mg) as a colorless oil. Rf (20% EtOAc/hexane) 0.42. (M+H)$^+$=162.10.

Example 420

A mixture of Example 420a (108 mg, 0.67 mmol), 2-(2-tert-butyl-phenoxy)-3-isothiocyanato-pyridine (Example 1c, 160 mg, 0.56 mmol) and triphenyl phosphine resin bound (1.6 mmol/g resin, 525 mg, 0.84 mmol) in dioxane (5 mL) was heated at 90° C. for 4 h. The mixture was filtered and evaporated. The residue was purified by flash chromatography (12 g ISCO silica column, 10-30% EtOAc/hexane gradient) to give Example 420 (139 mg) as an orange solid. (M+H)$^+$= 386.33; $^1$H NMR (400 MHz, CDCl$_3$) δ ppm 1.48 (s, 9 H), 7.00 (dd, J=7.91, 1.32 Hz, 1H), 7.10 (dd, J=7.91, 4.83 Hz, 1H), 7.21-7.35 (m, 4 H), 7.45 (t, J=7.69 Hz, 2 H), 7.61 (dd, J=8.57, 1.10 Hz, 2 H), 7.70 (s, 1 H), 7.84 (dd, J=4.83, 1.76 Hz, 1H), 8.80 (dd, J=7.91, 1.76 Hz, 1 H), 8.70 (dd, J=8.13, 1.54 Hz, 1 H).

Examples 421-422 listed in Table 12 were prepared according a similar procedure described for Example 420.

TABLE 12

| Example | R$^{1a}$ | R$^{1b}$ | (M + H)$^+$ |
|---------|----------|----------|-------------|
| 420 | Ph | H | 386.3 |
| 421 | 4-Me-Ph | H | 400.3 |
| 422 | 4-OCF$_3$-Ph | H | 470.3 |
| 437 | CO$_2$Et | CF$_3$ | 450.3 |
| 439 | CO$_2$Et | Me | 396.3 |
| 440 | CO$_2$Et | H | 382.3 |

Example 423

2-(2-tert-Butylphenoxy)-N-(5-o-tolyl-4H-1,2,4-triazol-3-yl)pyridin-3-amine

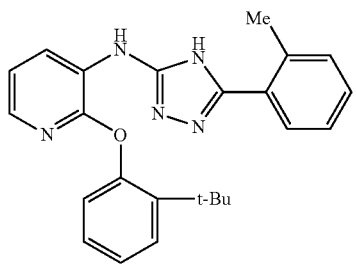

Example 423a

1-(2-(2-tert-Butylphenoxy)pyridin-3-yl)-3-(2-methylbenzoyl)thiourea

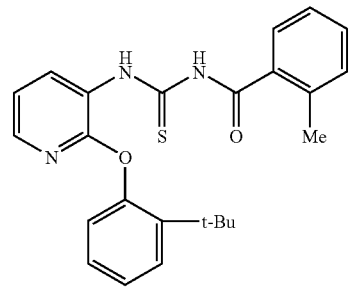

A mixture of 2-(2-tert-Butylphenoxy)-3-aminopyridine (Intermediate 1) (50 mg, 0.20 mmol) and 2-methylbenzoyl isothiocyanate (36 μL, 0.24 mmol, 1.2 eq) in DCM (10 mL) was heated at reflux for 1 h. The mixture was cooled to rt and evaporated to give the crude product. Purification by flash chromatography (silica, 0-20% EtOAc/hexane gradient) provided Example 423a (91 mg) as white crystals. (M+H)$^+$= 420.25.

Example 423

A mixture of Example 423a (50 mg, 0.12 mmol), hydrazine monohydrate (29 μL, 0.6 mmol, 5.0 eq) in 2:1 MeOH:THF (3 mL) was heated at 60° C. overnight. The solvent was removed and the residue was purified by reveres phase preparative HPLC to give Example 423 (139 mg) as a light yellow powder. (M+H)$^+$=400.36; $^1$H NMR (400 MHz, CDCl$_3$) δ ppm 1.32 (s, 9 H), 2.46 (s, 3H), 6.86-6.89 (m, 1H), 7.00 (dd, J=7.69, 5.05 Hz, 1H), 7.08-7.15 (m, 2H), 7.23-7.30 (m, 2 H), 7.37-7.41 (m, 2H), 7.48 (d, J=7.48 Hz, 1 H), 7.76-7.78 (m, 1 H), 8.32 (dd, J=7.91, 1.76 Hz, 1H), 11.11 (s, broad, 2H).

Examples 424-427 listed in Table 13 were prepared according a similar procedure described for Example 423.

TABLE 13

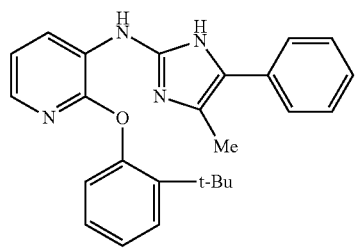

| Example | $R^{1c}$ | (M + H)+ |
|---|---|---|
| 423 | 2-Me-Ph | 400.4 |
| 424 | Ph | |
| 425 | 3-Me-Ph | |
| 426 | 4-Me-Ph | |
| 427 | 2-Cl-Ph | |

Example 428

2-(2-tert-Butylphenoxy)-N-(4-methyl-5-phenyl-1H-imidazol-2-yl)pyridin-3-amine

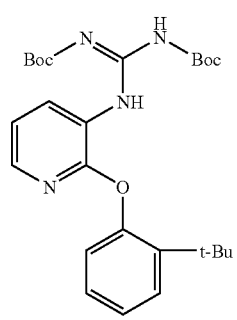

Example 428a 1,2-Bis-tert-butoxycarbonyl-3-(2-(2-tert-butylphenoxy)pyridin-3-yl)guanidine To a mixture of 2-(2-tert-Butylphenoxy)-3-aminopyridine (Intermediate 1) (500 mg, 2.06 mmol) and 1,3-bis-boc-2-methyl-2-thiopseudourea (658 mg, 2.26 mmol, 1.1 eq) in DMF (30 mL) was added triethylamine (1.1 mL, 8.24 mmol, 4.0 eq) and $HgCl_2$ (643 mg, 2.36 mmol, 1.15 eq). The resulting mixture was stirred at rt for 4 h. The reaction was diluted with EtOAc (150 mL) and filtered through a Celite® cake. The filtrate was washed with water. The aqueous layer was extracted with EtOAc (2×20 mL). The combined organic layers were filtered through Celite® again. The filtrate was washed with brine, dried ($MgSO_4$), filtered and concentrated to give Example 428a (600 mg) as a white foam. (M+H)+= 485.40.

Example 428b 1-(2-(2-tert-Butylphenoxy)pyridin-3-yl)guanidine

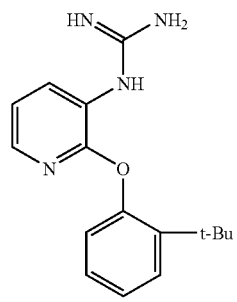

A mixture of Example 428a (560 mg, 1.15 mmol) and 50% TFA/DCM (10 mL) was stirred at rt for 2 h. The reaction was concentrated and the residue was coevaporated with toluene to give the TFA salt of Example 428b as a white foam (550 mg). (M+H)+=285.39.

Example 428

A mixture of Example 428b (30 mg, 0.11 mmol), 2-bromopropiophenone (26 mg, 0.12 mmol) and triethylamine (30 µL) in ethanol (1.0 mL) was heated at 60° C. overnight. The solvent was removed and the residue was purified by reveres phase preparative HPLC to give Example 428 (16 mg) as a white solid. (M+H)+=399.38; $^1$H NMR (400 MHz, $CDCl_3$) δ ppm 1.25 (s, 9 H), 2.15 (s, 3H), 7.10 (d, J=7.91 Hz, 1H), 7.15-7.18 (m, 1H), 7.22-7.26 (m, 1 H), 7.38-7.45 (m, 4H), 7.48-7.53 (m, 5 H), 8.17 (dd, J=7.91, 1.76 Hz, 1H), 8.36 (dd, J=4.83, 1.76 Hz, 1H).

Examples 429-431 listed in Table 14 were prepared according to a similar procedure described for Example 428.

TABLE 14

| Example | $R^{1a}$ | $R^{1b}$ | (M + H)+ |
|---|---|---|---|
| 428 | Ph | Me | 399.4 |
| 429 | Ph | H | 385.4 |
| 430 | 4-OCF$_3$-Ph | H | 469.3 |
| 431 | Et | H | 337.4 |

Example 432

N-(5-(1H-1,2,4-Triazol-3-yl)-4-(trifluoromethyl)thiazol-2-yl)-2-(2-tert-butylphenoxy)pyridin-3-amine

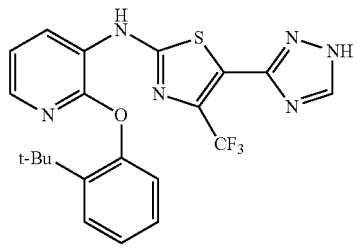

A solution of 2-(2-(2-tert-butylphenoxy)pyridin-3-ylamino)-4-(trifluoromethyl)thiazole-5-carboxamide (Example 269, 33 mg, 0.075 mmol) in N,N-dimethylformamide dimethyl acetal (0.5 mL) was stirred at rt for 1 h. The solvent was removed and the residue was dissolved in HOAc (1 mL) followed by the addition of hydrazine monohydrate (7 µL). The mixture was heated at 70° C. for 1 h. The reaction was concentrated and the residue was dissolved in EtOAc (10 mL), washed with saturated sodium bicarbonate solution (2×5 mL), dried over magnesium sulfate, filtered and evaporated to give the crude product. Purification by reverse phase preparative HPLC provided Example 432a (16 mg) as a white solid. (M+H)+=461.3.

Example 433

2-(2-(2-tert-Butylphenoxy)pyridin-3-ylamino)-4-(trifluoromethyl)thiazole-5-carbonitrile

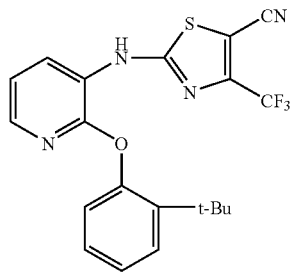

Example 433a 2-(2-tert-Butylphenoxy)-3-iodopyridine

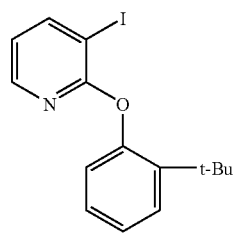

To a solution of 2-(2-tert-butylphenoxy)-3-aminopyridine (3.30 g, 13.6 mmol) in conc. HCl:water (3:4, 70 mL) at 0° C. was added NaNO$_2$ (1.04 g, 15.0 mmol). Gas evolution is immediately observed. The reaction was stirred at 0° C. for ±25 min. and then the reaction was slowly poured into a rt solution of KI (6.8, 40.8 mmol) in water (150 ml) to produce a dark liquid containing an amount of a black. After heating the reaction at 60° C. for 2 h, the reaction was cooled to rt and extracted with ethyl acetate (2×200 mL). The combined ethyl acetate extracts were then washed with saturated aqueous Na$_2$SO$_3$ (2×300 mL) and saturated aqueous Na$_2$CO$_3$ (1×300 mL). The ethyl acetate extracts were then dried over MgSO$_4$, filtered and concentrated. Purification of the residue by flash chromatography—(110 g ISCO silica gel column, 0 to 5% EtOAc in hexane step gradient)—gave Example 433a (3.35 g) as a pale yellow solid. $^1$H NMR (400 MHz, CDCl$_3$) δ ppm 1.39 (s, 9H); 6.74 (dd, J=7.47, 4.83 Hz, 1H); 6.93 (dd, J=7.91, 1.32 Hz, 1H); 7.12-7.25 (m, 2H); 7.45 (dd, J=7.91, 1.76 Hz, 1 H); 8.10 (dd, J=4.83, 1.76 Hz, 1H); 8.15 (dd, J=7.69, 1.54 Hz, 1H).

Example 433b 2-(2-tert-Butylphenoxy)-pyridine-3-boronic acid

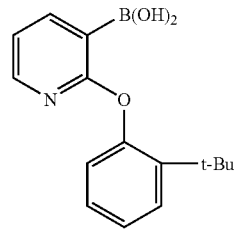

To a solution of Example 433a (3.35 g, 9.49 mmol) in THF (60 ml) under nitrogen at −78° C. was added 2.0 M nBuLi in pentane (14.2 mL, 28.47 mmol, 3 eq) over ~3 min. The reaction was stirred at −78° C. for 10 min & then B(OiPr)$_3$ (6.54 mL, 28.47 mmol, 3 eq) was added in a single aliquot. The reaction was stirred at −78° C. for 40 min. & then the reaction was poured into water (~60 mL) followed by the addition of LiOH (~3.5 g). The reaction was stirred for 2 hr at rt. Partition the reaction mixture between water (~200 ml additional) and EtOAc (~200 mL). Separate layers and wash the aqueous once more with EtOAc. Pour aqueous into a large erlenmyer flask & add EtOAc (~200 mL). With vigorous stirring add conc. HCl dropwise until pH ~2. Separate layers in sep funnel & extract aqueous once more with EtOAc (~200 mL). Combine these last two EtOAc extracts, dry over sodium sulfate, filter and concentrate. Azeotrope twice with toluene to give Example 433b (2.38 g) as a white solid. $^1$H NMR (400 MHz, CDCl$_3$) δ ppm 1.31 (s, 9H); 4.1 (bs, 1H); 5.61 (bs, 1H); 6.91 (d, J=7.47 Hz, 1H); 7.05 (dd, J=6.37, 3.74 Hz, 1 H); 7.15-7.3 (m, 2H); 7.48 (dd, J=7.47, 1.32 Hz, 1H); 8.23 (bs, 1H); 8.27 (dd, J=7.03 Hz, 1H).

Example 433

To a solution of Example 433b (48 mg, 0.177 mmol) in dichloromethane (2.5 mL) in a scintillation vial under air at rt was added 2-amino-4-(trifluoromethyl)thiazole-5-carbonitrile (52 mg, 0.27 mmol), powdered 4 Å molecular sieves (~100 mg), Et$_3$N (50 μL), pyridine (50 μL) and lastly Cu(OAc)$_2$ (35 mg, 0.19 mmol). The reaction vessel was capped and the reaction was stirred at rt overnight. The reaction mixture was diluted with hexane (2.5 mL), loaded to a silica gel column and purified by flash chromatography (0-10% EtOAc in hexane, step gradient) to provide Example 433 (30 mg) as a tan solid. (M+H)$^+$=407.3.

Examples 434-440 listed in Table 15 were prepared following the procedures described for Example 433 using the amines shown in the table.

TABLE 15

| Example | Amine | Structure | (M + H)$^+$ |
| --- | --- | --- | --- |
| 434 | | 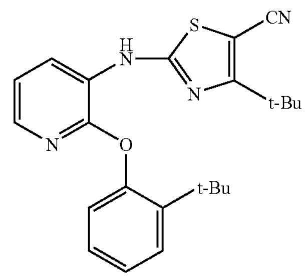 | 407.3 |
| 435 | | 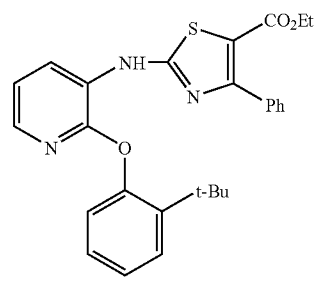 | 474.3 |
| 436 | | 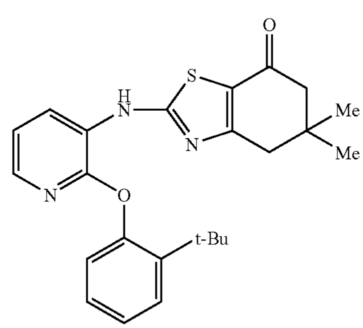 | 422.3 |
| 437 | | 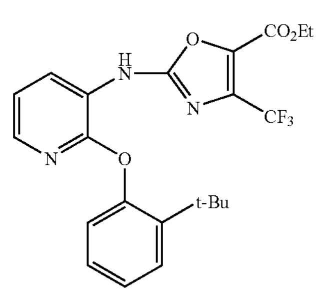 | 450.3 |

TABLE 15-continued

| Example | Amine | Structure | (M + H)+ |
|---------|-------|-----------|----------|
| 438 | | 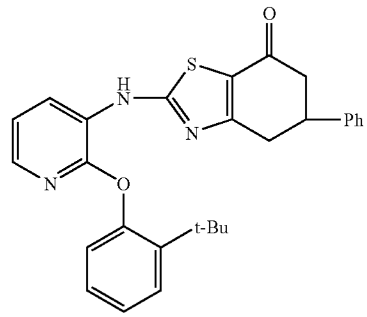 | 470.3 |
| 439 | | 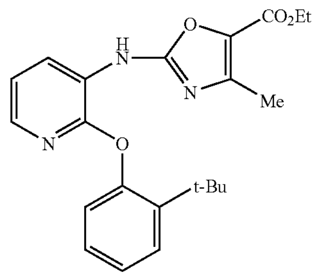 | 396.3 |
| 440 | | 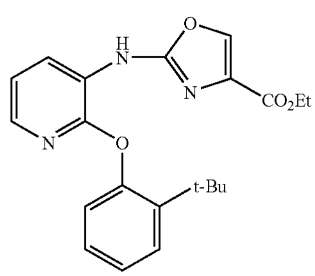 | 382.3 |

Example 441

2-[2-(2-tert-Butylphenoxy)-pyridin-3-ylamino]-4-methyl-thiazole-5-sulfonic acid benzyl-methyl-amide

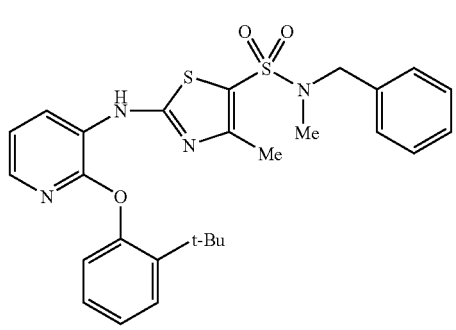

Example 441a

N-[5-(Benzyl-methyl-sulfamoyl)-4-methyl-thiazol-2-yl]-acetamide

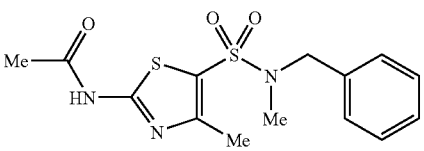

To a solution of 2-acetamido-4-methylthiazole-5-sulfonyl-chloride (440 mg, 1.73 mmol) in dichloroethane (5 mL) at rt was added N-methylbenzylamine (418 mg, 3.46 mmol) and iPr$_2$Net (400 μL). Reaction set at rt for 48 h. After solvent was reduced under vacuum, the residue was diluted with EtOAc (~30 mL) and washed twice with 1N HCl and once with saturated aqueous NaHCO$_3$. The EtOAc extract was dried over MgSO$_4$, filtered and concentrated. The residue was then diluted with dichloromethane and hexane was added to ini-

Example 441b

2-Amino-4-methyl-thiazole-5-sulfonic acid benzyl-methyl-amide

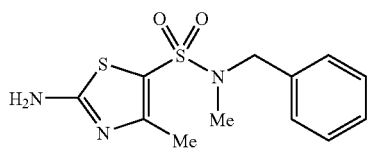

Example 441a (432 mg, 1.27 mmol) was diluted with a solution of conc. HCl:water:EtOH (15:20:15 by volume, 5 mL). The reaction mixture was heated at 65° C. for 18 h. The reaction was partitioned between EtOAc (25 mL) and 1:1 sat. NaHCO3:1N NaOH (25 mL). Extract the aqueous layer twice with EtOAc. Dry the combined organic extracts over MgSO$_4$, filter and concentrate to provide Example 441b (335 mg) as a white solid. (M+H)$^+$=298.3.

Example 441

To a solution of Example 433b (25 mg, 0.092 mmol) in dichloromethane (2.5 mL) in a scintillation vial under air at rt was added the product from Example 441b (30 mg, 0.101 mmol), powdered 4 Å molecular sieves (~100 mg), Et$_3$N (30 µL), pyridine (30 µL) and lastly Cu(OAc)$_2$ (20 mg, 0.11 mmol). The reaction vessel was capped and the reaction was stirred at rt overnight. The reaction mixture was diluted with hexane (2.5 mL) and filtered through a pad of silica gel eluting with 50% EtOAc in dichloromethane. After removing the solvent under vacuum, purification by preparative TLC (silica gel, 20×20 cm$^2$×1000 µm thick, 20% EtOAc in hexane) gave Example 441 as a white solid. (M+H)$^+$=523.3.

Examples 442-446 listed in Table 9 were prepared following the procedures described for Example 441.

Example 450

6-Bromo-2-(2-isopropylphenoxy)-N-(4-(trifluoromethyl)thiazol-2-yl)pyridin-3-amine

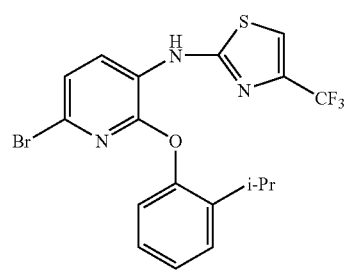

Example 450a

6-Bromo-2-(2-isopropylphenoxy)pyridin-3-amine

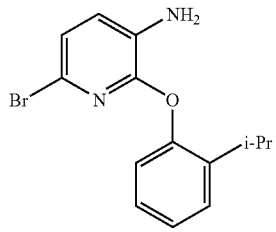

A solution of N-bromosuccinimide (2.32 g, 13.0 mmol) in DMF (20 ml) was added to a cold (−20° C.) solution of Intermediate 2 (2.76 g, 11.4 mmol) in DMF (25 mL). The reaction rapidly turned dark red. HPLC analysis after 5 min showed that the reaction was complete. The reaction was quenched with a freshly prepared solution of sodium thiosulfate (40 mL, 10% aqueous). A precipitate formed. The mixture was warmed to rt and was diluted with water (60 mL). The solid was filtered, washed with water and dried overnight under reduced pressure to give Example 450a (3.82 g, 96% yield) as brown solid. [M+H]$^+$=321.14. $^1$H NMR (500 MHz, CDCl$_3$) δ ppm 1.40 (s, 9 H), 3.91 (s, 2 H), 6.93 (m, 2 H), 7.00 (d, J=8.07 Hz, 1H), 7.12 (t, J=7.73 Hz, 1 H), 7.20 (t, J=7.73 Hz, 1 H), 7.41 (d, J=8.07 Hz, 1 H).

Example 450b 1-(6-Bromo-2-(2-isopropylphenoxy)pyridin-3-yl)thiourea

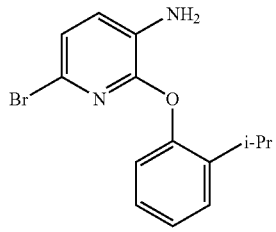

To a solution of Example 450a (1.7 g, 5.54 mmol) in THF (35 mL) at rt was added benzoylisothiocyanate (0.83 mL, 6.09 mmol). After heating this reaction mixture at 40° C. for 2 h, methanol (10 mL) and 1.0 M KOH (10 mL) was added and the reaction was stirred at 40° C. for an additional 3 h. The reaction was taken up in EtOAc (200 mL) and washed once with 50:50 sat. aq. NaCl:sat. aq. NaHCO$_3$ (200 mL) and once with water (200 mL). The organic layer was dried over MgSO$_4$, filtered and concentrated. The residue was taken up in Et$_2$O (~25 mL) and, while sonicating, hexane (~50 mL) was added slowly to provide a precipitate. The solid was collected, rinsed with 25% Et$_2$O in hexane (~10 mL) and dried under vacuum to give Example 450b (1.89 g). (M+H)$^+$= 366.2, 368.2 (Br isotopic pattern).

Example 450

To a solution of Example 450b (1.2 g, 3.28 mmol) in ethanol (20 ml) in a pressure vessel was added 2,6-lutidine (1.0 mL) and 3-bromo-1,1,1-trifluoropropan-2-one (0.63 g, 3.28 mmol). The vessel was sealed and the reaction was heated at 90° C. for ±18 h. After cooling to rt, solvent was removed. The residue was taken up in Et$_2$O and solids removed. After reducing the solvent again, purification by flash chromatography (silica gel, 10% EtOAc in hexanes) provided Example 450 (1.48 g). (M+H)$^+$=458.2, 460.2 (Br isotopic pattern).

Example 451

2-(2-Isopropylphenoxy)-N-(4-(trifluoromethyl)thiazol-2-yl)pyridin-3-amine

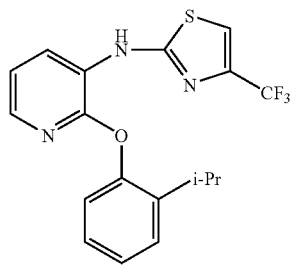

To a solution of Example 450 (20 mg, 0.044 mmol) in methanol (5 mL) was added 10% Pd/C (50% H$_2$O type, 5 mg). The flask was fitted with a hydrogen balloon and H$_2$ was bubbled through the solution for 5 min and then the reaction was stirred under H$_2$ for 3 h. The reaction was filtered through Celite® and eluted with methanol. Purification by prep HPLC (Method A) provided Example 451 (13 mg) as an off white solid. (M+H)$^+$=380.3.

Example 452

6-Cyano-2-(2-isopropylphenoxy)-N-(4-(trifluoromethyl)thiazol-2-yl)pyridin-3-amine

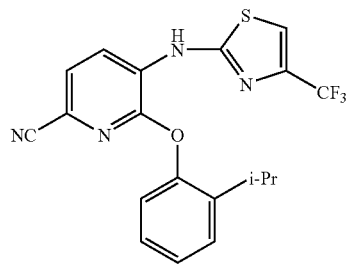

To a solution of Example 450 (200 mg, 0.437 mmol) in dry, nitrogen degassed DMF (4 mL) at rt was added Zn(CN)$_2$ (102 mg, 0.874 mmol) and Zn dust (8.5 mg, 0.131 mmol). After the reaction was degassed for an additional 5 min, Pd (tBu$_3$P)$_2$ (20 mg, 0.039 mmol) was added and the reaction was heated to 60° C. overnight (~18 h). The reaction was cooled to rt, diluted with EtOAc and washed twice with saturated aqueous NaHCO$_3$. The organic layer was dried over MgSO$_4$, filtered and concentrated. Purification by flash chromatography (40 g ISCO silica gel cartridge, 0 to 10% EtOAc in hexane single step gradient) provided Example 452 (178 mg). (M+H)$^+$=405.3.

Example 453

6-Dimethylamino-2-(2-isopropylphenoxy)-N-(4-(trifluoromethyl)thiazol-2-yl)pyridin-3-amine

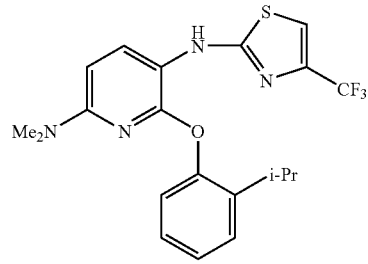

To a solution of Example 450 (34 mg, 0.074 mmol) in dry, nitrogen degassed toluene (1.0 mL) at rt was added Me$_2$NH (2.0 M in THF, 170 µL, 0.34 mmol), KOtBu (1.0 M in THF, 200 µL, 0.2 mmol) and Pd(tBu$_3$P)$_2$ (5 mg, 0.0098 mmol). The reaction was sealed and heated to 70° C. for 3 h. The reaction was diluted with hexane (0.25 mL), loaded to a prep TLC plate (20×20 cm$^2$×2000 µm) and eluted up the plate with 15% EtOAc in hexanes. After identification by UV and HPLC, the desired material was removed from the plate and eluted from the silica gel with 3:1 dichlormethane:EtOAc. Repurification by prep HPLC (YMC-PAC-ODS column (20 mm×100 mm) at 20 mL/min, 10 min gradient from 20% to 100% B where solvent A is 10% MeOH/Water+0.1% TFA and solvent B is 90% MeOH/Water+0.1% TFA) provided Example 453 (5.5 mg). (M+H)$^+$=423.3.

Example 454

6-(4-Methoxybenzyl)amino-2-(2-isopropylphenoxy)-N-(4-(trifluoromethyl)thiazol-2-yl)pyridin-3-amine

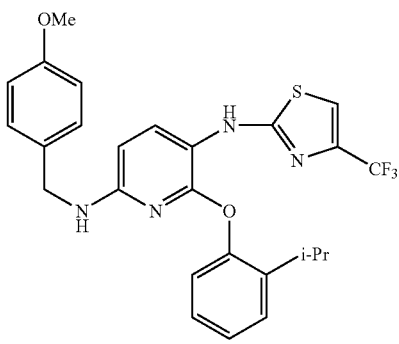

Example 454 was prepared using the method described for Example 453 except using 4-methoxybenzylamine in place of dimethylamine. (M+H)⁺=515.3.

Example 455

6-Amino-2-(2-isopropylphenoxy)-N-(4-(trifluoromethyl)thiazol-2-yl)pyridin-3-amine

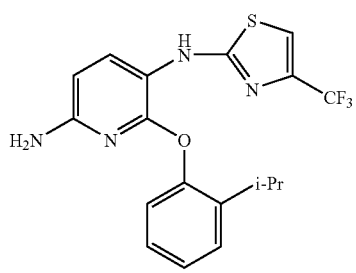

Example 454 (≦0.085 mmol, semi-crude) was taken up 50% TFA in dichloromethane and allowed to set overnight. Solvent was removed under vacuum and purification by prep HPLC (YMC-PAC-ODS column (20 mm×100 mm) at 20 mL/min, 10 min gradient from 20% to 100% B where solvent A is 10% MeOH/Water+0.1% TFA and solvent B is 90% MeOH/Water+0.1% TFA) provided Example 455 (7 mg). (M+H)⁺=395.3.

Example 456

5-Bromo-2-(2-isopropylphenoxy)-N-(4-(trifluoromethyl)thiazol-2-yl)pyridin-3-amine

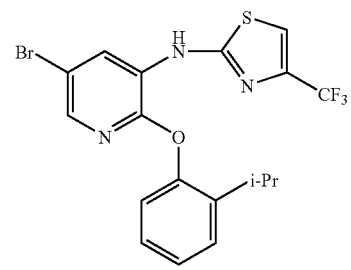

Example 456a

5-Bromo-2-(2-tert-butylphenoxy)pyridine-3-amine

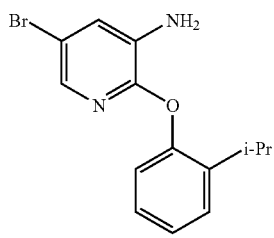

To a solution of 5-bromo-2-chloro-3-nitropyridine (4.9 g, 20.7 mmol) and 2-isopropylphenol (2.87 g, 21.1 mmol) in NMP (45 ml) in a 500 mL pressure vessel at rt was added K₂CO₃ (5.7 g). The reaction was fitted with a stir bar, sealed and heated at 115° C. for 48 h. The reaction was extracted with Et₂O (350 mL), washing with water (3×). The aqueous layers were then back extracted with Et₂O. The combined organic layers were dried over MgSO₄, filtered and concentrated. The crude material was then flash filtered through silica gel, eluting with 10% EtOAc in hexanes. Solvent was removed under vacuum. The residue was taken up into MeOH (150 mL) to which Zn powder (6 g) was added followed by slow addition of NH₄Cl (6 g). After stirring at rt for 20 min, the reaction was filtered through Celite® and the pad washed with MeOH. The solvent was remove under vacuum & the residue taken up into dichloromethane. The solid material formed was filtered off and discarded. Hexane was added to the dichloromethane eluent to initiate precipitation. The solid formed here was collected by filtration to provide Example 456a (385 mg). (M+H)⁺=307.3, 309.3 (Br isotopic pattern).

Example 456b 1-(5-Bromo-2-(2-isopropylphenoxy)pyridin-3-yl)thiourea

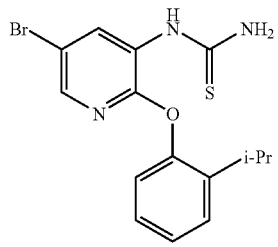

Prepared from Example 456a (385 mg, 1.25 mmol) as described previously for Example 451b to afford Example 456b (405 mg). (M+H)⁺=366.2, 368.2 (Br isotopic pattern).

Example 456

Example 456 (380 mg) was prepared from Example 456b (405 mg, 1.25 mmol) as described previously for Example 451. (M+H)⁺=458.2, 460.2 (Br isotopic pattern).

Example 457

5-Cyano-2-(2-isopropylphenoxy)-N-(4-(trifluoromethyl)thiazol-2-yl)pyridin-3-amine

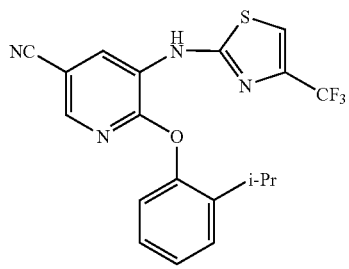

Prepared from Example 456 (103 mg, 0.225 mmol) as described previously for 452 to afford Example 457 (83 mg). (M+H)⁺=405.3.

Example 458

5-Dimethylamino-2-(2-isopropylphenoxy)-N-(4-(trifluoromethyl)thiazol-2-yl)pyridin-3-amine

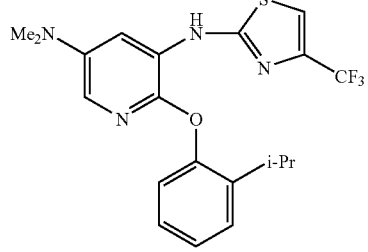

Prepared from Example 456 (25 mg, 0.055 mmol) as described previously for Example 453 to afford Example 458 (14 mg). (M+H)⁺=423.3.

Example 459

5-(4-Methoxybenzyl)methylamino-2-(2-isopropylphenoxy)-N-(4-(trifluoromethyl)thiazol-2-yl)pyridin-3-amine

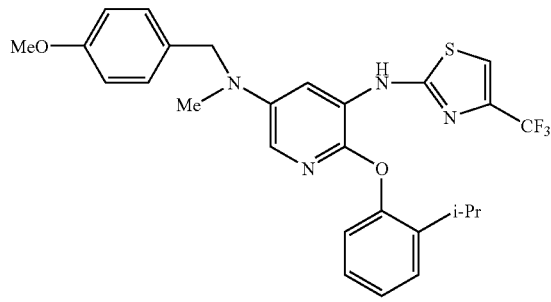

Prepared from Example 456 (25 mg, 0.055 mmol) as described previously for 453 except using (4-methoxybenzyl)methylamine in place of dimethylamine to afford Example 459 (16 mg). (M+H)⁺=529.3.

Example 460

N-(2-(2-tert-Butylphenoxy)thiophen-3-yl)-4-(pentafluoroethyl)thiazol-2-amine

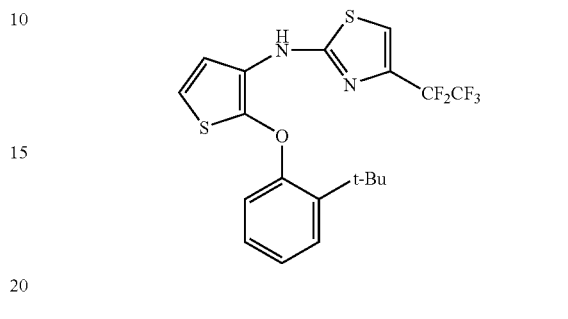

Example 460a 1-(2-(2-tert-Butylphenoxy)thiophen-3-yl)thiourea

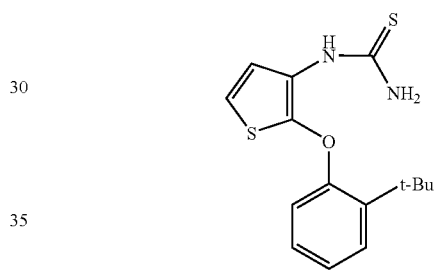

Prepared from Intermediate 3 (2.0 g, 8.10 mmol) as described previously for Example 450b to afford Example 460a (1.8 g). (M+H)⁺=307.3.

Example 460

Prepared from Example 460a (30 mg, 0.098 mmol) and 1-bromo-3,3,4,4,4-pentafluorobutan-2-one (0.098 mmol) following the procedure for the preparation of Example 450 to provide Example 460 (26 mg). (M+H)⁺=449.2.

Examples 461-464 listed in Table 16 were prepared following the procedures described for Example 460 using the commercially available α-haloketone shown.

TABLE 16

| Example | α-haloketone | Structure | (M + H)⁺ |
|---|---|---|---|
| 461 | ![F₃C-C(=O)-CH₂Br] | ![structure] | 399 |

TABLE 16-continued

| Example | α-haloketone | Structure | (M + H)+ |
|---|---|---|---|
| 462 | F3C-C(O)-CH(Cl)-CO2Et | thiophene-3-NH-thiazole(4-CF3, 5-CO2Et), 2-O-(2-t-Bu-phenyl) | 471 |
| 463 | Br-CH2-C(O)-C(O)-OEt | thiophene-3-NH-thiazole(4-CO2Et), 2-O-(2-t-Bu-phenyl) | 403 |
| 464 | Ph-C(O)-CH2Br | thiophene-3-NH-thiazole(4-Ph), 2-O-(2-t-Bu-phenyl) | 407 |

Examples 465-466 listed in Table 17 were prepared following the procedures described for Example 450 using Intermediates 5-7 and the appropriate α-haloketone.

TABLE 17

| Example | α-haloketone | Structure | (M + H)+ |
|---|---|---|---|
| 465 | t-Bu-C(O)-CH2Br | pyridine-3-NH-thiazole(4-t-Bu), 2-O-(2,2-dimethyl-2,3-dihydrobenzofuran-7-yl) | 396 |
| 466 | F3C-C(O)-CH(Cl)-CO2Et | pyridine-3-NH-thiazole(4-CF3, 5-CO2Et), 2-O-(2-OCF3-phenyl) | 494 |

TABLE 17-continued

| Example | α-haloketone | Structure | (M + H)+ |
|---|---|---|---|
| 467 | F₃C-C(=O)-CH(Cl)-CO₂Et | pyridine with NH-thiazole(CO₂Et,CF₃), O-linked 2,2-dimethyl-2,3-dihydrobenzofuran | 480 |
| 468 | t-Bu-C(=O)-CH₂Br | pyridine with NH-thiazole(t-Bu), O-linked 2-OCF₃-phenyl | 410 |
| 469 | t-Bu-C(=O)-CH₂Br | pyridine with NH-thiazole(t-Bu), O-linked 2,2-dimethyl-benzo[1,3]dioxole | 398 |

Example 470
2-(2-tert-Butylphenoxy)-N-(3-(phenylthiomethyl)-1,2,4-thiadiazol-5-yl)pyridin-3-amine

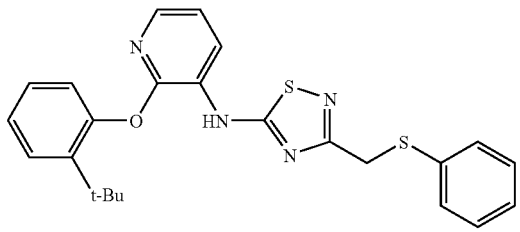

Example 470 was prepared from 2-(2-tert-butylphenoxy)-3-isothiocyanatopyridine (Example 1a) following the procedures described for Example 56. (M+H)+=449.

Example 471
2-(2-tert-Butylphenoxy)-N-(3-(phenylsulfinylmethyl)-1,2,4-thiadiazol-5-yl)pyridin-3-amine

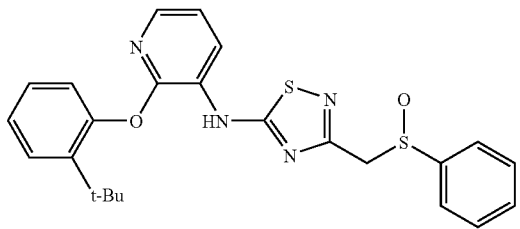

A mixture of 2-(2-tert-butylphenoxy)-N-(3-(phenylthiomethyl)-1,2,4-thiadiazol-5-yl)pyridin-3-amine (Example 470) (250 mg, 0.56 mmol), peracetic acid (32% wt/v, 132 µL, 0.56 mmol in DCM (3 mL) was stirred at rt for 2 h. The reaction mixture was diluted in ethyl acetate and washed with saturated sodium bicarbonate. The organic phase was separated, dried (MgSO₄), filtered and evaporated. The crude product was purified by preparative HPLC to give Example 471. (M+H)+=465; ¹H NMR (400 MHz, DMSO d₆) δ ppm 1.29 (s, 9 H), 4.33 (d, J=13.13 Hz, 1 H), 4.42 (d, J=13.13 Hz, 1 H), 6.91 (td, J=7.84, 1.51 Hz, 1 H), 7.08 (dd, J=7.84, 4.80, 1H), 7.16 (dt, J=7.58, 1.52, 1H), 7.22 (td, J=7.32, 1.76, 1H), 7.41 (dd, J=7.83, 1.52 Hz, 1 H), 7.5-7.7 (m, 5H), 7.75 (dd, J=4.80, 1.51 Hz, 1 H), 8.45 (dd, J=7.83, 1.51 Hz, 1H), 10.84 (s, 1 H).

Example 472
4-(2-(2-tert-Butylphenoxy)pyridin-3-yl)thiosemicarbazide

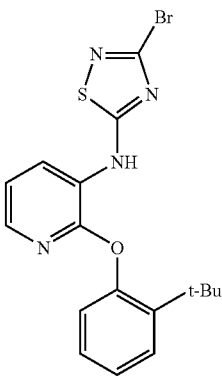

A mixture of sodium hydride (140 mg, 3.51 mmol) and cyanamide (148 mg, 3.51 mmol) in EtOH (10 mL) was stirred at rt for 15 min. 2-(2-tert-butylphenoxy)-3-isothiocyanatopyridine (Example 1a) (1 g, 3.51 mmol) was added and mixture was stirred for 2 h. The solvent was removed and the residue was dissolved in EtOAc (10 mL), bromine (562 mg, 3.51 mmol) was added and mixture was stirred for 18 h. The reaction mixture was washed with water, dried (anh. MgSO$_4$), filtered and evaporated. The crude material was purified by flash chromatography on silica gel (10% EtOAc/Hexanes) and by preparative HPLC to give Example 472 (5 mg, TFA salt) as a white powder. (M+H)+=405. $^1$H NMR (400 MHz, DMSO d$_6$) δ ppm 1.30 (s, 9 H), 6.93 (dd, J=7.83, 1.52 Hz, 1 H), 7.1-7.3 (m, 3 H), 7.43 (dd, J=7.83, 1.77 Hz, 1 H), 7.83 (dd, J=4.80, 1.51 Hz, 1 H), 8.65 (dd, J=7.84, 1.51 Hz, 1 H), 11.13 (s, 1 H).

Example 473

N-(5-((Benzylmethyl)amino)methyl)-1,3,4-thiadiazol-2-yl)-2-(2-tert-butylphenoxy)pyridin-3-amine

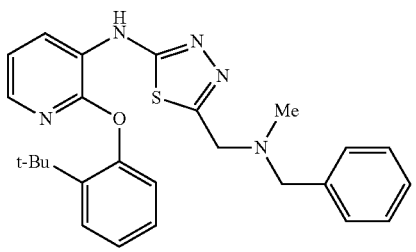

Example 473a 2-(2-tert-Butylphenoxy)-N-(5-(chloromethyl)-1,3,4-thiadiazol-2-yl)pyridin-3-amine

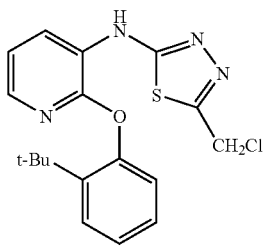

Example 473a was synthesized following the procedure for Example 1 using 4-(2-(2-tert-butylphenoxy)pyridin-3-yl)thiosemicarbazide (Example 1b) with chloroacetyl chloride.

Example 473

A mixture of Example 473a (25 mg, 0.07 mmol), N-benzylmethylamine (45 µL, 0.35 mmol) in DMF (2 mL) was agitated at rt for 3 h. The crude material was purified by preparative HPLC to give Example 473 (11 mg, 2 TFA salt) as a white solid. (M+H)+=460. $^1$H NMR (400 MHz, DMSO d$_6$) δ ppm 1.30 (s, 9 H), 2.07 (s, 3H), 6.93 (d, J=9.09 Hz, 1 H), 7.1-7.3 (m, 3H), 7.4-7.5 (m, 4H), 7.73 (d, J=4.29 Hz, 1 H), 7.96 (d, J=8.08 Hz, 1 H), 8.18 (d, J=8.33 Hz, 1 H) 8.83 (d, J=7.08 Hz, 1 H).

Example 474

N-(5-((4-Benzylpiperazin-1-yl)methyl)-1,3,4-thiadiazol-2-yl)-2-(2-tert-butylphenoxy)pyridin-3-amine

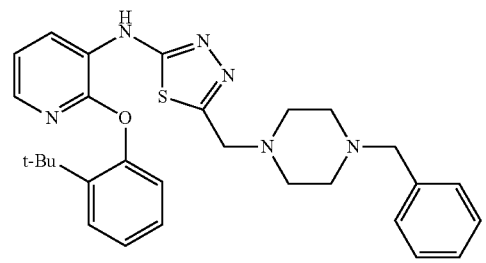

Example 474 was prepared following the procedures described for Example 473. (M+H)+=515.

Examples 475-476 listed in Table 18 were prepared following the procedures described for Example 1 using Intermediates 8-9.

TABLE 18

| Example | Structure | (M + H)+ |
|---------|-----------|----------|
| 475 | ![structure] | 460 |
| 476 | ![structure] | 453 |

Examples 477-495 listed in Table 6 were prepared following the procedure described for Example 172.

Example 496

Ethyl 3-(2-(2-tert-butylphenoxy)pyridin-3-ylamino)-1-(cyclopropylmethyl)-1H-pyrazole-5-carboxylate

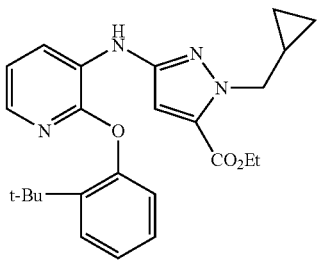

Example 496a 3-(2-(2-tert-Butylphenoxy)pyridin-3-ylamino)-1-(cyclopropylmethyl)-1H-pyrazole-5-carboxylic acid

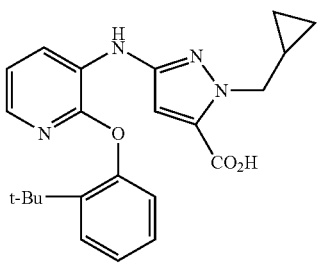

To a solution of 3-(2-(2-tert-butylphenoxy)pyridin-3-ylamino)-1-(cyclopropylmethyl)-1H-pyrazole-5-carbonitrile (Example 184) (64.9 mg, 0.17 mmol) in water (1 mL) was added the aqueous sodium hydroxide solution (2M in water, 418 µL, 0.84 mmol) and the mixture was heated at 200° C. for 10 min in the microwave. After cooling to 23° C., 1N HCl was added slowly till pH=2 and the mixture was extracted with ethyl acetate (3×). Combined organic layers were washed with water, brine, dried over $Na_2SO_4$, filtered and concentrated in vacuo. The residue was purified by preparative HPLC to yield 45 mg (65% TFA salt) of Example 496a. $(M+H)^+=407$.

Example 496

To a solution of 3-(2-(2-tert-butylphenoxy)pyridin-3-ylamino)-1-(cyclopropylmethyl)-1H-pyrazole-5-carboxylic acid (Example 20a) (38 mg, 0.073 mmol) in DCM (730 µL) was added 1-ethyl-3-(3-dimethylaminopropyl) carbodiimide (34 mg, 0.156 mmol), 1-hydroxybenzotriazole hydrate (24 mg, 0.156 mmol) and ethanol (10 µL, 0.156 mmol The mixture was stirred for 3 days at 23° C. then concentrated in vacuo. 1N HCl was added (25 mL) and the aqueous layer was extracted with ethyl acetate (3×). The combined organic layers were washed with water (50 mL), brine (50 mL) and dried (anh. $Na_2SO_4$), filtered and concentrated in vacuo. The residue was purified preparative HPLC to yield 26 mg (81%, TFA salt) of Example 496. $(M+H)^+=435$. $^1H$ NMR (400 MHz, DMSO-$d_6$) δ ppm 8.44 (s, 1H), 8.42 (dd, 1H, J=7.8, 1.5 Hz), 7.46 (dd, 1H, J=4.8, 1.5 Hz), 7.40 (dd, 1H, J=7.8, 1.5 Hz), 7.21 (td, 1H, J=7.8, 1.7 Hz), 7.13 (td, 1H, J=7.8, 1.5 Hz), 7.00 (dd, 1H, J=7.9, 4.8 Hz), 6.89 (dd, 1H, J=7.8, 1.2 Hz), 6.63 (s, 1H), 4.31-4.26 (m, 4H), 1.31 (s, 9H), 1.31-1.26 (m, 1H), 1.29 (t, 3H, J=7.1 Hz), 0.49-0.46 (m, 2H), 0.40-0.36 (m, 2H).

Example 497

2-(2-tert-Butylphenoxy)-N-(5-(3-(3-(dimethylamino)-2,2-dimethylpropoxy)phenyl)-4-(trifluoromethyl)thiazol-2-yl)pyridin-3-amine

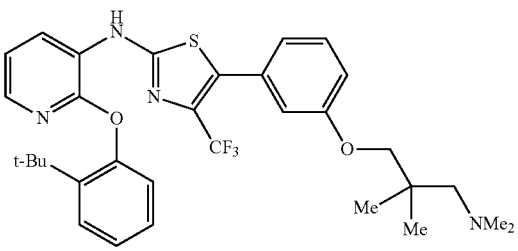

A suspension of $PPh_3$-resin (3.0 mmol/g resin, 167 mg, 0.5 mmol) in THF was stirred at rt for 15 min and 3-(dimethylamino)-2,2-dimethylpropan-1-ol (38 µL, 0.24 mmol) and DBAD (35 mg, 0.15 mmol) were added. The mixture was stirred at rt for 30 min and 3-(2-(2-(2-tert-butylphenoxy)pyridin-3-ylamino)-4-(trifluoromethyl)-1H-imidazol-5-yl)phenol (Example 117, 50 mg, 0.10 mmol) was added. The mixture was stirred at rt for 2 h. Another 38 µL of 3-(dimethylamino)-2,2-dimethylpropan-1-ol and 35 mg of DBAD were added and then stirred at rt for 30 min. LC-MS showed the formation of desired product and two by-products. The reaction was filtered and the filtrate was evaporated to give the crude product. Purification of the crude product by reverse phase preparative HPLC provided Example 497 as a colorless film (13.5 mg). $(M+H)^+=599.2$.

Example 498

N-(5-(4-(Benzyloxy)phenyl)-4-(trifluoromethyl)thiazol-2-yl)-2-(2-tert-butylphenoxy)pyridin-3-amine

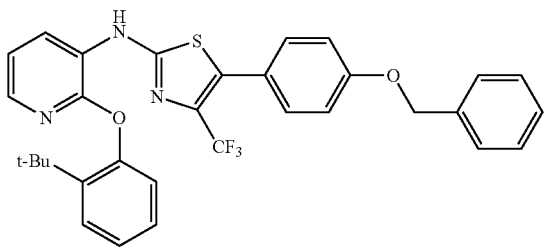

To a solution of compound 107a (340 mg, 0.72 mmol) in toluene/methanol (2:1, 4 mL) was added 4-benzyloxy phenyl boronic acid (328 mg, 1.44 mmol), 2 M $Na_2CO_3$ solution (1.44 ml, 2.88 mmol). The mixture was bubbled with nitrogen, added catalyst $Pd(PPh_3)_4$ (83 mg, 0.072 mmol) and heated at 85° C. overnight. The mixture was diluted with EtOAc, washed with brine, dried over magnesium sulfate, filtered and evaporated to give the crude product. Purification of crude product by flash chromatography (40 g silica, 0-20% EtOAc/hexane) provided Example 498 (245 mg) as a white foam. (M+H)⁺=576.3.

Example 499

4-(2-(2-(2-tert-Butylphenoxy)pyridin-3-ylamino)-4-(trifluoromethyl)thiazol-5-yl)phenol

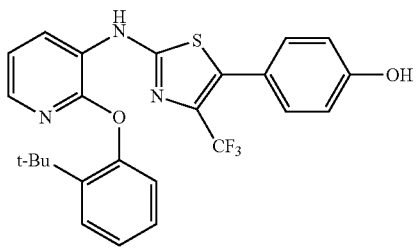

To a solution of Example 498 (164 mg, 0.28 mmol) in MeOH/EtOAc (1:1, 10 mL) was added a few drops of Raney Ni in water. The mixture was stirred under hydrogen atmosphere at rt overnight. The reaction was filtered through a layer of Celite®. The filtrate was concentrated to give the crude product. Purification of the crude product by flash chromatography (silica, 0-50% EtOAc/hexane) provided Example 499 (105 mg) as a white foam. (M+H)⁺=486.0.

Example 500

2-(2-tert-Butylphenoxy)-N-(5-(4-(3-(dimethylamino)-2,2-dimethylpropoxy)phenyl)-4-(trifluoromethyl)thiazol-2-yl)pyridin-3-amine

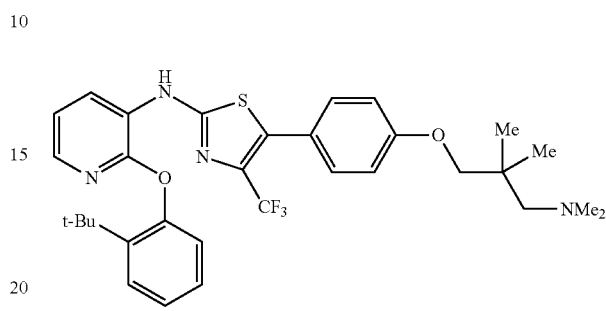

Example 500 was prepared according to a similar procedure described for Example 217 from Example 499 and 3-(dimethylamino)-2,2-dimethylpropan-1-ol. Example 500 was obtained as a colorless film (3 mg). (M+H)⁺=599.3.

Examples 501-502 listed in Table 19 were prepared following the procedure(s) indicated.

TABLE 19

| Example | Procedure(s) Used | Structure | (M + H)⁺ |
|---|---|---|---|
| 501 | Example 94 | 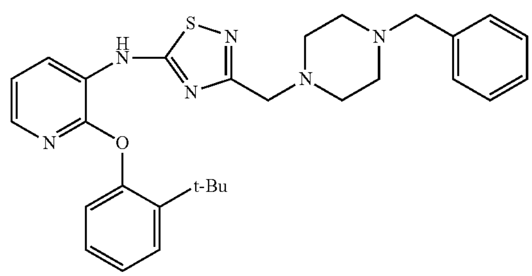 | 515 |
| 502 | Example 106 | 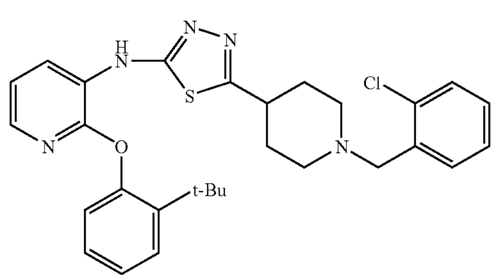 | 535 |

Example A1-A50 listed in Table 20 were prepared following the procedure(s) indicated.

TABLE 20

| Example | Procedure(s) Used | Structure | (M + H)+ |
|---|---|---|---|
| A1 | Example 315 | 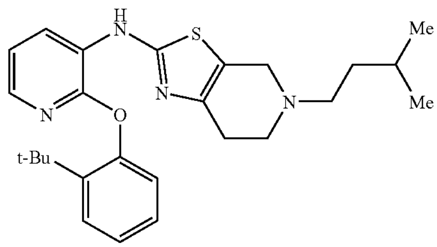 | 451.2 |
| A2 | Example 315 | 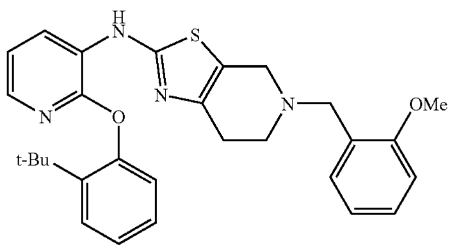 | 501.2 |
| A3 | Example 315 | 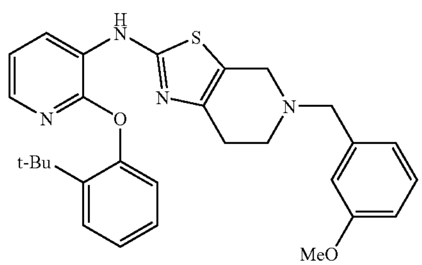 | 501.1 |
| A4 | Example 315 | 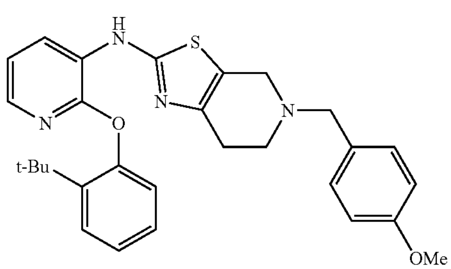 | 501.1 |
| A5 | Example 315 | 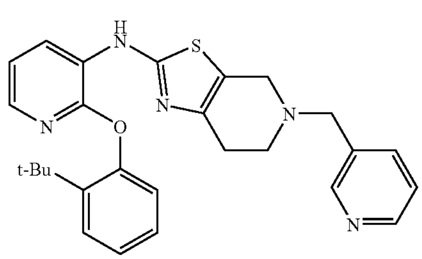 | 472.1 |

TABLE 20-continued

| Example | Procedure(s) Used | Structure | (M + H)+ |
|---|---|---|---|
| A6 | Example 315 | 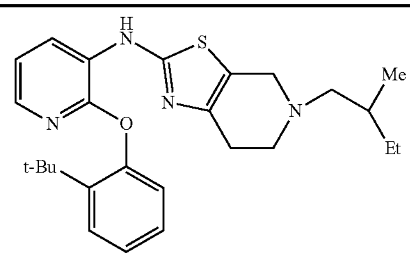 | 451.1 |
| A7 | Example 315 | 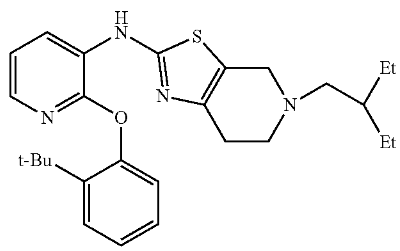 | 465.1 |
| A8 | Example 315 | 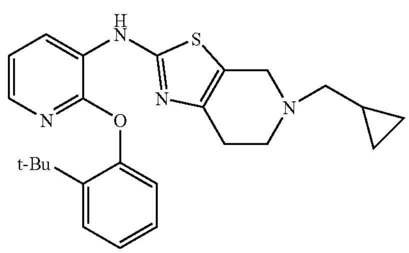 | 435.1 |
| A9 | Example 315 | 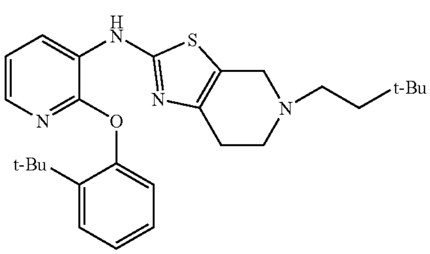 | 465.1 |
| A10 | Example 315 | 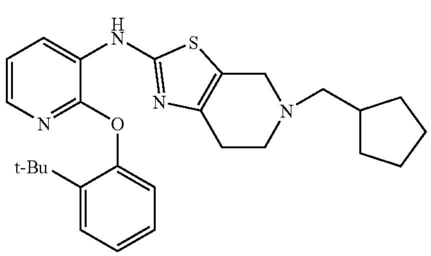 | 463.1 |
| A11 | Example 315 | 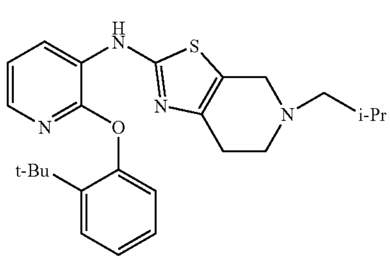 | 423.1 |

TABLE 20-continued
| Example | Procedure(s) Used | Structure | (M + H)+ |
|---|---|---|---|
| A12 | Example 315 | 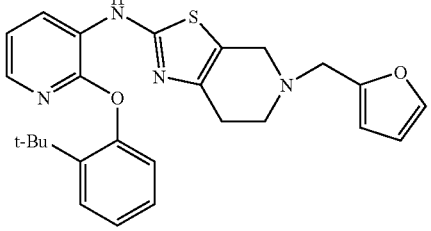 | 461.3 |
| A13 | Example 315 | 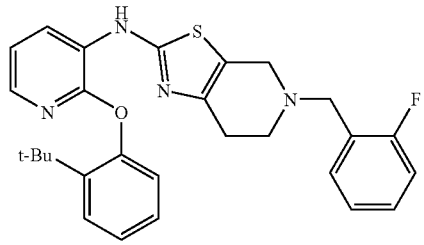 | 489.3 |
| A14 | Example 315 | 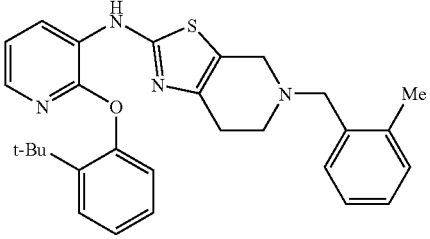 | 485.3 |
| A15 | Example 315 | 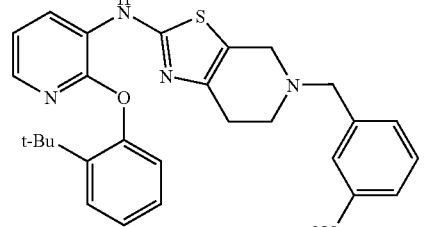 | 496.3 |
| A16 | Example 315 | 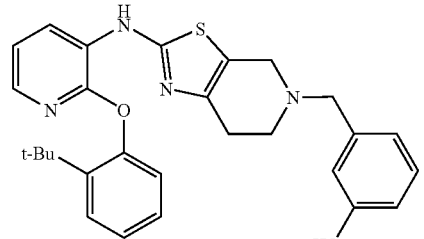 | 487.3 |
| A17 | Example 315 | 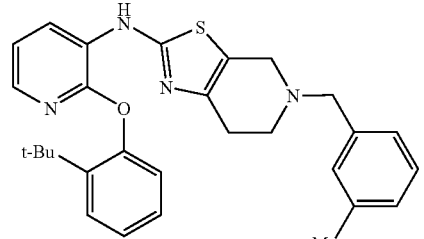 | 485.4 |

TABLE 20-continued

| Example | Procedure(s) Used | Structure | (M + H)+ |
|---|---|---|---|
| A18 | Example 315 | 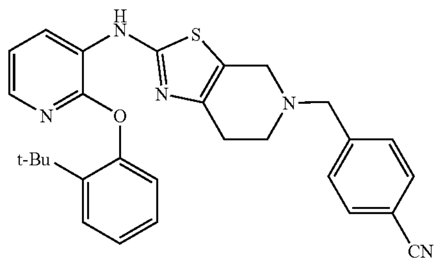 | 496.3 |
| A19 | Example 315 | 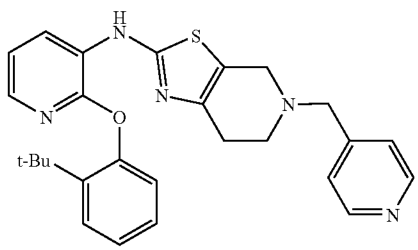 | 472.3 |
| A20 | Example 315 | 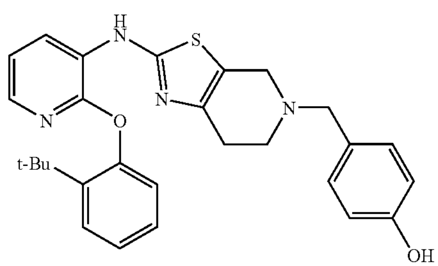 | 487.3 |
| A21 | Example 315 | 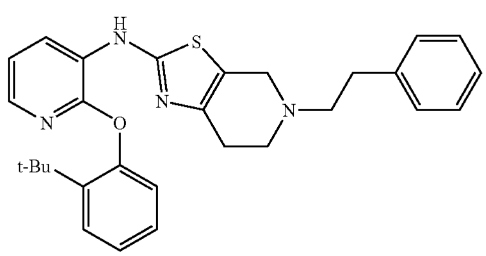 | 485.4 |
| A22 | Example 315 | 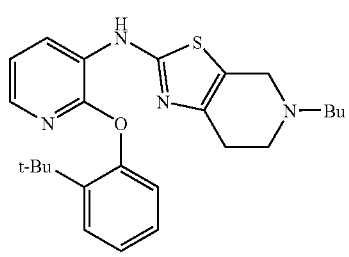 | 437.3 |
| A23 | Example 315 | 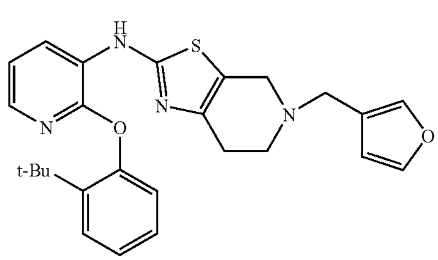 | 461.3 |

TABLE 20-continued

| Example | Procedure(s) Used | Structure | (M + H)+ |
|---|---|---|---|
| A24 | Example 315 | 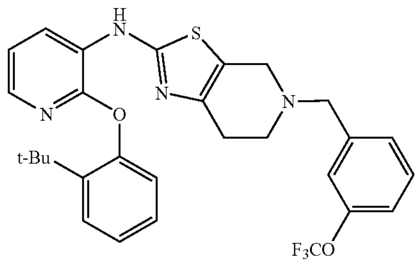 | 555.3 |
| A25 | Example 361 | 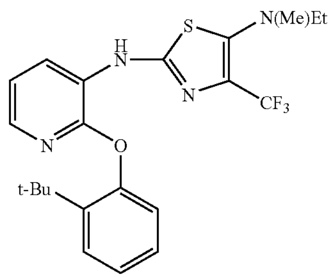 | 451.1 |
| A26 | Example 361 | 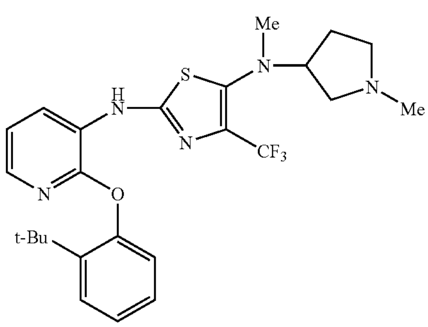 | 506.2 |
| A27 | Example 361 | 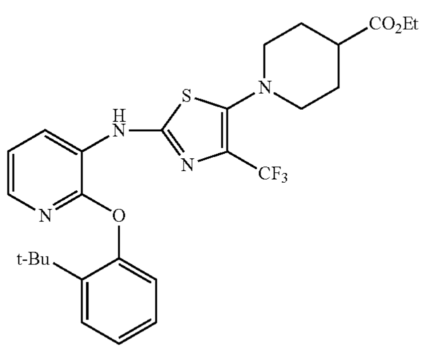 | 576.3 |
| A28 | Example 361 | 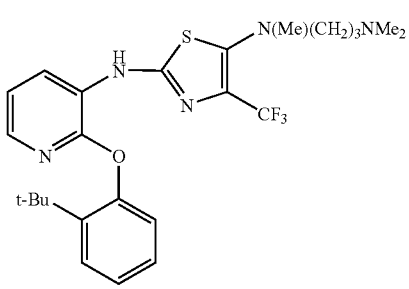 | 549.2 |

TABLE 20-continued

| Example | Procedure(s) Used | Structure | (M + H)+ |
|---------|-------------------|-----------|----------|
| A29 | Example 361 | [thiazole with N(CH₂CH₂OMe)₂, CF₃, NH-pyridine-O-(2-t-Bu-phenyl)] | 508.2 |
| A30 | Example 361 | [thiazole with piperazine-CO₂Et, CF₃, NH-pyridine-O-(2-t-Bu-phenyl)] | 525.2 |
| A31 | Example 361 | [thiazole with N-methyl-diazepane, CF₃, NH-pyridine-O-(2-t-Bu-phenyl)] | 550.2 |
| A32 | Example 361 | [thiazole with piperidine-CO₂Et, CF₃, NH-pyridine-O-(2-t-Bu-phenyl)] | 506.2 |

TABLE 20-continued

| Example | Procedure(s) Used | Structure | (M + H)+ |
|---|---|---|---|
| A33 | Example 361 | 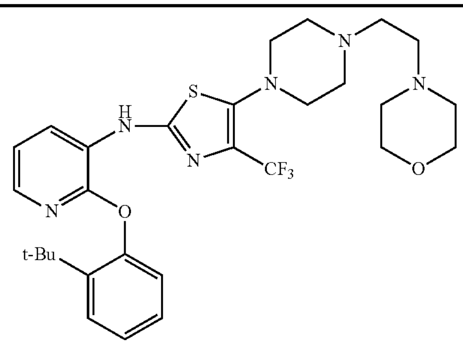 | 549.2 |
| A34 | Example 361 | 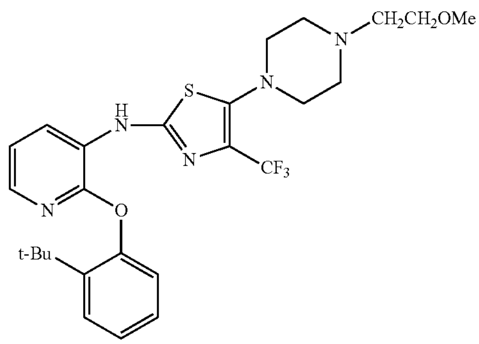 | 591.3 |
| A35 | Example 361 | 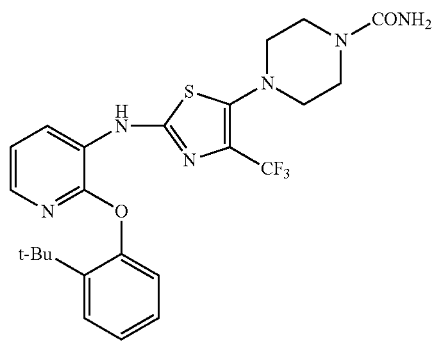 | 536.2 |
| A36 | Example 361 | 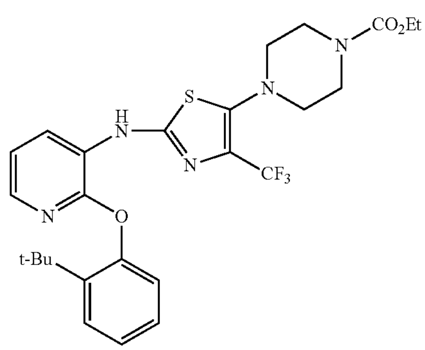 | 520.1 |

TABLE 20-continued

| Example | Procedure(s) Used | Structure | (M + H)+ |
|---|---|---|---|
| A37 | Example 361 | [structure with piperazine-N-CO2Me, thiazole-CF3, NH-pyridine-O-(t-Bu-phenyl)] | 520.1 |
| A38 | Example 361 | [structure with N(Me)(CH2)2NMe2, thiazole-CF3, NH-pyridine-O-(t-Bu-phenyl)] | 494.2 |
| A39 | Example 361 | [structure with piperazine-(CH2)2O(CH2)2OH, thiazole-CF3, NH-pyridine-O-(t-Bu-phenyl)] | 566.2 |
| A40 | Example 361 | [structure with H2NOC-pyrrolidine, thiazole-CF3, NH-pyridine-O-(t-Bu-phenyl)] | 506.1 |

TABLE 20-continued

| Example | Procedure(s) Used | Structure | (M + H)+ |
|---|---|---|---|
| A41 | Example 361 | 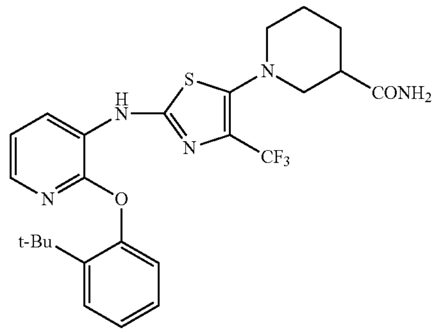 | 520.2 |
| A42 | Example 361 | 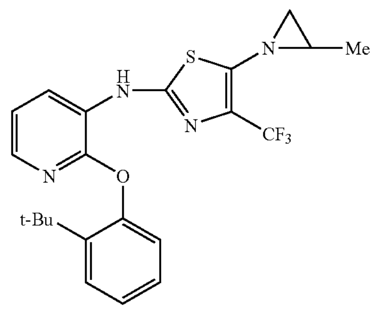 | 449.1 |
| A43 | Example 361 | 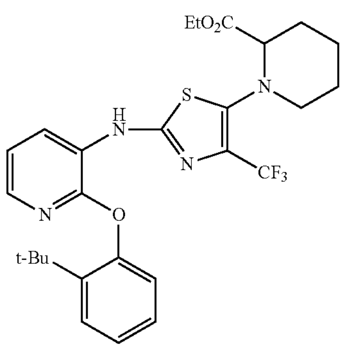 | 549.2 |
| A44 | Example 361 | 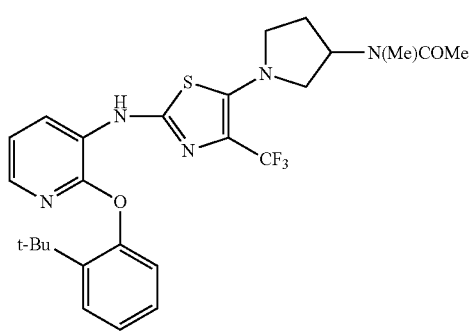 | 534.2 |

TABLE 20-continued

| Example | Procedure(s) Used | Structure | (M + H)+ |
|---|---|---|---|
| A45 | Example 361 | 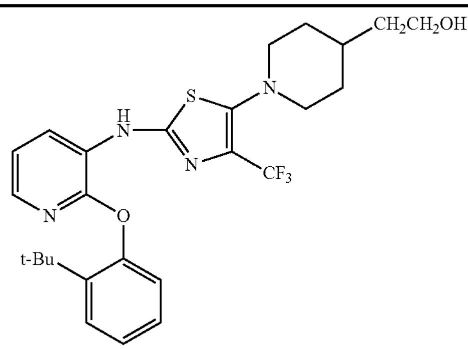 | 521.1 |
| A46 | Example 361 | 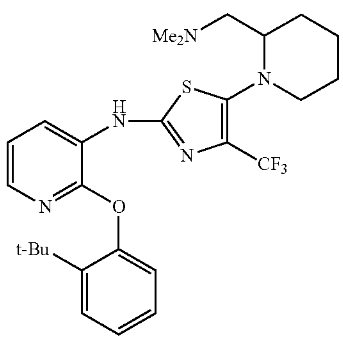 | 534.1 |
| A47 | Example 361 | 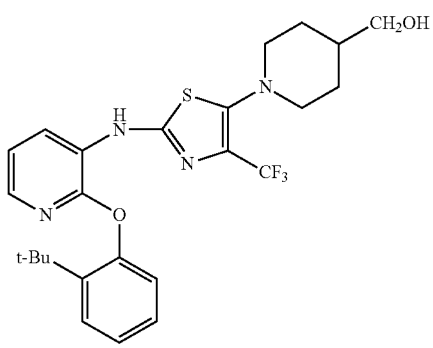 | 507.1 |
| A48 | Example 361 | 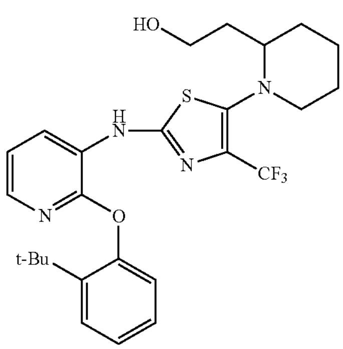 | 521.1 |

TABLE 20-continued

| Example | Procedure(s) Used | Structure | (M + H)⁺ |
|---|---|---|---|
| A49 | Example 361 | 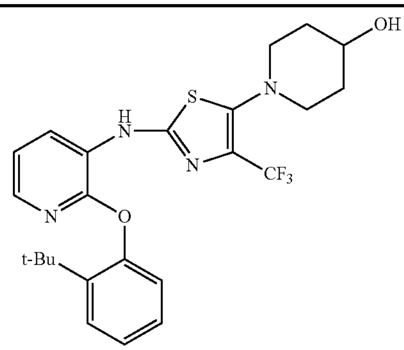 | 493.1 |
| A50 | Example 361 | 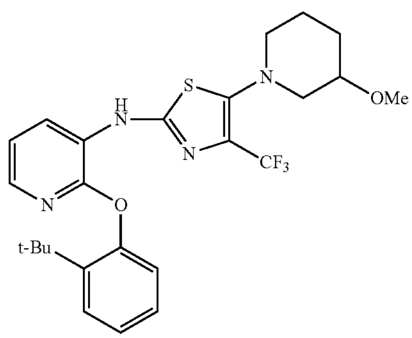 | 507.2 |

Example A51

2-(2-tert-Butylphenoxy)-N-(5-(3-methyl-1,2,4-oxadiazol-5-yl)-4-(trifluoromethyl)thiazol-2-yl)pyridin-3-amine

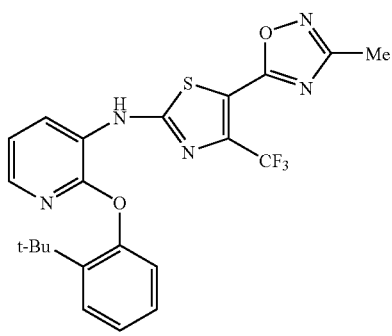

Example A51a 2-(2-(2-tert-Butylphenoxy)pyridin-3-ylamino)-4-(trifluoromethyl)thiazole-5-carboxylic acid

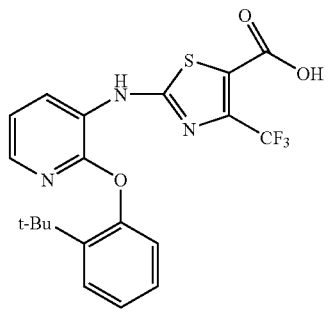

Example A51a was prepared from ethyl 2-(2-(2-tert-butylphenoxy)pyridin-3-ylamino)-4-(trifluoromethyl)thiazole-5-carboxylate (Example 238) according to the procedure described for Example 251a.

Example A51

A mixture of Example A51a (40 mg, 0.091 mmol), N-hydroxyacetamidine (10 mg, 0.14 mmol, DIC (43 μL, 0.27 mmol), HOBt (12 mg, 0.091 mmol) in acetonitrile (1.5 mL) was heated at 160° C. under microwave for 15 min. The reaction was cooled and concentrated. The residue was purified by reverse preparative HPLC to give Example A51 (25 mg). (M+H)+=476.2.

Example A52

2-(2-tert-Butylphenoxy)-N-(5-(3-phenyl-1,2,4-oxadiazol-5-yl)-4-(trifluoromethyl)thiazol-2-yl)pyridin-3-amine

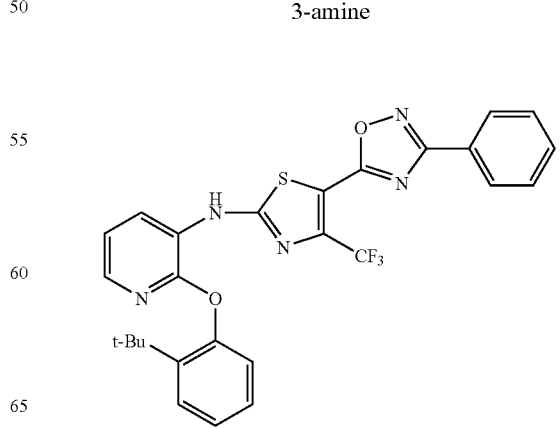

Example A52 was prepared following the procedure described for Example A51 as a yellow film. (M+H)+=538.3.

Example A53

2-(2-tert-Butylphenoxy)-N-(5-(5-methyl-1,2,4-oxadiazol-3-yl)-4-(trifluoromethyl)thiazol-2-yl)pyridin-3-amine

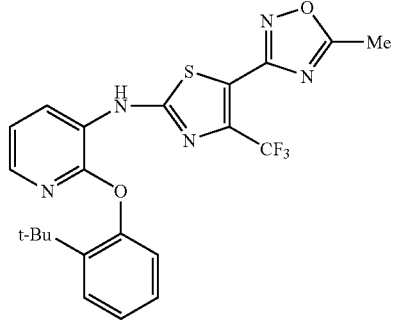

Example A53a (Z)-2-(2-(2-tert-Butylphenoxy)pyridin-3-ylamino)-N'-hydroxy-4-(trifluoromethyl)thiazole-5-carboxamidine

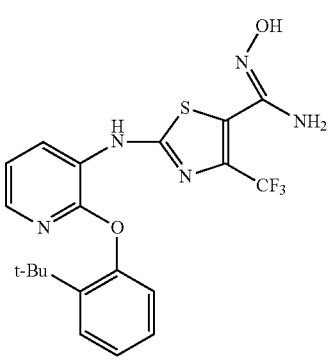

A mixture of 2-(2-(2-tert-butylphenoxy)pyridin-3-ylamino)-4-(trifluoromethyl)thiazole-5-carbonitrile (Example 404, 177 mg, 0.42 mmol), hydroxylamine hydrochloride salt (145 mg, 2.1 mmol), DIPEA (732 µL, 4.2 mmol) in ethanol (5 mL) was heated at 60° C. for 5 h. The reaction was diluted with ethyl acetate and washed with brine. The organic layer was separated and evaporated to give the crude product. Purification of the crude product by flash chromatography (silica, 0-80% EtOAc/hexane gradient) gave Example A53a (120 mg) as white crystals. (M+H)+=452.1.

Example A53

A mixture of Example A53a (40 mg, 0.091 mmol), acetic acid (10 µL, 0.16 mmol), DIC (43 µL, 0.27 mmol), HOBt (12 mg, 0.091 mmol) in acetonitrile (1.5 mL) was heated at 160° C. under microwave for 15 min. The reaction was cooled and concentrated. The residue was purified by reverse preparative HPLC to give Example A53 (13 mg). (M+H)+=476.1.

Example A54

(2-(2-(2-tert-Butylphenoxy)pyridin-3-ylamino)-5-phenylthiazol-4-yl)methanol

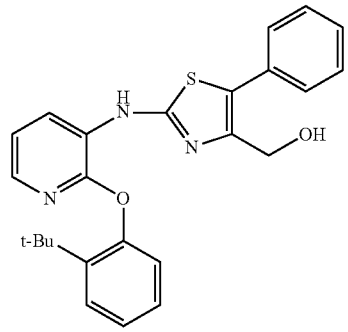

Example A54 was prepared according to a similar procedure described for Example 251. (M+H)+=432.2.

Example A55

2-(2-tert-Butylphenoxy)-N-(4-(ethoxymethyl)-5-phenylthiazol-2-yl)pyridin-3-amine

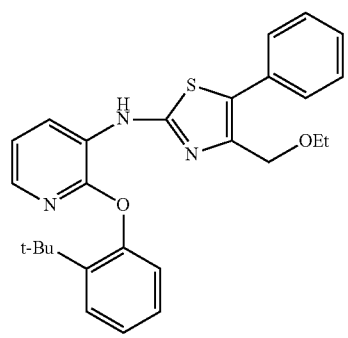

Example A55a 2-(2-tent-Butylphenoxy)-N-(4-(chloromethyl)-5-phenylthiazol-2-yl)pyridin-3-amine

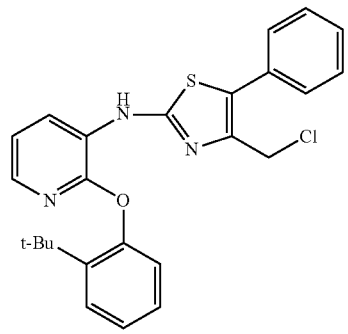

To a solution of Example A54 (170 mg, 0.39 mmol) in DCM (6 mL) at rt was added sulfonyl chloride (114 µL, 1.57 mmol). The mixture was stirred at rt for 2 h. The solvent was removed to give Example A55a (170 mg) as a yellow foam. (M+H)⁺=450.2.

Example A55

A small piece of sodium was added to ethanol (2 mL) and stirred at rt until the sodium was completely disappeared to give a light yellow solution. A solution of Example A55a (20 mg) in THF (1 mL) was added. The reaction was stirred at rt overnight and then quenched with water. The mixture was concentrated and the residue was partitioned between EtOAc and brine. The organic layer was isolated and evaporated. The residue was purified by reverse phase preparative HPLC to Example A55 (2.5 mg) as a colorless film. (M+H)⁺=486.0.

Example A56-A124 listed in Table 21 were prepared following the procedure(s) indicated.

TABLE 21

| Example | Procedure(s) Used | Structure | (M + H)⁺ |
|---|---|---|---|
| A56 | Example A55 | 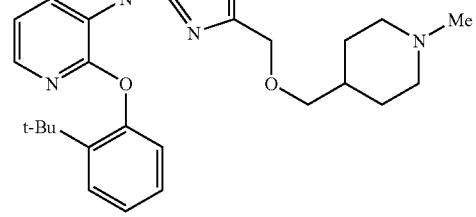 | 543.2 |
| A57 | Example A55 | 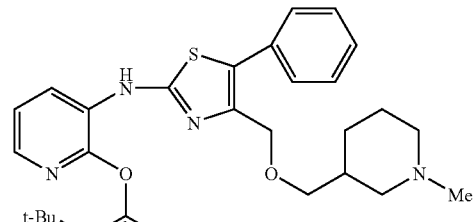 | 543.2 |
| A58 | Example A55 | 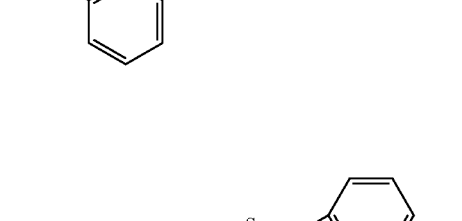 | 488.2 |
| A59 | Example A55 | 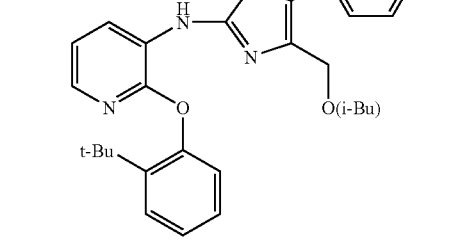 | 531.2 |

TABLE 21-continued

| Example | Procedure(s) Used | Structure | (M + H)+ |
|---|---|---|---|
| A60 | Example A55 | 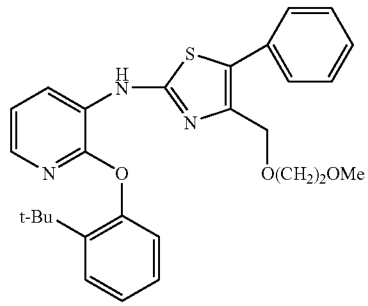 | 490.1 |
| A61 | Example A55 | 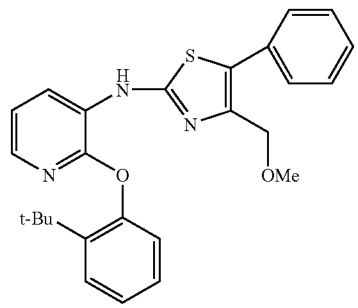 | 446.2 |
| A62 | Example 217 | 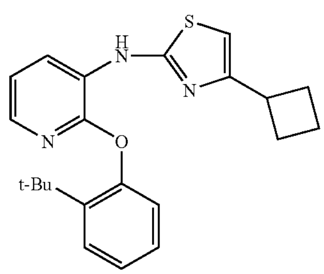 | 380.3 |
| A63 | Example 217 | 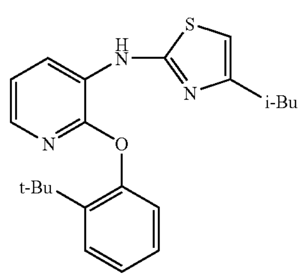 | 382.3 |
| A64 | Example 217 | 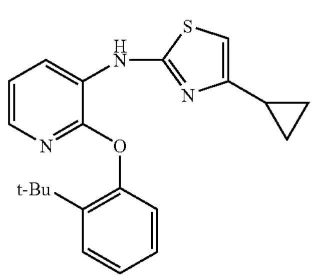 | 366.3 |

TABLE 21-continued

| Example | Procedure(s) Used | Structure | (M + H)⁺ |
|---|---|---|---|
| A65 | Example 217 | 3-(t-Bu-phenoxy)pyridin-2-yl-NH-thiazole-4-i-Pr | 368.3 |
| A66 | Example 217 | 3-(t-Bu-phenoxy)pyridin-2-yl-NH-thiazole-4-Me | 340.3 |
| A67 | Example 217 | 3-(t-Bu-phenoxy)pyridin-2-yl-NH-thiazole-4-CH₂CF₃ | 408.4 |
| A68 | Example 217 | 3-(t-Bu-phenoxy)pyridin-2-yl-NH-thiazole-5-Me-4-CF₃ | 408.3 |
| A69 | Example 217 | 3-(t-Bu-phenoxy)pyridin-2-yl-NH-thiazole-5-CF₃ | 394.3 |

TABLE 21-continued

| Example | Procedure(s) Used | Structure | (M + H)+ |
|---|---|---|---|
| A70 | Example 217 | (pyridine-NH-thiazole-i-Pr, pyridine-O-(2-t-Bu-phenyl)) | 368.4 |
| A71 | Example 217 | (pyridine-NH-thiazole-Et, pyridine-O-(2-t-Bu-phenyl)) | 354.3 |
| A72 | Example 217 | (pyridine-NH-(tetrahydrobenzothiazole-CH₂OH), pyridine-O-(2-t-Bu-phenyl)) | 410.4 |
| A73 | Example 217 | (pyridine-NH-(dihydropyrano-thiazole), pyridine-O-(2-t-Bu-phenyl)) | 382.4 |
| A74 | Example 217 | (pyridine-NH-(tetrahydrobenzothiazole-CO₂Et), pyridine-O-(2-t-Bu-phenyl)) | 452.4 |

TABLE 21-continued

| Example | Procedure(s) Used | Structure | (M + H)+ |
|---------|-------------------|-----------|----------|
| A75 | Example 323 | 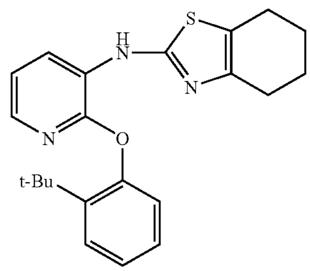 | 380.3 |
| A76 | Example 323 | 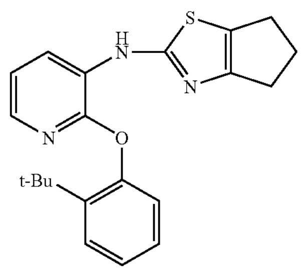 | 366.3 |
| A77 | Example 323 | 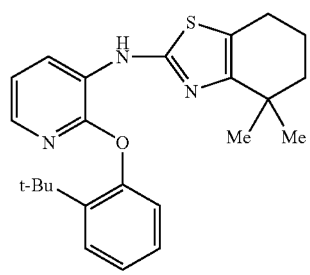 | 408.4 |
| A78 | Example 323 | 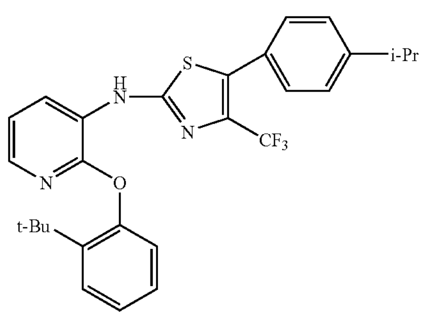 | 512.3 |
| A79 | Example 323 | 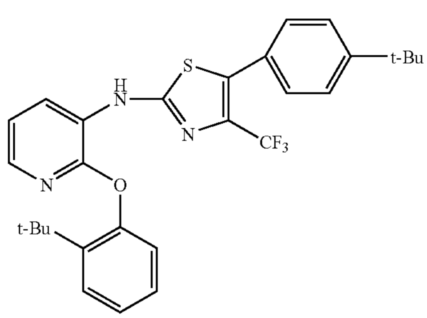 | 526.3 |

TABLE 21-continued

| Example | Procedure(s) Used | Structure | (M + H)+ |
|---------|-------------------|-----------|----------|
| A80 | Example 323 | 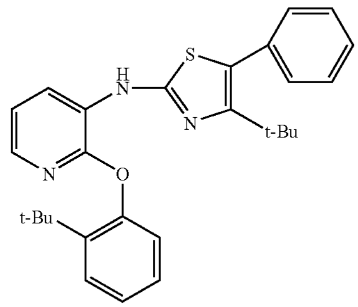 | 458.3 |
| A81 | Example 323 | 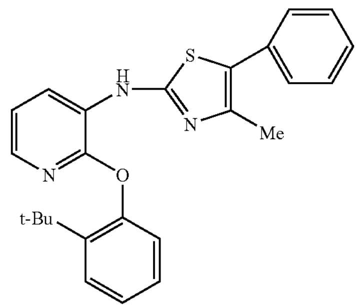 | 416.3 |
| A82 | Example 323 | 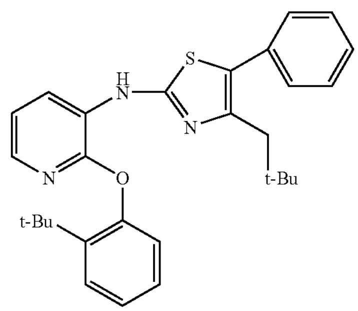 | 472.3 |
| A83 | Example 323 | 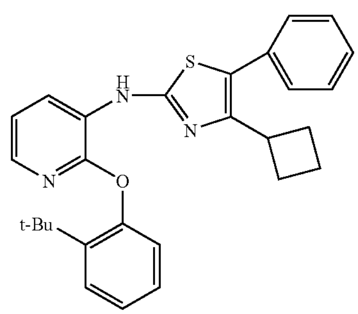 | 456.3 |
| A84 | Example 323 | 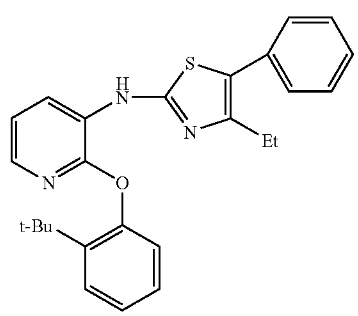 | 430.3 |

TABLE 21-continued

| Example | Procedure(s) Used | Structure | (M + H)+ |
|---|---|---|---|
| A85 | Example 323 | 3-pyridyl-NH-thiazole (5-phenyl, 4-i-Bu); 2-position O-linked to 2-t-Bu-phenyl | 458.3 |
| A86 | Example 323 | 3-pyridyl-NH-thiazole (5-phenyl, 4-i-Pr); 2-position O-linked to 2-t-Bu-phenyl | 444.3 |
| A87 | Example 323 | 3-pyridyl-NH-thiazole (5-[4-(CH$_2$)$_3$N(Me)Et-phenyl], 4-CF$_3$); 2-position O-linked to 2-t-Bu-phenyl | 569.2 |
| A88 | Example 323 | 3-pyridyl-NH-thiazole (5-[3-(CH$_2$)$_3$NH(Me)Et-phenyl], 4-CF$_3$); 2-position O-linked to 3-t-Bu-phenyl | 569.2 |
| A89 | Example 323 | 3-pyridyl-NH-thiazole (5-phenyl, 4-C(Me)$_2$(CH$_2$)$_2$N(Me)Et); 2-position O-linked to 2-t-Bu-phenyl | 529.3 |

TABLE 21-continued

| Example | Procedure(s) Used | Structure | (M + H)+ |
|---|---|---|---|
| A90 | Example 323 | 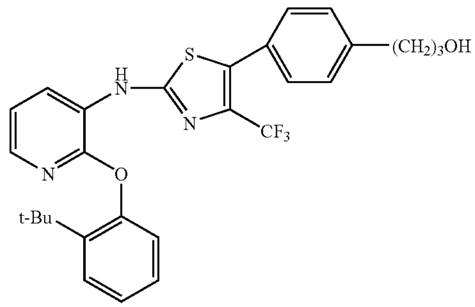 | 528.1 |
| A91 | Example 323 | 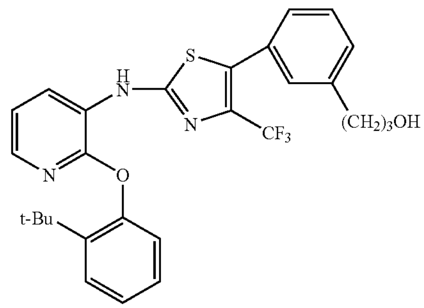 | 528.2 |
| A92 | Example 323 | 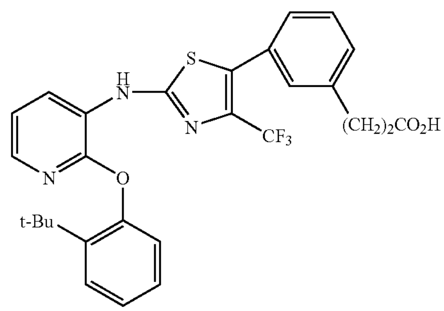 | 542.1 |
| A93 | Example 323 | 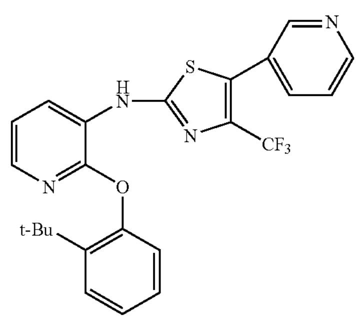 | 471.1 |
| A94 | Example 323 | 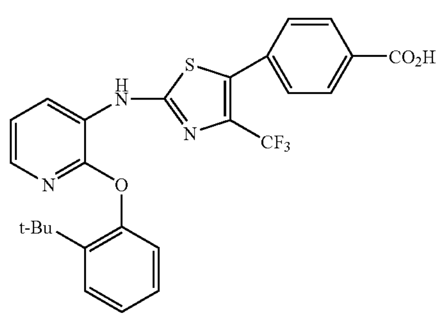 | 514 |

TABLE 21-continued
| Example | Procedure(s) Used | Structure | (M + H)+ |
|---|---|---|---|
| A95 | Example 323 | 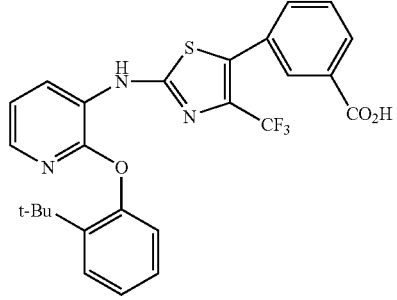 | 514 |
| A96 | Example 323 | 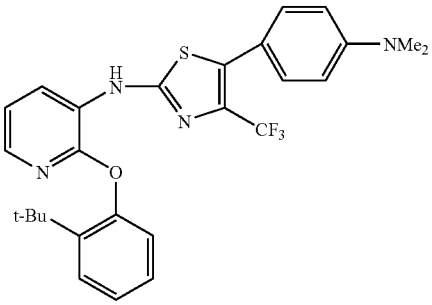 | 513.1 |
| A97 | Example 323 | 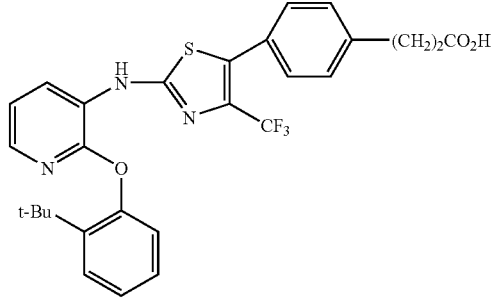 | 542.1 |
| A98 | Example 323 | 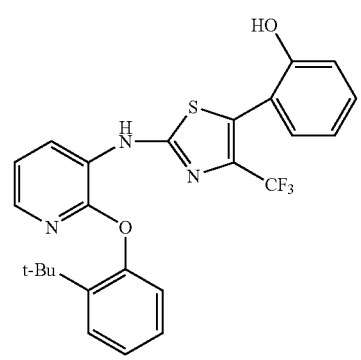 | 486 |

TABLE 21-continued

| Example | Procedure(s) Used | Structure | (M + H)+ |
|---|---|---|---|
| A99 | Example 323 | 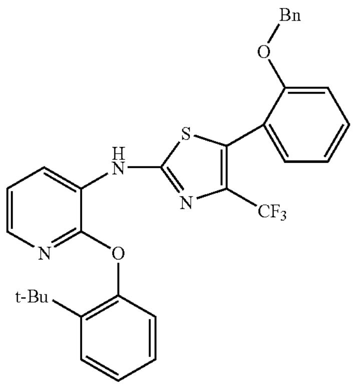 | 576 |
| A100 | Example 323 | 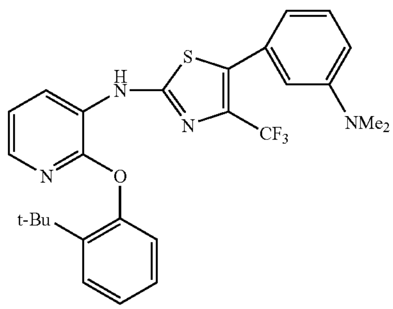 | 513.1 |
| A101 | Example 323 | 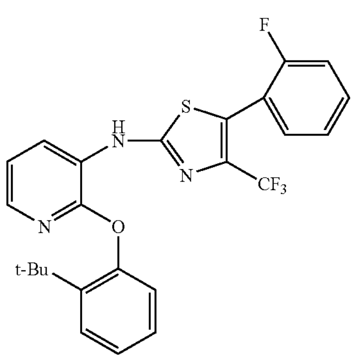 | 488.1 |
| A102 | Example 323 | 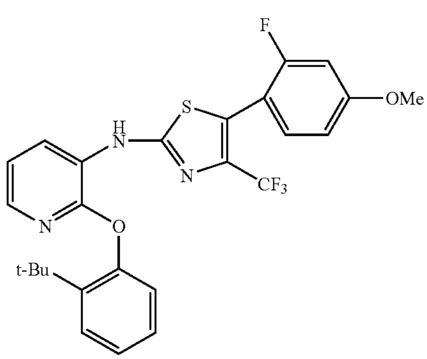 | 518 |

TABLE 21-continued

| Example | Procedure(s) Used | Structure | (M + H)+ |
|---|---|---|---|
| A103 | Example 323 | thiazole with NH-pyridine-O-(2-t-Bu-phenyl); thiazole 4-CF3, 5-(2-F-4-Me-phenyl) | 502.1 |
| A104 | Example 323 | thiazole with NH-pyridine-O-(2-t-Bu-phenyl); thiazole 4-CF3, 5-(3-(CH2)2CO2Me-phenyl) | 556 |
| A105 | Example 323 | thiazole with NH-pyridine-O-(2-t-Bu-phenyl); thiazole 4-C(Me)2CH2CO2Et, 5-phenyl | 530.1 |
| A106 | Example 323 | thiazole with NH-pyridine-O-(2-t-Bu-phenyl); thiazole 4-C(Me)2CH2CO2H, 5-phenyl | 502.1 |
| A107 | Example 323 | thiazole with NH-pyridine-O-(2-t-Bu-phenyl); thiazole 4-C(Me)2CH2CO2Me, 5-phenyl | 502.2 |

TABLE 21-continued

| Example | Procedure(s) Used | Structure | (M + H)+ |
|---|---|---|---|
| A108 | Example 323 | pyridine-NH-thiazole(5-phenyl)-C(Me)₂CO₂H; pyridine-O-(2-t-Bu-phenyl) | 488.2 |
| A109 | Example 323 | pyridine-NH-thiazole(5-phenyl)-C(Me)₂(CH₂)₃CO₂H; pyridine-O-(2-t-Bu-phenyl) | 530.2 |
| A110 | Example 323 | pyridine-NH-thiazole(5-phenyl)-C(Me)₂(CH₂)₂CO₂H; pyridine-O-(2-t-Bu-phenyl) | 516.2 |
| A111 | Example 323 | pyridine-NH-thiazole(5-cyclopentyl, 4-CF₃); pyridine-O-(2-t-Bu-phenyl) | 462.3 |
| A112 | Example 323 | pyridine-NH-thiazole(5-cyclohexyl, 4-CF₃); pyridine-O-(2-t-Bu-phenyl) | 476.3 |

TABLE 21-continued

| Example | Procedure(s) Used | Structure | (M + H)+ |
|---|---|---|---|
| A113 | Example 323 | 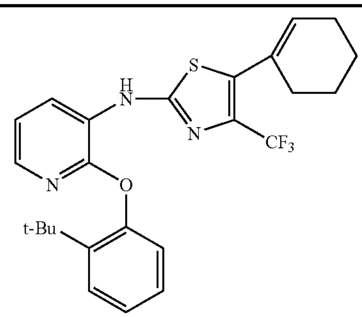 | 474.1 |
| A114 | Example 323 | 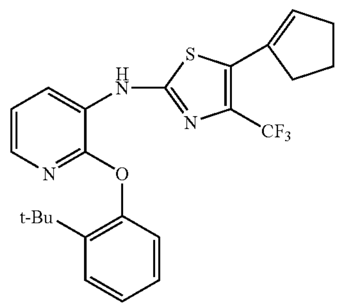 | 460.3 |
| A115 | Example 361 | 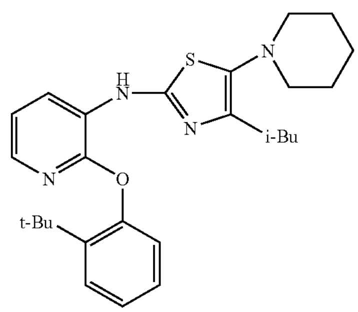 | 465.4 |
| A116 | Example 361 | 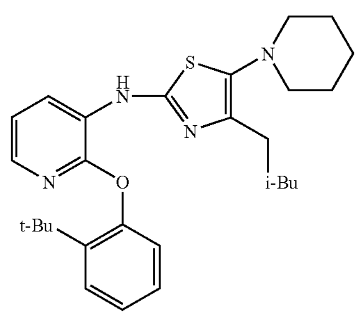 | 479.4 |
| A117 | Example 361 | 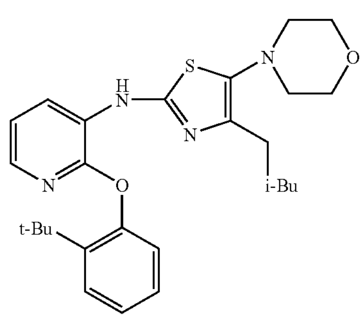 | 481.3 |

TABLE 21-continued

| Example | Procedure(s) Used | Structure | (M + H)+ |
|---|---|---|---|
| A118 | Example 361 | 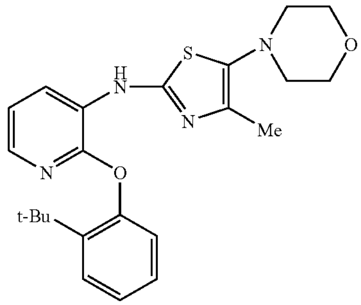 | 423.3 |
| A119 | Example 361 | 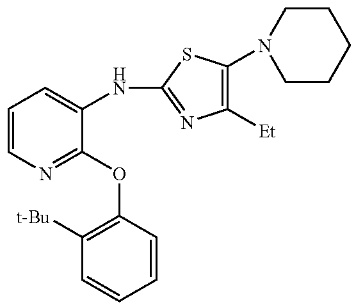 | 437.3 |
| A120 | Example 361 | 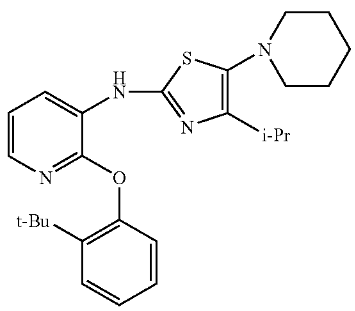 | 451.3 |
| A121 | Example 361 | 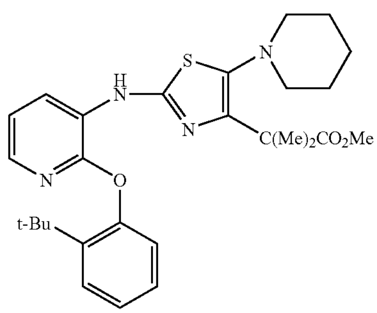 | 509.3 |
| A122 | Example 361 | 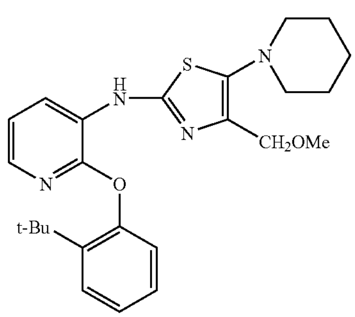 | 453.2 |

TABLE 21-continued

| Example | Procedure(s) Used | Structure | (M + H)+ |
|---------|-------------------|-----------|----------|
| A123 | Example 361 | 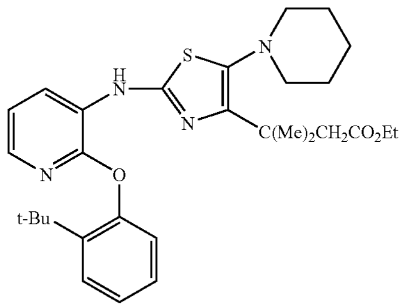 | 537.2 |
| A124 | Example 361 | 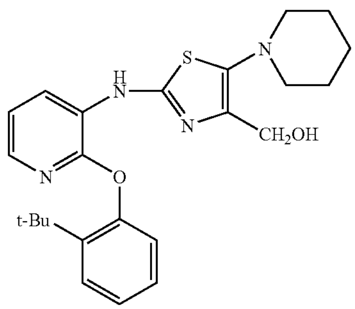 | 439.2 |

Example A125 tert-Butyl 2-(2-tert-butylphenoxy)pyridin-3-yl(5-(3-(3-(dimethylamino)-2,2-dimethylpropoxy)phenyl)-4-(trifluoromethyl)thiazol-2-yl)carbamate

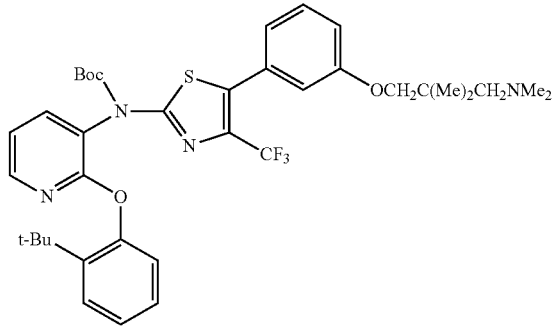

Example A125a tert-Butyl 5-bromo-4-(trifluoromethyl)thiazol-2-yl (2-(2-tert-butylphenoxy)pyridin-3-yl)carbamate

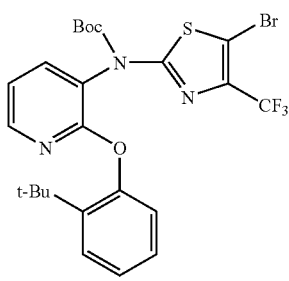

A mixture of N-(5-bromo-4-(trifluoromethyl)thiazol-2-yl)-2-(2-tert-butylphenoxy)pyridin-3-amine (Example 323a, 135 mg, 0.29 mmol), $BOC_2O$ (75 mg, 0.34 mmol), DMAP (5 mg) and DIPEA (59 μL, 0.34 mmol) in THF (5 mL) was stirred at rt for 5 h. The solvent was removed and the residue was purified by flash chromatography (silica, 0-50% EtOAc/hexane gradient) provided Example A125a (149 mg) as a white foam. $(M+H)^+ = 574.2$.

Example A125b tert-Butyl 2-(2-tert-butylphenoxy)pyridin-3-yl(5-(3-hydroxyphenyl)-4-(trifluoromethyl)thiazol-2-yl)carbamate

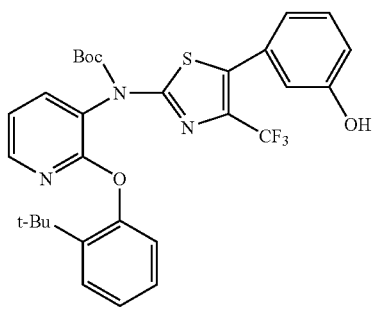

Example A125b was prepared from Example A125a according to a similar procedure described for 2-(2-tert-butylphenoxy)-N-(4-(trifluoromethyl)-5-(4-(trifluoromethyl)phenyl)thiazol-2-yl)pyridin-3-amine (Example 323).

Example 125

To a suspension of PS—PPh$_3$ (124 mg, 0.37 mmol) in THF (1 mL) was added a solution of Example A125b (50 mg, 0.085 mmol) in THF (0.5 mL) and was stirred at rt for 5 min. A solution of DBAD (62 mg, 0.27 mmol) in THF (0.5 mL) was added and stirred at rt for 5 min. Finally 3-(dimethylamino)-2,2-dimethylpropan-1-ol (32 µL, 0.21 mmol) was added and the mixture was stirred at rt overnight. The reaction was filtered and the filtrate was concentrated. The residue was purified by flash chromatography (silica, 0-100% EtOAc/hexane gradient) provided example 125 as an off-white solid (40 mg). (M+H)$^+$=712.3.

Example A126

2-(2-tert-Butylphenoxy)-N-(5-(3-((1-methylpiperidin-4-yl)methoxy)phenyl)-4-(trifluoromethyl)thiazol-2-yl)pyridin-3-amine

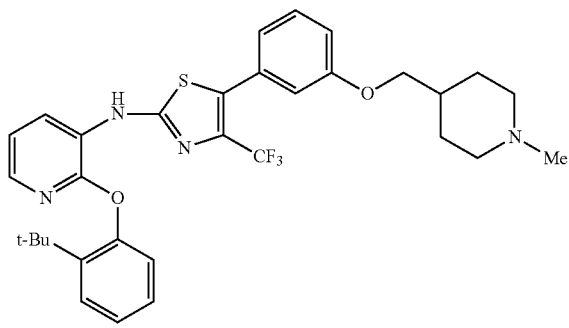

Example A126 was prepared according to a similar procedure described for Example 500. (M+H)$^+$=597.3.

Example A127

N-(5-(1H-1,2,4-Triazol-3-yl)-4-(trifluoromethyl)thiazol-2-yl)-2-(2-tert-butylphenoxy)pyridin-3-amine

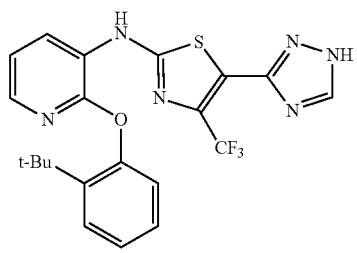

A solution of 2-(2-(2-tert-butylphenoxy)pyridin-3-ylamino)-4-(trifluoromethyl)thiazole-5-carboxamide (Example 269, 33 mg) in N,N-dimethylformamide dimethyl acetal (0.5 mL) was stirred at rt for 1 h. The reaction was concentrated and the residue was treated with HOAc (1.0 mL) and hydrazine monohydrate (7 µL) at 70° C. for 1 h. The solvent was removed and the residue was diluted with EtOAc, washed with sodium bicarbonate solution, dried with magnesium sulphate and evaporated to give the crude product. Purification of the crude product by reverse phase preparative HPLC provided Example A127 (17 mg) as a colorless film. (M+H)$^+$=461.3.

Example A132

2-(2-tert-butylphenoxy)-N-(5-(2-methyl-2H-tetrazol-5-yl)thiazol-2-yl)pyridin-3-amine

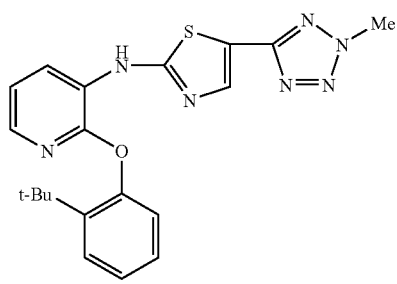

A mixture of N-(5-(1H-tetrazol-5-yl)-4-(trifluoromethyl)thiazol-2-yl)-2-(2-tert-butylphenoxy)pyridin-3-amine (Example 407, 19 mg, 0.048 mmol), MeI (5 µL), sodium bicarbonate (8 mg) and acetone was stirred at rt overnight. The solvent was removed and the residue was purified by reverse phase preparative HPLC to give Example A132 as a colorless film (16 mg). (M+H)$^+$=408.2.

Example A133

2-(2-tert-butylphenoxy)-N-(5-(2-methyl-2H-tetrazol-5-yl)-4-(trifluoromethyl)thiazol-2-yl)pyridin-3-amine

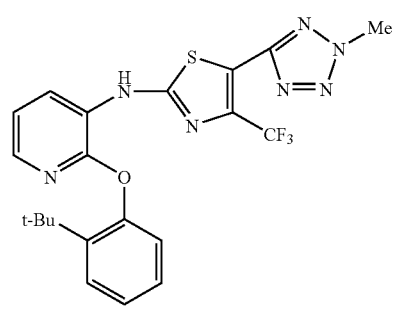

Example A133 was prepared from N-(5-(1H-tetrazol-5-yl)-4-(trifluoromethyl)thiazol-2-yl)-2-(2-tert-butylphenoxy)pyridin-3-amine (Example 404) following the procedure described for Example A132.

Example A128-A131 and A134-153 listed in Table 22 were prepared following the procedure(s) indicated.

TABLE 22

| Example | Procedure(s) Used | Structure | (M + H)+ |
|---|---|---|---|
| A128 | Example A125 | (structure with thiazole-triazole, i-Pr, CF3, pyridine-O-phenyl-t-Bu) | 503.3 |
| A129 | Example A125 | (structure with thiazole-triazole, tetrahydropyran, CF3, pyridine-O-phenyl-t-Bu) | 545.1 |
| A130 | Example A125 | (structure with thiazole-triazole, CH2-cyclopropyl, CF3, pyridine-O-phenyl-t-Bu) | 515.1 |
| A131 | Example A125 | (structure with thiazole-triazole, (CH2)2OH, CF3, pyridine-O-phenyl-t-Bu) | 505.1 |
| A134 | Example A272 | (structure with thiazole, phenyl, CH2NHMe, pyridine-O-phenyl-t-Bu) | 445.2 |

TABLE 22-continued

| Example | Procedure(s) Used | Structure | (M + H)+ |
|---|---|---|---|
| A135 | Example 272 | pyridine-NH-thiazole(Ph)(CH2NMe), 2-O-(2-t-Bu-phenyl) | 459.2 |
| A136 | Example 272 | pyridine-NH-thiazole(Ph)(C(Me)2(CH2)2N(Me)Et), 2-O-(2-t-Bu-phenyl) | 529.3 |
| A137 | Example 272 | pyridine-NH-thiazole(Ph)(C(Me)2(CH2)2N-pyrrolidine), 2-O-(2-t-Bu-phenyl) | 541.3 |
| A138 | Example 272 | pyridine-NH-thiazole(Ph)(C(Me)2(CH2)2N(Me)(i-Bu)), 2-O-(2-t-Bu-phenyl) | 557.3 |
| A139 | Example 272 | pyridine-NH-thiazole(Ph)(C(Me)2CH2N(Me)Et), 2-O-(2-t-Bu-phenyl) | 515.3 |

TABLE 22-continued

| Example | Procedure(s) Used | Structure | (M + H)+ |
|---|---|---|---|
| A140 | Example 390 | Pyridine-NH-thiazole(Ph)(CONH2), 2-O-(2-t-Bu-phenyl) | 459.2 |
| A141 | Example 390 | Pyridine-NH-thiazole(Ph)(CONMe2), 2-O-(2-t-Bu-phenyl) | 473.2 |
| A142 | Example 390 | Pyridine-NH-thiazole(Ph)(CONHMe), 2-O-(2-t-Bu-phenyl) | 459.2 |
| A143 | Example 390 | Pyridine-NH-thiazole(Ph)(C(Me)2CH2CON(Me)Et), 2-O-(2-t-Bu-phenyl) | 543.3 |
| A144 | Example 390 | Pyridine-NH-thiazole(Ph)(C(Me)2CH2CONHEt), 2-O-(2-t-Bu-phenyl) | 529.3 |

TABLE 22-continued

| Example | Procedure(s) Used | Structure | (M + H)⁺ |
|---|---|---|---|
| A145 | Example 390 | [structure with pyridine-NH-thiazole-phenyl, t-Bu-phenoxy, C(Me)₂CH₂CON(Me)(i-Bu) substituent] | 571.3 |
| A146 | Example 390 | [structure with pyridine-NH-thiazole-phenyl, t-Bu-phenoxy, C(Me)₂CH₂CONH₂ substituent] | 501.2 |
| A147 | Example 390 | [structure with pyridine-NH-thiazole-phenyl, t-Bu-phenoxy, C(Me)₂CON(Me)Et substituent] | 529.3 |
| A148 | Example 251 | [structure with pyridine-NH-thiazole-phenyl, t-Bu-phenoxy, C(Me)₂(CH₂)₂OH substituent] | 509.3 |
| A149 | Example 251 | [structure with pyridine-NH-thiazole-phenyl, t-Bu-phenoxy, C(Me)₂CH₂OH substituent] | 474.3 |

TABLE 22-continued

| Example | Procedure(s) Used | Structure | (M + H)+ |
|---|---|---|---|
| A150 | Example 404 | 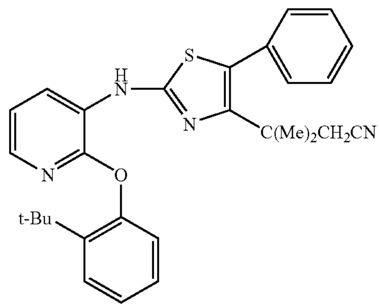 | 483.3 |
| A151 | Example A132 | 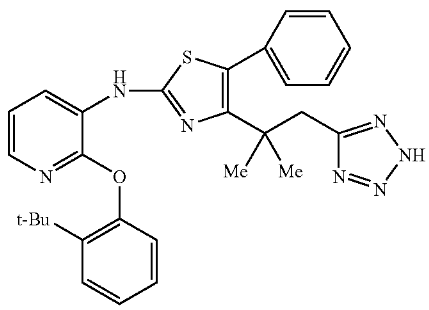 | 526.2 |
| A152 | Example A132 | 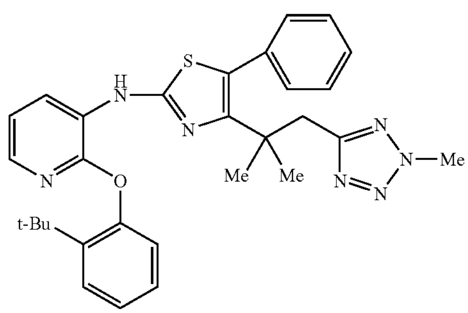 | 540.2 |
| A153 | Example A132 | 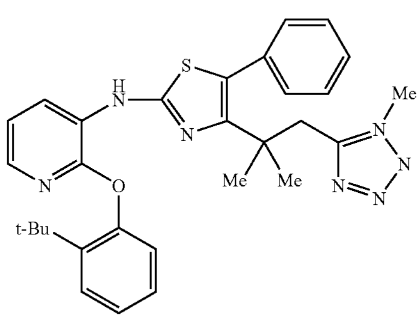 | 540.2 |

Example A154

1-(2-(2-(2-tert-Butylphenoxy)pyridin-3-ylamino)-4-(trifluoromethyl)thiazol-5-yl)ethanone

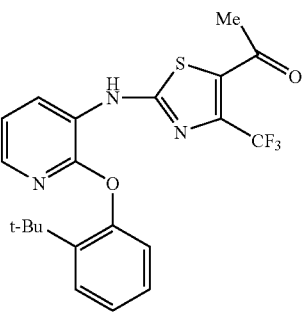

Example A154a 2-(2-tert-Butylphenoxy)-N-(5-(1-ethoxyvinyl)-4-(trifluoromethyl)thiazol-2-yl)pyridin-3-amine

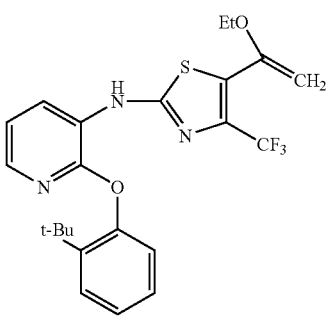

A solution of N-(5-bromo-4-(trifluoromethyl)thiazol-2-yl)-2-(2-tert-butylphenoxy)pyridin-3-amine (Example 323a, 1.3 g, 2.75 mmol) in dioxane (30 mL) was added tributyl(1-ethoxyvinyl)tin (1.1 mL, 3.3 mmol) was degassed and Pd(PPh$_3$)$_4$ (160 mg, 0.14 mmol) was added. The mixture was degassed and heated at 100° C. overnight. The mixture was concentrated on vacuum, dissolved in EtOAc and treated with saturated KF solution. The solid was removed by filtering through a pad of Celite®. The filtrate was extracted with EtOAc. The organic layers were combined, washed with bring, dried over magnesium sulfate and concentrated to give crude Example A154a (1.12 g) as a brown oil.

Example A154

Example A154a (crude, 1.12 g) was dissolved in diethyl ether (30 mL) and treated with 4 N HCl/ether solution at rt for 2 h. The solvent was removed and the residue was purified by flash chromatography (120 g ISCO silica gel column, 0-70% EtOAc/hexane) to give Example A154 (890 mg) as a yellow solid.

Example A155

2-(2-tert-Butylphenoxy)-N-(5-(prop-1-en-2-yl)-4-(trifluoromethyl)thiazol-2-yl)pyridin-3-amine

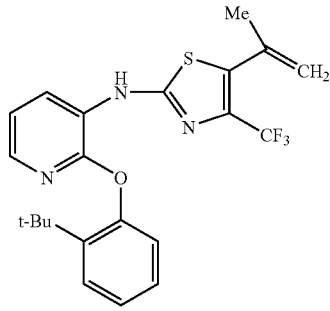

To a solution of Example A154 (105 mg, 0.24 mmol) in THF (3 mL) at 0° C. was added Tebbe reagent (C$_{13}$H$_{18}$AlClTi) (0.5 M in toluene, 580 μL, 0.29 mmol). The mixture was stirred at 0° C. for 15 min and was allowed to warm to rt and stirred at rt for 10 days. The reaction was diluted with diethyl ether (10 mL) and quenched with 5 drops of 1 N NaOH. The mixture was dried over sodium sulfate and filtered. The filtrate was concentrated and purified by flash chromatography (12 g ISCO silica gel column, 0-40% EtOAc/hexane) to give Example A155 (24 mg) as a yellow film. (M+H)$^+$=434.3.

Example A156

2-(2-tert-Butylphenoxy)-N-(5-isopropyl-4-(trifluoromethyl)thiazol-2-yl)pyridin-3-amine

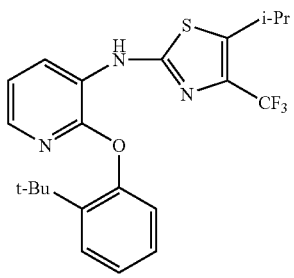

A mixture of Example A155 (15 mg) and 10% Pd/C (5 mg) in methanol (2 mL) was stirred under hydrogen atmosphere for 3 h. The mixture was filtered and the filtrate was concentrated to give Example A156 (12 mg) as a colorless film. (M+H)⁺=436.3.

Example A157

2-(2-tert-Butylphenoxy)-N-(4-(trifluoromethyl)-5-vinylthiazol-2-yl)pyridin-3-amine

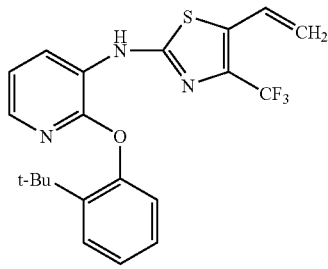

Example A157 was prepared from N-(5-bromo-4-(trifluoromethyl)thiazol-2-yl)-2-(2-tert-butylphenoxy)pyridin-3-amine (Example 323a) according to the procedure described for Example A154a. (M+H)⁺=420.3.

Example A158

2-(2-tert-Butylphenoxy)-N-(5-ethyl-4-(trifluoromethyl)thiazol-2-yl)pyridin-3-amine

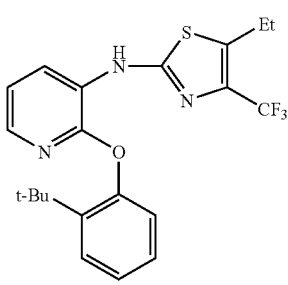

Example A158 was prepared from Example A157 according to the procedure described for Example A156. (M+H)⁺=420.3.

Example A159

2-(2-(2-(2-tert-Butylphenoxy)pyridin-3-ylamino)-4-(trifluoromethyl)thiazol-5-yl)ethanol

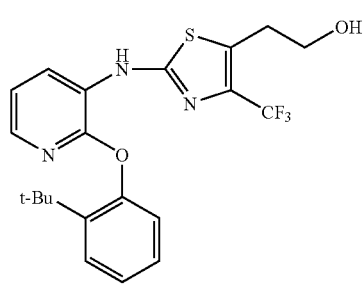

A solution of Example A157 (105 mg, 0.25 mmol) in THF (1.5 mL) at 0° C. was added BH₃-THF (1.0 M, 500 μL, 0.5 mmol). The mixture was stirred at 0° C. for 1 h, warmed to rt and stirred at rt for 1 h. The reaction was cooled to 0° C. and 1 N NaOH solution (750 μL, 0.75 mmol) was added followed by H₂O₂ solution (35%, 500 μL). The mixture was stirred at rt overnight. The mixture was extracted with EtOAc. The organic layers were combined, washed with saturated sodium bicarbonate solution, brined, dried over sodium sulfate and filtered. The filtrate was concentrated and purified by flash chromatography (40 g ISCO silica gel column, 0-100% EtOAc/hexane) to give Example A159 (57 mg) as a white foam. (M+H)⁺=438.1.

Example A160

2-(2-tert-Butylphenoxy)-N-(5-((isobutyl(methyl)amino)methyl)-4-(trifluoromethyl)thiazol-2-yl)pyridin-3-amine

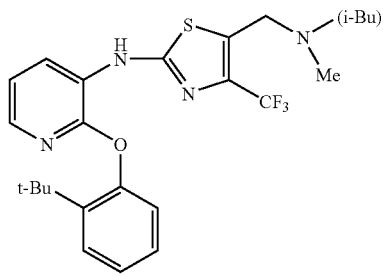

Example A160 was prepared according to the procedure described for Example 272. (M+H)⁺=493.2.

Example A161

N-(4-tert-Butyl-5-(((isobutyl(methyl)amino)methyl)thiazol-2-yl)-2-(2-tert-butylphenoxy)pyridin-3-amine

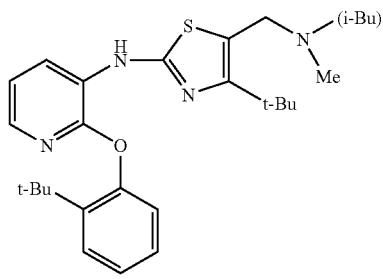

Example A161 was prepared from (4-tert-butyl-2-(2-(2-tert-butylphenoxy)pyridin-3-ylamino)thiazol-5-yl)methanol (Example 252) and isobutyl methyl amine according to the procedure described for Example 272. (M+H)⁺=493.2.

Example A162

N-(4-tert-Butyl-5-(1H-imidazol-1-yl)thiazol-2-yl)-2-(2-tert-butylphenoxy)pyridin-3-amine

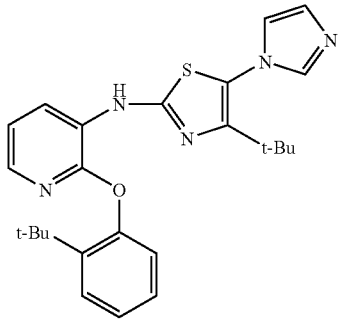

A mixture of N-(5-bromo-4-(trifluoromethyl)thiazol-2-yl)-2-(2-tert-butylphenoxy)pyridin-3-amine (Example 323a, 30 mg) and imidazole (100 mg) in dioxane (200 μL) was heated at 100° C. for 18 h. The reaction was diluted with methanol and purified by reverse preparative HPLC to give Example A162 (11 mg) as an off-white solid. (M+H)+=460.1.

Example A162-A165 listed in Table 23 were prepared from N-(5-bromo-4-(trifluoromethyl)thiazol-2-yl)-2-(2-tert-butylphenoxy)pyridin-3-amine (Example 323a) using the same procedure described for Example A161.

TABLE 23

| Example | Structure | (M + H)+ |
|---|---|---|
| A163 | 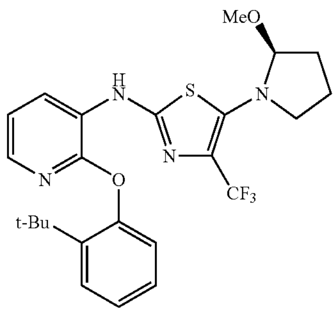 | 507.1 |
| A164 | 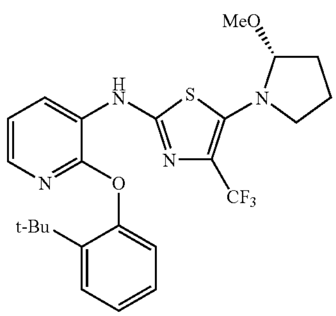 | 507.1 |
| A165 | 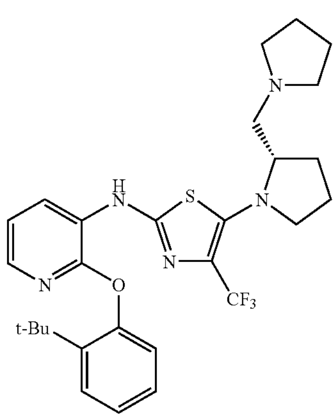 | 546.1 |

Example A166

2-(2-(2-Methylbut-3-en-2-yl)phenoxy)-N-(4-(trifluoromethyl)thiazol-2-yl)pyridin-3-amine

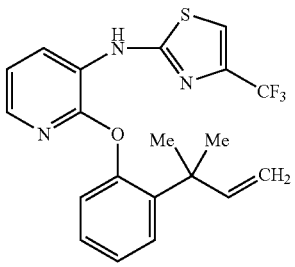

Example A166a 2-(2-Methylbut-3-en-2-yl)phenol

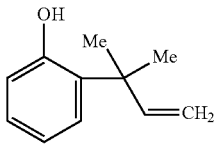

A mixture of 1-(3-methylbut-2-enyloxy)benzene (2.8 g, 11.1 mmol), Ac₂O (25 mL) and AcOK (2.8 g) were placed in a steel bomb, degassed and bubbled with N₂ for 10 min. The reaction was heated at 200° C. for 16 h. The reaction was cooled to rt, quenched with water (150 mL) and stirred at rt for 1 h. The mixture was extracted with diethyl ether. The combined organic layers were washed with water, dried over magnesium sulfate and evaporated. The residue was dissolved in THF:MeOH:H₂O (3:2:1, 200 mL), adjusted pH=9 with KOH and stirred at rt overnight. To the mixture was added HCl until pH=6 and then NaHCO₃ till neutralized. The mixture was extracted with diethyl ether. The combined organic layers were washed with water, dried over magnesium sulfate and evaporated to give the crude product. Purification of the crude product by flash chromatography (20 g silica gel, 5% EtOAc/hexane) provided Example A166a (1.55 g).

Example A166b 2-(2-(2-Methylbut-3-en-2-yl)phenoxy)pyridin-3-amine

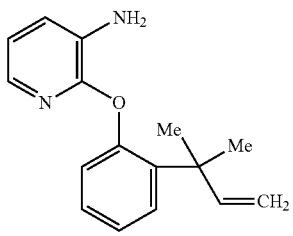

A mixture of Example A166a (1.55 g, 9.51 mmol), 2-fluoro-3-nitropyridine (1.34 g, 9.51 mmol) and potassium carbonate (1.55 g) in dioxane (5 mL) was stirred at rt overnight. The reaction was diluted with EtOAc (50 mL), filtered and evaporated. The residue was combined with MeOH (5 mL), HOAc (7.5 mL), i-PrOH (12.5 mL) and Fe (2 g). The mixture was heated at 100° C. for 2.5 h. The solvent was remover and the residue was partitioned between EtOAc and 1 N NaOH. The mixture was filtered through Celite® and the Celite® cake was washed with EtOAc. The organic layer was separated from the filtrate, washed with water, dried over magnesium sulfate, filtered and evaporated to give the crude product. Purification of the crude product by flash chromatography (20 g silica gel, 5% EtOAc/hexane) provided Example A166b (1.3 g). (M+H)$^+$=255.

Example A166 was prepared from Example A166b following the same procedure as for Example 217. (M+H)$^+$=406.1.

Example A167

2-(2-Bromophenoxy)-N-(4-(trifluoromethyl)thiazol-2-yl)pyridin-3-amine

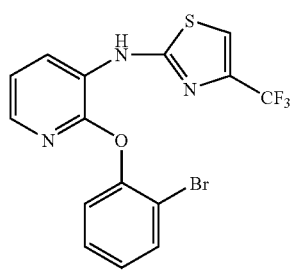

Example A167 was prepared from 2-fluoro-3-nitropyridine and 2-bromophenol following the same procedure as for Example A166. (M+H)$^+$=415.9, 418.0.

Example A168

2-(2-Iodophenoxy)-N-(4-(trifluoromethyl)thiazol-2-yl)pyridin-3-amine

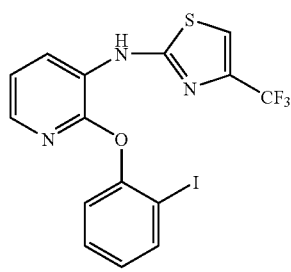

Example A168 was prepared from 2-fluoro-3-nitropyridine and 2-iodophenol following the same procedure as for Example A166. (M+H)$^+$=463.9.

Example A169

3-(5-(2-(2-tert-butylphenoxy)pyridin-3-ylamino)-1,3,4-thiadiazol-2-yl)phenol

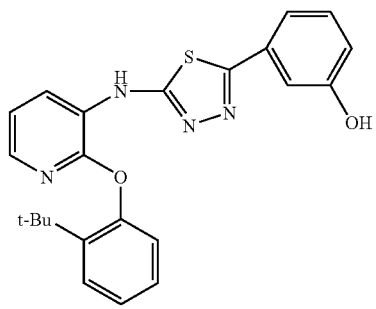

Example A169 was prepared according to the procedure described for Example 1. (M+H)$^+$=419.

Example A170

N-(5-Phenyl-1,3,4-thiadiazol-2-yl)-2-(1,2,3,4-tetrahydroquinolin-5-yloxy)pyridin-3-amine

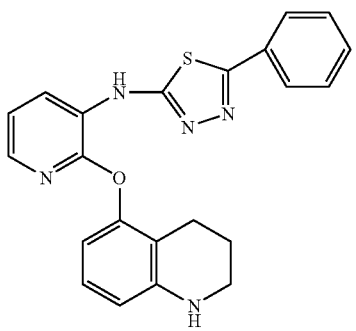

Example A170a

1-Benzoyl-1,2,3,4-tetrahydroquinolin-5-yl benzoate

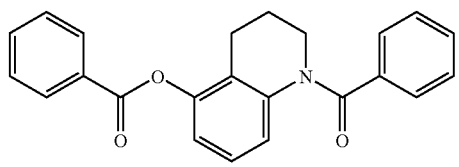

A mixture of quinolin-5-ol (540 mg, 3.72 mmol), 10% palladium on charcoal (Degussa 50% wet, 100 mg) were diluted in ethyl acetate and hydrogenated under 1 atmosphere of hydrogen for 18 h. The mixture was filtered over Celite® and evaporated in vacuo. The crude material was diluted in dichloromethane. Benzoyl chloride (906 μl, 7.8 mmol) and diisopropylethylamine (1.97 mL, 11.2 mmol) were added and mixture was stirred at rt for 3 h. The mixture was dissolved in EtOAc, washed with a saturated solution of ammonium chloride and a 1N HCl solution, dried (MgSO₄), filtered and evaporated to afford the crude product (1.31 g). (M+H)⁺=358.

Example A170b (5-Hydroxy-3,4-dihydroquinolin-1(2H)-yl)(phenyl)methanone

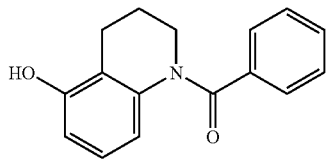

Example A170a (1.31 g, 3.66 mmol) is diluted in THF (20 mL). A solution of lithium hydroxide monohydrate (769 mg, 18.3 mmol) in water (10 mL) was added and mixture was stirred for 18 h. The mixture was dissolved in EtOAc, washed with a saturated solution of sodium bicarbonate, dried (MgSO₄), filtered and evaporated to afford the crude product (560 mg). (M+H)⁺=254.

Example A170c (5-(3-Nitropyridin-2-yloxy)-3,4-dihydroquinolin-1(2H)-yl)(phenyl)methanone

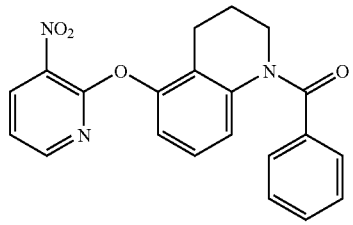

A mixture of Example A170b (560 mg, 2.21 mmol), 2-chloro-2-nitropyridine (525 mg, 3.31 mmol) and cesium carbonate (1.08 g, 3.31 mmol) in DMF (10 mL) was stirred at rt for 18 h. Water (25 mL) was added and mixture was extracted twice using ethyl acetate. The organic phases was dried (MgSO₄), filtered and evaporated to afford the crude product (800 mg). (M+H)⁺=376.

Example A170d (5-(3-Aminopyridin-2-yloxy)-3,4-dihydroquinolin-1(2H)-yl)(phenyl)methanone

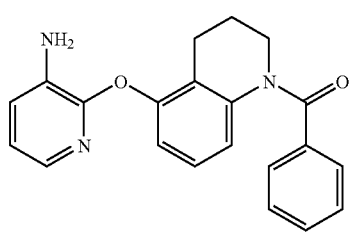

A mixture of Example A170c (800 mg, 2.13 mmol), zinc (697 mg, 10.7 mmol) and ammonium chloride (572 mg, 10.7 mmol) in ethanol (20 mL) was heated to reflux for 24 h. The solution was filtered over a pad of Celite® and evaporated in vacuo to afford the crude final product. The crude material was directly used in the next step. (M+H)⁺=346.

Example A170e

Phenyl(5-(3-(5-phenyl-1,3,4-thiadiazol-2-ylamino)pyridin-2-yloxy)-3,4-dihydroquinolin-1(2H)-yl)methanone

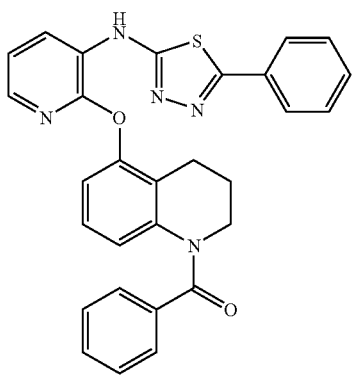

A mixture of Example A170d (400 mg, 1.16 mmol), 1,1'-thiocarbonyldi-2(1H)-pyridone (269 mg, 1.16 mmol) in DCM (10 mL) was agitated at rt for 4 h. The mixture was evaporated and diluted in THF (5 mL), benzohydrazide (79 mg, 0.58 mmol) was added and mixture was stirred for 18 h. The solution was evaporated in vacuo and diluted in sulfuric acid (conc. 5 mL) and stirred 2 h. Water was added and the solid formed was collected by filtration and purified using preparative HPLC to afford the final product (110 mg). (M+H)⁺=506.

Example A170

Example A170e (100 mg, 0.2 mmol) was diluted in THF (5 mL) and cooled to −78° C. Butyllithium (1.6 M/hexanes, 0.63 mL, 1 mmol) was added and the reaction mixture was stirred for 30 min. A saturated solution of ammonium chloride was added. The solution was warmed to r.t. and extracted twice using ethyl acetate. Organic phase were combined, dried (MgSO₄) and evaporated. The crude material was directly purified using preparative HPLC to afford the final product as 2 TFA salt (100 mg). (M+H)⁺=402. ¹H NMR (400 MHz, DMSO-D6) δ ppm 1.70-1.79 (m, 2H) 2.07 (s, 1 H) 2.44 (t, J=6.32 Hz, 3 H) 3.13-3.20 (m, 2 H) 6.42 (d, J=5.31 Hz, 1 H) 6.50 (d, J=7.07 Hz, 1 H) 6.99 (t, J=7.83 Hz, 1 H) 7.12 (dd, J=7.83, 4.80 Hz, 1 H) 7.48-7.55 (m, 3 H) 7.67 (dd, J=4.93, 1.64 Hz, 1 H) 7.87 (dd, J=7.45, 2.15 Hz, 2 H) 8.86 (dd, J=7.96, 1.64 Hz, 1 H) 10.50 (s, 1 H).

Example A171

N-(5-phenyl-1,3,4-thiadiazol-2-yl)-2-(1,2,3,4-tetrahydroquinolin-8-yloxy)pyridin-3-amine

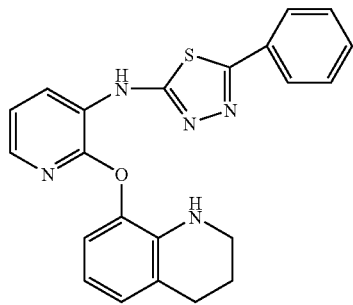

The 3-amino-phenoxypyridyl intermediate ((8-(3-aminopyridin-2-yloxy)-3,4-dihydroquinolin-1(2H)-yl)(phenyl)methanone) leading to Example A171 was made according to the sequence described in Scheme 13 in U.S. patent application Ser. No. 11/126,915, which is hereby incorporated by reference.

Example A172

N-(3-tert-Butyl-1,2,4-thiadiazol-5-yl)-2-(1,2,3,4-tetrahydroquinolin-5-yloxy)pyridin-3-amine

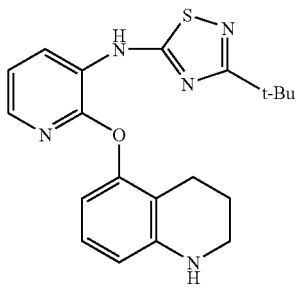

Example A172a (5-(3-(3-tert-butyl-1,2,4-thiadiazol-5-ylamino)pyridin-2-yloxy)-3,4-dihydroquinolin-1(2H)-yl)(phenyl)methanone

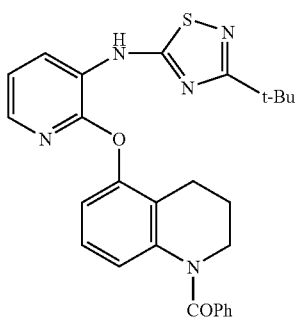

A mixture of (5-(3-aminopyridin-2-yloxy)-3,4-dihydroquinolin-1(2H)-yl)(phenyl)methanone (Example A171d) (224 mg, 0.58 mmol), 1,1'-thiocarbonyldi-2(1H)-pyridone (269 mg, 1.16 mmol) in DCM (10 mL) was agitated at rt for 4 h. The mixture was evaporated and diluted in THF (5 mL), pivalamidine (79 mg, 0.58 mmol) and DIPEA (205 µL, 1.16 mmol) were added and mixture was heated at 80° C. in a sealed tube for 24 h. The solution was cooled down and DEAD (183 µL, 1.16 mmol) was added, mixture was stirred for 2 h. The reaction mixture was evaporated in vacuo and purified using preparative HPLC to afford the final product (40 mg). $(M+H)^+=486$.

Example A172

Example A172a (35 mg, 0.06 mmol) was diluted in THF (5 mL) and cooled to −78° C. Butyllithium (1.6 M/hexanes, 0.19 mL, 0.3 mmol) was added and the reaction mixture was stirred for 30 min. A saturated solution of ammonium chloride was added. The solution was warmed to rt and extracted twice using ethyl acetate. Organic phase were combined, dried ($MgSO_4$) and evaporated. The crude material was directly purified using preparative HPLC to afford the final product as 2 TFA salt (4 mg). $(M+H)^+=382$. $^1$H NMR (400 MHz, DMSO-$D_6$) δ ppm 1.35 (s, 9H) 1.66-1.75 (m, 2 H) 2.39 (t, J=6.06 Hz, 2 H) 3.13 (s, 2 H) 6.28 (dd, J=7.71, 5.18 Hz, 1 H) 6.34-6.44 (m, 1 H) 6.88-6.95 (m, 1 H) 7.13 (dd, J=7.83, 4.80 Hz, 1 H) 7.68 (dd, J=4.93, 1.64 Hz, 1 H) 8.87 (dd, J=7.83, 1.52 Hz, 1 H) 10.76 (s, 1 H).

Example A173

N-(3-tert-Butyl-1,2,4-thiadiazol-5-yl)-2-(1,2,3,4-tetrahydroquinolin-8-yloxy)pyridin-3-amine

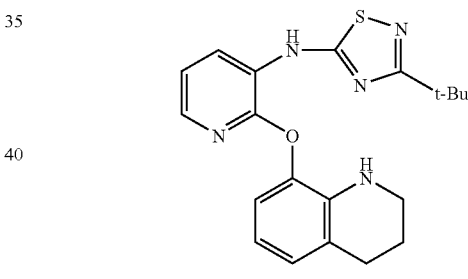

The 3-amino-phenoxypyridyl intermediate ((8-(3-aminopyridin-2-yloxy)-3,4-dihydroquinolin-1(2H)-yl)(phenyl)methanone) leading to Example A173 was made according to the sequence described in Scheme 13 in U.S. patent application Ser. No. 11/126,915, which is hereby incorporated by reference.

Example A174

Methyl 2-(3-(3-tert-butyl-1,2,4-thiadiazol-5-ylamino)pyridin-2-yloxy)benzoate

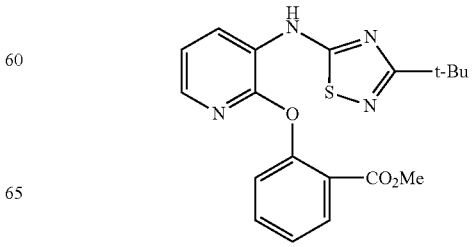

Example A174a

Methyl 2-(3-aminopyridin-2-yloxy)benzoate

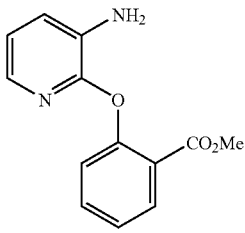

Example A174a was prepared according to the procedures described in U.S. patent application Ser. No. 11/126,915, which is hereby incorporated by reference, using methyl salicylate and 2-chloro-3-nitro pyridine in the first step. (M+H)⁺= 245.

Example A174

A mixture of Example A174a (163 mg, 0.66 mmol), diisopropylethylamine (219 µL, 1.25 mmol) and tert-butyl amidine (86 mg, 0.63 mmol) in DMF (2.1 mL) was stirred at rt for 18 h. Diethylazodicarboxylate (196 µL, 1.25 mmol) was added and mixture was stirred for 4 h. The reaction mixture was purified by preparative HPLC to give the title compound (152 mg) as a white solid. (M+H)⁺=385. ¹H NMR (400 MHz, DMSO-D6) δ ppm 1.36 (s, 9 H) 3.53 (s, 3 H) 7.13 (dd, J=7.96, 4.93 Hz, 1 H) 7.35 (d, J=8.08 Hz, 1 H) 7.40 (t, J=7.20 Hz, 1 H) 7.61 (dd, J=4.80, 1.52 Hz, 1 H) 7.70 (td, J=7.77, 1.64 Hz, 1 H) 7.92 (dd, J=7.83, 1.52 Hz, 1 H) 8.91 (dd, J=8.08, 1.52 Hz, 1 H) 10.77 (s, 1 H).

Example A175

2-(3-tert-Butyl-2-ethylisoindolin-4-yloxy)-N-(5-methyl-4-(trifluoromethyl)thiazol-2-yl)pyridin-3-amine

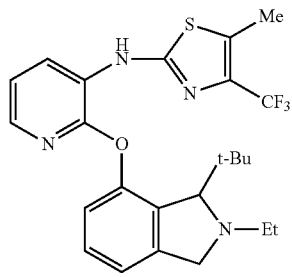

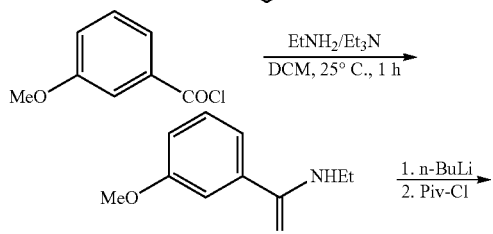

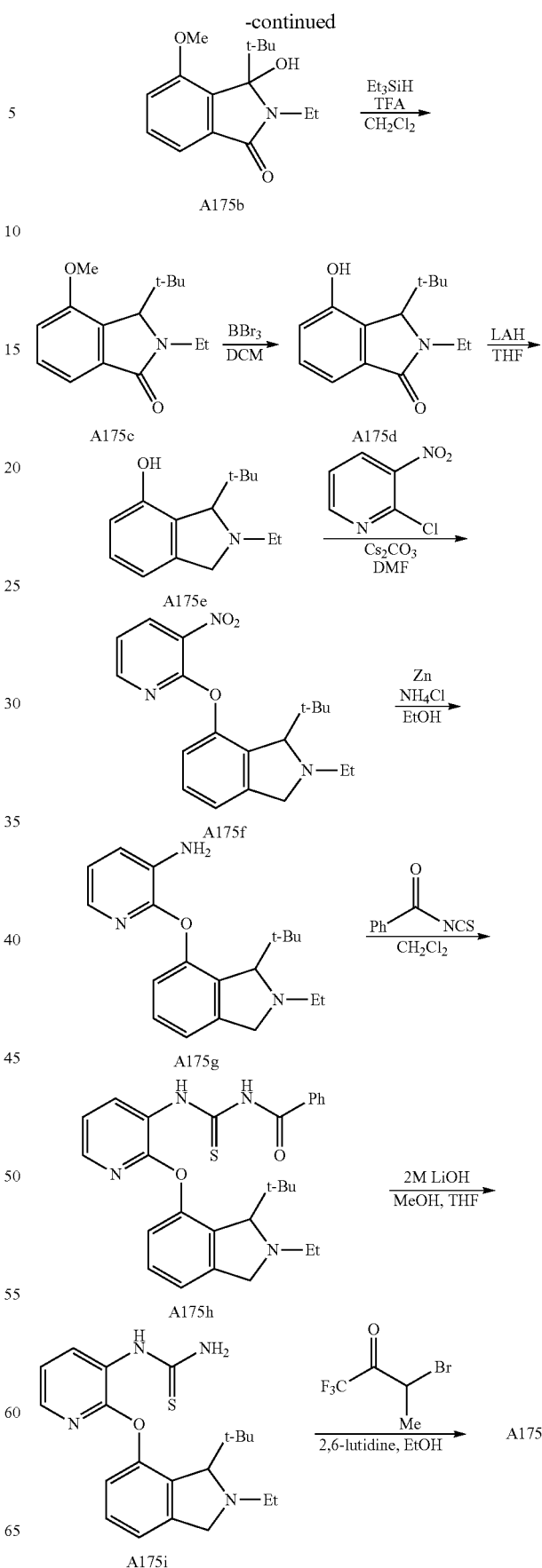

Example A175a

N-Ethyl-3-methoxybenzamide

To a solution of 3-methoxybenzoyl chloride (commercially available from Aldrich, 5 mL, 35 mol) and Et$_3$N (10 mL) in 100 mL of DCM was added and EtNH$_2$ (2 M/THF, 30 mL, 60 mmol) dropwise for 30 min at 0° C. and the resulting solution was stirred for additional 1 h. The reaction mixture was washed with aq. NaHCO$_3$ and brine, consecutively. The organic layer was dried over Na$_2$SO$_4$ and concentrated in vacuo, yielding oily residue, which was subjected to column chromatography to yield Example A175a (6.2 g, >95%) as a colorless oil.

Example A175b 3-tert-Butyl-2-ethyl-3-hydroxy-4-methoxyisoindolin-1-one

Example A175a (6.1 g, 34 mmol) in THF (200 mL) was stirred at 0° C. n-Butyllithium (1.6 M in hexanes, 50 mL, 80 mmol) was added dropwise for 1 h and the mixture was stirred for 2 h. Trimethylacetylchloride (4.5 mL, 36 mmol) was added and stirring was continued for 1 h. A saturated solution of ammonium chloride was added and the solution was warmed to rt and extracted twice using ethyl acetate (150 mL×2). Organic phases were combined, dried using MgSO$_4$ and evaporated. The oily mixture was purified on column chromatography (0-100% EtOAc/Hexane) to yield 5.1 g (19.4 mmol, 57%) of Example A175b as an oil.

Example A175c 3-tert-Butyl-2-ethyl-4-methoxyisoindolin-1-one

To a solution of Example A175b (5.1 g, 19.4 mmol) in a solution of TFA (20 mL) and DCM (20 ml) was added Et$_3$SiH (6.5 mL, 42 mmol) dropwise for 30 min. The resulting solution was stirred for 12 h at 25° C. It was then concentrated in vacuo, yielding oily residue, which was diluted with DCM (150 ml) and washed with aq. NaHCO$_3$ (30 mL×2). The organic layer was dried over MgSO$_4$ and concentrated to provide oily residue, which was purified on column chromatography (0-100% ethyl acetate, hexane) to yield 2.7 g (10.9 mmol, 56%) of Example A175c.

Example A175d 3-tert-Butyl-2-ethyl-4-hydroxyisoindolin-1-one

To a solution of Example A175c (2.7 g, 10.9 mmol) in DCM (30 mL) was added BBr$_3$ (20 mL, 1M in DCM) dropwise for 0.5 h and the resulting solution was stirred for 0° C. for 12 h. The mixture was then cooled down to −78° C. and 5 mL of MeOH was added into the solution. The resulting solution was stirred for additional 2 h at 25° C. It was concentrated in vacuo to provide Example A175d as a dark brown oil, which was subjected to following reaction without further purification.

Example A175d 3-tert-Butyl-2-ethylisoindolin-4-ol

A mixture of Example A175d (2.5 g, 10.7 mmol) and lithium aluminium hydride (20 mL, 1M in THF, 20 mmol) in 100 mL of THF was stirred at reflux for 18 h. The reaction mixture was cooled down and Sodium sulfate decahydrate was added. The mixture was stirred for 30 min. The reaction mixture was filtered over a pad of Celite® and washed with ethylacetate. The organic phase was concentrated in vacuo to provide Example A175d as an oil (2.3 g, >95%), which was identified by $^1$H NMR and subjected to the following reaction without further purification.

Example A175e 1-tert-Butyl-2-ethyl-7-(3-nitropyridin-2-yloxy)isoindoline

A mixture of Example A175d (2.5 g, 10.7 mmol), 2-chloro-2-nitropyridine (2.4 g, 16.0 mmol) and cesium carbonate (10 g, 32.1 mmol) in DMF (30 mL) was stirred at 60° C. for 2 h. The mixture directly purified on column chromatography (0-100%, EtOAc/hexane) to give Example A175e (2.6 g, 7.6 mmol).

Example A175g 2-(3-tert-Butyl-2-ethylisoindolin-4-yloxy)pyridin-3-amine

A mixture of Example A175e (2.6 g, 7.6 mmol), zinc (6.5 g, 100 mmol) and ammonium chloride (5.4 g, 100 mmol) in ethanol (100 mL) was heated to reflux for 24 h. The solution was allowed to cool and filtered over a pad of Celite® and evaporated in vacuo. The crude material was purified using column chromatography (0-10%, methanol, dichloromethane) to give Example A175g (1.3 g, 4.1 mmol).

Example A175h

1-Benzoyl-3-(2-(3-tert-butyl-2-ethylisoindolin-4-yloxy)pyridin-3-yl)thiourea

Example A175g (145 mg, 0.466 mmol) was dissolved in 5 mL of dichloromethane. Benzoylisothiocyanate (75 μL, 0.559 mmol) was added and the mixture was heated to 40° C. for 2 h. The reaction mixture was cooled and purified on flash chromatography (20 g SiO$_2$; column packed with hexane saturated with ammonia then eluted with dichloromethane) to provide 167 mg (76%) of Example A175h as a yellow oil. HPLC; LC/MS; $^1$H NMR (400 MHz, CDCl$_3$).

Example A175i 1-(2-(3-tert-Butyl-2-ethylisoindolin-4-yloxy)pyridin-3-yl)thiourea Example A175h (155 mg, 0.327 mmol) was dissolved in 4 mL of 50% methanol and 50% tetrahydrofuran. Lithium hydroxide (2.0 M aq, 0.327 mL, 0.653 mmol) was added and the mixture was heated to 50° C. for 3 h. The reaction mixture was purified by flash chromatography (20 g SiO$_2$; column packed with 2% of 7 M ammonia in methanol and dichloromethane then eluted with 2% methanol in dichloromethane) to provide 99 mg (82%) of Example A175i as an orange solid.

Example A175

Example A175i (46 mg, 0.124 mmol) and 1,1,1-trifluoro-3-bromo-2-butanone (51 mg, 0.248 mmol, commercially available) were dissolved in 1 mL of ethanol. 2,6-Lutidine (29 μL, 0.248 mmol) was added and the mixture was heated to 100° C. for 4 h in a sealed tube. The reaction mixture was cooled to room temperature and the solvent removed. The residue was purified by flash chromatography (15 g SiO$_2$; eluted with 3% i-propanol, dichloromethane) to provide Example A175 that was only 88% pure. Further purification by preparative thin layer chromatography (plate eluted with 3% i-propanol, dichloromethane) provided 22 mg (37%) of pure Example A175. HPLC, LC/MS, $^1$H NMR (400 MHz, CDCl$_3$), MS (ESI) 477 (M+H). HRMS (ESI) m/e calc'd for C$_{24}$H$_{28}$F$_3$N$_4$OS: 477.1936. Found (M): 477.1927.

Example A176

2-(3-tert-Butyl-2-ethylisoindolin-4-yloxy)-N-(5-phenyl-4-(trifluoromethyl)thiazol-2-yl)pyridin-3-amine

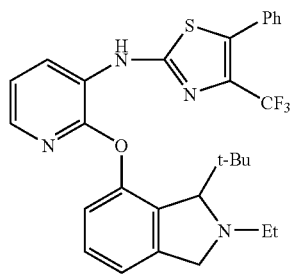

Example A176a 3-bromo-1,1,1-trifluoro-3-phenylpropan-2-one

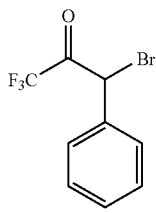

1,1,1-trifluoro-3-phenylpropanone (0.50 mL, 3.2 mmol) was dissolved in 5 mL of diethyl ether and the mixture was cooled to 0° C. Bromine (0.16 mL, 3.2 mmoL) was added and the mixture was stirred for 18 h and allowed to warm to rt. The solvent was removed to provide a 2:1 mixture of Example A176a as a starting material which was used in the subsequent reaction without further purification.

Example A176

Example A175i (43 mg, 0.124 mmol) and Example A176a (124 mg) were dissolved in 1 mL of ethanol. Pyridine (19 μL, 0.232 mmol) was added and the mixture was heated to 100° C. for 3 h in a sealed tube. The reaction mixture was cooled to rt and the solvent was removed. The residue was purified by preparative thin layer chromatography (plate eluted with 5% i-propanol, dichloromethane) to provide 14 mg (22%) of Example A176. HPLC, LC/MS, $^1$H NMR (400 MHz, CDCl$_3$), MS (ESI) m/e 539 (M+H); HRMS (ESI) m/e calc'd for C$_{29}$H$_{30}$F$_3$N$_4$OS: 539.2092. Found (M$^+$): 539.2085.

Example A177

2-(2-Neopentyl-1,2,3,4-tetrahydroisoquinolin-5-yloxy)-N-(5-phenyl-4-(trifluoromethyl)thiazol-2-yl)pyridin-3-amine

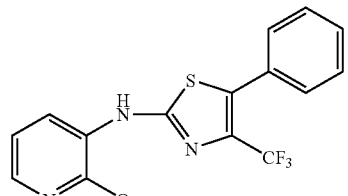

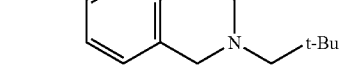

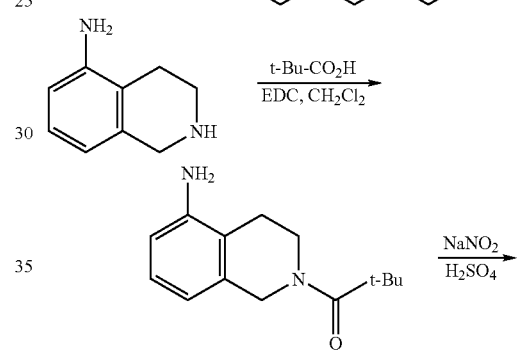

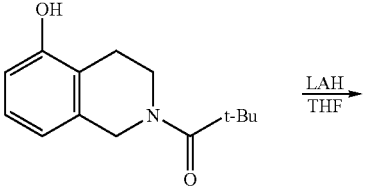

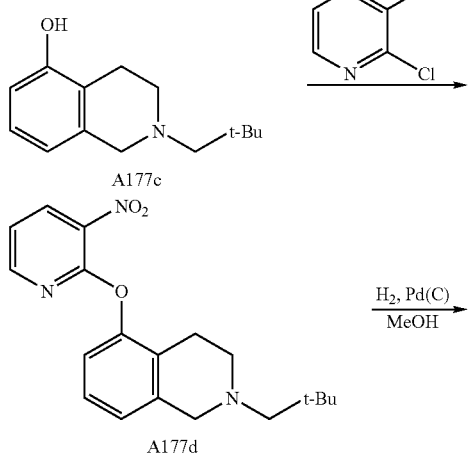

243

-continued

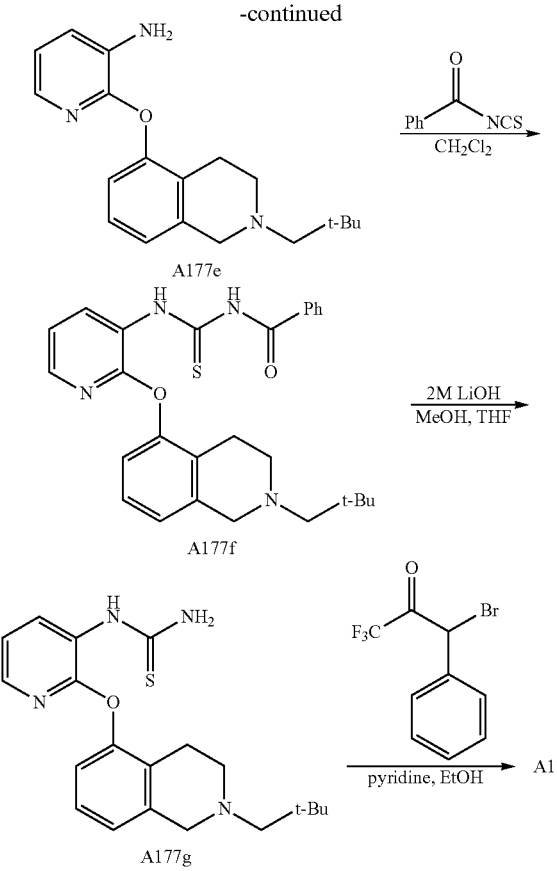

Example A177a 1-(5-Amino-3,4-dihydroisoquinolin-2(1H)-yl)-2,2-dimethylpropan-1-one 1,2,3,4-tetrahydroisoquinolin-5-amine (commercially available from Aldrich, 1 g, 6.7 mmol) was dissolved in 20 mL of dichloromethane. 1,1-dimethylpropanoic acid (0.68 g, 6.7 mmol) and EDC (1.28 g, 6.7 mmol) were added and the mixture was stirred for 6 h at rt. The solvent was removed and the residue purified by flash chromatography (SiO$_2$; 0-100% ethyl acetate hexane) to provide 0.48 g (31%) of Example A177a as a yellow oil. HPLC; $^1$H NMR (400 MHz, CDCl$_3$).

Example A177b 1-(5-Hydroxy-3,4-dihydroisoquinolin-2(1H)-yl)-2,2-dimethylpropan-1-one Example A177a (0.48 g, 2.1 mmol) was dissolved in 25 mL of 15% sulfuric acid. The reaction mixture was stirred at 60° C. for 0.5 h and NaNO$_2$ (0.15 g, 2.1 mmol) in 4 mL of H$_2$O was added dropwise. The reaction mixture was stirred at 60° C. for additional 1 h, then cooled to 25° C. The aqueous layer was extracted with EtOAc (40 mL×2). The organic solution was dried over sodium sulfate and concentrated in vacuo, yielding oily residue which was purified on column chromatography (0-100% ethyl acetate, hexane) to provide 0.27 g (1.15 mmol, 55%) of Example A177b.

244

Example A177c

2-Neopentyl-1,2,3,4-tetrahydroisoquinolin-5-ol

Example A177b (0.27 g, 1.15 mmol) was dissolved in 10 mL of THF. Lithium aluminum hydride (1.0 M in THF, 5 mL, 5 mmol) was added an the mixture was heated to 50° C. for 6 h. The reaction was cooled and quenched with a few drops of water. The reaction mixture was filtered and the solvent removed. The residue was purified by flash chromatography (ISCO system 40 g SiO$_2$; eluted with 0-100% ethyl acetate, hexane) to provide 0.26 g (>95%) of Example A177c as a yellow oil. HPLC; $^1$H NMR (400 MHz, CDCl$_3$).

Example A177d

2-Neopentyl-5-(3-nitropyridin-2-yloxy)-1,2,3,4-tetrahydroisoquinoline

Example A177c (260 mg, 1.2 mmol) and 2-chloro-3-nitrobenzene (225 mg, 1.4 mmol) were heated to 60° C. for 3 h. The mixture was cooled and the mixture was purified by flash chromatography (ISCO system 40 g SiO$_2$; eluted with 0-100% ethyl acetate hexane) to provide 170 g (41%) of Example A177d as a yellow oil. HPLC; $^1$H NMR (400 MHz, CDCl$_3$).

Example A177e 2-(2-Neopentyl-1,2,3,4-tetrahydroisoquinolin-5-yloxy)pyridin-3-amine Example A177d was dissolved in 5 mL of methanol. Palladium (5% on charcoal, 20 mg) was added and the mixture was stirred for 12 h at rt under 1 atm hydrogen. The mixture was purged with nitrogen then filtered through Celite®. The solvent was removed to provide Example A177e which was subjected to the subsequent reaction without further purification (150 mg, >95%). HPLC; $^1$H NMR (400 MHz, CDCl$_3$).

Example A177f

1-Benzoyl-3-(2-(2-neopentyl-1,2,3,4-tetrahydroisoquinolin-5-yloxy)pyridin-3-yl)thiourea Example A177e (50 mg, 0.16 mmol) was dissolved in 2 mL of dichloromethane. Benzoylisothiocyanate (26 µL, 0.19 mmol) was added and the mixture was heated to 40° C. for 6 h. The reaction mixture was cooled and the solvent removed to provide Example A177f (LC/MS 475 M+H) as a brown oil that was used in the subsequent reaction without purification or further characterization.

Example A177g 1-(2-(2-Neopentyl-1,2,3,4-tetrahydroisoquinolin-5-yloxy)pyridin-3-yl)thiourea Example A177f was dissolved in 2 mL of 50% methanol and 50% tetrahydrofuran. Lithium hydroxide (2.0 M aq, 0.16 mL, 0.32 mmol) was added and the mixture was heated to 50° C. for 3 h. The reaction mixture was concentrated then partitioned between water and ethyl acetate. The aqueous phase was extracted with ethyl acetate. The combined organic extracts were dried over magnesium sulfate, filtered and the solvent removed to provide 65 mg of a brown oil. The residue was purified by flash chromatography (15 g SiO$_2$; eluted with 5% methanol, 25% ethyl acetate, hexane) to provide 35 mg of a yellow oil that contained the desired product with some impurities. Repurification using the same flash chromatography conditions provided 18 mg (30% over 2 steps) of pure Example A177g. HPLC; ¹H NMR (400 MHz, CDCl₃).

Example A177

Example A177g (18 mg, 0.049 mmol) and Example 176a (43 mg) were dissolved in 0.5 mL of ethanol. Pyridine (8 μL, 0.1 mmol) was added and the mixture was heated to 100° C. for 1.5 h in a sealed tube. The reaction mixture was cooled to rt and the solvent removed. The residue was purified by preparative HPLC (YMC Pack ODS-A 5μ, 30 mm×100 mm column, eluted with 42-90% methanol and water with 0.1% TFA, linear gradient over 10 min, 40 mL/min) to provide 20 mg (77%) of the TFA salt of compound J (2-(2-neopentyl-1,2,3,4-tetrahydroisoquinolin-5-yloxy)-N-(5-phenyl-4-(trifluoromethyl)thiazol-2-yl)pyridin-3-amine) as a tan powder. HPLC, LC/MS, ¹H NMR (400 MHz, CDCl₃), MS (ESI) m/e 539 (M+H); HRMS (ESI) m/e calc'd for $C_{29}H_{30}F_3N_4OS$: 539.2092. Found (M⁺): 539.2081.

Example A178

2-(2-(1-Neopentylpiperidin-4-yl)phenoxy)-N-(5-phenyl-4-(trifluoromethyl)thiazol-2-yl)pyridin-3-amine

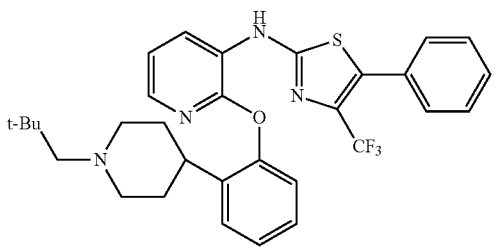

Example A178a 2-(Piperidin-4-yl)phenol

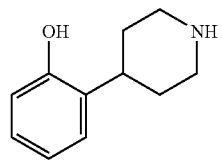

A solution of 4-(2-methoxyphenyl)piperidine (Fluka, 5 g, 26.1 mmol) in 48% hydrobromic acid (45 mL) was heated to 100° C. for 3 days. The mixture was then allowed to cool down to rt and it was concentrated under reduced pressure to give 2-(piperidin-4-yl)phenol as a light pink solid which was used directly in the next step. M+H=178.1.

Example A178b 2-(1-Neopentylpiperidin-4-yl)phenol

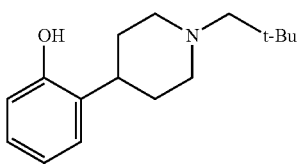

Example A178b was made from Example A178a using the reductive amination procedure previously described. The crude product was used directly without further purification. M+H=248.2.

Example A178c 2-(2-(1-Neopentylpiperidin-4-yl)phenoxy)-3-nitropyridine

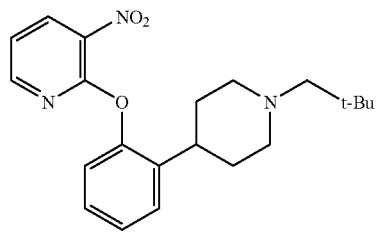

Example A178c was made from Example A178b using the standard procedure described above. M+H=370.2.

Example A178d 2-(2-(1-Neopentylpiperidin-4-yl)phenoxy)pyridin-3-amine

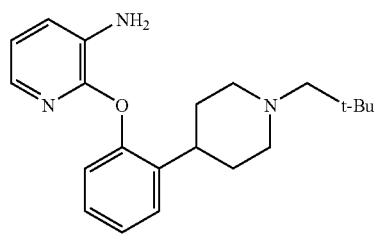

Example A178d was made from the reaction of zinc dust, ammonium chloride and Example A178c as described above. M+H=340.2.

Example A178

Example A178 was prepared from Example A178a using the similar procedure described for Example 217. (M+H)$^+$= 567.0. $^1$H nmr (400 MHz, MeOH-d$_4$) δ ppm 8.95 (m, 1H), 7.65-7.07 (m, 11H), 3.67 (m, 2H), 3.15 (m, 3H), 2.99 (s, 2H), 2.13 (m, 4H), 1.11 (s, 9H).

Utility

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; kidney embolisms; peripheral occlusive arterial disease (e.g., peripheral arterial disease, intermittent claudication, critical leg ischemia, prevention of amputation, prevention of cardiovascular morbidity such as MI, transient ischemic attack, stroke or ischemic sudden death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation (e.g., thrombophlebitis); ischemia (such as that resulting from vascular occlusion, cerebral infarction, transient ischemic attack, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously); thrombosis resulting from medical implants, devices, or procedures in which blood is exposed to an artificial surface that promotes thrombosis. The medical implants or devices include, but not limited to: prosthetic valves, indwelling catheters, stents, and vessel grafts. The procedures include, but not limited to: cardiopulmonary bypass and hemodialysis.

In general, a thromboembolic disorder is a circulatory disease caused by blood clots (i.e., diseases involving fibrin formation, platelet activation, and/or platelet aggregation). The term "thromboembolic disorders" as used herein also includes arterial or venous cardiovascular or cerebrovascular thromboembolic disorders, and thromboembolic disorders in the chambers of the heart.

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for P2Y$_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

P2Y$_1$ Assays

A. Binding Assay

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pcDNA 3.1 (Invitrogen) to produce a P2Y$_1$ expression construct. This construct was then transfected into the human embryonic kidney cell line HEK-293 and stable transfectants selected in Genetcin®(G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete® protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCL$_2$, 5 mM EDTA, 5 mM KCl) and stored at −70° C. until used.

Binding reactions were performed in WGA FlashPlates (PerkinElmer Life Sciences, Cat # SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 μM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (KO calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

Compounds tested in the P2Y$_1$ binding assay are considered to be active if they exhibit a K$_i$ of equal to or less than 10 μM. Preferred compounds of the present invention have K$_i$'s of equal to or less than 1 μM. More preferred compounds of the present invention have K$_i$'s of equal to or less than 0.1 μM. Even more preferred compounds of the present invention have K$_i$'s of equal to or less than 0.01 μM. Compounds of the present invention have demonstrated K$_i$ values of equal to or less than 10 μM in the assay for P2Y$_1$ binding, thereby confirming that they act to modulate P2Y$_1$ activity.

The compounds of the present invention may be used in combination with each other, or with other anti-platelet agents. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phosphodiesterase inhibitors; cholesterol/lipid lowering agents and lipid profile therapies; anti-diabetic agents; antidepressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in U.S. Application Publication US 20030022890.

Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable anti-platelet agents for use in combination with the compounds of the present invention include: GPIIb/IIIa blockers (e.g., abciximab, eptifibatide, tirofiban, integrelin); other P2Y$_{12}$ antagonists (e.g., clopidogrel, ticlopidine, Prasugrel); thromboxane receptor antagonists (e.g., ifetroban); aspirin; and PDE-III inhibitors (e.g., dipyridamole) with or without aspirin.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); factor VIIa inhibitors; factor Xa inhibitors; factor XIa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phosphodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiazolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in U.S. Pat. No. 6,548,529.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabeled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (II):

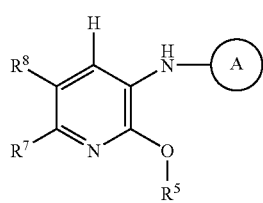

or a stereoisomer, a tautomer, or a pharmaceutically acceptable salt thereof, wherein:
ring A is

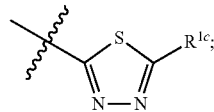

$R^{1c}$ is independently $C_{1-6}$ alkyl substituted with 0-2 $R^a$, $C_{2-6}$ alkenyl substituted with 0-2 $R^a$, $C_{2-6}$ alkynyl substituted with 0-2 $R^a$, Br, CN, $CF_3$, $-CF_2CF_3$, $-C(NH_2)=N(OH)$, $C(O)R^c$, $-CH(=NOH)$, $-C(O)OR^c$, $NR^{12}R^{13}$, $-C(O)NR^{12}R^{13}$, $-CON(Me)(CH_2)_2OH$, $-S(O)_pNR^{12}R^{13}$, $-(CH_2)_r-C_{3-6}$ cycloalkyl substituted with 0-2 $R^b$, $-(CH_2)_r$-adamantyl substituted with 0-2 $R^b$, $-(CH_2)_r$-phenyl substituted with 0-4 $R^b$, or $-(CH_2)_r$-naphthyl substituted with 0-4 $R^b$;

$R^5$ is phenyl substituted with 1-4 $R^{5a}$;

$R^{5a}$ is, independently at each occurrence, F, Cl, Br, I, $-(CR^fR^f)_r-OR^c$, $SR^c$, CN, $CF_3$, $-CF_2CF_3$, $OCF_3$, $-OCF_2CF_2H$, $-OCF_2CF_3$, $-NR^{12}R^{13}$, $-C(O)R^c$, $-C(O)OR^c$, $-C(O)NR^{12}R^{13}$, $-NR^{14}C(O)R^d$, $-S(O)_p NR^{12}R^{13}$, $-S(O)R^d$, $-S(O)_2R^d$, $-Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, or $-(CR^fR^f)_r-C_{3-10}$ carbocycle substituted with 0-3 $R^e$;

alternatively, two $R^{5a}$ groups attached to two adjacent carbon atoms, together with the carbon atoms to which they are attached, form a 5- to 7-membered carbocyclic ring, wherein said carbocyclic ring is substituted with 0-3 $R^e$;

$R^7$ is H, Br, CN, $NH_2$, $NMe_2$, or $-NH(4-OMe-Ph)$;

$R^8$ is H, Br, CN, $NMe_2$, or $-N(Me)(4-OMe-Ph)$;

$R^{11}$ is, independently at each occurrence, H, $-COPh$, $-COBn$, $-SO_2Me$, $-SO_2Ph$, $-SO_2Bn$, $C_{1-6}$ alkyl substituted with 1-5 fluorine, $-(CR^fR^f)_rC(O)NR^{12}R^{13}$, $C_{1-4}$ alkyl substituted with 0-2 $R^a$, $-(CH_2)_r-C_{3-6}$ cycloalkyl substituted with 0-2 $R^b$, $-(CH_2)_r$-phenyl substituted with 0-3 $R^b$, or $-CHMe$-phenyl substituted with 0-3 $R^b$;

$R^{12}$ is, independently at each occurrence, H, $C_{1-6}$ alkyl substituted with 1-5 fluorine, $-(CR^fR^f)_rC(O)NR^fR^f$, $C_{1-6}$ alkyl, $-(CH_2)_r-C_{3-6}$ cycloalkyl, or $-(CH_2)_n$-phenyl; wherein said alkyl and phenyl are substituted with 0-2 $R^g$;

$R^{13}$ is, independently at each occurrence, H, $C_{1-6}$ alkyl, or $-(CH_2)_n$-phenyl;

$R^{14}$ is, independently at each occurrence, H, $C_{1-6}$ alkyl, $C_{2-6}$ alkenyl, or $-(CH_2)_r$-phenyl carbocycle substituted with 0-3 $R^g$;

$R^a$ is, independently at each occurrence, H, F, $OCF_3$, $CF_3$, $-(CR^fR^f)_rOR^c$, $-(CR^fR^f)_rSR^c$, CN, $-(CR^fR^f)_rNR^{12}R^{13}$, $-(CR^fR^f)_rC(O)R^c$, $-(CR^fR^f)_rC(O)OR^c$, $-(CR^fR^f)_rC(O)NR^{12}R^{13}$, $-(CR^fR^f)_rNR^{14}C(O)R^d$, $-(CR^fR^f)_rS(O)_pNR^{12}R^{13}$, $-(CR^fR^f)_rS(O)R^d$, $-(CR^fR^f)_rS(O)_2R^d$, $C_{1-4}$ alkyl substituted with 1-5 fluorine, or $-(CH_2)_r-C_{3-10}$ carbocycle substituted with 0-3 $R^e$;

$R^b$ is, independently at each occurrence, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, F, Cl, Br, $CF_3$, $-OCF_3$, $-(CH_2)_r-OR^c$, $-(CH_2)_r-C(O)OR^c$, $-(CR^fR^f)_rNR^{12}R^{13}$, $-(CH_2)_r-C(O)NR^{12}R^{13}$, CN, —OCH$_2$C(Me)$_2$CH$_2$NMe$_2$, NO$_2$, —SO$_2$Me, OBn, —(CH$_2$)$_r$—C$_{3-6}$ cycloalkyl, —(CH$_2$)$_r$-phenyl substituted with 0-2 R$^e$, or —(CH$_2$)$_r$-naphthyl substituted with 0-3 R$^e$;

R$^d$ is, independently at each occurrence, CF$_3$, OH, C$_{1-4}$ alkoxy, C$_{1-6}$ alkyl, or —(CH$_2$)$_r$—C$_{3-10}$ carbocycle substituted with 0-2 R$^e$;

R$^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, Si(C$_{1-4}$ alkyl)$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, or —(CH$_2$)$_r$—C$_{6-10}$ aryl substituted with 0-2 R$^g$;

alternatively, two R$^e$ groups, together with the atoms to which they are attached, form a 5- to 7-membered carbocyclic ring, wherein said carbocyclic ring is substituted with 0-2 R$^g$;

R$^f$ is, independently at each occurrence, H, F, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

R$^i$ is, independently at each occurrence, H or C$_{1-6}$ alkyl;

n, at each occurrence, is selected from 0, 1, 2, 3, and 4;

p, at each occurrence, is selected from 0, 1, and 2; and r, at each occurrence, is selected from 0, 1, 2, 3, and 4.

2. A compound according to claim 1, wherein:

R$^{1c}$ is independently C$_{1-6}$ alkyl substituted with 0-2 R$^a$, C$_{2-6}$ alkenyl substituted with 0-2 R$^a$, C$_{2-6}$ alkynyl substituted with 0-2 R$^a$, Br, CF$_3$, C(O)R$^c$, —C(O)OR$^c$, NR$^{12}$R$^{13}$, —C(O)NR$^{12}$R$^{13}$, —(CH$_2$)$_r$—C$_{3-6}$ cycloalkyl substituted with 0-2 R$^b$, —(CH$_2$)$_r$-adamantyl substituted with 0-2 R$^b$, —(CH$_2$)$_r$-phenyl substituted with 0-3 R$^b$, or —(CH$_2$)$_r$-naphthyl substituted with 0-3 R$^b$;

R$^a$ is, independently at each occurrence, —O(CH$_2$)$_2$OMe, —C(O)OR$^c$, —(CR$^f$R$^f$)$_r$NR$^{12}$R$^{13}$, —(CR$^f$R$^f$)$_r$C(O) NR$^{12}$R$^{13}$, C$_{1-4}$ alkyl substituted with 1-5 fluorine, SPh, phenoxy substituted with 0-2 R$^e$, or benzoxy substituted with 0-2 R$^e$;

R$^b$ is, independently at each occurrence, C$_{1-6}$ alkyl, C$_{1-4}$ alkoxyl, F, Cl, CF$_3$, —OCF$_3$, OH, —CH$_2$OH, CN, —(CR$^f$R$^f$)$_r$NR$^{12}$R$^{13}$, —CH$_2$NMe$_2$, NO$_2$, —SO$_2$Me, —(CH$_2$)$_r$—C$_{3-6}$ cycloalkyl, CH(Ph)$_2$, —(CH$_2$)$_r$-phenyl substituted with 0-2 R$^e$, or —(CH$_2$)$_r$-naphthyl substituted with 0-3 R$^e$; and R$^e$ is, independently at each occurrence, C$_{1-6}$ alkyl, F, Cl, CN, or Bn.

3. A compound according to claim 1, wherein the compound is of Formula (IIb):

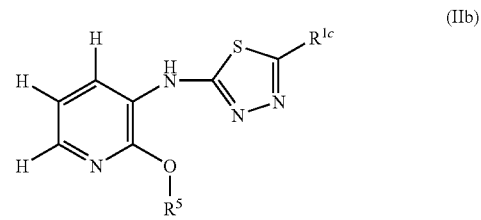

(IIb)

or a stereoisomer, a tautomer, or a pharmaceutically acceptable salt thereof, wherein:

R$^{1c}$ is H, i-Pr, t-Bu, neopentyl, cyclopropyl, 1-Ph-cyclopropyl, cyclobutyl, cycopentyl, cyclohexyl, 4-NHBn-cyclohexyl, 4-N(Me)Bn-cyclohexyl, —CH$_2$OBn, —CH$_2$O(CH$_2$)$_2$OMe, CO$_2$H, CO$_2$Et, —C(Me)$_2$(CH$_2$)$_2$CO$_2$Me, —CH$_2$N(Me)Bn, —(CH$_2$)$_3$N(Me)Bn, —C(Me)$_2$(CH$_2$)$_3$N(Me)Bn, —CON(Me)Bn, —C(Me)$_2$CH$_2$CON(Me)Bn, —C(Me)$_2$(CH$_2$)$_2$CON(Me)Bn, Ph, phenethyl, 3-Me-Ph, 4-Me-Ph, 4-t-Bu-Ph, 3-OH-Ph, 2-OMe-Ph, 4-OMe-Ph, 4-F-Ph, 2-Cl-Ph, 3-Cl-Ph, 4-CF$_3$-Ph, 3-OCF$_3$-Ph, 4-OCF$_3$-Ph, 4-CN-Ph, 3-NMe$_2$-Ph, 4-NMe$_2$-Ph, 2-CH$_2$NMe$_2$-Ph, 3-CH$_2$NMe$_2$-Ph, 4-CH$_2$NMe$_2$-Ph, 4-NO$_2$-Ph, 4-Ph-Ph, 3,5-diCl-Ph, 4-F-Bn, 4-OMe-Bn, 4-NMe$_2$-Bn, naphth-2-yl, or

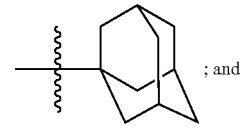; and

R$^5$ is 2-t-Bu-Ph, 2-Br-Ph, 2-CO$_2$Me-Ph, or 3-CO$_2$Et-Ph.

4. A compound according to claim 1, wherein the compound is the following formula:

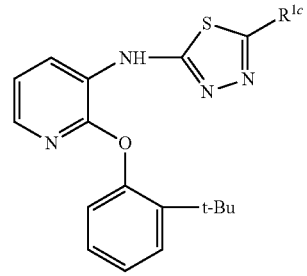

or a stereoisomer or a pharmaceutically acceptable salt thereof; wherein:

R$^{1c}$ is H, i-Pr, t-Bu, neopentyl, —CH$_2$O(CH$_2$)$_2$OMe, —C(Me)$_2$(CH$_2$)$_2$CO$_2$Me, —(CH$_2$)$_3$N(Me)(Bn, —C(Me)$_2$(CH$_2$)$_3$N(Me)Bn, —C(Me)$_2$CH$_2$CON(Me) Bn, —C(Me)$_2$(CH$_2$)$_2$CON(Me)Bn, cyclopropyl, cyclobutyl, cyclopentyl, cyclohexyl, Ph, 3-Me-Ph, 4-Me-Ph, 4-t-Bu-Ph, 2-OMe-Ph, 4-OMe-Ph, 4-F-Ph, 2-Cl-Ph, 3-Cl-Ph, 4-CF$_3$-Ph, 3-OCF$_3$-Ph, 4-OCF$_3$-Ph, 4-CN-Ph, 3-NMe$_2$-Ph, 4-NMe$_2$-Ph, 3-CH$_2$NMe$_2$-Ph, 4-CH$_2$NMe$_2$-Ph, 4-NO$_2$-Ph, 3,5-diCl-Ph, 4-Ph-Ph, 4-F-

Bn, —CH$_2$OBn, 4-OMe-Bn, 4-NMe$_2$-Bn, phenethyl, 1-Ph-cyclopropyl, —CON(Me)Bn,

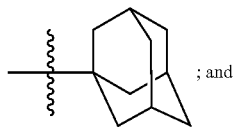 ; and naphth-2-yl, or

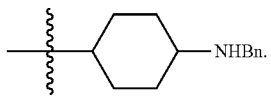

5. A compound according to claim 1, wherein the compound is selected from the group consisting of:

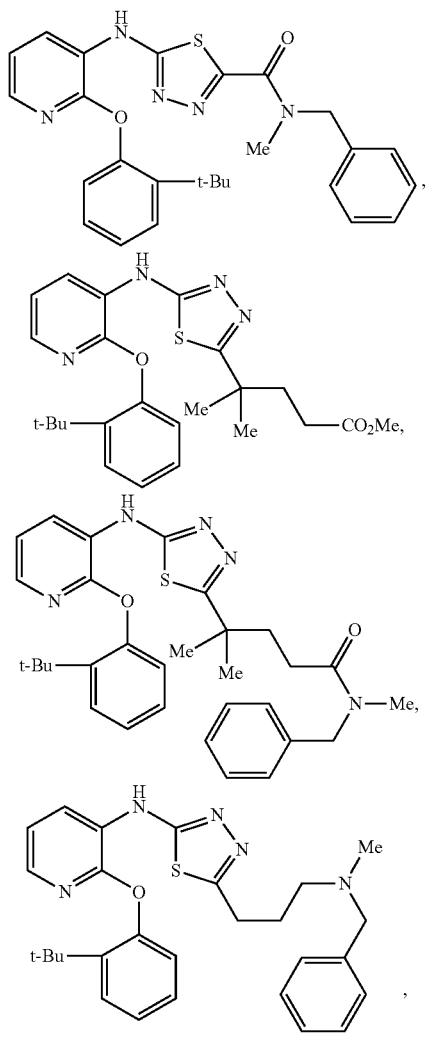

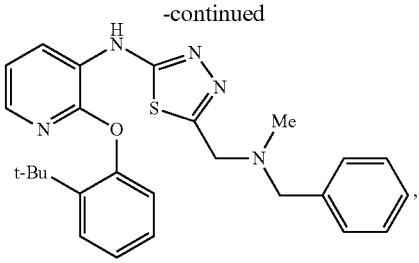

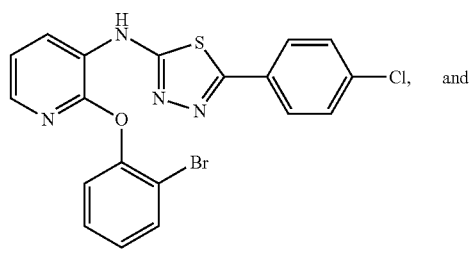

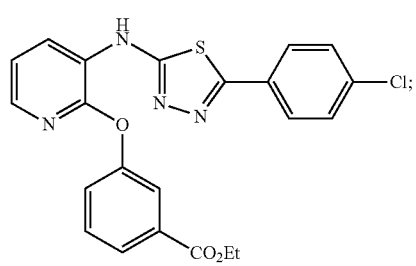

or a stereoisomer or a pharmaceutically acceptable salt thereof.

6. A pharmaceutical composition, comprising: a pharmaceutically acceptable carrier and a therapeutically effective amount of a compound of claim 1.

7. A pharmaceutical composition, comprising: a pharmaceutically acceptable carrier and a therapeutically effective amount of a compound of claim 2.

8. A pharmaceutical composition, comprising: a pharmaceutically acceptable carrier and a therapeutically effective amount of a compound of claim 3.

9. A pharmaceutical composition, comprising: a pharmaceutically acceptable carrier and a therapeutically effective amount of a compound of claim 4.

10. A pharmaceutical composition, comprising: a pharmaceutically acceptable carrier and a therapeutically effective amount of a compound of claim 5.

* * * * *

UNITED STATES PATENT AND TRADEMARK OFFICE
CERTIFICATE OF CORRECTION

PATENT NO. : 8,273,772 B2
APPLICATION NO. : 12/619702
DATED : September 25, 2012
INVENTOR(S) : James C. Sutton et al.

It is certified that error appears in the above-identified patent and that said Letters Patent is hereby corrected as shown below:

Page 1 Column 1
Line 8, "2005" should read -- 2006, now issued Patent No. 7,645,778 --.

Column 258
Line 18, "cycopentyl" should read -- cyclopentyl --.

Column 259

Line 6, " 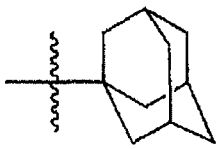 ; and " should read -- 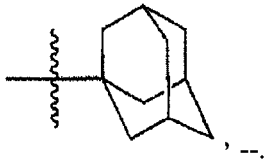 , --.

Signed and Sealed this
Fifteenth Day of January, 2013

David J. Kappos
Director of the United States Patent and Trademark Office